United States Patent
Deisher

(10) Patent No.: US 11,219,628 B2
(45) Date of Patent: Jan. 11, 2022

(54) REPLACEMENT OF CYTOTOXIC PRECONDITIONING BEFORE CELLULAR IMMUNOTHERAPY

(71) Applicant: AVM BIOTECHNOLOGY, LLC, Seattle, WA (US)

(72) Inventor: Theresa Deisher, Seattle, WA (US)

(73) Assignee: AVM Biotechnology, LLC, Seattle, WA (US)

( * ) Notice: Subject to any disclaimer, the term of this patent is extended or adjusted under 35 U.S.C. 154(b) by 0 days.

(21) Appl. No.: 15/976,630

(22) Filed: May 10, 2018

(65) Prior Publication Data

US 2018/0296572 A1 Oct. 18, 2018

Related U.S. Application Data

(63) Continuation of application No. PCT/US2018/025517, filed on Mar. 30, 2018.

(60) Provisional application No. 62/480,414, filed on Apr. 1, 2017, provisional application No. 62/613,697, filed on Jan. 4, 2018, provisional application No. 62/624,454, filed on Jan. 31, 2018.

(51) Int. Cl.
| | |
|---|---|
| *A61K 31/573* | (2006.01) |
| *A61P 35/00* | (2006.01) |
| *A61K 35/17* | (2015.01) |
| *A61K 45/00* | (2006.01) |
| *A61P 37/00* | (2006.01) |
| *A61P 31/18* | (2006.01) |
| *A61K 39/00* | (2006.01) |

(52) U.S. Cl.
CPC ........ *A61K 31/573* (2013.01); *A61K 39/0011* (2013.01); *A61K 45/00* (2013.01); *A61P 31/18* (2018.01); *A61P 35/00* (2018.01); *A61P 37/00* (2018.01); *A61K 35/17* (2013.01); *A61K 2039/515* (2013.01); *A61K 2039/5158* (2013.01)

(58) Field of Classification Search
CPC .......... A31K 35/17; A61K 31/56; A61K 8/63; A61K 2039/5154; A61K 2039/5158; A61K 35/17; A61K 31/573; A61P 37/06
See application file for complete search history.

(56) References Cited

U.S. PATENT DOCUMENTS

| | | | |
|---|---|---|---|
| 5,728,388 A | 3/1998 | Terman | |
| 7,282,222 B2 | 10/2007 | Phillips | |
| 8,030,469 B2 | 10/2011 | Aoyagi | |
| 9,855,298 B2 | 1/2018 | Bot et al. | |
| 9,962,408 B2* | 5/2018 | Deisher | A61K 31/00 |
| 2002/0006409 A1 | 1/2002 | Wood | |
| 2004/0247574 A1 | 12/2004 | Christopherson et al. | |
| 2006/0233766 A1 | 10/2006 | Messina et al. | |
| 2007/0196331 A1 | 8/2007 | Phillips et al. | |
| 2007/0243173 A1 | 10/2007 | Phillips et al. | |
| 2007/0243174 A1 | 10/2007 | Phillips et al. | |
| 2007/0243175 A1 | 10/2007 | Phillips et al. | |
| 2007/0248577 A1 | 10/2007 | Phillips et al. | |
| 2009/0047263 A1 | 2/2009 | Yamanaka | |
| 2009/0191201 A1* | 7/2009 | Heiss | A61K 31/573 424/136.1 |
| 2009/0299269 A1 | 12/2009 | Foley et al. | |
| 2010/0047215 A1 | 2/2010 | Phillips et al. | |
| 2010/0055107 A1* | 3/2010 | Zeng | C07K 16/2809 424/141.1 |
| 2011/0091434 A1 | 4/2011 | Miller | |
| 2012/0045435 A1* | 2/2012 | Deisher | A61K 31/00 424/133.1 |
| 2013/0287748 A1 | 10/2013 | June et al. | |
| 2014/0050708 A1 | 2/2014 | Powell et al. | |
| 2014/0099309 A1 | 4/2014 | Powell, Jr. et al. | |
| 2014/0154228 A1 | 6/2014 | Volk et al. | |
| 2014/0227237 A1 | 8/2014 | June et al. | |
| 2015/0283178 A1* | 10/2015 | June | A61K 35/17 424/85.2 |
| 2018/0296572 A1 | 10/2018 | Deisher | |

FOREIGN PATENT DOCUMENTS

| | | |
|---|---|---|
| JP | 2002508335 | 3/2002 |
| JP | 2011520959 A | 7/2011 |
| WO | 1995/13093 A1 | 5/1995 |
| WO | 9930738 A2 | 6/1999 |
| WO | 2003/047616 A1 | 6/2003 |
| WO | 2003/097052 A2 | 11/2003 |
| WO | 2004/098644 A1 | 11/2004 |
| WO | 2008/081035 A1 | 7/2008 |
| WO | 2008081035 A1 | 7/2008 |
| WO | 2008/094689 A2 | 8/2008 |
| WO | 2009142759 A1 | 11/2009 |

(Continued)

OTHER PUBLICATIONS

Hinrichs et al., J. Immunother., 2005, 28(6):517-524.*
International Search Report and Written Opinion dated Aug. 10, 2018 in PCT/US2018/025517 (13 pages).
Hinrichs et al: "Glucocorticoids do not inhibit antitumor activity of activated CD8+ T cells.", J Immunother. 2005 ; 28(6): 517-524.
Dudley et al."A Phase I Study of Nonmyeloablative Chemotherapy and Adoptive Transfer of Autologous Tumor Antigen-Specific T Lymphocytes in Patients With Metastatic Melanoma", Journal of Immunotherapy, vol. 25, No. 3, Jan. 1, 2002 (Jan. 1, 2002), pp. 243-251.
Bracci et al., "Cyclophosphamide enhances the antitumor efficacy of adoptively transferred inmune cells through the induction of cytokine expression, B-cell and T-cell homeostatic proliferation, and specific tumor infiltration", Clin Cancer Research, vol. 113. No. 2. Jan. 15, 2007 (Jan. 15, 2007), pp. 644-653.

(Continued)

*Primary Examiner* — Hong Sang
(74) *Attorney, Agent, or Firm* — McNeill Baur PLLC

(57) ABSTRACT

Provided herein are novel therapeutic compositions and methods that keep cellular immunotherapies in the circulation or at the site of injection for extended periods of time without resorting to the use of cytotoxic preconditioning. For example, the compositions and methods herein lymphodeplete and reduce or ablate sites in the secondary lymphatics where the cellular immunotherapy is bound and sequestered, without the use of cytotoxic preconditioning.

19 Claims, 23 Drawing Sheets

(56) References Cited

FOREIGN PATENT DOCUMENTS

| WO | 2009/152186 A1 | 12/2009 | | |
|---|---|---|---|---|
| WO | 2016120216 A1 | 8/2016 | | |
| WO | 2016/191756 A1 | 12/2016 | | |
| WO | WO-2018102606 A1 | * | 6/2018 | ........... A61K 38/191 |
| WO | 2018183927 A1 | 10/2018 | | |

OTHER PUBLICATIONS

Bierer et al., "Cyclosporin A and FK506: molecular mechanisms of immunosuppression and probes for transplantation biology", Current Opinion in Immunology 1993, 5:763-773.
Braitch et al., "Glucocorticoids increase CD4+CD25high cell percentage and Foxp3 expression in patients with multiple sclerosis", Acta Neurol Scand. Apr. 2009 ; 119(4): 239-245. doi:10.1111/j.0600-0404.2008.01090.x.
Brendolan et al., "Development and function of the mammalian spleen", BioEssays, 2007, 29:166-177.
Burger et al., "Coming full circle: 70 years of chronic lymphocytic leukemia cell redistribution, from glucocorticoids to inhibitors of B-cell receptor signaling", Blood. Feb. 28, 2013; 121(9): 1501-1509.
Chang et al., "Egress of CD19 CD5 cells into peripheral blood following treatment with the Bruton tyrosine kinase inhibitor ibrutinib in mantle cell lymphoma patients", Blood. Oct. 3, 2013; 122(14): 2412-2424.
Chatenoud et al., "Adaptive human regulatory T cells: myth or reality?", J. Clin. Invest. 116:2325-2327 (2006). doi:10.1172/JCI29748.
Cheadle et al., "Differential Role of Th1 and Th2 Cytokines in Autotoxicity Driven by CD19-Specific Second-Generation Chimeric Antigen Receptor T Cells in a Mouse Model", J Immunol 2014; 192:3654-3665; Prepublished Wine Mar. 12, 2014; doi: 10.4049/jimmunol.1302148.
Elmore, Susan, "Enhanced Histopathology of the Spleen", Toxicologic Pathology, 34:648-655, 2006.
Fauci, A.S., "Mechanisms of corticosteroid action on lymphocyte suhpopulations II. Differential Effects of In Vivo Hvdrocortisone, Prednisone and Dexamethasone on In Vitro Expression of Lymphocyte Function", Clin. exp. Immunol. (1976) 24, 54-62.
Fehervari and Sakaguchi, "Development and function of CD25RCD4R regulatory T cells", Current Opinion in Immunology 2004, 16:203-208.
Gaur and Ganguly, "Effect of Single Dose Betamethasone Administration in Pregnancy on Maternal and Newborn Parameters", Journal of Clinical and Diagnostic Research. May 2017, vol. 11(5): FC15-FC18.
Henderson et al., "Comparison of the effects of FK-506, cyclosporin a and rapamycin on IL-2 production", Immunology, 1991, 73:316-321.
Kershaw et al., "A Phase I Study on Adoptive Immunotherapy Using Gene-Modified T Cells for Ovarian Cancer", Clin Cancer Res 2006;12(20) Oct. 15, 2006, pp. 6106-6115.
Klingemann et al., "Autologous Stem Cell Transplant Recipients Tolerate Haploidentical Related-Donor Natural Killer Cell Enriched Infusions", Transfusion. Feb. 2013 ; 53(2): 412-418. doi:10.1111/j.1537-2995.2012.03764.x.
Kunder et al., "A Comprehensive Antibody Panel for Immunohistochemical Analysis of Formalin-Fixed, Paraffin-Embedded Hematopoietic Neoplasms of Mice: Analysis of Mouse Specific and Human Antibodies Cross-Reactive with Murine Tissue", Toxicologic Pathology, 35:366-375, 2007.
Liu et al., "Calcineurin Is a Common Target of Cyclophilin-Cyclosporin A and FKBP-FK506 Complexes", Cell, vol. 66, 807-815, Aug. 23, 1991.
Mathian et al., "Regulatory T Cell Responses to High-Dose Methylprednisolone in Active Systemic Lupus Erythematosus". 2015, PLoS One 10(12): e0143689. doi:10.1371/journal.pone.0143689.

Moriyama et al., "Pathological Effects in Lymphoid Tissues of the Spleen, Lymph Nodes, and Peyer's Patches in Cyclosporin-Treated Cynomolgus Monkeys", J. Vet. Med. Sci. 74(11): 1487-1491, 2012.
Ritchie et al., "Persistence and Efficacy of Second Generation CAR T Cell Against the LeY Antigen in Acute Myeloid Leukemia", The American Society of Gene & Cell Therapy, vol. 21, No. 11, 2122-2129, Nov. 2013.
Schleimer et al., "An assessment of the effects of glucocorticoids on degranulation, chemotaxis, binding to vascular endothelium and formation of leukotriene B4 by purified human neutrophils.", J Phamiacol Exp Ther. Aug. 1989;250(2):598-605.
Serafin et al., "Glucocorticoid resistance is reverted by LCK inhibition in pediatric T-cell acute lymphoblastic leukemia", Blood. 2017;130(25):2750-2761.
Shi et al., "Infusion of haplo-identical killer immunoglobulin-like receptor ligand mismatched NK cells for relapsed myeloma in the setting of autologous stem cell transplantation", Br J Haematol. Dec. 2008 ; 143(5): 641-653. doi:10.1111/j.1365-2141.2008.07340.x.
Suzuki et al., "Neutrophil infiltration as an important factor in liver ischemia and reperfusion injury. Modulating effects of FK506 and cyclosporine." Transplantation. Jun. 1993;55(6):1265-72.
Ulrich et al., "Validation of immune function testing during a 4-week oral toxicity study with FK506", Toxicology Letters 149 (2004) 123-131.
Yan et al., "Prednisone treatment inhibits the differentiation of B lymphocytes into plasma cells in MRL/MpSlac-lpr mice", Acta Pharmacologica Sinica (2015) 36: 1367-1376.
Wulffraat et al., "Prolonged remission without treatment after autologous stem cell transplantation for refractory childhood systemic lupus erythematosus". Arthritis & Rheumatism, 2001, vol. 44, pp. 728-734.
Childs et al. "Regression of Metastatic Renal-Cell Carcinoma after Nonmyeloablative Allogeneic Peripheral-Blood Stem-Cell Transplantation." New England J. Med., 2000, vol. 343, pp. 750-758.
Kreisel et al. "Complete remission of Crohn's disease after high-dose cyclophosphamide and autologous stem cell transplantation." Bone Marrow Transplantation, 2003, vol. 32, pp. 337-340.
Kolf et al., "Mesenchymal stromal cells. Biology of adult mesenchymal stem cells: regulation of niche, self-renewal and differentiation", 2007, Arthritis Research & Therapy, vol. 9, p. 204, 10 pages.
Alenzi et al., "Stem cells: Biology and clinical potential", 2011, African Journal of Biotechnology, vol. 10(86), pp. 19929-19940.
Wu et al., "Cell delivery in cardiac regenerative therapy.", 2012, Aging Research reviews, vol. 11, p. 32-40.
Steinert et al., "Major biological obstacles for persistent cell-based regeneration of articular cartilage", 2007, Arthritis Research & therapy, vol. 9, No. 3, 213, p. 1-15.
Li et al., "Xenotransplantation: role of natural immunity.", 2009, Transplant Immunology, vol. 21, p. 70-74.
Sprangers et al., "Xenotransplantation: where are we in 2008?", 2008, Kidney International, vol. 74, p. 14-21.
Kalos et al., "T cells with chimeric antigen receptors have potent antitumor effects and can establish memory in patients with advanced leukemia." Sci Transl Med. Aug. 10, 2011;3(95):95ra73. doi: 10.1126/scitranslmed.3002842.
Rosenberg et al., Durable complete responses in heavily pretreated patients with metastatic melanoma using T-cell transfer immunotherapy. Clin Cancer Res. Jul. 1, 2011;17(13):4550-7. doi: 10.1158/1078-0432.CCR-11-0116. Epub Apr. 15, 2011.
Muranski et al., "Increased intensity lymphodepletion and adoptive immunotherapy—how far can we go?", Nat Clin Pact Oncol. Dec. 2006;3(12):668-81.
Rytel and Kilbourne, "The Influence of Cortisone on Experimental Viral Infection VIII: Suppression by Cortisone of Interferon Formation in Mice Injected with Newcastle Disease Virus," J Exp Med, 123:767-75 (1966).
Savage et al., Urinary levels of triclosan and parabens are associated with aeroallergen and food sensitization. J. Allergy Clin. Immunol. 130, 453-60.e7 (2012).
Secord et al., "The Eμ-bcl-2 Transgene Enhances Antigen-Induced Germinal Center Formation in Both BALB/c and SJL Mice but

(56) References Cited

OTHER PUBLICATIONS

Causes Age-Dependent Germinal Center Hyperplasia Only in the Lymphoma-Prone SJL Strain," Am J Pathol, 147:422-33 (PMID: 7639335), (1995).

Shlomchik et al., From T to B and back again: positive feedback in systemic autoimmune disease. Nat Rev Immunol; 1:147-153 (2001).

Snarski E. et al. Immunoablation and autologous hematopoietic stem cell transplantation in the treatment of new-onset type 1 diabetes mellitus: long-term observations. Bone Marrow Transplant. 51, 398-402 (2016).

Spain et al., "Effect of Cortisone on Inflammation in Mice, Minimum Dose Required to Affect Eosinophil Count, Inflammation, Wound Healing and Size of Spleen," Am J Clin Pathol, 22:944-7 (1952).

Spanier et al., The associations of triclosan and paraben exposure with allergen sensitization and wheeze in children. Allergy asthma Proc. 35, 475-481 (2014).

Sullivan et al., Hematopoietic cell transplantation for Autoimmune disease: Updates from Europe and the United States. Biol Blood Marrow Transplant; 16(1 Suppl): S48-S56. doi:10.1016/j.bbmt.2009. 10.034 (2010).

Swart et al. Haematopoietic stem cell transplantation for autoimmune diseases. Nat. Rev. Rheumatol. 13, 244-256 (2017).

Thangavelu et al., Programmed death-1 is required for systemic self-tolerance in newly generated T cells during the establishment of immune homeostasis. J. Autoimmunity, 36, 301-312 (2011).

Thomas et al., Burden of Mortality Associated With Autoimmune Diseases Among Females in the United Kingdom. American Journal of Public Health. 100(11):2279-2287. doi:10.2105/AJPH.2009. 180273 (2010).

U.S Department of Health and Human Services Food and Drug Administration Center for Drug Evaluation and Research (CDER) Guidance for Industry: Estimating the Maximum Safe Starting Dose in Initial Clinical Trials for Therapeutics in Adult Healthy Volunteers. Pharmacology and Toxicology Jul. 2005.

Voltarelli et al., Autologous nonmyeloablative hematopoietic stem cell transplantation in newly diagnosed type 1 diabetes mellitus. JAMA 297, 1568-1576 (2007).

Wang et al., "Early administration of tumor necrosis factor-alpha antagonist promotes survival of transplanted neural stem cells and axon myelination after spinal cord injury in rats," Brain Res, 1575:87-100 (PMID: 24887643), (2014).

Zhang et al., "Repeated System Administration of Human Adipose-Derived Stem Cells Attenuates Overt Diabetic Nephropathy in Rats," Stem Cells Dev, 22:3074-86 (PMID: 23844841), (2013).

Zwang, Homeostatic expansion as a barrier to lymphocyte depletion strategies Curr Opin Organ Transplant. 19(4): 357-362 (2014).

Activate clinical trial, clinical trial identifier: NCT03158935; https://clinicaltrials.gov/ct2/show/NCT03158935, first posted May 18, 2017.

Aicher et al., "Assessment of the Tissue Distribution of Transplanted Human Endothelial Progenitor Cells by Radioactive Labeling," Circulation, 107(16):2134-9 (2003).

Aker, A. M. et al. Phenols and parabens in relation to reproductive and thyroid hormones in pregnant women. Environ. Res. 151, 30-37 (2016).

Alexander, T. et al. Hematopoietic stem cell therapy for autoimmune diseases—Clinical experience and mechanisms. J. Autoimmun. 92, 35-46 (2018).

American Diabetes Association. Diagnosis and classification of diabetes mellitus. Diabetes Care 37 Suppl 1, S81-90 (2014).

Atkinson, M. A., Eisenbarth, G. S. & Michels, A. W. Type 1 diabetes. Lancet (London, England) 383, 69-82 (2014).

Barbash et al., "Systemic Delivery of Bone Marrow-Derived Mesenchymal Stem Cells to the Infarcted Myocardium," Circulation, 108:863-8 (PMID: 12900340), (2003).

Barbosa Da Fonseca et al., "Migration and homing of bone-marrow mononuclear cells in chronic ischemic stroke after intra-arterial injection," Exp Neurol, 221(1):122-8 (PMID: 19853605), (2010).

Bone, R. N. & Evans-Molina, C. Combination Immunotherapy for Type 1 Diabetes. Curr. Diab. Rep. 17, 50 (2017).

Boroujeni et al., "Transplantation and Homing of Mouse Embryonic Stem Cells Treated with Erythropoietin in Spleen and Liver of Irradiated Mice," Iran Biomed J, 13(2):87-94 (PMID: 19471548), (2009).

Broder, M. S. et al. The Cost of Hematopoietic Stem-Cell Transplantation in the United States. Am. Heal. drug benefits 10, 366-374 (2017).

Cantu-Rodriguez, O. G. et al. Long-Term Insulin Independence in Type 1 Diabetes Mellitus Using a Simplified Autologous Stem Cell Transplant. J. Clin. Endocrinol. Metab. 101, 2141-2148 (2016).

Cell Therapy Catapult Phase I/II Study of Gene-modified WT1 TCR Therapy in MDS & AML Patients (https://clinicaltrials.gov/ct2/show/NCT02550535), first posted Sep. 15, 2015.

Chen et al., "Cyclosporine-assisted adipose-derived mesenchymal stem cell therapy to mitigate acute kidney Ischemia-reperfusion injury," Stem Cell Res Ther, 4(3):62 (PMID: 23726287) (2013).

Couri, C. E. B., Malmegrim, K. C. R. & Oliveira, M. C. New Horizons in the Treatment of Type 1 Diabetes: More Intense Immunosuppression and Beta Cell Replacement. Front. Immunol. 9, 1086 (2018).

Craddock et al., "The Immune Response to Foreign Red Blood Cells and the Participation of Short-Lived Lymphocytes," J Exp Med, 125:1149-72 (PMID: 6025321) (1967).

Daikeler, T., Tichelli, A. & Passweg, J. Complications of autologous hematopoietic stem cell transplantation for patients with autoimmune diseases. Pediatr. Res. 71, 439-444 (2012).

Darbre, P. D. & Harvey, P. W. Parabens can enable hallmarks and characteristics of cancer in human breast epithelial cells: a review of the literature with reference to new exposure data and regulatory status. J. Appl. Toxicol. 34, 925-938 (2014).

Defranco, A. L. Germinal centers and autoimmune disease in humans and mice. Immunol. Cell Biol. 94, 918-924 (2016).

Ettinger et al., "Effects of tumor necrosis factor and lymphotoxin on peripheral lymphoid tissue development," Int Immunol, 10(5):727-41 (PMID: 9678753), (1998).

Flammer, J. R. & Rogatsky, I. Minireview: Glucocorticoids in autoimmunity: unexpected targets and mechanisms. Mol. Endocrinol. 25, 1075-1086 (2011).

Gholamrezanezhad et al., "In vivo tracking of 111 In-oxine labeled mesenchymal stem cells following infusion in patients with advanced cirrhosis," Nucl Med Biol, 38:961-7 (PMID: 21810549), (2011).

Haba et al., "An immunohistochemical study on the effects of cyclosporin on the gut-associated lymphoid tissue of rats," Gastroenterol Jpn, 26(5):593-602 (PMID: 1836439), (1991).

Haddad-Mashadrizeh et al., Evidence for crossing the blood barrier of adult rat brain by human adipose-derived mesenchymal stromal cells during a 6-month period of post-transplantation, Cytotherapy, 15:951-60 (PMID: 23732047), (2013).

Henig, I. & Zuckerman, T. Hematopoietic stem cell transplantation-50 years of evolution and future perspectives. Rambam Maimonides Med. J. 5, e0028 (2014).

Jackson et al., "Tirilazad Mesylate—Effects of the 21-Aminosteriod on the Lymphoid System of Laboratory Animals: A Comparison with the Glucocorticoid Methylpredinsolone," Fundam Appl Toxicol, 26:246-57 (PMID: 7589913), (1995).

Jasmin et al., "Mesenchymal Bone Marrow Cell Therapy in a Mouse Model of Chagas Disease. Where Do the Cells Go?," PLoS Negl Trop Dis, 6(12):e1971 (2012).

Kang et al., "Tissue Distribution of 18F-FDG-Labeled Peripheral Hematopoietic Stem Cells After Intracoronary Administration in Patients with Myocardial Infarction," J Nucl Med, 47(8):1295-301 (PMID: 16883008), (2006).

Kim, J. H., Jin, S.-M., Kim, H. S., Kim, K.-A. & Lee, M.-S. Immunotherapeutic treatment of autoimmune diabetes. Crit. Rev. Immunol. 33, 245-281 (2013).

Lin et al., Pharmacological Mobilization of Endogenous Stem Cells Significantly Promotes Skin Regeneration after Full Thickness Excision: The Synergistic Activity of AMD3100 and Tacrolimus, J Invest Dermatol, 134(9):2458-2468 (PMID: 24682043), (2014).

Loh, Y. et al. Development of a secondary autoimmune disorder after hematopoietic stem cell transplantation for autoimmune diseases: role of conditioning regimen used. Blood 109, 2643-2648 (2007).

(56) References Cited

OTHER PUBLICATIONS

Lu, Y., Suzuki, J., Guillioli, M., Umland, O., & Chen, Z. Induction of self-antigen-specific Foxp3+ regulatory T cells in the periphery by lymphodepletion treatment with anti-mouse thymocyte globulin in mice. Immunology 134, 50-59 (2011).

Magdalena, W. et al. Lack of persistent remission following initial recovery in patients with type 1 diabetes treated with autologous peripheral blood stem cell transplantation. Diabetes Res. Clin. Pract. 143, 357-363 (2018). doi:10.1016/j.diabres.2018.07.020.

Malmegrim, K. C. R. et al. Immunological Balance Is Associated with Clinical Outcome after Autologous Hematopoietic Stem Cell Transplantation in Type 1 Diabetes. Front. Immunol. 8, 167 (2017).

Matsumoto et al., "Role of Lymphotoxin and the Type I TNF Receptor in the Formation of Germinal Centers," Science Reports, 271:1289-91 (PMID: 8638112), (1996).

Menke, A. et al. The prevalence of type 1 diabetes in the United States. Epidemiology (Cambridge, Mass.) 24, 773-774 (2013).

Miller et al., "Resistance of Long-Lived Lymphocytes and Plasma Cells in Rat Lymph Nodes to Treatment with Prednisone, Cyclophosphamide, 6-Mercaptopurine, and Actinomycin D," J Exp Med, 126:109-25 (PMID: 6027642) (1967).

Murray et al., "Overproduction of corticotropin-releasing hormone blocks germinal center formation: role of corticosterone and impaired follicular dendritic cell networks," J Neuroimmunol, 156:31-41 (PMID: 15465594) (2004).

Orem, J., et al. Burkitt's Lymphoma in Africa, a Review of the Epidemiology and Etiology: African Health Sciences, vols. 7.3: 166-175 (2007).

Pallera, A. M. & Schwartzberg, L. S. Managing the toxicity of hematopoietic stem cell transplant. J. Support. Oncol. 2, 223-228-247 (2004) (Abstract).

Pasparakis et al., "Immune and Inflammatory Responses in TNFα-deficient Mice: A Critical Requirement for TNFα in the Formation of Primary B Cell Follicles, Follicular Dendritic Cell Networks and Germinal Centers, and in the Maturation of the Humoral Immune Response," J Exp Med, 184(4):1397-411 (PMID: 8879212), (1996).

Pasricha, J. Current regimen of pulse therapy for pemphigus: Minor modifications, improved results. Indian J Dermatol Venereol Leprol 74;3, pp. 217-221 (2008).

Peng, B.-Y. et al. Addressing Stem Cell Therapeutic Approaches in Pathobiology of Diabetes and Its Complications. J. Diabetes Res. 2018, 7806435 (2018).

Petranyi et al., The Effect of Single Large Dose Hydrocortisone Treatment on IgM Antibody Production, Morphological Distribution of Antibody Producing Cells and Immunological Memory, Immunology, 21:151-8 (PMID: 4934137) (1971).

Ponchel et al., Interleukin-7 deficiency in rheumatoid arthritis: consequences for therapy-induced lymphopenia. Arthritis Res Ther, 7:R80-R92 (DOI 10.1186/ar1452) (2005).

Patt et al., Management issues with exogenous steroid therapy. Indian Journal of Endocrinology and Metabolism. 17 (Suppl 3):S612-S617. doi:10.4103/2230-8210.123548 (2013).

Ren et al., "Insulin-producing cells from embryonic stem cells rescues hyperglycemia via intra-spleen migration," Sci Rep, 4:7586 (PMID: 25533571), (2014).

Rooman et al., "The effect of dexamethasone on body and organ growth of normal and IGF-II-transgenic mice," J Endocrinol, 163:543-52 (PMID: 10588828), (1999).

Bonifant et al., "Toxicity and management in Car T-cell therapy," Mol Ther Oncolytics 3:16011 (2016).

Davila et al., "Efficacy and Toxicity Management of 19-28z CAR T Cell Therapy in B Cell Acute Lymphoblastic Leukemia," Sci Transl Med 6(224):224ra25 (2014).

Maude et al., "CD19-targeted chimeric antigen receptor T-cell therapy for acute lymphoblastic leukemia," Blood 125(26):4017-23 (2015).

Shank, et al., "Chimeric Antigen Receptor T Cells in Hematologic Malignancies," Pharmacotherapy, 37(3):334-345 (2017), Abstract only.

Stadtmauer et al., "CAR T-Cell Therapy: On the Verge of Breakthrough in Many Hematologic Malignancies," J. Adv. Pract. Oncol. 8:228-231 (2017).

AVM, FIRM presentation, Oct. 31, 2016, https://www.slideshare.net/thu_pham/avmfirmpresentation2016-67942141, 22 pages.

Brown et al., "Low Dose Cyclophosphamide Improves Survival in a Murine Treatment Model of Sepsis," Shock. 43 (1): 92-98 (2015).

Brudno et al., "Toxicities of chimeric antigen receptor T cells: recognition and management," Blood 127 (26):3321-3330 (2016).

Gattinoni et al., "Adoptive immunotherapy for cancer: building on success," Nat Rev Immunol 6(5):383-393 (2006).

International Preliminary Report on Patentability issued in International Application No. PCT/US2018/025517, dated Oct. 10, 2019, 7 pages.

\* cited by examiner $n = 5$/group
*$p < 0.05$ ANOVA (Dunnett's post-hoc) vs. Vehicle IV
†$p < 0.05$ ANOVA (Dunnett's post-hoc) vs. Vehicle PO
‡$p < 0.05$ Student's $t$-test vs. Vehicle IV Groups 1-4 IV : 1 = 20 mg/kg, 2 = 40 mg/kg, 3 = 80 mg/kg, 4 = Placebo
Groups 5-9 PO : 5 = 20 mg/kg, 6 = 40 mg/kg, 7 = 80 mg/kg, 8 = Placebo 3 mg/kg oral dexamethasone base increases human Bone Marrow CFU-F per ml 48 hours later compared to 31 historical controls aspirated using the same Marrow Cellutions needle as for Patients M & P.

REPLACEMENT OF CYTOTOXIC PRECONDITIONING BEFORE CELLULAR IMMUNOTHERAPY

CROSS-REFERENCE TO RELATED APPLICATIONS

This application is a continuation of International Patent Application No. PCT/US2018/025517, filed Mar. 30, 2018, which claims priority to U.S. Provisional Application No. 62/480,414, filed Apr. 1, 2017, to U.S. Provisional Application No. 62/613,697, filed Jan. 4, 2018, and to U.S. Provisional Application No. 62/624,454, filed Jan. 31, 2018, each of which is incorporated herein by reference in its entirety

FIELD OF THE INVENTION

The field of the invention pertains to compositions and methods, including novel dosing regimens, that enhance the short and long term tumor and pathogen killing by cellular immunotherapies, by keeping the cellular immunotherapy in the circulation or at the site of injection for extended periods of time without resorting to the use of cytotoxic preconditioning. The field of invention additionally enhances long term engraftment of the cellular immunotherapy.

BACKGROUND OF THE INVENTION

Cellular immunotherapies need to remain in the circulation or at the site of injection for extended periods of time in order to effectively find and participate in killing cancer or autoimmune activated cells or infectious agents. Unfortunately, the cellular immunotherapies are rapidly, typically within one hour after injection, cleared from the circulation or site of injection unless cytotoxic chemotherapy or radiation preconditioning has been done (Muranski *Nat Clin Pract Oncol.* 2006 December; 3(12): 668-681.; Kalos M et al. *Sci Transl Med.* August 10; 3(95) (2011); Rosenberg et al., *Clin. Cancer. Res.* (2011)). The prevailing thought has been that preconditioning enhanced adoptive cell transfer or therapy (ACT) effectiveness by eliminating Tregs and competing elements of the immune system called 'cytokine sinks' that would use up cytokines needed for optimal activation of ACT (Muranski *Nat Clin Pract Oncol.* 2006 December; 3(12): 668-681 page 2 paragraph 3, page 4 paragraph 4; U.S. Pat. No. 9,855,298 B2 January/2018, Bot page 29 Detailed Description of the Invention first paragraph). Several investigators have observed that the cellular immunotherapies rapidly bind and accumulate in the lung, liver, spleen, and secondary lymphatics (Kershaw M H et al. *Clin Cancer Res.* October 15; 12(20 Pt 1):6106-15 (2006)); (Ritchie D S et al. *Mol Ther.* November; 21(11):2122-9 (2013); (Cheadle *J Immunol* Apr. 15, 2014, 192 (8) 3654-3665). Kershaw concluded that the cellular immunotherapy signal in the lung and spleen was due to the cells being sticky and non-selectively trapped (page 6114, paragraph 3), while Cheadle concluded that the spleen accumulation observed in mice was a chronic toxicity manifested as a granuloma formation (page 3654, abstract).

Because of the toxicities associated with chemotherapy or radiation and the contribution of the chemotherapy to neuroedema and cytokine release syndrome after ACT, there is a need to develop safer and less cytotoxic methods to precondition patients to allow cellular immunotherapies to remain in the circulation or at the site of injection for extended periods of time.

While chemotherapy and radiotherapy have often been used to precondition patients prior to ACT, most leaders in the field teach that steroids or other immunosuppressive medications are specifically excluded for at least 3 days prior to NK administration (Klingemann H, Transfusion. 2013 February;53(2):412-8 page 3 Study Design, paragraph 3), and in adoptive cell therapy clinical trials steroid use is commonly an exclusion criteria for patient enrollment. For instance see the ACTIVATE clinical trial exclusion criteria #2 which specifically excludes systemic steroid or other immunesuppressant therapy within 7 days of ACT which in this clinical trial is autologous tumor-infiltrating lymphocytes that have been culture expanded (clinical trial identifier: NCT03158935—current online address: clinicaltrials.gov/ct2/show/NCT03158935). Also see U.S. Pat. No. 9,855,298 1/2018 (Bot et al) which in Example 3 exclusion criteria p Column 54 specifically excludes patients from ACT treatment if they have a current or expected need for systemic corticosteroid therapy. This demonstrates that the field believed corticosteroids were detrimental prior to ACT, and would not have conceived of preconditioning just prior to ACT with glucocorticoids as described in the present patent application. While US2013/0287748 A1 10/2013 (June et al) paragraph 0227 does disclose "In further embodiments, the T cells of the invention [claimed in US2013/0287748 A1] may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., *Curr. Opin . Immun.* 5:763-773, 1993)", June does not explain whether the use of the listed agents "in combination" with the disclosed T cell therapy relates to prior, concurrent or subsequent use, e.g. to manage symptoms. Preconditioning is not suggested.

June references Liu who used cyclosporine, FK506 and rapamycin at 300 nM concentrations and Henderson who used about 100 nM concentrations, which translate to low in vivo doses, of below 0.05 mg/kg.

Prior studies into the use of steroids to precondition a patient prior to ACT had shown this approach to be ineffective. Hinrichs (*J Immunother.* 2005 November-December; 28(6):517-24.) had evaluated dexamethasone as a preconditioning treatment prior to ACT. In comparison to total body irradiation (TBI), Hinrichs demonstrated that an HED of 0.8 mg/kg administered on day −6, day −4, and day −2 lymphodepleted equivalently to 5Gy TBI. Hinrichs demonstrate that pretreatment with systemic intraperitoneal dexamethasone at 10 mg/kg (HED 0.81 mg/kg) on day −6, −4, and −2 before ACT induced equivalent lymphodepletion compared to radiation, but this pretreatment did not enhance ACT tumor killing. In contrast, Hinrichs discloses that pretreatment with radiation did enhance ACT tumor killing. In the Hinrichs paper, the dexamethasone reportedly caused lymphodepletion as demonstrated by 99% reduced spleen cellularity. However, while Hinrichs reported 99% lymphodepletion, no enhancement of ACT tumor killing was observed. In contrast, Hinrichs observed that radiation does enhance ACT tumor killing. Experiments to repeat Hinrichs reported lymphodepletion, however, demonstrate that the Hinrichs doses of intraperitoneal dexamethasone at 10 mg/kg (HED 0.81 mg/kg) on day −6, day −4, and day −2, do not effectively lymphodeplete peripheral blood lymphocytes. With Hinrichs dosing, only B lymphocytes in the peripheral blood were significantly lymphodepleted, from 10680 (vehicle control) to 3733 live events measured by flow cytometry of CD3-CD19+ cells, a 65% reduction. In contrast, CD3+ T lymphocytes were reduced from 3370 to 2441 live events, only a non-significant 33% reduction. CD3+CD4+ T lymphocytes were reduced from 1779 to 902 live events, only a non-significant 50% reduction. CD3+CD8_T lymphocytes were reduced from 1318 to 1277 live events, only a non-significant 3% reduction. CD3+CD4+CD25+FoxP3+ Tregs were reduced from 198 to 70 live events, only a non-significant 65% reduction. And natural killer (NK) cells were reduced from 1153 to 958 live events, only a non-significant 17% reduction.

Some studies have preconditioned patients with a chemotherapeutic agent, which was administered in combination with dexamethasone. For instance, Shi et al (Br J Haematol. 2008 December; 143(5):641-53.) preconditioned relapsed multiple myeloma patients with fludarabine (Flu, 25 mg/m$^2$ on day −5 to day −2), and dexamethasone (Dex, 40 mg/d on days −5 to −2). This dose of dexamethasone corresponds to approximately 1.14 to 1.6 mg/kg within 72 hours prior to administration of ACT. Lymphodepletion was complete as shown in FIG. 5 of Shi et al with absolute WBC reduced from 10.9e9/L to 0.7e9/L a 94% reduction. Shi et al did not suggest using higher dexamethasone doses. Cell Therapy Catapult has preconditioned patients with fludarabine×5 days 30 mg/m$^2$ intravenous (i.v.) and methylprednisolone×1 day 500 mg i.v. for their A Phase I/II Study of Gene-modified WT1 TCR Therapy in MDS & AML Patients (clinicaltrials.gov/ct2/show/NCT02550535). This dose of methylprednisolone corresponds to a 100 mg dose of Dexamethasone which translates to about 1.4 mg/kg to 2 mg/kg. Additionally, both the Shi publication and the Cell Therapy Catapult trial preconditioned with repetitive doses of chemotherapy. Furthermore, methylprednisone increases Tregs, an undesireable response in the cancer patient where Tregs limit T cell tumor killing (Braitch Acta Neurol Scand. 2009 April; 119(4): 239-245; Mathian PLoS One. 2015; 10(12): e0143689).

Because of the toxicities associated with chemotherapy or radiation and the contribution of the cytotoxic preconditioning to neuroedema and cytokine release syndrome after ACT, there is a need to develop safer and less cytotoxic methods to precondition patients to allow cellular immunotherapies to remain in the circulation or at the site of injection for extended periods of time.

SUMMARY OF THE INVENTION

The present inventors have shown the spleen accumulation of cellular immunotherapies to be a specific binding event, in contrast to the prior belief, discussed above, that spleen accumulation was due non-selective sequestration. The present inventors believe that prior art chemotherapy- and radiatiotherapy-based methods non-selectively destroy the cellularity of the spleen, to keep the administered cellular immunotherapies in circulation or at the site of injection for extended durations of time and enhancing patient outcome.

The present patent application shows that non-chemotherapeutic agents, such as glucorticoids and other non-toxic lymphodepleting agents (NTLAs), can be used to make cellular immunotherapies more effective without the need for chemotherapy (or at least, can reduce the need for chemotherapy to just one day of chemotherapy treatment). For instance, the present application shows that acute doses of dexamethasone, typically about 300 to about 840 mgs, can be highly effective. In particular, the present invention discloses the benefit to cancer patients of pretreating the patient with a steroid such as dexamethasone shortly before cellular immunotherapy administration.

Thus, the present invention fills the need to replace chemo- and radiotherapy preconditioning by providing for methods and compositions for inhibiting binding of cellular immunotherapies to lymphoid tissue comprising administering cellular immunotherapies to an individual in conjunction with a therapeutic agent or agents that inhibit binding of cellular immunotherapies to lymphoid tissue, in particular to germinal centers and marginal zones in lymph nodes and germinal centers and marginal zones in the spleen. The therapeutic agent or agents also lymphodepletes peripheral blood lymphocytes via a biologic rather than a cytotoxic mechanism. The term "in conjunction with" can mean before, and/or together with, and/or after the cellular immunotherapies.

Accordingly, in a first aspect, this invention provides a method of enhancing adoptive cellular therapy (ACT) in a patient, by administering to the patient a non-toxic lymphodepleting agent (NTLA) at a dose that is effective to cause substantial lymphodepletion and/or cause ablation of secondary lymphatic germinal centers, wherein the method does not include the administration of radiotherapy nor a chemotherapeutic agent for a duration of more than 1 day within about 2 weeks preceding the start of ACT.

In a second aspect, this invention provides an NTLA for use in a method of enhancing adoptive cellular therapy (ACT) in a patient, the method comprising administering to the patient a dose of the NTLA that is effective to cause substantial lymphodepletion and/or cause ablation of secondary lymphatic germinal centers, wherein the method does not include the administration of a chemotherapeutic agent for a duration of 1 day or more.

In a third aspect, this invention provides a method of performing adoptive cellular therapy (ACT) in a patient in need thereof, said method comprising performing a method of enhancing ACT by pretreating the patient according to the invention; and then performing the ACT by administering therapeutic cells to the patient. In some embodiments, the NTLA is a steroid. The steroid may be a glucocorticoid. In some embodiments, the steroid is selected from the group consisting of dexamethasone, dexamethasone base, prednisone, methylprednisone, and dexamethasone analogues. In other embodiments, the NTLA is selected from the group consisting of tacrolimus and cyclosporine.

In some embodiments, the dose of the NTLA achieves at least 60% CD3+ lymphodepletion. Preferably, the dose achieves at least 70%, at least 80% or at least 90% lymphodepletion. In preferred embodiments, the ACT involves administration of either a cell used to enhance the immune system in treating a disease in said patient or a cell derived from an immune lineage which directly treats said disease.

In embodiments in which the NTLA is dexamethasone, the dexamethasone may be administered at a dose of at least about 3 mg/kg, at least about 4 mg/kg, at least about 5 mg/kg, at least about 6 mg/kg, at least about 7 mg/kg, at least about 8 mg/kg, at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, at least about 20 mg/kg, at least about 21 mg/kg, at least about 22 mg/kg, at least about 23 mg/kg, at least about 24 mg/kg, at least about 25 mg/kg, or at least about 26 mg/kg. The NTLA dexamethasone dose may be chosen from a range delimited by dexamethasone dosage values as disclosed herein, e.g. in the present paragraph. For instance the NTLA dexamethasone may be expressed as being administered at a dose chosen from a range of between about 9 mg/kg to about 12 mg/kg. In some embodiments, the dexamethasone may be administered at a dose of up to about 26 mg/kg.

Preferably, the NTLA is administered before ACT commences. The NTLA may be administered at least 12 hours before ACT commences. The NTLA may be administered at one or more time points between about 72 to about 12 hours prior to commencement of ACT.

In a fourth aspect, this invention provides a method of ameliorating the binding and accumulation of a cellular immunotherapy in secondary lymphatic binding sites comprising: identifying a patient suffering from cancer; administering to said patient a cellular immunotherapy comprising either a cell used to enhance the immune system in treating said cancer or a cell derived from an immune lineage which directly treats said cancer; and administering a non-toxic lymphodepleting agent (NTLA), which lymphodepletes and ablates the secondary lymphatic binding sites where said cellular immunotherapy binds and accumulates, and is selected from the group consisting of: Tacrolimus delivered as an injection or oral dose of 0.48 mg/kg to about 10 mg/kg for about 1-4 weeks, Cyclosporine administered at about 15-100 mgs/kg/daily or about 7.5-50 mgs/kg/twice-daily for about 7-28 days, Dexamethasone base, or an equivalent dose of another glucocorticoid, between about 3-26 mg/kg for a single acute dose about 12-72 hours, and a TNF inhibitor administered for about 3 to about 4 weeks; wherein the administration of the NTLA occurs before administration said cellular immunotherapy, such as to ameliorate the binding and accumulation of said cellular immunotherapy in secondary lymphatic binding sites.

In preferred embodiments of the aspects described herein, the patient is a human. The NTLA may be administered at least 12 hours before ACT commences. In some embodiments, NTLA is administered within about 72 hours preceding commencement of ACT. In some embodiments, the ACT comprises administration of anticancer T cells and/or anticancer NK cells to the patient. In preferred embodiments, the cells administered for ACT include T cells. The ACT may be adoptive T cell therapy. Preferably, the method does not include the administration of radiotherapy or a chemotherapeutic agent for a duration of more than 1 day within about 2 weeks preceding the start of ACT. In some embodiments, no radiotherapy or chemotherapeutic agents are administered to the patient. In some embodiments, the NTLA induces an elevation of one or more plasma cytokine in the patient, selected from the group consisting of IL-2, IL-7, IL-12, and IL-15 to levels preferably of 20 pg/ml or greater. Levels of IL-6 may be unaffected by the NTLA.

The enhancement of ACT may comprise enhanced cancer killing in a cancer patient, or reduced autoimmune causing cell count in a patient with an autoimmune disorder, or reduced infectious agent load, in a patient with an infectious disease.

Preferably the NTLA is administered before ACT commences. For instance, NTLA may be administered at least 12 hours before ACT commences, or at another interval in advance of ACT, as described herein. In some embodiments, the NTLA is administered at one or more time points between about 12 to about 72 hours prior to commencement of ACT.

In some embodiments of this invention, the method according to any of the preceding claims, wherein the ACT is an adoptive T cell therapy, for instance based on the transfusion of CAR T cells. In some embodiments, the patient is a cancer patient and the ACT comprises administration of anticancer T cells and/or anticancer NK cells.

The ACT may be based on autologous cells (i.e. cells that have been harvested from the patient, before being optionally modified or stimulated prior to transfer/readministration) or heterologous (i.e. cells or cell lines originating from another donor).

In some embodiments of this invention, no chemotherapeutic agents are administered to the patient.

A non-toxic lympodepleting therapeutic agent is an agent that induces lymphodepletion and inhibits germinal centers in the spleen without killing other rapidly dividing cells such as hair cells, mucosal cells, intestinal cells, and which does not induce sepsis, organ dysfunction, capillary leak, myocarditis, lethal inflammatory syndrome, fatal infusion reactions or subsequent new cancers.

The non-toxic lymphodepleting therapeutic agent can be administered without cytotoxic preconditioning or in combination with cytotoxic preconditioning. "In combination with" means administered before, and/or together with and/or after cytotoxic lymphodepleting chemotherapy, preferably with only one day of cytotoxic chemotherapy dosing. Addition of non-toxic lymphodepleting therapy can reduce the total dose or needed duration of cytotoxic lymphodepleting chemotherapy for lower adverse events and toxicities to the patient. The non-toxic lymphodepleting therapeutic agent can also be administered in combination with other cytotoxic preconditioning agents that include rituximab and similar molecules that bind lymphocytes and induce antibody-dependent cellular cytotoxicity (ADCC) and complement mediated cytotoxicity (CMC), in combination with temodar, in combination with interleukins or toll-like receptor agonists that can activate endogenous cytotoxic pathways, in combination with radiolabeled antibodies that trigger immune cell destruction (immunotoxins) such as antibodies to CD45, for instance Iomab-B, or in combination with total body radiation (TBI).

BRIEF DESCRIPTION OF THE DRAWINGS

(FIG. 12, FIG. 13, FIG. 14 and FIG. 15 show data from the same four human patients.)

FIG. 17 is a representation of the dosing schedules in mice of 2 days Cy plus 4 days Flu (light grey), compared to 1 day Cy plus 1 day Flu plus Dexamethasone base HED 12 mg/kg on day −2 (dark grey) or to Dexamethasone base HED 12 mg/kg on day −2 alone (black). Below the dosing schedule are columns indicating the percent change compared to vehicle controls in body weights, CD3+ lymphocytes, CD4+ lymphocytes, CD8+ lymphocytes, Tregs, B lymphocytes, NK cells, neutrophils, absolute lymphocytes, platelets, and RBCs.

FIG. 18 shows graphs of individual CD3+ and CD4+ lymphocytes and averages measured by flow cytometry as relative counts and normalized to relative absolute counts using complete blood chemistries 48 hours after mice were treated IP with PBS (Vehicle 1), or with repeat IP Cyclophosphamide 166 mg/kg on day −5 and −4 and 4 days of IP Fludarabine 10 mg/kg (HED 30 mg/m$^2$) on days −5, −4, −3, −2 (Flu+Cy), or with a single IP dose of Cyclophosphamide 166 mg/kg (HED 500 mg/m$^2$) and IP Fludarabine 10 mg/kg both on day −5 and then with oral 12 mg/kg Dex base on day −2 (Flu+Cy+AVM0703), or with oral placebo (Vehicle 2), or with oral 12 mg/kg dexamethasone base.

FIG. 19 shows graphs of individual Treg and CD8+ lymphocytes and averages measured by flow cytometry as relative counts and normalized to relative absolute counts using complete blood chemistries 48 hours after mice were treated IP with PBS (Vehicle 1), or with repeat IP Cyclophosphamide 166 mg/kg on day −5 and −4 and 4 days of IP Fludarabine 10 mg/kg (HED 30 mg/m$^2$) on days −5, −4, −3, −2 (Flu+Cy), or with a single IP dose of Cyclophosphamide 166 mg/kg (HED 500 mg/m$^2$) and IP Fludarabine 10 mg/kg both on day −5 and then with oral 12 mg/kg Dex base on day −2 (Flu+Cy+AVM0703), or with oral placebo (Vehicle 2), or with oral 12 mg/kg dexamethasone base.

FIG. 20 graphs of individual B lymphocytes and NK cell lymphocytes and averages measured by flow cytometry as relative counts and normalized to relative absolute counts using complete blood chemistries 48 hours after mice were treated IP with PBS (Vehicle 1), or with repeat IP Cyclophosphamide 166 mg/kg on day −5 and −4 and 4 days of IP Fludarabine 10 mg/kg (HED 30 mg/m$^2$) on days −5, −4, −3, −2 (Flu+Cy), or with a single IP dose of Cyclophosphamide 166 mg/kg (HED 500 mg/m$^2$) and IP Fludarabine 10 mg/kg both on day −5 and then with oral 12 mg/kg Dex base on day −2 (Flu+Cy+AVM0703), or with oral placebo (Vehicle 2), or with oral 12 mg/kg dexamethasone base.

FIG. 21 shows graphs of individual absolute neutrophils and absolute lymphocytes and averages measured by complete blood chemistries 48 hours after mice were treated IP with PBS (Vehicle 1), or with repeat IP Cyclophosphamide 166 mg/kg on day −5 and −4 and 4 days of IP Fludarabine 10 mg/kg (HED 30 mg/m$^2$) on days −5, −4, −3, −2 (Flu+Cy), or with a single IP dose of Cyclophosphamide 166 mg/kg (HED 500 mg/m$^2$) and IP Fludarabine 10 mg/kg both on day −5 and then with oral 12 mg/kg Dex base on day −2 (Flu+Cy+AVM0703), or with oral placebo (Vehicle 2), or with oral 12 mg/kg dexamethasone base.

FIG. 22 shows graphs of individual absolute platelet and absolute RBCs and averages measured by complete blood chemistries 48 hours after mice were treated IP with PBS (Vehicle 1), or with repeat IP Cyclophosphamide 166 mg/kg on day −5 and −4 and 4 days of IP Fludarabine 10 mg/kg (HED 30 mg/m$^2$) on days −5, −4, −3, −2 (Flu+Cy), or with a single IP dose of Cyclophosphamide 166 mg/kg (HED 500 mg/m$^2$) and IP Fludarabine 10 mg/kg both on day −5 and then with oral 12 mg/kg Dex base on day −2 (Flu+Cy+AVM0703), or with oral placebo (Vehicle 2), or with oral 12 mg/kg dexamethasone base.

FIG. 23 shows graphs of individual body weight differences and averages calculated by subtracting body weight 48 hours after mice were treated IP with PBS (Vehicle 1), or with repeat IP Cyclophosphamide 166 mg/kg on day −5 and −4 and 4 days of IP Fludarabine 10 mg/kg (HED 30 mg/m$^2$) on days −5, −4, −3, −2 (Flu+Cy), or with a single IP dose of Cyclophosphamide 166 mg/kg (HED 500 mg/m$^2$) and IP Fludarabine 10 mg/kg both on day −5 and then with oral 12 mg/kg Dex base on day −2 (Flu+Cy+AVM0703), or with oral placebo (Vehicle 2), or with oral 12 mg/kg dexamethasone base from pretreatment body weights.

DESCRIPTION OF THE INVENTION

Overview

Figure 1:
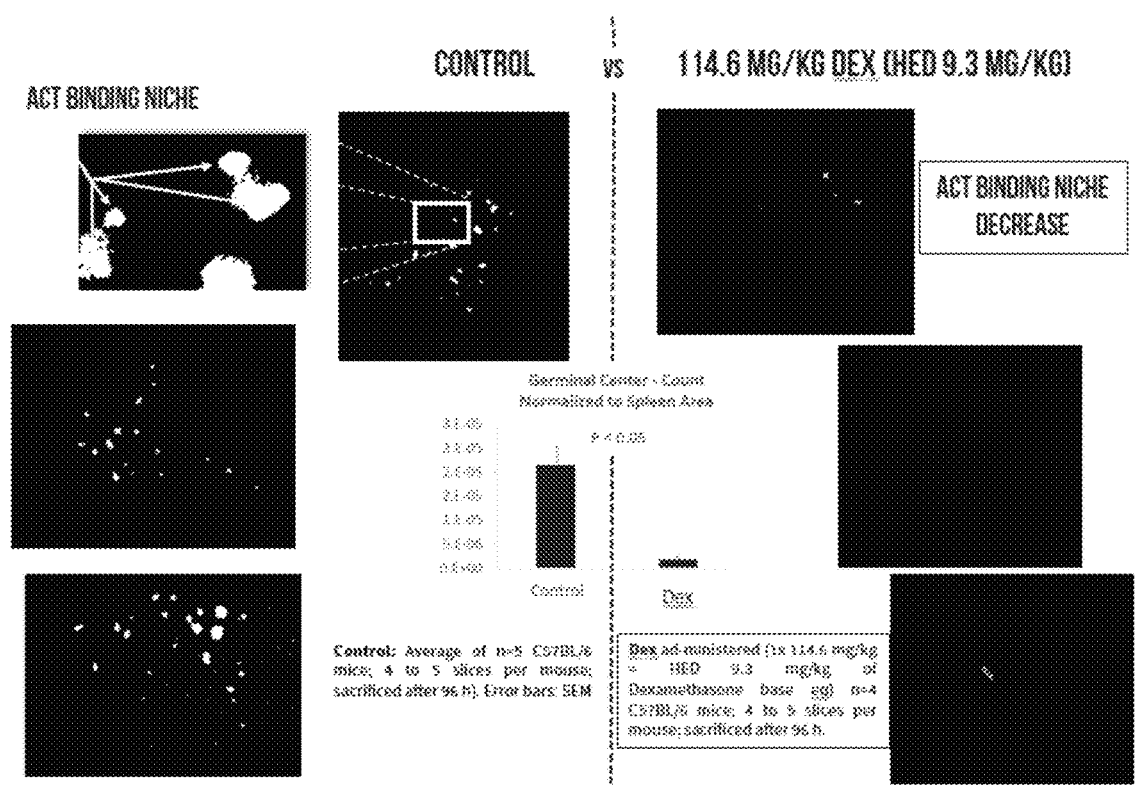
FIG. 1: Acute high dose Dex eliminates ACT binding niches in the mouse spleen and secondary lymphatics. Black and white scale immunofluorescent pictures of fresh thick spleen sections stained with FITC-PNA to quantitate germinal centers from IP administered placebo control and mice IP administered HED 9.3 mg kg dexamethasone base 96 hours before spleen harvest is shown. The graph shows column plots of average germinal cell count per spleen area plus standard area of the mean (SEM).

Provided herein are novel therapeutic compositions and methods that keep cellular immunotherapies in the circulation or at the site of injection for extended periods of time without resorting to the use of cytotoxic preconditioning. More specifically the compositions and methods herein lymphodeplete and reduce or ablate sites in the secondary lymphatics where the cellular immunotherapy is bound and sequestered, without the use of cytotoxic preconditioning.

Cytotoxic chemotherapeutic preconditioning agents trigger cell death via mechanisms or means that are not receptor mediated. Cytotoxic chemotherapeutic agents trigger cell death by interfering with functions that are necessary for cell division, metabolism, or cell survival. Because of this mechanism of action, cells that are growing rapidly (which means proliferating or dividing) or are active metabolically will be killed preferentially over cells that are not. The status of the different cells in the body as dividing or as using energy (which is metabolic activity to support function of the cell) determines the dose of the chemotherapeutic agent that triggers cell death. The skilled person will appreciate that the NTLA that is utilized in this invention is not a cytotoxic chemotherapeutic. Cytotoxic chemotherapeutic agents non-exclusively relates to alkylating agents, antimetabolites, plant alkaloids, topoisomerase inhibitors, antineoplastics and arsenic trioxide, carmustine, fludarabine, IDA ara-C, myalotang, GO, mustargen, cyclophosphamide, gemcitabine, bendamustine, total body irradiation, cytarabine, etoposide, melphalan, pentostatin and radiation.

Examples of alkylating agents non-exclusively relates to cisplatin and carboplatin, as well as oxaliplatin. TEMODAR® (temozolomide) is an alkylating agent. ACNU is also an alkylating agent. They impair cell function by forming covalent bonds with the amino, carboxyl, sulfhydryl, and phosphate groups in biologically important molecules.

Examples of antimetabolites non-exclusively relates to azathioprine, mercaptopurine, capecitabine, fluorouracil- which become the building blocks of DNA. They prevent these substances from becoming incorporated in to DNA during the "S" phase (of the cell cycle), stopping normal development and division. They also affect RNA synthesis. Due to their efficiency, these drugs are the most widely used cytostatics.

Alkaloids non-exclusively relates to the vinca alkaloids and taxanes. Vinca alkaloids non-exclusively relates to vincristin, vinblastin, vinorelbine, and vindesine. Taxanes non-exclusively relates totaxol, paclitaxel and docetaxel.

Topoisomerases are essential enzymes that maintain the topology of DNA. Inhibition of type I or type II topoisomerases interferes with both transcription and replication of DNA by upsetting proper DNA supercoiling. Some type I topoisomerase inhibitors non-exclusively relates to camptothecins: irinotecan and topotecan. Examples of type II inhibitors non-exclusively relates to amsacrine, etoposide, etoposide phosphate, and teniposide.

Antineoplastic non-exclusively relates to dactinomycin, doxorubicin, epirubicin, and bleomycin.

Other cytotoxic preconditioning agents non-exclusively relate to; rituximab and similar antibody molecules which activate antibody-dependent cellular cytotoxicity and complement mediated cytotoxicity upon binding their target cells; radiolabeled antibodies that trigger immune cell destruction (immunotoxins) such as antibodies to CD45, for instance Iomab-B; immunotoxins such as MYLOTARG® (gemtuzumab ozogamicin), Denileukin diftitox (ONTAK®), BL22 and 8H9; and pharmacologic doses of interleukins such as IL-2, IL12, or IL15 which activate cytotoxic T lymphocytes.

Agents which lymphodeplete and ablate the secondary lymphatic binding sites where cellular immunotherapies bind and accumulate but are not cytotoxic preconditioning agents are considered non-toxic lymphodepleting agents (NTLA).

NTLAs that reduce cellular immunotherapies binding to the spleen and other lymphatics and lymphodeplete thus augment the numbers of cellular immunotherapy cells at the site of injection or in the circulation that can thus find and participate in killing cancer or tumor cells or autoimmune causing cells or infectious agents. Therapeutic agents which have this affect via a biologic mechanism of action, rather than a cytotoxic mechanism of action, are considered NTLAs.

NTLAs that inhibit the binding of cellular immunotherapies to lymphoid tissues, particularly to the germinal centers of lymphoid tissues and cause lymphodepletion via a biologic mechanism of action, which are not cytotoxic preconditioning agents, non-exclusively relates to immunesuppressants, particularly agents that contain dexamethasone, glucocorticoid-receptor modulating agents, antagonists to CD40L or CD40, or antagonists to CD26. Thus, some of the NTLAs used in this invention may be termed NTLA immunosuppressants. NTLAs that inhibit the binding of cellular immunotherapies to lymphoid tissues, particularly to the germinal centers of lymphoid tissues and cause lymphodepletion via a biologic mechanism of action, which are not cytotoxic preconditioning agents, also non-exclusively relates to steroids, glucocorticoids including but not limited to; dexamethasone, prednisone, methylprednisone, beclomethasone, betamethasone, budesonide, cortisone, hydrocortisone, prednisolone, mometasone furoate, Triamcinolone Acetonide and methylprednisolone, and agents that enhance the expression of or activate CCR7, an agent that inhibits the binding of CD40L to CD40 (for example antagonistic antibodies to CD40 or to CD40L), antagonists or inhibitors of signaling lymphocyte activation molecule-associated protein, and antagonists or inhibitors of the following list: Interleukin 1, interleukin 2, Interleukin 4, interleukin 5, interleukin 6, Interleukin 12, Interleukin 13, interleukin 21, Interleukin 23, IgE, Vascular Adhesion Protein (VAP), Vascular Endothelial Growth Factor (VEGF), BAFF (BLyS), complement, CD2, CD23, CD25a, CD40, CD154 (CD40L), CD62L, CD147, LFA1, (CD11a), CD18, Adenosine deaminase, tumor necrosis factor (TNF).

In administering a glucocorticoid or glucocorticoid receptor modulating therapeutic NTLA agent that inhibits the binding of cellular immunotherapies to lymphatic tissues and causes lymphodepletion it is preferred to administer the therapeutic agents about 1-14 days prior to treatment with cellular immunotherapies, more preferably about 1-7 days prior to treatment with cellular immunotherapies, and most preferably about 36-48 hours prior to treatment with cellular immunotherapies.

Corticosteroids, which are NTLA immunesuppressants at certain doses, such as dexamethasone, prednisolone, methylprednisolone, dexamethasone sodium phosphate and betamethasone will cause lymphodepletion and prevent cellular immunotherapies from binding to the secondary lymphatics and thus keep the cellular immunotherapies in the circulation or retained at the site of injection so that they can find and kill cancer, tumor or autoimmune causing cells or infectious agents. Long term engraftment of the cellular immunotherapy will also be enhanced.

Glucocorticoids and glucocorticoid-receptor (GR) modulating agents exert their effects through both membrane glucocorticoid receptors and cytoplasmic GRs which activate or repress gene expression. Some of the desireable lymphodepletion effects of the glucocorticoids and GR modulating agents appear to be mediated via membrane GRs or other non-genomic effects in addition to their genomic effects. Interestingly, co-treatment with dexamethasone has been shown to be able to reduce glucocorticoid resistance (Serafin Blood 2017 130:2750-2761).

The effects of glucocorticoids are complex and depend on each specific glucocorticoid's affinity for the GR and mineralocorticoid receptor (MR). Additionally, there are now 9 known isoforms of the cytosolic GR and additional membrane expressed GR receptors that have been identified but which are not fully characterized. Glucocorticoids have been reported to have varied effects on lymphocyte levels, depending on the concentration of the glucocorticoid administered and the duration of treatment. In general, at low doses typically used for chronic therapy, glucocorticoids have been reported to redistribute lymphocytes from the peripheral blood into the bone marrow, at medium doses glucocorticoids have been reported to cause leukocytosis thought to be a redistribution of leukocytes from the bone marrow, spleen and thymus into the peripheral blood, and at high doses glucocorticoids have a lymphotoxic action on lymphocytes by triggering apoptosis and necroptosis. The duration of effect also depends on the dose level, for instance Fauci (*Clin. exp. Immunol*. (1976) 24, 54-62.) reports a single oral 0.24 mg/kg dexamethasone dose suppresses peripheral blood T and B lymphocytes 80% with recovery beginning at 12 hours and normal levels by 24 hours. However, the present invention demonstrates that acute oral doses of 3 mg/kg or greater are necessary to reduce peripheral blood T and B cells 48 hours after administration, with return to baseline levels occurring around 5 to 14 days after dosing.

Figure 12:
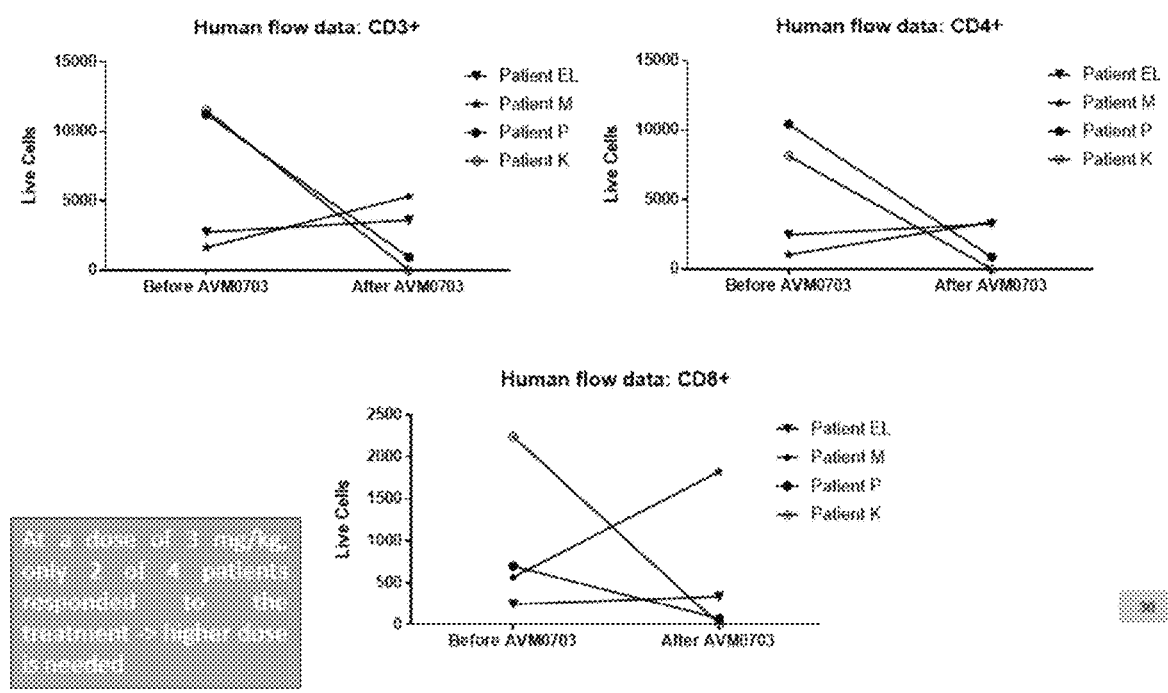
FIG. 12: Fifty percent (2 of 4) of human patients treated with 3 mg/kg dexamethasone base depleted CD3, CD4 and CD8 positive lymphocytes. Individual pre- and post-treatment, 48 hours after oral administration of 3 mg/kg dexamethasone base to four human patients, values and line plots of CD3+, CD4+, and CD8+ lymphocytes measured by flow cytometry. Each patients pre-treatment values are connected to post-treatment values by a connecting line. CD4+ cells are also CD3+. CD8+ cells are also CD3+.
Figure 15:
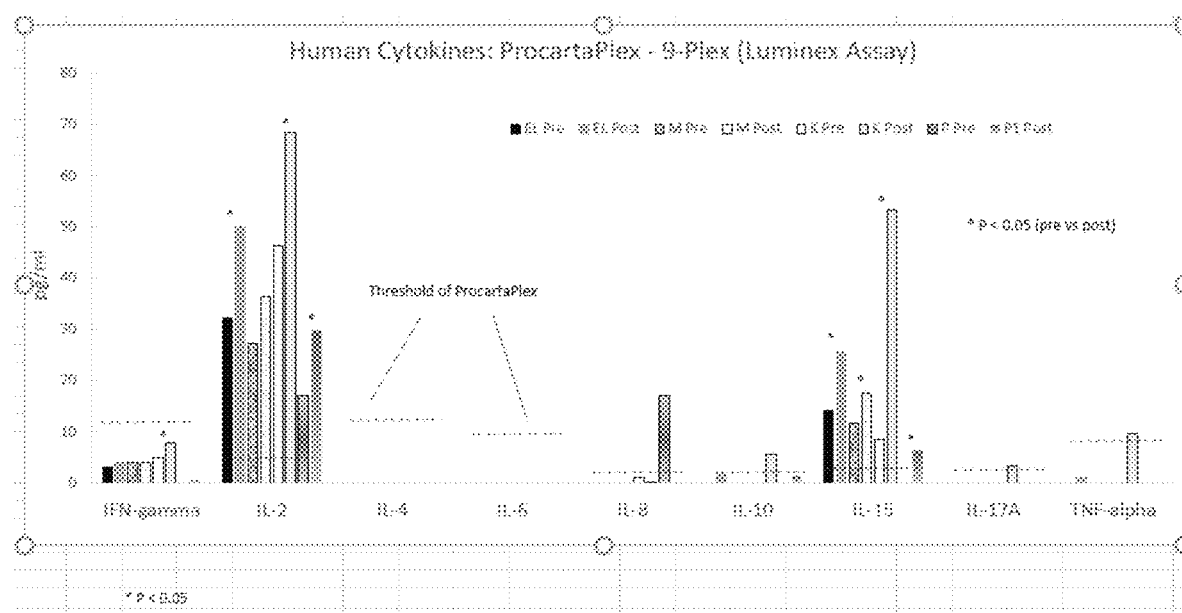
FIG. 15: 100% of human patients treated with 3 mg/kg dexamethasone base showed increased serum IL-2 and/or IL-15 levels, but no elevation in IL-6. Column plots of each patients pre- and post-treatment, 48 hours after oral administration of 3 mg/kg dexamethasone base to four human patients, plasma levels of interleukin 2 and interleukin 15 measured by ProCartaPlex-9 plx Luminex assay.

The desired in vivo effects of exemplary NTLAs would include reductions in germinal center and marginal zones in secondary lymphatics, direct tumor killing of some cancers particularly; multiple myeloma, renal cell carcinoma, leukemia and lymphoma, non-small cell lung cancer (NSCLC), prostate and breast cancer; depletion of all peripheral blood lymphocyte types, lack of lymphocyte redistribution to the BM or other organs, and elevation of plasma cytokines including IL-2, and/or IL-7, and/or IL-12, and/or IL-15 to levels preferably of 20 pg/ml or greater, among others. Exemplary NTLAs do not elevate plasma levels of IL-6, one of the major contributors to ACT induced cytokine release syndrome (CRS). Acute doses of dexamethasone of about HED 6 mg/kg and above reduce germinal centers and marginal zones in secondary lymphatics; acute doses of dexamethasone of about 1.6 mg/kg HED in a 48 hour period have about 50% direct tumor killing against multiple myeloma and other cancer cell lines which is maintained but not increased with doses up to about 12 mg/kg HED; acute doses of dexamethasone of greater than about HED 3 mg/kg are required for lymphodepletion demonstrated by the observation that 50% of patients treated with 3 mg/kg HED showed lymphocytosis (FIG. 12); plasma IL-2 and IL-15 cytokine elevations are observed at doses of dexamethasone base of about HED 3 mg/kg or higher (FIG. 15). Based on the desired in vivo effects in the indications disclosed in this application, the most preferred acute dexamethasone base doses, which can be converted to NTLA equivalent doses of other glucocorticoids based on known calculators or as disclosed in this description, will be most likely about HED 9 mg/kg and above.

NTLA dosing of Dexamethasone, or an equivalent dose of another glucocorticoid, should be between about 3 mg/kg and about 26 mg/kg single acute dose about 12 to about 72 hours prior to cellular immunotherapy administration or total dose of about 3 mg/kg to about 26 mg/kg given between about 12 to about 72 hours prior to cellular immunotherapy administration. The single acute dose would most preferably be given about 36 to about 48 hours prior to cell immunotherapy administration.

A single acute NTLA dose is an oral administration or about a one hour IV infusion. A total dose may be given as repetitive IV or oral doses in any quantity such that the total dose reaches about 3 mg/kg to about 26 mg/kg between about 12 to about 72 hours prior to cell immunotherapy administration.

Equivalent doses of another glucorticoid or glucocorticoid receptor modulating agent can be readily and easily calculated using publicly available corticoid conversion algorithms. For example, a 12 mg/kg dose of dexamethasone corresponds to 1) a 75 mg/kg dose of prednisolone that would require repeat dosing of about two to about three doses within about 48 hours before administration of ACT because of its shorter pharmacologic half life, 2) a 10 mg/kg dose of betamethasone that has a pharmacodynamic (biologic) half-life similar to dexamethasone. However, Betamethasone reduces RBC at doses of about 24 mg/50 kg (Gaur 2017).

An NTLA agent containing dexamethasone is preferably administered intravenously or orally about 36 to about 48 hours before administration of the cellular immunotherapy at a dose between about 3.0 to about 12.0 mgs dexamethasone base per kg of the patient's body weight. The most preferable dose in young children is between about 3.0 and about 12.0 mg/kg dexamethasone base and in adolescents and adults is between about 6.0 and about 12.0 mg/kg, with about 9.0 mg/kg to about 12.0 mg/kg dexamethasone base being most preferred. Dexamethasone, like the other glucocorticoid steroids at equivalent doses, inhibits the formation and proliferation of germinal centers in the lymph tissues and lymphodepletes peripheral blood.

An NTLA agent containing hydrocortisone is administered intravenously or orally about every 12 hours at a dose of about 75 to about 300 mg/kg between about 12 to about 72 hours before administration of the cellular immunotherapy. An NTLA agent containing cortisone is administered intravenously or orally about every 12 hours at a dose of about 93 to about 375 mg/kg between about 12 to about 72 hours before administration of the cellular immunotherapy. An NTLA agent containing prednisolone is administered intravenously or orally about every 24 hours at a dose of about 19 to about 75 mg/kg between about 12 to about 60 hours before administration of the cellular immunotherapy. An NTLA agent containing methylprednisolone is administered intravenously or orally about every 24 hours at a dose of about 15 to about 60 mg/kg between about 12 to about 60 hours before administration of the cellular immunotherapy. An NTLA agent containing triamcinolone is administered intravenously or orally about every 24 hours at a dose of about 15 to about 60 mg/kg between about 12 to about 60 hours before administration of the cellular immunotherapy. An NTLA agent containing paramethasone is administered in either a single acute dose or cumulative doses of about 7.5 to about 30 mg/kg, given between about 12-72 hours prior to cellular immunotherapy. An NTLA agent containing betamethasone is administered in either a single acute dose or cumulative doses of about 2.5 to 10 mg/kg, given between about 12-72 hours prior to cellular immunotherapy.

Clinically effective doses of NTLA, particularly Dexamethasone, achieve greater than 60% CD3+ lymphodepletion. More preferable clinically effective doses of NTLA, particularly Dexamethasone, achieve greater than 70% CD3+ lymphodepletion. The most preferable clinically effective doses of NTLA, particularly Dexamethasone, achieve greater than 80% CD3+ lymphodepletion. The skilled person will understand that CD3+ lymphodepletion can be measured readily by measuring complete blood counts (CBCs) with differentials and/or the percent of cells that are positive for CD3 by flow cytometry. Flow cytometry is a technology that is used to analyse the physical and chemical characteristics of particles in a fluid as it passes through at least one laser. Cell components are fluorescently labelled and then excited by the laser to emit light at varying wavelengths. Flow cytometry enables the identification and characterization of distinct subsets of cells within a heterogeneous sample.

Clinically effective doses of NTLA, particularly Dexamethasone, achieve greater than 60% Treg lymphodepletion.

More preferable clinically effective doses of NTLA, particularly Dexamethasone, achieve greater than 70% Treg lymphodepletion. The most preferable clinically effective doses of NTLA, particularly Dexamethasone, achieve greater than 80% Treg lymphodepletion. Clinically effective doses of Dexamethasone and other preferred agents for NTLA spare neutrophils and do not inhibit neutrophil function (Schleimer R P, J Pharmacol Exp Ther 1989; 250:598-605), and spare red blood cells (RBCs), platelets, mesenchymal stem cells (MSC) and hematopoietic stem cells (HSC). Neutrophil sparing in humans is an absolute neutrophil count (ANC) greater than 500 per $mm^3$. By sparing neutrophils, RBCs and platelets, preferred NTLA, particularly NTLA Dexamethasone, would reduce or eliminate the need for transfusions. NTLA Dexamethasone also spares bone marrow mesenchymal stem cells (MSCs) and does not affect the capacity of bone marrow MSCs to differentiate towards chondrocytes, osteocytes or adipocytes. NTLA Dexamethasone also increases the endogenous number of BM MSCs or their ex vivo survival in both humans and horses. Preferred NTLA, particularly NTLA Dexamethasone, increase plasma IL-2, IL-7, IL-12 and IL-15 levels, but not IL-6 levels.

Dexamethasone is approved for use with an initial dosage of dexamethasone sodium phosphate injection that varies from 0.5 to 9 mg a day depending on the disease being treated, which is a daily dose of 0.01 to 0.18 mg/kg based on a 50 kg BW. In less severe diseases doses lower than 0.5 mg may suffice. while in severe diseases doses higher than 9 mg may be required. There is a tendency in current medical practice to use high (pharmacologic) doses of corticosteroids for the treatment of unresponsive shock. For cerebral edema Dexamethasone sodium phosphate injection is generally administered initially in a dosage of 10 mg intravenously followed by four mg every six hours intramuscularly until the symptoms of cerebral edema subside. This total dose would correspond to a total 24 hour dose of about 0.34 to 0.48 mg/kg and a total 72 hour dose of 0.8 to 1.12 mg/kg in 72 hours, which is not an NTLA dose as disclosed in the present application, which are total doses between about 3 mg/kg and about 26 mg/kg given between about 12 to about 72 hours before ACT.

For acute allergic disorders Dexamethasone sodium phosphate injection, USP 4 mg/mL; is recommended: first day, 1 or 2 mL (4 or 8 mg), intramuscularly, then Dexamethasone sodium phosphate tablets, 0.75 mg; second and third days, 4 tablets in two divided doses each day; fourth day, 2 tablets in two divided doses; fifth and sixth days, I tablet each day; seventh day, no treatment; eighth day, follow-up visit. Dexamethasone has been used in the emergency room for severe acute pediatric asthma at 2 mg/kg, a dose which is below the NTLA doses as defined in this invention.

The human CD26 gene contains 26 exons and is located on chromosome 2q.24.3. The gene spans a region of circa 70 kb.vFlanking to the 5' end, a sequence of 300 base pairs is located that consists for not less than 72% of cytosine and guanine residues, implying that the sequence holds potential-binding sites for growth factors such as the nuclear factor kappa-light-chainenhancer of activated B cells (NF-κB) and hepatocyte nuclear transcription factor 1 (HNF-1). Absence of a TATA box and a high CG content, which characterize the CD26 gene, are typical features of a promotor region of a house keeping gene. As it results to the present invention, antagonists to CD26 do not effect the DPPIV activity of the molecule. The coding glycoprotein, as a monomer, has a size of 110 kDa and is multifunctional. CD26 exists both as a soluble molecule as well as in a membrane-bound form and functions as a serine protease, as a receptor, as an adhesion molecule for collagen and fibronectin, as a costimulatory signal for T lymphocytes, and is involved in apoptosis. Conditions of hypoxia promote CD26 expression and hypoxia-inducible protein-1α (HIP-1α) is a strong inducing factor for CD26 gene expression and protein production. Several cytokines including IFNs and IL-1β, retinoic acid, and HNF-1 can also stimulate activation of CD26 on fibroblasts, epithelial cells, endothelial cells, and leukocytes. Membrane-bound CD26 contains a transmembrane domain that is located 28 residues from the NH2-terminus and is a leukocyte surface marker. The protein shows catalytic proteolytic activity only as a dimer and can be found on the surface of T and B cells, NK cells, some types of macrophages, and hematopoietic stem and progenitor cells. In addition, fibroblasts, endothelial, acinar, and epithelial cells of different tissues like kidney and liver do also express CD26. Both termini of the protein contribute to the formation of a so called 3-propeller domain (amino acids 55-497). The β-propeller structure holds seven sheets and contains only hydrophobic bonds and salt bridges, implying that the region is extremely flexible. Furthermore, the protein contains an α/β hydroxylase domain (amino acid 39-51 and amino acid 506-766) that is covalently bound to the P3-propeller domain. All together, these properties imply that the catalytic pocket is situated in a locked hole. The other side of the β-propeller domain faces the extracellular environment. It cannot be excluded that the flexibility of the β-propeller domain plays a role in facilitating the passage of substrates toward the catalytic pocket of CD26. However, only entrance of substrates through a side opening of the enzyme is supported by experimental data at the moment. In addition to functional homodimeric CD26, active heterodimers with FAPα have also been described.

CD26 contains multiple regions that can be subjected to N-glycosylation. Research, however, suggests that glycosylation of these sequences does not have implications for dimerization of the protein, binding to adenosine deaminase (ADA), or the catalytic activity.

CD26, also called DPP4, is a multi-functional protein involved in T cell activation by co-stimulation via its association with adenosine deaminase (ADA), caveolin-1, CARMA-1, CD45, mannose-6-phosphate/insulin growth factor-II receptor (M6P/IGFII-R) and C-X-C motif receptor 4 (CXC-R4). CD26 is a T-cell activation antigen. Antagonists to CD26 would prevent CD26 co-stimulation of T cells. Without T cell activation, B cells cannot be activated and germinal center formation cannot occur.

CD26 is expressed in all organs, primarily on apical surfaces of epithelial and acinar cells and at lower levels on lymphocytes and capillary endothelial cells. Immunohistochemical analysis has detected CD26 in human tissue sections of the gastrointestinal tract, biliary tract, exocrine pancreas, kidney, uterus, placenta, prostate and epidermis, the adrenal, parotid, sweat, salivary and mammary glands and on endothelia of all organs examined including liver, spleen, lungs and brain. Similar studies of rat tissues produced identical data by immunohistochemistry and showed that endothelial cells of capillaries in all organs including lymphoid organs, muscle and brain express CD26.

CD26 in addition to its DPPIV enzymatic activity can directly bind adenosine deaminase, fibronectin, collagen and other extracellular matrix proteins, gp120, fibroblast activation protein alpha, CARD11, gelatin, CAV1, BCL10, GPC3, CXRC4, TAT, coronavirus-EMC spike protein, IGF2R, and PTPRC and CD45. CD26 also has signal transduction activity (www.uniprot.org/uniprot/P27487). Residues of Leucine_<340>, Valine_<341>, Alanine_<342> and Arginine_<343> on the CD26 molecule were essential amino acids for ADA binding. These interactions were specified to involve fibronectin and collagen: collagen binds to a region in the cysteine domain 14 between residues 238 and 495, whereas fibronectin binds residues 469 to 479. The residues 340-343 on the CD26 molecule proved to be essential for ADA binding 21. GP120 bocks ADA binding to CD26. The receptor-binding subdomain of MERS-CoV RBD binds to the DPP4 b-propeller, contacting blades four and five and a small bulged helix in the blade-linker. Structural analysis and mutational analysis have identified Y499, L506, W533, and E513 in the RBD to be critical for receptor binding and viral entry, and mutations of these significantly abrogate its interaction with DPP4.

In certain embodiments of the invention it would be desireable to have an antagonist to CD26 that prevented cellular immunotherapies from binding to the secondary lymphatics but that did not affect or impact the DPPIV proteolytic activity of CD26.

The complete cDNA and derived amino acid sequence for human CD26 was first published in 1992. The CD26 gene5 encodes a type II transmembrane protein of 766 amino acids, which is anchored to the lipid bilayer by a single hydrophobic segment located at the N-terminus, and has a short cytoplasmic tail of six amino acids. A flexible stalk links the membrane anchor to a large glycosylated region, a cysteine-rich region and a C-terminal catalytic domain. Alignment of the amino acid sequences reveals a high degree of conservation between different species, with the C-terminal segment showing the highest level of identity.

The present invention also provides a means to achieve adequate lymphodepletion by combining NTLA, particularly NTLA Dexamethasone, with reduced intensity cytotoxic preconditioning administered as only one day of dosing to reduce the toxicities of the cytotoxic preconditioning or by significantly reducing an acute dose of cytotoxic preconditioning. Standard chemotherapy preconditioning regimens include cyclophosphamide (about 200 to about 2100 mg/m2/day from about day −14 to about day−2) with or without fludarabine (about 10 mg/m2/day to about 9000 mg/m2/day from about day −14 to about day −2) in various combinations and daily duration of dosing. A single treatment of cyclophosphamide (Cy) 167 mg/kg (equivalent to a HED of about 500 mg/m2) for mice on day −5 and fludarabine (Flu) 10 mg/kg (equivalent to a HED of about 30 mg/m2) for mice on day −5 plus 12 mg/kg HED dose of Dexamethasone base on day −2 was equally effective for lymphodepletion compared to more standard cyclophosphamide 167 mg/kg dose on day −5 and −4 and fludarabine 10 mg/kg on day −5, −4, −3, −2, however, toxicity of the preconditioning was reduced as evidenced by lower BW reductions in the Dexamethasone plus single CyFlu compared to standard CyFlu repeat dosing. A reduced dose of cytotoxic preconditioning would be a single dose of a standard chemotherapy preconditioning regime dose used in repetitive dosing or a cumulative dose of a cytotoxic preconditioning agent below cumulative standard chemotherapy preconditioning regimens. For example a reduced dose of cyclophosphamide would be a single dose of cyclophosphamide between about 200 to about 3000 mg/m$^2$ or a cumulative dose below about 200 mg/m$^2$.

To reduce the toxicity of preconditioning, a single dose of any standardly used preconditioning therapy or combination preconditioning therapy can be given between about day 0 and about day −9, followed by a dose of NTLA, particularly NTLA Dexamethasone. NTLA Dexamethasone should be administered between about 3 mg/kg and about 26 mg/kg single acute dose about 12 to about 72 hours prior to cell immunotherapy administration or total dose of about 3 mg/kg to about 26 mg/kg given between about 12 to about 72 hours before cell therapy administration. Preconditioning agents that can be used in lower doses in combination with NTLA Dexamethasone between about 3 mg/kg and about 26 mg/kg single acute dose about 12 to about 72 hours prior to cell immunotherapy administration or total dose of about 3 mg/kg to about 26 mg/kg given between about 12 to about 72 hours before cell therapy administration non-exclusively relate to Abiraterone, Alemtuzumab, Anastrozole, Aprepitant, Aranose, Arsenic trioxide, Atezolizumab, Azacitidine, Bevacizumab, Bleomycin, Bortezomib, Cabazitaxel, Capecitabine, Carboplatin, Cetuximab, Cisplatin, Crizotinib, Cyclophosphamide, Cytarabine, Chlorozotocin, Chlorambucil, Denosumab, Docetaxel, Doxorubicin, Eribulin, Erlotinib, Etoposide, Everolimus, Exemestane, Filgrastim, Fluorouracil, Fotemustine, Fulvestrant, Gemcitabine, HPV Vaccine, Imatinib, Imiquimod, Ipilimumab, Ixabepilone, Lapatinib, Lenalidomide, Letrozole, Leuprolide, Mesna, Melphalan, Methotrexate, Mechlorethamine, Nivolumab, Oxaliplatin, Paclitaxel, Palonosetron, Pembrolizumab, Pemetrexed, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine, Zoledronic acid, Abitrexate (Methotrexate Injection), Abraxane® (Paclitaxel Injection), Adcetris® (Brentuximab Vedotin Injection), Adriamycin® (Doxorubicin), Adrucil® Injection (5-FU (fluorouracil)), Afinitor® (Everolimus), Afinitor® Disperz (Everolimus), Alimta® (PEMETREXED), Alkeran® Injection (Melphalan Injection), Alkeran® Tablets (Melphalan), Aredia® (Pamidronate), Arimidex® (Anastrozole), Aromasin® (Exemestane), Arranon® (Nelarabine), Arzerra® (Ofatumumab Injection), Avastin® (Bevacizumab), Beleodaq® (Belinostat Injection), Bexxar (Tositumomab), BiCNU® (Carmustine), Blenoxane® (Bleomycin), Blincyto® (Blinatumomab Injection), Bosulif® (Bosutinib), Busulfex® Injection (Busulfan Injection), Campath® (Alemtuzumab), Camptosar® (Irinotecan), Caprelsa® (Vandetanib), Casodex® (Bicalutamide), CeeNU® (Lomustine), CeeNU® Dose Pack (Lomustine), Cerubidine® (Daunorubicin), Clolar® (Clofarabine Injection), Cometriq® (Cabozantinib), Cosmegen® (Dactinomycin), Cotellic® (Cobimetinib), Cyramza® (Ramucirumab Injection), CytosarU® (Cytarabine), Cytoxan® (Cytoxan), Cytoxan® Injection (Cyclophosphamide Injection), Dacogen® (Decitabine), DaunoXome® (Daunorubicin Lipid Complex Injection), DepoCyt® (Cytarabine Lipid Complex Injection), Docefrez® (Docetaxel), Doxil® (Doxorubicin Lipid Complex Injection), Droxia® (Hydroxyurea), DTIC® (Decarbazine), Eligard® (Leuprolide), Ellence® (Ellence (epirubicin)), Eloxatin® (oxaliplatin), Elspar® (Asparaginase), Emcyt® (Estramustine), Erbitux® (Cetuximab), Erivedge® (Vismodegib), Erwinaze® (Asparaginase *Erwinia chrysanthemi*), Ethyol® (Amifostine), Etopophos® (Etoposide Injection), Eulexin® (Flutamide), Fareston® (Toremifene), Farydak® (Panobinostat), Faslodex® (Fulvestrant), Femara® (Letrozole), Firmagon® (Degarelix Injection), Fludara® (Fludarabine), Folex® (Methotrexate Injection), Folotyn® (Pralatrexate Injection), FUDR® (floxuridine), Gazyva® (Obinutuzumab Injection), Gemzar® (Gemcitabine), Gilotrif® (Afatinib), Gleevec® (Imatinib Mesylate), Gliadel® Wafer (Carmustine wafer), Halaven® (Eribulin Injection), Herceptin® (Trastuzumab), Hexalen® (Altretamine), Hycamtin® (Topotecan), Hydrea® (Hydroxyurea), Ibrance® (Palbociclib), Iclusig®

(Ponatinib), Idamycin® PFS (Idarubicin), Ifex® (Ifosfamide), Imbruvica® (Ibrutinib), Inlyta® (Axitinib), Intron® A alfab (Interferon alfa-2a), Iressa® (Gefitinib), Istodax (Romidepsin Injection), Ixempra® (Ixabepilone Injection), Jakafi® (Ruxolitinib), Jevtana® (Cabazitaxel Injection), Kadcyla® (Ado-trastuzumab Emtansine), Keytruda® (Pembrolizumab Injection), Kyprolis® (Carfilzomib), Lanvima® (Lenvatinib), Leukeran® (Chlorambucil), Leukine® (Sargramostim), Leustatin® (Cladribine), Lonsurf® (Trifluridine and Tipiracil), Lupron® (Leuprolide), Lupron® Depot (Leuprolide), Lupron® DepotPED (Leuprolide), Lynparza® (Olaparib), Lysodren® (Mitotane), Marqibo® Kit (Vincristine Lipid Complex Injection), Matulane® (Procarbazine), Megace® (Megestrol), Mekinist® (Trametinib), Mesnex® (Mesna), Mesnex® (Mesna Injection), Metastron® (Strontium-89 Chloride), Mexate® (Methotrexate Injection), Mustargen® (Mechlorethamine), Mutamycin® (Mitomycin), Myleran® (Busulfan), Mylotarg® (Gemtuzumab Ozogamicin), Navelbine® (Vinorelbine), Neosar® Injection (Cyclophosphamide Injection), Neulasta® (filgrastim), Neulasta® (pegfilgrastim), Neupogen® (filgrastim), Nexavar® (Sorafenib), Nilandron® (nilutamide), Nipent® (Pentostatin), Nolvadex® (Tamoxifen), Novantrone® (Mitoxantrone), Odomzo® (Sonidegib), Oncaspar® (Pegaspargase), Oncovin® (Vincristine), Ontak® (Denileukin Diftitox), Onxol® (Paclitaxel Injection), Opdivo® (Nivolumab Injection), Panretin® (Alitretinoin), Paraplatin® (Carboplatin), Perjeta® (Pertuzumab Injection), Platinol® (Cisplatin), Platinol® (Cisplatin Injection), Platinol® AQ (Cisplatin), Platinol® AQ (Cisplatin Injection), Pomalyst® (Pomalidomide), Proleukin® (Aldesleukin), Purinethol® (Mercaptopurine), Reclast® (Zoledronic acid), Revlimid® (Lenalidomide), Rheumatrex® (Methotrexate), Rituxan® (Rituximab), Roferon® A alfaa (Interferon alfa-2a), Rubex® (Doxorubicin), Sandostatin® (Octreotide), Sandostatin® LAR Depot (Octreotide), Soltamox® (Tamoxifen), Sprycel® (Dasatinib), Stivarga® (Regorafenib), Supprelin® LA (Histrelin Implant), Sutent® (Sunitinib), Sylatron® (Peginterferon Alfa-2b Injection), Sylvant® (Siltuximab Injection), Synribo® (Omacetaxine Injection), Tabloid® (Thioguanine), Taflinar® (Dabrafenib), Tarceva® (Erlotinib), Targretin® Capsules (Bexarotene), Tasigna® (Decarbazine), Taxol® (Paclitaxel Injection), Taxotere® (Docetaxel), Temodar® (Temozolomide), Temodar® (Temozolomide Injection), Tepadina® (Thiotepa), Thalomid® (Thalidomide), TheraCys® BCG (BCG), Thioplex® (Thiotepa), TICE® BCG (BCG), Toposar® (Etoposide Injection), Torisel® (Temsirolimus), Treanda® (Bendamustine hydrochloride), Trelstar® (Triptorelin Injection), Trexall® (Methotrexate), Trisenox® (Arsenic trioxide), Tykerb® (lapatinib), Unituxin® (Dinutuximab Injection), Valstar® (Valrubicin Intravesical), Vantas® (Histrelin Implant), Vectibix (Panitumumab), Velban® (Vinblastine), Velcade (Bortezomib), Vepesid® (Etoposide), Vepesid® (Etoposide Injection), Vesanoid® (Tretinoin), Vidaza® (Azacitidine), Vincasar® PFS (Vincristine), Vincrex® (Vincristine), Votrient® (Pazopanib), Vumon® (Teniposide), Wellcovorin® IV (Leucovorin Injection), Xalkori® (Crizotinib), Xeloda® (Capecitabine), Xtandi® (Enzalutamide), Yervoy® (Ipilimumab Injection), Yondelis® (Trabectedin Injection), Zaltrap® (Ziv-aflibercept Injection), Zanosar® (Streptozocin), Zelboraf® (Vemurafenib), Zevalin® (Ibritumomab Tiuxetan), Zoladex® (Goserelin), Zolinza® (Vorinostat), Zometa® (Zoledronic acid), Zortress® (Everolimus), Zydelig® (Idelalisib), Zykadia® (Ceritinib), Zytiga® (Abiraterone), ABVD (combination of doxorubicin (Adriamycin®), bleomycin, vinblastine, and dacarbazine (DTIC)), AC (combination of Adriamycin® (doxorubicin) and cyclophosphamide), ACE (combination of Adriamycin® (doxorubicin), cyclophosphamide, and etoposide (Eposin, Etopophos, Vepesid)), Abiraterone (Zytiga®), Abraxane® (Nab-paclitaxel), Abstral® (fentanyl), Actinomycin D, Actiq®, Adriamycin, Afatinib (Giotrif®), Afinitor® (Everolimus), Aflibercept (Zaltrap®), Aldara® imiquimod cream), Aldesleukin (IL-2, Proleukin® or interleukin 2), Alemtuzumab (MabCampath®), Alkeran® (melphalan), Amsacrine (Amsidine®, m-AMSA), Amsidine®, Anastrozole (Arimidex®), Ara C (cytarabine), Aredia®, Arimidex®, Aromasin®, Arsenic trioxide (Trisenox™, ATO), Asparaginase (Crisantaspase, Erwinase®), Axitinib (Inlyta®), Azacitidine (Vidaza®), BEACOPP, BEAM, Bendamustine (Levact®), Bevacizumab (Avastin®), Bexarotene (Targretin®), Bicalutamide (Casodex®), Bleomycin, [Bleomycin, etoposide and platinum (BEP)], Bortezomib (Velcade®), Bosulif®, Bosutinib (Bosulif®), Brentuximab (Adcetris®), Brufen, Buserelin (Suprefact®), Busilvex®, Busulfan (Myleran®, Busilvex®), CAPE-OX (oxaliplatin and capecitabine (XELOX)), CAPOX (oxaliplatin and capecitabine (XELOX)), CAV (cyclophosphamide, doxorubicin (Adriamycin®), vincristine), CAVE (cyclophosphamide, doxorubicin (Adriamycin®), vincristine, etoposide), CCNU (Lomustine), CHO (combination of cyclophosphamide, doxorubicin hydrochloride (Adriamycin®), vincristine (Oncovin®), CMF (combination of cyclophosphamide, methotrexate, and fluorouracil (5FU)), CMV (combination of cisplatin, methotrexate, and vinblastine), CT (combination of cyclophosphamide, thalidomide), CV (a combination of cyclophosphamide, vincristine (Oncovin®), Cabazitaxel (Jevtana®), Cabozantinib (Cometriq®), Caelyx®, Calpol®, Campto®, Capecitabine (Xeloda®), Caprelsa®, Carbo® MV (combination of carboplatin, methotrexate, and vinblastine), CarboTaxol®, Carboplatin®, Carboplatin® and etoposide, Carboplatin® and paclitaxel, Carmustine (BCNU, Gliadel®), Casodex®, Celebrex®, Celecoxib (Celebrex®), Ceritinib (Zykadia®), Cerubidin®, Cetuximab (Erbitux®), ChlVPP, Chlorambucil (Leukeran®), Cisplatin®, Cisplatin® and Teysuno®, Cisplatin® and capecitabine (CX), Cisplatin®, etoposide and ifosfamide (PEI), Cisplatin®, fluorouracil (5-FU) and trastuzumab, Cladribine (Leustat, LITAK®), Clasteon®, Clofarabine (Evoltra®), Co-codamol (Kapake®, Solpadol®, Tylex®), Cometriq®, Cosmegen®, Crisantaspase®, Crizotinib (Xalkori®), Cyclophosphamide, Cyprostat®, Cyproterone acetate (Cyprostat®), Cytarabine (Ara C, cytosine arabinoside), Cytarabine into spinal fluid, Cytosine arabinoside, HAP (combination of HA (high dose Ara C, also known as cytarabine), and cisplatin), DTIC (dacarbazine), Dabrafenib (Tafinlar®), Dacarbazine (DTIC), Dacogen®, Dactinomycin (actinomycin D, Cosmegen®), Dasatinib (Sprycel®), Daunorubicin, De Gramont, Decapeptyl® SR, Decitabine (Dacogen®), Degarelix (Firmagon®), Denosumab (Prolia®, Xgeva®), Depocyte®, Diamorphine, Disodium pamidronate, Disprol, Docetaxel (Taxotere®), Docetaxel, cisplatin and fluorouracil (TPF), Doxifos®, Doxil®, Doxorubicin (Adriamycin®), Doxorubicin and ifosfamide (Doxifos®), Drogenil®, Durogesic®, E-CMF (Epi-CMF), EC, ECF, EOF, EOX, EP, ESHAP, Effentora®, Efudix®, Eldisine®, Eloxatin®, Enzalutamide (Xtandi®), Epirubicin (Pharmorubicin®), Epirubicin, carboplatin and capecitabine (ECarboX), Epirubicin, cisplatin and capecitabine (ECX), Eposin®, Erbitux®, Eribulin (Halaven®), Erlotinib (Tarceva®), Erwinase®, Estracyt, Estramustine (Estracyt®), Etopophos®, Etoposide (Eposin, Etopophos®, Vepesid), Etoposide, leucovorin and fluorouracil (ELF), Everolimus (Afinitor®), Evoltra, Exemestane (Aromasin®), FAD, FC, FEC, FEC-T chemotherapy, FMD, FOLFIRINOX, Faslodex®, Femara®, Fentanyl, Firmagon®, Fludara®, Fludarabine (Fludara®), [Fludarabine, cyclophosphamide and rituximab (FCR)], Fluorouracil (5FU), Flutamide, [Folinic acid, fluorouracil and irinotecan (FOLFIRI)], [Folinic acid, fluorouracil and oxaliplatin (FOL.,FOX)], Fulvestrant (Faslodex®), G-CSF, Gefitinib (Iressa®), GemCarbo (gemcitabine and carboplatin), GemTaxol, Gemcitabine (Gemzar®), Gemcitabine and capecitabine (GemCap), Gemcitabine and cisplatin (GC), Gemcitabine and paclitaxel (GemTaxol), Gemzar®, Giotrif®, Gliadel@, Glivec®, Gonapeptyl® Depot, Goserelin (Zoladex®), Goserelin (Zoladex@, Novgos®), Granulocyte colony stimulating factor (G-CSF), Halaven®, Herceptin®, Hycamtin®, Hydrea, Hydroxycarbamide (Hydrea®), Hydroxyurea, I-DEX, ICE, IL-2, IPE, Ibandronic acid, Ibritumomab (Zevalin®), Ibuprofen (Brufen®, Nurofen®), Iclusig, Idarubicin (Zavedos®), Idelalisib (Zydelig®), Ifosfamide (Mitoxana®), Imatinib (Glivec®), Imiquimod cream (Aldara®), Imnovid®, Instanyl®, Interferon (Intron A®), Interleukin, Intron A®, Ipilimumab (Yervoy®), Iressa@, Irinotecan (Campto®), Irinotecan and capecitabine (XELIRI®), Irinotecan de Gramont, Irinotecan modified de Gramont, Javlor™, Jevtana®, Kadcyla®, Kapake@, Keytruda®, Lanvis™, Lapatinib (Tyverb®), Lenalidomide (Revlimid®), Letrozole (Femara®), Leukeran®, Leuprorelin (Prostap®, Lutrate®), Leustat®, Levact®, Liposomal doxorubicin, Litak®, Lomustine (CCNU, Gleostine®), Lynparza®, Lysodren®, MIC, MM, MMM, MST Continus, MVAC, MVP, MabCampath®, Mabthera®, Maxtrex®, Medroxyprogesterone acetate (Provera®), Megace®, Megestrol acetate (Megace®), Melphalan (Alkeran®), Melphalan, thalidomide, Mepact®, Mercaptopurine (Xaluprine®), Methotrexate (Maxtrex®), Mifamurtide (Mepact®), Mitomycin C, Mitotane, Mitoxana®, Mitoxantrone (Mitozantrone®), Morphgesic® SR, Morphine, Myleran®, Myocet®, Nab-paclitaxel, Nab-paclitaxel (Abraxane®), Navelbine@, Nelarabine (Atriance®), Nexavar®, Nilotinib (Tasigna®), Nintedanib (Vargatef®), Nipent™, Nivolumab (Opdivo®), Novgos®, Nurofen®, Ofatumumab (Arzerra®), Olaparib (Lynparza®), Oncovin®, Onkotrone®, Opdivo®, Oramorph®, Oxaliplatin (Eloxatin®), Oxaliplatin and capecitabine (XELOX), PAD, PC (paclitaxel and carboplatin, CarboTaxol®), PCV, PE, PMitCEBO, POMB/ACE, Paclitaxel (Taxol®), Paclitaxel and carboplatin, Pamidronate, Panadol®, Panitumumab (Vectibix®), Paracetamol, Pazopanib (Votrient®), Pembrolizumab (Keytruda®), Pemetrexed (Alimta®), Pemetrexed and carboplatin, Pemetrexed and cisplatin, Pentostatin (Nipent®), Perjeta®, Pertuzumab (Perjeta®), Pixantrone (Pixuvri®), Pixuvri@, Pomalidomide (Imnovid®), Ponatinib (Iclusig®), Potactasol, Procarbazine, Proleukin@, Prolia®, Prostap®, Provera®, Purinethol, R-CHOP, R-CVP, R-DHAP, R-ESHAP, R-GCVP, RICE, Raloxifene, Raltitrexed (Tomudex®), Regorafenib (Stivarga®), Revlimid, Rituximab (Mabthera®), Sevredol®, Sodium clodronate (Bonefos®, Clasteon®), Solpadol®, Sorafenib (Nexavar®), Stanford V, Streptozocin (Zanosar®), Sunitinib (Sutent®), Sutent®, TAC, TIP, Tafinlar®, Tamoxifen, Tarceva®, Targretin®, Tasigna®, Taxol®, Taxotere®, Taxotere® and cyclophosphamide (TC), Temodal®, Temozolomide (Temodal®), Temsirolimus (Torisel®), Tepadina®, Teysuno®, Thalidomide, Thiotepa (Tepadina®), Tioguanine (thioguanine, 6-TG, 6-tioguanine), Tomudex®, Topotecan (Hycamtin®, Potactasol®), Torisel®, Trabectedin (Yondelis®), Trastuzumab (Herceptin®), Trastuzumab emtansine (Kadcyla®), Treosulfan®, Tretinoin (Vesanoid®, ATRA), Triptorelin (Decapeptyl® SR, Gonapeptyl® Depot), Trisenox®, Tylex®, Tyverb®, VIDE, Vandetanib (Caprelsa®), Vargatef®, VeIP, Vectibix®, Velbe®, Velcade®, Vemurafenib (Zelboraf®), Vepesid®, Vesanoid®, Vidaza®, Vinblastine (Velbe®), Vincristine, [Vincristine, actinomycin D (dactinomycin) and cyclophosphamide (VAC)], [Vincristine, actinomycin and ifosfamide (VAI)], [Vincristine, doxorubicin (VA)], Vindesine (Eldisine®), Vinflunine (Javlor®), Vinorelbine (Navelbine®), Vismodegib (Erivedge®), Votrient®, XELOX®, Xalkori®, Xeloda®, Xgeva®, Xtandi®, Yervoy®, Yondelis, Z-DEX, Zaltrap®, Zanosar®, Zavedos®, Zelboraf®, Zevalin®, Zoladex® (breast cancer), Zoladex® (prostate cancer), Zoledronic acid (Zometa®), Zometa®, Zomorph®, Zydelig®, Zytiga®, Abemaciclib, Abiraterone Acetate, Abitrexate (Methotrexate®), Abraxane® (Paclitaxel Albumin-stabilized Nanoparticle Formulation), ABVD, ABVE, ABVE-PC, AC, Acalabrutinib, AC-T, Adcetris® (Brentuximab Vedotin), ADE, Ado-Trastuzumab Emtansine, Adriamycin (Doxorubicin Hydrochloride), Afatinib Dimaleate, Afinitor (Everolimus®), Akynzeo® (Netupitant and Palonosetron Hydrochloride), Aldara® (Imiquimod), Aldesleukin, Alecensa® (Alectinib), Alectinib, Alemtuzumab, Alimta® (Pemetrexed Disodium), Aliqopa® (Copanlisib Hydrochloride), Alkeran® for Injection (Melphalan Hydrochloride), Alkeran® Tablets (Melphalan), Aloxi® (Palonosetron Hydrochloride), Alunbrig® (Brigatinib), Ambochlorin (Chlorambucil), Amifostine, Aminolevulinic Acid, Anastrozole, Aprepitant, Aredia® (Pamidronate Disodium), Arimidex® (Anastrozole), Aromasin® (Exemestane), Arranon® (Nelarabine), Arsenic Trioxide, Arzerra® (Ofatumumab), Asparaginase *Erwinia chrysanthemi*, Atezolizumab, Avastin® (Bevacizumab), Avelumab, Axicabtagene Ciloleucel, Axitinib, Azacitidine, Bavencio® (Avelumab), BEACOPP, Becenum (Carmustine™), Beleodaq (Belinostat™,), Belinostat™, Bendamustine Hydrochloride, BEP, Besponsa™ (Inotuzumab Ozogamicin), Bevacizumab, Bexarotene, Bicalutamide, BiCNU (Carmustine™), Bleomycin, Blinatumomab, Blincyto® (Blinatumomab), Bortezomib, Bosulif® (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Calquence (Acalabrutinib), Campath (Alemtuzumab), Camptosar (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin® (Oxaliplatin), Eltrombopag Olamine, Emend® (Aprepitant), Empliciti® (Elotuzumab), Enasidenib Mesylate, Enzalutamide, Epirubicin Hydrochloride, EPOCH, Erbitux® (Cetuximab), Eribulin Mesylate, Erivedge® (Vismodegib), Erlotinib Hydrochloride, Erwinaze (Asparaginase *Erwinia chrysanthemi*), Ethyol® (Amifostine), Etopophos® (Etoposide Phosphate), Etoposide, Etoposide Phosphate, Evacet™ (Doxorubicin Hydrochloride Liposome), Everolimus, Evista® (Raloxifene Hydrochloride), Evomela® (Melphalan Hydrochloride), Exemestane, 5-FU (Fluorouracil Injection), 5-FU (Fluorouracil—Topical), Fareston® (Toremifene), Farydak® (Panobinostat), Faslodex® (Fulvestrant), FEC, Femara® (Letrozole), Filgrastim, Fludara® (Fludarabine Phosphate), Fludarabine Phosphate, Fluoroplex® (Fluorouracil—Topical), Fluorouracil Injection, Fluorouracil-Topical, Flutamide, Folex® (Methotrexate), Folex® PFS (Methotrexate), FOLFIRI®, FOLFIRI-BEVACIZUMAB, FOLFIRI-CETUXIMAB, FOLFIRINOX, FOLFOX, Folotyn® (Pralatrexate), FU-LV, Fulvestrant, Gardasil® (Recombinant HPV Quadrivalent Vaccine), Gardasil® 9 (Recombinant HPV Nonavalent Vaccine), Gazyva® (Obinutuzumab), Gefitinib, Gemcitabine Hydrochloride, GEMCITABINE-CISPLATIN, GEMCITABINE-OXALIPLATIN, Gemtuzumab Ozogamicin, Gemzar® (Gemcitabine Hydrochloride), Gilotrif® (Afatinib Dimaleate), Gleevec® (Imatinib Mesylate), Gliadel® (Carmustine Implant), Gliadel® wafer (Carmustine Implant), Glucarpidase, Goserelin Acetate, Halaven® (Eribulin Mesylate), Hemangeol® (Propranolol Hydrochloride), Herceptin® (Trastuzumab), [HPV Bivalent Vaccine, Recombinant], [HPV Nonavalent Vaccine, Recombinant], [HPV Quadrivalent Vaccine, Recombinant], Hycamtin® (Topotecan Hydrochloride), Hydrea® (Hydroxyurea), Hydroxyurea, Hyper-CVAD, Ibrance® (Palbociclib), Ibritumomab Tiuxetan, Ibrutinib, ICE, Iclusig® (Ponatinib Hydrochloride), Idamycin® (Idarubicin Hydrochloride), Idarubicin Hydrochloride, Idelalisib, Idhifa® (Enasidenib Mesylate), Ifex® (Ifosfamide), Ifosfamide, Ifosfamidum® (Ifosfamide), IL-2 (Aldesleukin), Imatinib Mesylate, Imbruvica® (Ibrutinib), Imfinzi® (Durvalumab), Imiquimod, Imlygic® (Talimogene Laherparepvec), Inlyta® (Axitinib), Inotuzumab Ozogamicin, [Interferon Alfa-2b, Recombinant], Interleukin-2 (Aldesleukin), Intron A (Recombinant Interferon Alfa-2b), Ipilimumab, Iressa® (Gefitinib), Irinotecan Hydrochloride, Irinotecan Hydrochloride Liposome, Istodax® (Romidepsin), Ixabepilone, Ixazomib Citrate, Ixempra® (Ixabepilone), Jakafi® (Ruxolitinib Phosphate), JEB, Jevtana® (Cabazitaxel), Kadcyla® (Ado-Trastuzumab Emtansine), Keoxifene® (Raloxifene Hydrochloride), Kepivance® (Palifermin), Keytruda® (Pembrolizumab), Kisqali® (Ribociclib), Kymriah® (Tisagenlecleucel), Kyprolis® (Carfilzomib), Lanreotide Acetate, Lapatinib Ditosylate, Lartruvo® (Olaratumab), Lenalidomide, Lenvatinib Mesylate, Lenvima® (Lenvatinib Mesylate), Letrozole, Leucovorin Calcium, Leukeran® (Chlorambucil), Leuprolide Acetate, Leustatin® (Cladribine), Levulan® (Aminolevulinic Acid), Linfolizin® (Chlorambucil), LipoDox® (Doxorubicin Hydrochloride Liposome), Lomustine, Lonsurf® (Trifluridine and Tipiracil Hydrochloride), Lupron® (Leuprolide Acetate), Lupron® Depot (Leuprolide Acetate), Lupron® Depot-Ped (Leuprolide Acetate), Lynparza® (Olaparib), Marqibo® (Vincristine Sulfate Liposome), Matulane® (Procarbazine Hydrochloride), Mechlorethamine Hydrochloride, Megestrol Acetate, Mekinist® (Trametinib), Melphalan, Melphalan Hydrochloride, Mercaptopurine, Mesna, Mesnex® (Mesna), Methazolastone® (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex® (Mitomycin C), MOPP, Mozobil® (Plerixafor), Mustargen® (Mechlorethamine Hydrochloride), Mutamycin® (Mitomycin C), Myleran® (Busulfan), Mylosar® (Azacitidine), Mylotarg® (Gemtuzumab Ozogamicin), Nanoparticle Paclitaxel (Paclitaxel Albumin-stabilized Nanoparticle Formulation), Navelbine® (Vinorelbine Tartrate), Necitumumab, Nelarabine, Neosar® (Cyclophosphamide), Neratinib Maleate, Nerlynx® (Neratinib Maleate), Netupitant and Palonosetron Hydrochloride, Neulasta® (Pegfilgrastim), Neupogen® (Filgrastim), Nexavar® (Sorafenib Tosylate), Nilandron® (Nilutamide), Nilotinib, Nilutamide, Ninlaro® (Ixazomib Citrate), Niraparib Tosylate Monohydrate, Nivolumab, Nolvadex® (Tamoxifen Citrate), Nplate® (Romiplostim), Obinutuzumab, Odomzo® (Sonidegib), OEPA, Ofatumumab, OFF, Olaparib, Olaratumab, Omacetaxine Mepesuccinate, Oncaspar® (Pegaspargase), Ondansetron Hydrochloride, Onivyde® (Irinotecan Hydrochloride Liposome), Ontak® (Denileukin Diftitox), Opdivo® (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat® (Carboplatin), Paraplatin® (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta® (Pertuzumab), Pertuzumab, Platinol® (Cisplatin), Platinol®-AQ (Cisplatin), Plerixafor, Pomalidomide, Pomalyst® (Pomalidomide), Ponatinib Hydrochloride, Portrazza® (Necitumumab), Pralatrexate, Procarbazine Hydrochloride, Proleukin® (Aldesleukin), Prolia® (Denosumab), Promacta® (Eltrombopag Olamine), Propranolol Hydrochloride, Provenge® (Sipuleucel-T), Purinethol® (Mercaptopurine), Purixan® (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor® (Methylnaltrexone Bromide), R-EPOCH, Revlimid® (Lenalidomide), Rheumatrex® (Methotrexate), Ribociclib, R-ICE, Rituxan® (Rituximab), Rituxan® Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca® (Rucaparib Camsylate), Rucaparib Camsylate, Ruxolitinib Phosphate, Rydapt® (Midostaurin), Sclerosol® Intrapleural Aerosol (Talc), Siltuximab, Sipuleucel-T, Somatuline® Depot (Lanreotide Acetate), Sonidegib, Sorafenib Tosylate, Sprycel® (Dasatinib), STANFORD V, Sterile Talc Powder (Talc), Steritalc® (Talc), Stivarga® (Regorafenib), Sunitinib Malate, Sutent® (Sunitinib Malate), Sylatron® (Peginterferon Alfa-2b), Sylvant® (Siltuximab), Synribo® (Omacetaxine Mepesuccinate), Tabloid® (Thioguanine), TAC, Tafinlar (Dabrafenib), Tagrisso® (Osimertinib), Talc, Talimogene Laherparepvec, Tamoxifen Citrate, Tarabine® PFS (Cytarabine), Tarceva® (Erlotinib Hydrochloride), Targretin® (Bexarotene), Tasigna® (Nilotinib), Taxol® (Paclitaxel), Taxotere® (Docetaxel), Tecentriq® (Atezolizumab), Temodar® (Temozolomide), Temozolomide, Temsirolimus, Thalidomide, Thalomid® (Thalidomide), Thioguanine, Thiotepa, Tisagenlecleucel, Tolak® (Fluorouracil—Topical), Topotecan Hydrochloride, Toremifene, Torisel® (Temsirolimus), Totect® (Dexrazoxane Hydrochloride), TPF, Trabectedin, Trametinib, Trastuzumab, Treanda® (Bendamustine Hydrochloride), Trifluridine and Tipiracil Hydrochloride, Trisenox® (Arsenic Trioxide), Tykerb® (Lapatinib Ditosylate), Unituxin® (Dinutuximab), Uridine Triacetate, VAC, Valrubicin, Valstar® (Valrubicin), Vandetanib, VAMP, Varubi® (Rolapitant Hydrochloride), Vectibix® (Panitumumab), VeIP, Velban® (Vinblastine Sulfate), Velcade® (Bortezomib), Velsar® (Vinblastine Sulfate), Vemurafenib, Venclexta® (Venetoclax), Venetoclax, Verzenio® (Abemaciclib), Viadur® (Leuprolide Acetate), Vidaza® (Azacitidine), Vinblastine Sulfate, Vincasar® PFS (Vincristine Sulfate), Vincristine Sulfate, Vincristine Sulfate Liposome, Vinorelbine Tartrate, VIP, Vismodegib, Vistogard® (Uridine Triacetate), Voraxaze® (Glucarpidase), Vorinostat, Votrient® (Pazopanib Hydrochloride), Vyxeos® (Daunorubicin Hydrochloride and Cytarabine Liposome), Wellcovorin® (Leucovorin Calcium), Xalkori® (Crizotinib), Xeloda® (Capecitabine), XELIRI, XELOX, Xgeva® (Denosumab), Xofigo® (Radium 223 Dichloride), Xtandi® (Enzalutamide), Yervoy® (Ipilimumab), Yescarta® (Axicabtagene Ciloleucel), Yondelis® (Trabectedin), Zaltrap® (Ziv-Aflibercept), Zarxio® (Filgrastim), Zejula® (Niraparib Tosylate Monohydrate), Zelboraf® (Vemurafenib), Zevalin® (Ibritumomab Tiuxetan), Zinecard® (Dexrazoxane Hydrochloride), Ziv-Aflibercept, Zofran® (Ondansetron Hydrochloride), Zoladex® (Goserelin Acetate), Zoledronic Acid, Zolinza® (Vorinostat), Zometa® (Zoledronic Acid), Zydelig® (Idelalisib), Zykadia® (Ceritinib), Zytiga® (Abiraterone Acetate), Monoclonal antibodies—approved by FDA abciximab (Reopro), adalimumab (Humira®, Amjevita®), ado-trastuzumab emtansine (Kadcyla®), alefacept (Amevive®), alemtuzumab (Campath®, Lemtrada®), Alirocumab (Praluent®), Atezolizumab (Tecentriq®), Avelumab (Bavencio®), basiliximab (Simulect®), belimumab (Benlysta®), blinatumomab (Blincyto®), Brentuximab vedotin (Adcentris), Bevacizumab (Avastin®), bezlotoxumab (Zinplava®), Brodalumab (Siliz®), Canakinumab (Ilaris®), Capromab pendetide (Prostascint®), Catumaxomab (Removab®), canakinumab (Ilaris®), certolizumab pegol (Cimzia®), cetuximab (Erbitux®), cixutumumab, daclizumab (Zenapax@, Zinbryta®), daratumumab (Darzalex®), denosumab (Prolia®, Xgeva®), dinutuximab (Unituxin®), dupilumab (Dupixent®), durvalumab (Imfinzi®), eculizumab (Soliris®), elotuzumab (Repatha®), efalizumab (Raptiva®), emicizumab (Hemlibra®), ertumaxomab (Rexomun®), etaracizumab (Abegrin®), evolocumab (Repatha®), gemtuzumab ozogamicin (Mylotarg®), girentuximab (Rencarex®), golimumab (Simponi®, Simponi® Aria), Guselkumab, ibritumomab tiuxetan (Zevalin®), idarucizumab (Praxbind®), imciromab (Myoscint®), infliximab/inflectra (Remicade®), ipilimumab (Yervoy®), ixekizumab (Taltz®), mepolizumab (Bosatria®), natalizumab (Tysabri®), necitumumab (Portrazza®), nivolumab (Opdivo®), obiltoxaximab, obinutuzumab (Gazyva®), ocrelizumab (Ocrevus®), ofatumumab (Arzerra®), olaratumab (Lartruvo®), omalizumab (Xolair®), palivizumab (Synagis®, Abbosynagis®), panitumumab (Vectibix®), pembrolizumab (Keytruda®), pertuzumab (Omnitarg®), ramucirumab (Cyramza@), ranibizumab (Lucentis®), raxibacumab, reslizumab, rituximab (Rituxan®, MabThera®), rovelizumab (LeukArrest®), Rupluzimab (Antova®), secukinumab (Cosentyx®), siltuximab (Sylvant®), tocilizumab (Actemra®, RoActemra®), tositumomab (Bexxar®), trastuzumab (Herceptin®), trastuzumab emtansine (Kadcyla®), ustekinumab (Stelara®), vedolizumab (Entyvio®), Pertuzumab, alpha interferon, Galiximab, humanized SMART Anti-IL-12 Antibody, Dinutuximab, Oregovomab, Epratuzumab, anti-CD22 Recombinant Immunotoxin Moxetumomab Pasudotox, CAT-5001 (formerly SS1P), Labetuzumab, anti-alpha5Beta1-integrin antibody, NVS antibody, Efmoroctocog alfa, 3f8 (CAS #339169-93-6), 8H9 MAb, Abagovomnab, Abituzurnab, Abrilumab, Actoxurnab, Adecatumumab, Aducanurmab, Afasevikumab, Afelimomab, Afutuzumab, Alacizumab pegol, Altumomab pentetate, Amatuxirnab, Anatumomab mafenatox, Anetumab ravtansine, Anifrolumab, Anrukinzumab, Apolizumab, Arcitumomab, Ascrinvacumab, Aselizumab, Atinumab, Atorolimumab, Bapineuzumab, Bavituximab, Bectumomab, Begelomab, Benralizumab, Bertilimumab, Besilesomab (Scintimun®), Biciromab (FibriScint®), Bimagrumab, Bimekizumab, Bivatuzumab mertansine, Bleselumab, Blontuvetmab (Blontress®), Blosozumab, Bococizurnab, Brazikumab, Briakinumab, Brolucizumab, Brontictuzumab, Burosumab, Cabiralizumab, Cantuzumrab mertansine, Cantuzurnab ravtansine, Caplacizurnab, Carlnumab, Carotuxumab, cBR96-doxorubicinimmunoconjugate, Cedelizumab. Cergutuzumab amunaleukin, Citatuzumab bogatox, Clazakizumnab, Clenolixinab, Clivatuzumab tetraxetan (hPAM4-cide), Codrituzumab, Coltuximab ravtansine, Conatumumab, Concizumab, Crenezumab, Crotedumab, CR6261, Dacetuzumrab, Dalotuzumab, Dapriolizumab pegol, Dectrekurnab, Derncizumnab, Denintuzumab mafodotin, Depatuxizumab mafodotin, Derlotuxirnab biotin, deturmomab, diridavumab, domagrozumab, dorlirnmomab aritox, drozitumab, duligotumab, dusigitumab, ecrorneximab, edobacomnab, edrecolomab, efalizumab, efungumnab, eldelumab, elgemtumab, elsilimomab, emactuzumab, eribetuzumab, enavatuzumab, enfortumabvedotin, enlimomabpegol, enoblituzurnab, enokizumab, enoticurnab, ensituximab, epiturnornabcituxetan, epratuzumnab, erenumab, erlizumrab, etrolizumrab, evinacumab, exbivirumab, fanolesomab (NeutroSpec), faralimomrnab, farletuzumab, Fasinumab, FBTAO5 (Lymphornun), Felvizurnab, Fezakinumab, Fibatuzumab. Ficlatuzurmab, Figitumumab, Firivumab, Flanvotumab. Fletikumab, Fontolizumnab (HIuZAF), Foralumab, Foravirumab, Fresolimunab, Fulranumab, Futuximab, Galcanezumrab, Galiximab, Ganiturnab, Gantenerurnab, Gavilinmomnab, Gevokizumab, Glembatumumab vedotin, Gomriliximab, ibalizumab, icrucumab, igovomab (Indimacis-125™), IMAB362, Imralumab, lrngatuzumab, INTLAcumab, indatuximab ravtansine, indusatumnab vedotin, inebilizurnab, inteturnmumab, inolimomab, inotuzumrab ozogarnicin, iraturnmumab, isatuximab, itolizumab, keliximab, labetuzurnab (CEA-cide), lampalizumrab, lanadelumrab, landogrozumnab, laprituximab emtansine, lebrikizumab, lemalesomab, lendalizurmab, lenzilurnab, lerdelimumab, lexatumumab, libivirumab, lifastuzumab vedotin, liglizumrab, lilotomrab satetraxetan, lintuzurnab, lirilumab, lodelcizumab, lorvotuzumab mertansine, lucatumumab, lulizurmab pegol, lumiliximab, lumretuzumab, MABpl (Xilonix™), mapaturnmumab, margetuximnab, maslimomab, mapaturnurnab, margetuximab, maslimomab, mavrilimumab, matuzunab, metelimumnab, milatuzumrab, minretumomab, mirvetuximab soravtansine, Mitumomab, mogarnulizumab, monalizumab, morolirnunab, motavizumab (Nurmaxi™), Moxetumomab pasudotox, Muromonab-CD3 (orthocione OKT3), nacolomnab tafenatox, namilumab, naptumomab estafenatox, naratuxirnab erntansine, narnaturab, navicixizumab, navivumab, nebacumab, nemolizumab, nerelimomab, nesvacumab, nimotuzumab (Theracim®, Theraloc®), nofetumomab merpentan (Verluma®), ocaratuzumab, odulimomab, olokizumab, onartuzumab, ontuxizumab, opicinumab, oportuzumab monatox, oregovomab, orticumab, otelixizumab, otlertuzumab, oxelumab, ozanezumab, ozoralizumab, pagibaximab, pamrevlumab, pankomab, panobacumab, parsatuzumab, pascolizumab, pasotuxizumab, pateclizumab, patritumab, pemtumomab, perakizumab, pexelizumab, pidilizumab, pinatuzumab vedotin, pintumomab, placulumab, plozalizumab, pogalizumab, polatuzumab vedotin, ponezumab, prezalizumab, priliximab, pritoxaximab, pritumumab, PRO 140, Quilizumab, Racotumomab, radretumab, rafivirumab, ralpancizumab, refanezumab, regavirumab, rilotumumab, rinucumab, resankizumab, rivabazumab pego, robatumumab, roledumab, romosozumab, rontalizumab, rovalpituzumab tesirine, sacituzumab govitecan, samalizumab, sapelizumab, sarilumab, satumomab pendetide, seribantumab, setoxaximab, sevirumab, sibrotuzumab, SGN-CD19A, SGN-CD33A, sifalimumab, simtuzumab, siplizumab, sirukumab, sofituzumab vedotin, solanezumab, solitomab, sonepcizumab, sontuzumab, stamulumab, sulesomab (LeukoScan®), suvizumab, tabalumab, tacatuzumab tetraxetan, tadocizumab, talizumab, tarntuvetmab, tanezumab, taplitumomab paptox, tarextumab, tefibazumab (Aurexis), telimomab aritox, tenatumomab, teneliximab, teplizumab, teprotumumab, tesidolumrnab, tetulrnomab, tezepelumab, TGN 1412, ticilimumab, tildrakizumnab, tigatuzumnab, timolumab, tisotumnab vedotin, TNX-650, Toralizumab, tosatoxumab, tovetumab, tralokinumab, TRBS07 (Ektomab), tregalizumab, tremelimumab, trevogrumab, tucotuzumab celmoleukin, tuvirumab, ublituximab, ulocuplumab, urelumab, urtoxazumab, utomilumab, vadastuximab talirine, vandortuzumab vedotin, vanticturnab, vanucizumab, vapaliximab, varlilumab, vatelizumab, veltuzumab, vepalimomab, vesencumab, visilizumab (Nuvion), vobarilizumab, volociximab, vorsetuzumab mafodotin, votumumab (HumaSPECT®), xentuzumab, zalutumumab (HuMax-EGFr), Zanolimumab (HuMax-CD4), Zatuximab, Ziralimumab, zolimomab aritox, Digoxin Immune Fab (Ovine), Recombinant Cholera Toxin B Subunit, Denileukin diftitox, Ranimustine (approved in Japan), Resimmune (A-dmDT390-bisFv(UCHT1), MOC31PE, BL22, Anti-CD22 Recombinant Immunotoxin BL22 (CAT-3888), and immunotoxin CMD-193.

NTLA, particularly NTLA Dexamethasone dosed between about 3 mg/kg and about 26 mg/kg single acute dose about 12 to about 72 hours prior to cell immunotherapy administration or total dose of about 3 mg/kg to about 26 mg/kg given between about 12 to about 72 hours of cell therapy administration increases plasma IL-2 and IL-15 levels.

NTLA, particularly NTLA Dexamethasone dosed between about 3 mg/kg and about 26 mg/kg single acute dose or total dose of about 3 mg/kg to about 26 mg/kg given over about a 72 hour period, either alone, or in combination with reduced intensity cytotoxic preconditioning can be useful for the treatment of autoimmune diseases. For the treatment of autoimmune disease an ACT could be targeted to the immune cells driving the disease in an effort to eradicate the autoimmune recognizing cells. Additionally, for autoimmune diseases the ACT could be a Treg targeted by a CAR or TCR or expressed antibody for an antigen expressed specifically or selectively by the region or organ of the body where the autoimmune attack goes on. The Tregs could non-exclusively relate to CD4+ Tregs, CD4+ CD45RA+ Tregs, CD4+CD25+CD45RA+ Tregs, FoxP3+ Tregs, CD4+CD25+FoxP3+CD152+ Tregs, CD4+CD25+ CD152+ Tregs, CD8+ Tregs, CD8+CD28− Tregs, CD4+ CD25int/high, CD127low, CTLA4+, GITR+, FoxP3+, CD127low, CD4+CD25−⁻ induced Tregs, or Type I T regs.

"Natural" regulatory T cells originally recognised by their constitutive expression of CD4 and CD25 can be further defined by expression of the transcription factor foxP3 and surface CD152. Their generation and some of their suppressive activity is dependent on TGF-beta, and it has been shown that they can induce IDO in appropriate DCs by CD152 mediated ligation of CD80/86. Anergic CD4+ T cells generated by antigen stimulation in the absence of costimulation seem to be characterised by an intrinsic raising of their threshold for antigen stimulation, that may be maintained by expression of E3 ubiquitin ligases such as GRAIL, c-cbl and Itch. Anergic cells can act as regulatory T cells by competing at the sites of antigen presentation and adsorbing out stimulatory cytokines such as IL-2. Trl cells represent an induced subset of CD4 helper T cells that are dependent on IL-10 for their differentiation and for some of their regulatory properties. They do not express foxP3 but may express markers associated with Th2 cells and repressor of GATA (ROG). Like natural Tregs, they express high levels of surface CD152 and can induce IDO and trypophan catabolism in appropriate DCs. CD8+CD28− suppressor T (Ts) cells were first characterised in human, but have recently also been demonstrated in rodents. Like Trl cells, they are induced in the presence of IL-10, and IL-10 may be involved in the downregulation of dendritic cell costimulation and the upregulation of ILT-3 and ILT-4 (in human DC) that seem to play an important role in presenting antigen to tolerise further cohorts of T cells.

Regulatory T cells (Tregs) play an important role in maintaining immune homeostasis. Tregs suppress the function of other T cells to limit the immune response. Alterations in the number and function of Tregs has been implicated in several autoimmune diseases including multiple sclerosis, active rheumatoid arthritis, and type 1 diabetes. High levels of Tregs have been found in many malignant disorders including lung, pancreas, and breast cancers. Tregs may also prevent antitumor immune responses, leading to increased mortality.

Two major classes of Tregs have been identified to date: CD4 and CD8 Tregs. CD4 Tregs consist of two types, "natural" Tregs (nTregs) that constitutively express CD25 and FoxP3, and so-called adaptive or inducible Tregs (iTregs).

Natural Tregs originate from the thymus as CD4⁺ cells expressing high levels of CD25 together with the transcription factor (and lineage marker) FoxP3. nTregs represent approximately 5-10% of the total CD4⁺ T cell population, and can first be seen at the single-positive stage of T lymphocyte development.[2] They are positively selected thymocytes with a relatively high avidity for self-antigens. (Fehérvari Z, Sakaguchi S. Development and function of CD25⁺CD4⁺ regulatory T cells. *Curr Opin Immunol.* 2004; 16:203-208.)

The signal to develop into Treg cells is thought to come from interactions between the T cell receptor and the complex of MHC II with self peptide expressed on the thymic stroma. nTregs are essentially cytokine independent.

Adaptive or inducible Tregs originate from the thymus as single-positive CD4 cells. They differentiate into CD25 and FoxP3 expressing Tregs (iTregs) following adequate antigenic stimulation in the presence of cognate antigen and specialized immunoregulatory cytokines such as TGF-β, IL-10, and IL-4. (Chatenoud L, Bach J F. Adaptive human regulatory T cells: myth or reality? *J Clin Invest.* 2006; 116:2325-2327.)

FoxP3 is currently the most accepted marker for Tregs, although there have been reports of small populations of FoxP3⁻ Tregs. The discovery of transcription factor FoxP3 as a marker for Tregs has allowed scientists to better define Treg populations leading to the discovery of additional Treg markers including CD127.

NTLA, particularly NTLA Dexamethasone dosed between about 3 mg/kg and about 26 mg/kg single acute dose or total dose of about 3 mg/kg to about 26 mg/kg given over about a 72 hour period, either alone or in combination with reduced intensity cytotoxic preconditioning can be useful for the treatment of residual HIV disease, and for the treatment of germinal center lymphomas such as Burkitt's Lymphoma.

Follicular helper CD4 T cells, $T_{FH}$, residing in B-cell follicles within secondary lymphoid tissues, are readily infected by AIDS viruses and are a major source of persistent virus despite relative control of viral replication. This persistence is due at least in part to a relative exclusion of effective antiviral CD8 T cells from B-cell follicles. AIDS virus persistence in individuals under effective drug therapy or those who spontaneously control viremia remains an obstacle to definitive treatment. Infected follicular helper CD4 T cells, $T_{FH}$, present inside B-cell follicles represent a major source of this residual virus. While effective CD8 T-cell responses can control viral replication in conjunction with drug therapy or in rare cases spontaneously, most antiviral CD8 T cells do not enter B-cell follicles, and those that do fail to robustly control viral replication in the $T_{FH}$ population. Thus, these sites are a sanctuary and a reservoir for replicating AIDS viruses. Here, we demonstrate that engineering unselected CD8 T cells to express CXCR5, a chemokine receptor on $T_{FH}$ associated with B-cell follicle localization, redirects them into B-cell follicles. Lymphodepletion and reduction of germinal centers and marginal zones in the spleen would force residual HIV infected cells into the blood stream where they could be killed by existing therapies. Latently infected resting CD4 T cells have been detected in the peripheral blood, gastrointestinal (GI) tract, and lymph nodes of HIV-1-infected individuals and are also likely to exist in other organs containing lymphoid tissue.

Highly active antiretroviral therapy (HAART) enables long-term suppression of plasma HIV-1 loads in infected persons, but low-level virus persists and rebounds following cessation of therapy. During HAART, this virus resides in latently infected cells, such as resting CD4 T cells, and in other cell types that may support residual virus replication. Therapeutic eradication will require elimination of virus from all reservoirs.

Burkitt's Lymphoma is a germinal center lymphoma originating and growing within the secondary lymphatic system, always associated with a c-Myc activating chromosomal translocation. It is one of the fastest growing cancers and can double in size every 14-18 hours.

Clinical observations on the ability of a Bruton's Tyrosine Kinase inhibitor ibrutinib for treatment of chronic lymphocytic leukemia has demonstrated that redistribution of CLL cells from the lymphatics into the bloodstream is a contributing mechanism of action to its benefit in CLL. Circulating CLL cells are not proliferative, with proliferation of the clone limited to the lymphatic microenvironment. Therefore, redistribution into the blood stream reduces cancerous proliferation. Similarly, redistribution of ALL from the bone marrow to the bloodstream, has also been reported to enhance sensitivity to standard chemotherapy (Chang B Y, Blood 2013 122: 2412-24;).

Among B-cell malignancies, CLL is the most responsive to ibrutinib, and thus unfortunately ibrutinib is not likely to significantly benefit people afflicted with Burkitt's Lymphoma and other germinal center lymphomas. However, the same result to redistribute B-cell cancers into the circulation where they are more susceptible to chemotherapy and less proliferative can be achieved for germinal center lymphomas such as Burkitt's lymphoma with the use of agents that ablate secondary lymphatic germinal centers.

Glucocorticoids have been reported to have multiple and contradictory actions on lymphocytes, depending on the dose, the duration of dosing and the species investigated. Glucocorticoids have been investigated as lymphocytosis inducing agents, agents which increase circulating lymphocyte numbers, since 1943 (for review see Burger J A, Blood 2013 121: 1501-9), typically with the use of prednisone between 0.5 and 1 mg/kg, which would be an equivalent 0.1-0.2 mg/kg dexamethasone dose. High dose methylprednisone (HDMP) used for refractory CLL, in contrast, does not appear to induce lymphocytosis at the methylprednisone equivalent to the 0.5-1.0 mg/kg dose at which prednisone did. Lymphotoxic high-dose steroids are typically considered to be approximately 100 mg daily of prednisone equivalent, which would be a dexamethasone equivalent dose of 16 mg which is approximately 0.23 to 0.32 mg/kg, and which we have demonstrated is not an NTLA dose. NTLA Dexamethasone does not reduce germinal centers in mice until an HED of 3 mg/kg is administered. Prednisone does not significantly impact spleen weights or germinal centers until used at doses in mice over 2.5 mg/kg po daily for 13 weeks (Yan S X[1], Acta Pharmacol Sin. 2015 November; 36(11):1367-76.), a human dose which would have unacceptable mineralocorticoid activity as a dose of 30 mgs per day (~0.48-0.72 mg/kg) is considered a high dose in human lupus patients.

For Burkitt's lymphoma (BL) treatment with standard chemotherapy regimens such as COPADM, prednisone is included in various cycles typically at 60 mg/m², which converts to 1.62 mg/kg prednisone and an equivalent 0.3 mg/kg dexamethasone dose, which is not an NTLA dose. Dexamethasone is also used clinically for the treatment of B-cell cancers, typically in an oral four-five day 40 mg daily regimen or 6 mg/m² for 5 days. In some indications such as ALL, dexamethasone is given daily for weeks and can be associated with osteonecrosis, particularly in adolescent boys. Risk of osteonecrosis can be substantially eliminated by alternate week dosing of dexamethasone and may be particularly present in ALL because of the asparaginase regimen that is part of the treatment for ALL (Chang B Y, Blood 2013 122: 2412-24).

BL is an aggressive B-cell lymphoma found in germinal centers of the spleen and secondary lymphatics. Epstein-Barr virus (EBV) infection is found in nearly all African BL patients, and chronic malaria is believed to reduce resistance to EBV, allowing it to take hold. The disease characteristically involves the jaw or other facial bone, distal ileum, cecum, ovaries, kidney, or breast. Additionally, BL strike immunocompromised people, such as those with HIV.

BL is classified into three main clinical variants: Endemic, Sporadic, and the Immunodeficiency-associated variants, with the Endemic variant (also called the "African variant") most commonly occurring in children living in malaria endemic regions of the world.

The use of NTLA which ablate germinal centers to selectively drive BL and other germinal center cancer cells from the germinal centers into circulation where they can be more easily killed with chemotherapy or other agents could dramatically, safely and cost-effectively advance BL treatment outcomes.

NTLA, particularly NTLA Dexamethasone dosed between about 3 mg/kg and about 26 mg/kg single acute dose or total dose of about 3 mg/kg to about 26 mg/kg given over about a 72 hour period, either alone, or in combination with reduced intensity cytotoxic preconditioning, preferably one day of cytotoxic preconditioning dosing, can be useful for preconditioning prior to allogeneic or autologous bone marrow transplant or hematopoietic stem cell transplant (HSCT).

DEX (dexamethasone base) doses in the examples in the present application are given as human equivalent doses (HED). AVM0703 (also referred to as AugmenStem™ or PlenaStem™) in the examples given is Dex (dexamethasone base) as dexamethasone sodium phosphate in a proprietary buffer.

The specific NTLA drugs listed below at standard or novel high doses would prevent cellular immunotherapies from binding to and accumulating in the secondary lymphatics and cause peripheral blood lymphodepletion because they are also immunesuppressants:

Tacrolimus is a calcineurin inhibitor delivered as an NTLA as an injection or oral dose of about 0.48 mg/kg/day to about 10 mgs/kg/day for about 1 to about 4 weeks. The doses of tacrolimus needed for NTLA are higher than doses typically used for approved indications. Tacrolimus (Prograf™) is approved for adult kidney transplant In combination with azathioprine at 0.2 mg/kg/day and in combination with MMF/IL-2 receptor antagonist 0.1 mg/kg/day, for adult liver transplant at 0.1 to 0.15 mg/kg/day, for pediatric liver transplant at 0.15-0.20 mg/kg/day, and for adult heart transplant 0.075 mg/kg/day, much lower doses than disclosed in this invention for NTLA. Tacrolimus suppressed interleukin 2. Tacrolimus Sandoz® is approved for: Primary immunosuppression in liver, kidney, pancreas, lung or heart allograft recipients LIVER: Administration should start approximately 6 hours after the completion of surgery. When commencing oral therapy, an initial dose of 0.10-0.20 mg/kg/day should be administered in two divided doses. KIDNEY, PANCREAS or KIDNEY-PANCREAS: Administration should start approximately 6 hours after the completion of surgery. When commencing oral therapy, an initial dose of 0.15-0.30 mg/kg/day should be administered in two divided doses. HEART: Administration should start no sooner than 6 hours after the completion of surgery. When commencing oral therapy, an initial dose of 0.075 mg/kg/day should be administered in two divided doses. LUNG: Administration should start no sooner than 6 hours after the completion of surgery. When commencing oral therapy, an initial dose of 0.10-0.30 mg/kg/day should be administered in two divided doses. Tacrolimus is associated with an increased risk of malignancy, particularly lymphomas. Tacrolimus inhibits neutrophil function (Suzuki 1993). Ulrich et al (Toxicol Lett 149, 123-31, 2004) showed that 1 to 4 weeks of daily FK506 (tacrolimus) dosing at about 0.48 mg/kg/day to about 10 mgs/kg/day is required to reduce germinal centers.

Cyclosporine is a cyclic polypeptide immunosuppressant agent orally administered as an NTLA at about 20 to about 100 mgs/kg/daily for about 7 to about 28 days. The daily dose is divided by two and administered every 12 hours. The doses of cyclosporine needed for NTLA are in general higher than doses typically used for approved indications. Sandimmune® (cyclosporine) is approved for an initial single oral dose of 15 mg/kg and should be given 4 to 12 hours prior to transplantation. Although a daily single dose of 14 to 18 mg/kg was used in most clinical trials, few centers continue to use the highest dose, most favoring the lower end of the scale. There is a trend towards use of even lower initial doses for renal transplantation in the ranges of 10 to 14 mg/kg/day. The initial single daily dose is continued postoperatively for 1 to 2 weeks and then tapered by 5% per week to a maintenance dose of 5 to 10 mg/kg/day. Some centers have successfully tapered the maintenance dose to as low as 3 mg/kg/day in selected renal transplant patients without an apparent rise in rejection rate. Cyclosporine inhibits neutrophil function (Suzuki 1993). If cyclosporine trough blood concentrations are used, the target range is the same for Neoral® as for Sandimmune®. Cyclosporine causes significant nephrotoxicity. Moriyama et al (J Vet Med Sci 74, 1487-1491 2012) showed that 7 to 28 days of 20 to 100 mg/kg cyclosporine dosing is required to reduce germinal centers.

Anakinra (trade name KINERET®, BIOVITRUM, Stockholm, Sweden) is a recombinant, non-glycosylated version of human IL-RA (RA for receptor antagonist) delivered as injection concentrate containing about 100 mg each single dose, weekly preferably for 3-4 weeks prior to the administration of the cellular immunotherapies.

Infliximab (trade name REMICADE®, CENTOCOR ORTHO BIOTECH, Horsham, Pa.) is a monoclonal antibody against tumour necrosis factor alpha (TNFα). administered by intravenous infusion at a dose of from about 3 mg/kg up to about 10 mg/kg, weekly preferably for 3-4 weeks prior to the administration of the cellular immunotherapies.

Golimumab (CNTO 148) is a human monoclonal antibody and is marketed under the brand name SIMPONI®, CENTOCOR ORTHO BIOTECH, Horsham, Pa. Golimumab targets TNF-alpha. administered by intravenous infusion, a once monthly subcutaneous injection preferably for 3-6 months prior to administration of the cellular immunotherapy.

Adalimumab (HUMIRA®, ABBOTT LABORATORIES, North Chicago, Ill.) is a TNF inhibitor, adalimumab binds to TNFα, preventing it from activating TNF receptors; adalimumab was constructed from a fully human monoclonal antibody, marketed in both preloaded 0.8 mL syringes and also in preloaded pen devices each containing 40 mg of adalimumab. To down-regulate the germinal centers prior to stem cell administration of at least 40 mg of adalimumab should be administered weekly preferably for 3-4 weeks prior to the administration of the cellular immunotherapies.

Certolizumab pegol (trade name CIMZIA®, UCB Inc., Atlanta, Ga.) is a monoclonal antibody directed against tumor necrosis factor alpha. More precisely, it is a PEGylated Fab' fragment of a humanized TNF inhibitor monoclonal antibody. It is administered as two subcutaneous injections of 200 mg, injections, weekly preferably for 3-4 weeks prior to the administration of the cellular immunotherapies.

Eculizumab (trade name SOLIRIS®, ALEXION PHARMACEUTICALS, Cheshire, Conn.) is a monoclonal antibody directed against the complement protein C5. This antibody blocks the clea CIMZIA® age of C5 and halts the process of complement-mediated cell destruction. Soliris® is administered as an IV infusion administered in 600-mg doses or 900-mg doses, weekly preferably for 3-4 weeks prior to the administration of the cellular immunotherapies.

Mepolizumab (proposed trade name BOSATRIA, GLAXO SMITH KLINE, King of Prussia, Pa.) is a humanized monoclonal antibody that recognizes interleukin-5 (IL-5) administered in subcutaneously (SC) at 750 mg every four weeks, preferably for 1 to 6 months prior to the administration of the cellular immunotherapies.

Omalizumab (trade name XOLAIR®, GENENTECH/ NOVARTIS) is a humanized antibody Omalizumab is a recombinant DNA-derived humanized IgG1k monoclonal antibody that selectively binds to human immunoglobulin E (IgE). XOLAIR® (Omalizumab) 150 to 375 mg is administered SC every 2 to 4 weeks, preferably for 4 to 12 weeks prior to the administration of the cellular immunotherapies.

Nerelimomab (BAYX®) is a mouse anti-TNF antibody, and can be administered at 10 mg/kg sc weekly, preferably for 1 to 3 months prior to the administration of the cellular immunotherapies.

Faralimomab is a mouse anti-TNF antibody, and can be administered at 10 mg/kg weekly preferably for 3-4 weeks prior to the administration of the cellular immunotherapies.

Elsilimomab (also known as B-E8) is a mouse monoclonal antibody and an immunosuppressive drug that blocks interleukin 6. According to the present invention, it can be administered at a dose of 10 mg/kg weekly preferably for 3-4 weeks prior to the administration of the cellular immunotherapies.

Lebrikizumab (GENENTECH, South San Francisco, Calif.) is a humanized monoclonal antibody that is designed to bind specifically to IL-13 and can be administered at 10 mg/kg weekly preferably for 3-4 weeks prior to the administration of the cellular immunotherapies.

Ustekinumab (experimental name CNTO 1275, proprietary commercial name STELARA®, CENTOCOR) is a human monoclonal antibody. It is directed against interleukin 12 and interleukin 23, naturally occurring proteins that regulate the immune system and immune-mediated inflammatory disorders. 2 injections, one-month apart, of either 90 or 45 milligrams, preferably given for 2 months before administration of the cellular immunotherapy.

Efalizumab (trade name RAPTIVA®, GENENTECH, MERCK SERONO) is a recombinant humanized monoclonal antibody. Efalizumab binds to the CD11a subunit of lymphocyte function-associated antigen 1. According to the present invention, it can be administered once weekly by subcutaneous injection at a dose of 20 mg/kg, weekly preferably for 3-4 weeks prior to the administration of the cellular immunotherapies.

Erlizumab, also known as rhuMAb, is a recombinant humanized monoclonal antibody developed by GENENTECH under a partnership with ROCHE. According to the present invention, it can be administered once weekly by subcutaneous injection at a dose of 20 mg/kg, weekly preferably for 3-4 weeks prior to the administration of the cellular immunotherapies. The drug works by blocking a growth factor in blood vessels. Specifically, erlizumab targets CD18 and an LFA-1 integrin.

Pascolizumab is an anti-IL-4 humanized monoclonal antibody. According to the present invention, it can be administered once weekly by subcutaneous injection at a dose of 20 mg/kg, weekly preferably for 3-4 weeks prior to the administration of the cellular immunotherapies.

Lumiliximab (BIOGEN IDEC) is a monoclonal antibody that targets CD23. According to the present invention, it can be dosed at 50 mg/m2, to 450 mg/m2, to 500 mg/m2 weekly preferably for 3-4 weeks prior to the administration of the cellular immunotherapies. The drug is a chimeric antibody from *Macaca irus* and *Homo sapiens*.

Teneliximab is a chimeric monoclonal antibody binding to the immune stimulatory protein CD40. According to the present invention, it can be administered once weekly by subcutaneous injection at a dose of 20 mg/kg, weekly preferably for 3-4 weeks prior to the administration of the cellular immunotherapies.

Toralizumab (IDEC 131, IDEC Pharmaceuticals Corporation) is a humanized monoclonal antibody to IL-6. According to the present invention, it can be administered once weekly by subcutaneous injection at a dose of 20 mg/kg, weekly preferably for 3-4 weeks prior to the administration of the cellular immunotherapies.

Aselizumab is an anti-CD62L administered by I.V. infusion at doses ranging from 0.5-mg/kg, 1.0-mg/kg, and 2.0-mg/kg weekly preferably for 3-4 weeks prior to the administration of the cellular immunotherapies.

Gavilimomab is a mouse monoclonal antibody (also known as ABX-CBL, developed by ABGENIX. It binds to the antigen CD147. According to the present invention it can be administered by I.V. infusion at a dose of 20 mg/kg weekly preferably for 3-4 weeks prior to the administration of the cellular immunotherapies.

BG9588, a humanized anti-CD40L administered at 20 mg/kg weekly preferably for 3-4 weeks prior to the administration of the cellular immunotherapies. Administration of antibodies to CD154, also called CD40 ligand or CD40L, is a protein that is primarily expressed on activated T cells and is a member of the TNF superfamily of molecules. It binds to CD40 on antigen-presenting cells (APC), which leads to many effects depending on the target cell type. In general, CD40L plays the role of a costimulatory molecule and induces activation in APC in association with T cell receptor stimulation by MHC molecules on the APC. In total CD40L has three binding partners: CD40, 5031 integrin and αIIbβ3.

(Hu5c8) 5c8, a monoclonal antibody that binds CD154 (CD40 ligand), thus blocking the interaction between CD40 and CD154, administered at 20 mg/kg weekly preferably for 3-4 weeks prior to the administration of the cellular immunotherapies.

Belimumab (registered name BENLYSTA® previously known as LymphoStat-B), is a fully human monoclonal antibody that specifically recognizes and inhibits the biological activity of B-Lymphocyte stimulator (BLyS), also known as B cell activation factor of the TNF family (BAFF) HUMAN GENOME SCIENCES. According to the present invention, it can be administered at a dose of 10 mg/kg weekly preferably for 3-4 weeks prior to the administration of the cellular immunotherapies.

Bertilimumab is a human monoclonal antibody that binds to eotaxin-1. (iCo Therapeutics Inc. Vancouver, B.C.) According to the present invention, it is administered at a dose of 10 mg/kg weekly preferably for 3-4 weeks prior to the administration of the cellular immunotherapies.

Natalizumab is a humanized monoclonal antibody against the cellular adhesion molecule α4-integrin. It is co-marketed by Biogen Idec and Elan as TYSABRI®, and was previously named Antegren. Natalizumab is administered at a dose of 300 mg infused intravenously over approximately one hour every 4 weeks preferably for 1 to 6 months prior to the administration of the cellular immunotherapies.

Tocilizumab or atlizumab, developed by Hoffmann-La Roche and Chugai under the trade names ACTEMRA® and ROACTEMRA®, is a humanized monoclonal antibody against the interleukin-6 receptor (IL-6R). According to the present invention, it can be administered by intravenous infusions at 8 mg/kg, weekly preferably for 3-4 weeks prior to the administration of the cellular immunotherapies.

Odulimomab is a mouse monoclonal antibody directed against the alpha chain of the protein lymphocyte function-associated antigen 1 which is involved in immune reactions. It is administered 10 mg/kg active drug weekly preferably for 3-4 weeks prior to the administration of the cellular immunotherapies.

Atorolimumab is mouse monoclonal antibody directed against the Rhesus factor. According to the present invention, it can be administered at a dose of 10 mg/kg weekly preferably for 3-4 weeks prior to the administration of the cellular immunotherapies.

Fontolizumab (trade name HuZAF®, PDL Biopharma) is anti-interferon gamma humanized monoclonal antibody. According to the present invention, it can be administered at an I.V. dose of fontolizumab given as 4.0 mg/kg or 10.0 mg/kg weekly preferably for 3-4 weeks prior to the administration of the cellular immunotherapies.

Gantenerumab is anti-beta amyloid monoclonal antibody (ROCHE). It is administered at a dose of 10 mg/kg of active drug weekly preferably for 3-4 weeks prior to the administration of the cellular immunotherapies.

Gomiliximab is a monoclonal antibody that targets the low affinity IgE receptor (FcεRII or CD23). According to the present invention, it can be administered at a dose of 10 mg/kg weekly preferably for 3-4 weeks prior to the administration of the cellular immunotherapies.

Morolimumab is a human monoclonal antibody against the human Rhesus factor. According to the present invention, it can be administered at a dose of 10 mg/kg weekly preferably for 3-4 weeks prior to the administration of the cellular immunotherapies.

Pexelizumab is a single chain variable fragment of a monoclonal antibody targeted against component 5 of the complement system. According to the present invention, it can be administered at a dose of 10 mg/kg weekly preferably for 3-4 weeks prior to the administration of the cellular immunotherapies.

Reslizumab (CEPTION THERAPEUTICS Inc) is an anti-IL-5 humanized monoclonal antibody. According to the present invention, It can administered as an infusion at a preferred dose of reslizumab 3.0 mg/kg weekly preferably for 3-4 weeks prior to the administration of the cellular immunotherapies.

Rovelizumab, also known as LEUKARREST® and Hu23F2G, is an anti-CD 11/CD18 humanized monoclonal antibody that suppresses white blood cells. According to the present invention, it can be administered at a dose of 10 mg/kg weekly preferably for 3-4 weeks prior to the administration of the cellular immunotherapies.

Talizumab (TNX-901) is a humanized monoclonal antibody being developed by TANOX in Houston, Tex. It was designed to target immunoglobulin E (or IgE) and IgE-expressing B lymphocytes specifically, without binding to IgE already bound by the IgE receptors on mast cells and basophils. According to the present invention, it can be administered at a dose of 10 mg/kg weekly preferably for 3-4 weeks prior to the administration of the cellular immunotherapies.

Omalizumab is an anti-IgE monoclonal antibody, developed by TANOX, NOVARTIS, and GENENTECH. According to the present invention, it can be administered at a dose of 10 mg/kg preferably 3-4 weeks days prior to the administration of the cellular immunotherapies.

Vapaliximab is an anti-VAP-1 chimeric monoclonal antibody. According to the present invention, it can be administered at a dose of 10 mg/kg preferably 3-4 weeks days prior to the administration of the cellular immunotherapies.

Vepalimomab is an anti-VAP1 (vascular adhesion protein 1) mouse monoclonal antibody According to the present invention, it can be administered at a dose of 10 mg/kg preferably 3-4 weeks days prior to the administration of the cellular immunotherapies.

Etanercept (trade name ENBREL®, AMGEN, Thousand Oaks, Calif.) is a drug that treats autoimmune diseases by interfering with the tumor necrosis factor (TNF, a part of the immune system) by acting as a TNF inhibitor. Etanercept can be administered subcutaneously (s.c.) at a dose 25 mg or 50 mg one to three times weekly for preferably 3-4 weeks prior to the administration of the cellular immunotherapies.

Pegsunercept is a pegylated soluble tumor necrosis factor receptor. According to the present invention, it can be administered at a preferable dose of 9 mg/kg s.c., preferably 3-4 weeks prior to the administration of the cellular immunotherapies.

Aflibercept is protein comprised of segments of the extracellular domains of human vascular endothelial growth factor receptors 1 (VEGFR1) and 2 (VEGFR2) fused to the constant region (Fc) of human IgG1 with potential antiangiogenic activity and is being co-developed by SANOFI-AVENTIS and REGENERON Pharmaceuticals. Aflibercept (VEGF Trap), an anti-angiogenic agent, is a fusion protein specifically designed to bind all forms of Vascular Endothelial Growth Factor-A (called VEGF-A). In addition, aflibercept binds Placental Growth Factor (PLGF), which has also been implicated in tumor angiogenesis. Aflibercept can be administered by injection or IV infusion at preferable doses of 2 milligrams per kilogram (mg/kg) or 4 mg/kg, preferably 3-4 weeks prior to the administration of the cellular immunotherapies.

Alefacept (trade name AMEVIVE®, ASTELLAS Pharma US, Inc. Deerfield, Ill. 60015) is a fusion protein: it combines part of an antibody with a protein that blocks the growth of some types of T cells. Alefacept is an immunosuppressive dimeric fusion protein that consists of the extracellular CD2-binding portion of the human leukocyte function antigen-3 (LFA-3) linked to the Fc (hinge, CH2 and CH3 domains) portion of human IgG. The preferred dosage is either 7.5 mg IV or 15 mg IM weekly preferably 3-4 weeks prior to the administration of the cellular immunotherapies.

Rilonacept also known as IL-1 Trap (marketed under the trade name ARCALYST®), is a dimeric fusion protein consisting of the extracellular domain of human interleukin-1 receptor and the FC domain of human IgG1 that binds and neutralizes IL-1h. Treatment should be initiated with a loading dose of 320 mg delivered as two, 2 mL, subcutaneous injections of 160 mg each given on the same day at two different sites, weekly preferably 3-4 weeks prior to the administration of the cellular immunotherapies. Pediatric patients aged 12 to 17 years: Treatment should be initiated with a loading dose of 4.4 mg/kg, up to amaximum of 320 mg, delivered as one or two subcutaneous injections with a maximum single-injection volume of 2 mL, preferably 3-4 days prior to administration of the cellular immunotherapies. Produced by REGENERON.

Dacetuzumab (also known as SGN-40 or huS2C6, SEATTLE GENETICS, Inc.) is an anti-CD40 humanized monoclonal antibody. The CD40 antigen is highly expressed on most B-lineage hematologic malignancies including multiple myeloma, non-Hodgkin lymphoma and chronic lymphocytic leukemia. CD40 is also found on many types of solid tumors, including bladder, renal and ovarian cancer and on cells that play a role in immunologic disorders. It is administered at a preferred dose of 10 mg/kg of active drug weekly preferably 3-4 weeks prior to the administration of the cellular immunotherapies.

HCD122 is a fully human antagonist anti-CD40 monoclonal antibody. CD40 is a cell-surface receptor that plays a pivotal role in immune responses, as well as cell growth and survival signaling, through its activation by CD40 ligand (CD40L). It is commonly overexpressed and activated in B-cell malignancies. According to the present invention, it can be administered at a dose of 10 mg/kg of active drug weekly preferably 3-4 weeks prior to the administration of the cellular immunotherapies. This is being developed by XOMA/NOVARTIS ONCOLOGY.

Adenosine deaminases deficiency will also lead to reduced active germinal center formation and cause lymphodepletion as will agents which trigger the accumulation of deoxyATP (J Immunol 171: 5562-5570, 2003). Similarly, agents which enhance the expression of or activate CCR7 will lead to diminished active germinal center formation and cause lymphodepletion.

Of all of the immune suppressant immunomodulators disclosed, an agent that contains dexamethasone that can be given at a dose between about 3.0 to about 12.0 mg dexamethasone base/kg body weight about 12 to about 72 hours before cellular immunotherapy administration, most preferred given at a dose between about 6.0 to 12.0 mg/kg, is the most preferred method to lymphodeplete and prevent cellular immunotherapies binding to the secondary lymphatics so that they remain in the circulation where they can find and participate in killing cancer, tumor or autoimmune causing cells or infection because of dexamethasone's long biological half-life, short pharmacokinetic half-life and limited to no toxicity.

Definitions

Definitions used to describe the embodiments of the invention:

The antibody-dependent cell-mediated cytotoxicity (ADCC), also referred to as antibody-dependent cellular cytotoxicity, is a mechanism of cell-mediated immune defense whereby an effector cell of the immune system actively lyses a target cell, whose membrane-surface antigens have been bound by specific antibodies. A type of immune reaction in which a target cell or microbe is coated with antibodies and killed by certain types of white blood cells. The white blood cells bind to the antibodies and release substances that kill the target cells or microbes. Also called antibody-dependent cell-mediated cytotoxicity and antibody-dependent cellular cytotoxicity. Antibody-dependent cell-mediated cytotoxicity (ADCC) is the killing of an antibody-coated target cell by a cytotoxic effector cell through a nonphagocytic process, characterised by the release of the content of cytotoxic granules or by the expression of cell death-inducing molecules. ADCC is triggered through interaction of target-bound antibodies (belonging to IgG or IgA or IgE classes) with certain Fc receptors (FcRs), glycoproteins present on the effector cell surface that bind the Fc region of immunoglobulins (Ig). Effector cells that mediate ADCC include natural killer (NK) cells, monocytes, macrophages, neutrophils, eosinophils and dendritic cells. ADCC is a rapid effector mechanism whose efficacy is dependent on a number of parameters (density and stability of the antigen on the surface of the target cell; antibody affinity and FcR-binding affinity). ADCC involving human IgG, the most used IgG subclass for therapeutic antibodies, is highly dependent on the glycosylation profile of its Fc portion and on the polymorphism of Fcγ receptors.

Complement-Mediated Cytotoxicity (CMC): CMC is the mechanism by which antibody-coated target cells recruit and activate components of the complement cascade, leading to the formation of a Membrane Attack Complex (MAC) on the cell surface and subsequent cell lysis.

Biologic mechanism of lymphodepletion means induction of programmed cell death via apoptosis or necroptosis or pyroptosis or autophagy or oncosis. Various stimuli can engage a non-apoptotic form of cell death called necroptosis, which occurs when caspases required for apoptosis are inhibited. Pyroptosis is a caspase-dependent form of programmed cell death that differs in many respects from apoptosis. Unlike apoptosis, it depends on the activation of caspase-1 or caspase-11 (caspase-5 in humans). Autophagy is a lysosome-dependent process.

Apoptosis: A form of cell death in which a programmed sequence of events leads to the elimination of cells without releasing harmful substances into the surrounding area. Apoptosis plays a crucial role in developing and maintaining the health of the body by eliminating old cells, unnecessary cells, and unhealthy cells.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; Band C; A (alone); B (alone); and C (alone).

The term "about' when referring to a measurable value such as an amount or a temporal duration and the like refers to variations of +/−20% or +/−10%.

Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically.

A pharmacologic dose is a dose far in excess of normal levels in the body.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A therapeutic agent is an agent that enhances the efficacy of cellular immunotherapies compared to the cellular immunotherapies without said therapeutic agent.

The term "autologous" refers to any material derived from the same individual to which it is later to be re-introduced, whether the individual is a human or other animal.

The term "allogeneic" refers to any material derived from one individual which is then introduced to another individual of the same species, whether the individual is a human or other animal.

The term dexamethasone (also referred to as Dex) non-exclusively relates to any formulation whether a liquid solution, liquid suspension, oral solution, tablet form, tablet form dissolved in a liquid containing the active ingredient of dexamethasone, injectable form, gel formulation, patch formulation or any formulation containing the active ingredient dexamethasone.

The term glucocorticoid-receptor modulating agents non-exclusively relates to glucocorticoid receptor agonists or glucocorticoid receptor modulators including but not limited to: compound A [CpdA; (2-((4-acetophenyl)-2-chloro-N-methyl)ethylammonium-chloride)] and N-(4-methyl-1-oxo-1H-2,3-benzoxazine-6-yl)-4-(2,3-dihydrobenzofuran-7-yl)-2-hydroxy-2-(trifluoromethyl)-4-methylpentanamide (ZK216348), AL-438, Mapracorat, LGD-5552, RU-24858, Fosdagrocorat, PF-802, Compound 10, MK5932, C108297, LGD5552, and ORG 214007-0.

Immunotoxins are proteins that contain a toxin along with an antibody or growth factor that binds specifically to target cells. Immunotoxins are created by chemically conjugating an antibody to a whole protein toxin, devoid of its natural binding domain. Immunologic proteins that are smaller than monoclonal antibodies (MoAbs), like growth factors and cytokines, have also been chemically conjugated and genetically fused to protein toxins. Toxins used in immunotoxin constructs are derived from bacteria, fungi, and plants, and most function by inhibiting protein synthesis. Bacterial toxins commonly used in immunotoxins include Diphtheria toxin (DT) and the toxin from *Pseudomonas* exotoxin (PE). Plant toxins utilized in immunotoxins include the A chain of ricin (RTA), and the ribosome inactivating proteins (RIPs) gelonin, pokeweed antiviral protein, and dodecandron. Because it is an enzyme, one toxin molecule can work on many substrate molecules, having a devastating effect on the cell. Toxins such as diphtheria toxin (DT) and *Pseudomonas* exotoxin (PE) prevent protein synthesis by an effect on elongation factor 2 (EF-2).

The term systemic injection as used herein non-exclusively relates to a route of administration that rapidly, within seconds or a few hours, leads to circulating levels of cellular immunotherapies, and non-exclusively relates to intravenous, intraperitoneally, subcutaneous, via nasal submucosa, lingual, via bronchoscopy, intravenous, intra-arterial, intramuscular, intro-ocular, intra-striatal, subcutaneous, intradermal, by dermal patch, by skin patch, by patch, into the cerebrospinal fluid, into the portal vein, into the brain, into the lymphatic system, intra-pleural, retro-orbital, intra-dermal, into the spleen, intra-lymphatic, among others.

The term 'site of injection' as used herein non-exclusively relates to intra-tumor, or intra-organ such as the kidney or liver or pancreas or heart or lung or brain or spleen or eye, intra-muscular, intro-ocular, intra-striatal, intradermal, by dermal patch, by skin patch, by patch, into the cerebrospinal fluid, into the brain, among others.

The term 'chimeric antigen receptor(s)' (CAR) as used herein non-exclusively relates to constructs that contain an antigen-binding domain of an antibody fused to a strong T-cell activator domain. T-cells modified with the CAR construct can bind to the antigen and be stimulated to attack the bound cells. Artificial T cell receptors (also known as chimeric T cell receptors, chimeric immunoreceptors, chimeric antigen receptors (CARs)) are engineered receptors, which graft an arbitrary specificity onto an immune effector cell. The receptors are called chimeric because they are composed of parts from different sources.

The term lymphodepletion as used herein non-exclusively relates to the reduction of lymphocyte number in the peripheral blood without causing redistribution of lymphocytes to another organ such as the bone marrow, thymus, lymph nodes, lung or spleen or another organ.

The term cytotoxic lymphodepletion as used herein relates to the reduction of lymphocyte number in the peripheral blood by a mechanism of ADCC, CMC or direct lysis or cytotoxic elimination of lymphocyte.

The term 'cellular immunotherapy', 'adoptive cellular immunotherapy', 'adoptive cellular therapy' (ACT) or cell immunotherapy or cell therapy as used herein non-exclusively relates to treatments that contain a cell used to help the immune system fight diseases or a cell from the immune lineage which directly fights diseases such as cancer, autoimmune diseases and infections with certain viruses. The cellular immunotherapy can be from either an autologous or allogeneic source. In preferred embodiments, the adoptive immunotherapy used in the methods disclosed herein may be an adoptive T cell immunotherapy, i.e. 'T cell therapy'.

The term preconditioning as used herein relates to the preparation of a patient with a cytotoxic lymphodepleting agent or a NTLA prior to ACT.

The term immunotherapy, also called biologic therapy, as used herein non-exclusively relates to a type of treatment for cancer, autoimmune disease or infection treatment designed to boost the body's natural defenses to fight the cancer, autoimmune disease or infection. It uses substances either made by the body or in a laboratory to improve or restore immune system function. The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The term 'immune modulation' as used herein non-exclusively relates to, in cancer, autoimmune disease or infection, a range of treatments aimed at harnessing a patient's immune system to achieve tumour, autoimmune causing cell or viral control, stabilization, and potential eradication of disease.

The term immunomodulator as used herein non-exclusively relates to a chemical agent (such as dexamethasone) or biologic agent (such as HUMIRA® and rituximab) that modifies the immune response or the functioning of the immune system (as by the stimulation of antibody formation or the inhibition of white blood cell activity). Traditional immune modulating drugs that are immunesuppressants non-exclusively relates to glucocorticoids, calcineurin inhibitors, antimetabolites, and alkylating agents. Antimetabolites non-exclusively relates topurine analogues (e.g., azathioprine and mycophenolate mofetil), and folate antagonists (e.g., methotrexate and dapsone).

Immunesuppressants (also termed immunosuppressants) can be chemical or biologic agents that can suppress or prevent the immune response. For instance, antagonists to CD26 and dexamnethasone are immunesuppressants. The NTLAs used in this invention may be NTLA immunesuppressants.

The term 'T cell therapy' as used herein non-exclusively relates to immune cells or antibodies that can be produced in the laboratory under tightly controlled conditions and then given to patients to treat diseases such as cancer, autoimmunity or infection. T cell therapy is a type of immunotherapy, and it involves taking a patient's own immune cells—specifically, white blood cells called T-cells—and reprogramming them to attack tumours.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FI COLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising a costimulatory domain and an activating domain. The costimulatory domain can be derived from, e.g., CD28, and the activating domain can be derived from, e.g., CD3-zeta. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. Example CAR+ T cell therapies and constructs are described in U.S. Patent Publication Nos. 2013/0287748, 2014/0227237, 2014/0099309, and 2014/0050708, and these references are incorporated by reference in their entirety.

The terms "conditioning" and "pre-conditioning" are used interchangeably herein and indicate preparing a patient or animal in need of a T cell therapy for a suitable condition. Conditioning as used herein includes, but is not limited to, reducing the number of germinal centers and marginal zones, reducing the number of endogenous lymphocytes, removing a cytokine sink, increasing a serum level of one or more homeostatic cytokines or pro-inflammatory factors, enhancing an effector function of T cells administered after the conditioning, enhancing antigen presenting cell activation and/or availability, or any combination thereof prior to a T cell therapy.

The term 'adoptive immunotherapy' or 'cellular adoptive immunotherapy' as used herein non-exclusively relates to immune cells that are collected from a patient (autologous or autogenic) or a donor (allogeneic), either related or unrelated, and grown in the laboratory. This increases the number of immune cells that are able to kill cancer cells, autoimmune causing cells or fight infections. These immune cells are given back to the patient to help the immune system fight disease. This is also called cellular adoptive immunotherapy. The immune cell can be a T cell and/or other cell of the immune system non-exclusively relating to macrophages, monocytes, dendritic cells, neutrophils, granulocytes, phagocytes, mast cells, basophils, thymocytes, or innate lymphoid cells, or any combination thereof.

The term agonist as used herein non-exclusively relates to any entity that activates a specific receptor or downstream signaling pathway essential to mediate the receptor's effect(s). Agonists may non-exclusively relates tobut are not limited to antibodies, antibody fragments, soluble ligands, small molecules, cyclic peptides, cross-linking agents.

The term antagonist as used herein non-exclusively relates to any entity that interferes with the binding of a receptor's counter structure(s), or with the activation of a specific receptor or downstream signaling pathway essential to mediate the receptor's effect(s). Antagonists may non-exclusively relates tobut are not limited to antibodies, antibody fragments, soluble ligands, Fc fusion receptors, chimeric receptors, small molecules, cyclic peptides, peptides.

The term inhibitor as used herein non-exclusively relates to any entity that diminishes the target effect of a specific receptor. Inhibitors may be small molecules, antisense agents, nucleic acids including siRNA and microRNA.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CDS+ T-cells or killer T cell), Memory T-cells ((i) stem memory T scM cells, like naive cells, are CD45RO−, CCR 7+, CD45RA+, CD62L+(L-selectin), CD27+, CD28+ and IL-7Ra+, but they also express large amounts of CD95, IL-2R~, CXCR3, and LFA-1, and show numerous functional attributes distinctive of memory cells); (ii) central memory TcM cells express L-selectin and the CCR7, they secrete IL-2, but not IFNy or IL-4, and (iii) effector memory T EM cells, however, do not express L-selectin or CCR 7 but produce effector cytokines like IFNy and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen presenting cells (APCs) and turns into memory B-cells after activation by antigen interaction. In mammals, immatureB-cells are formed in the bone marrow, where its name is derived from.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" is assessed by measurement of malignant lesions on radiographs or other methods should not be reported as adverse events. Death due to disease progression in the absence of signs and symptoms should be reported as the primary tumor type (e.g., DLBCL).

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

Doses described herein can be presented as a "weight based dose" or as a "body surface area (BSA) based dose." A weight based dose is a dose that is administered to a patient that is calculated based on the weight of the patient, e.g., mg/kg. A BSA based dose is a dose that is administered to a patient that is calculated based on the surface area of the patient, e.g., mg/m2. The two forms of dose measurement can be converted for human dosing by multiplying the weight based dose by 37 or dividing the BSA based dose by 37.

The terms "subject" and "patient" are used interchangeably herein, and refer to a human or animal.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20% (i.e., ±20%). For example, about 3 mg can include any number between 2.3 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Ranges: Various aspects of the invention are presented in range format. The description in range format is for convenience and brevity and should not be construed as an inflexible limitation on the scope of the invention. Accordingly, the description of a range should be considered to have specifically disclosed all the possible subranges as well as individual numerical values within that range. For example, a range from 3 to 12 includes 3.1, 3.2, 3.3 etc.

The spleen contains both a white pulp and a red pulp. The red pulp of the spleen holds macrophages that normally filter and remove senescent or defective red blood cells (RBCs) and antibody-coated bacteria or red blood cells from the circulation. The white pulp of the spleen contains the lymphoid compartments and is crucial for immune surveillance and response: it synthesizes antibodies against invading pathogens and releases platelets and neutrophils in response to bleeding or infection. During development the spleen is believed to have multiple roles including being the first site of hematopoiesis (at six weeks of gestation). Preclinical and clinical trials have demonstrated that without cytotoxic chemotherapy preconditioning, cellular immunotherapies are cleared from the circulation, largely within one hour after administration, and accumulate in the spleen. The cytotoxic chemotherapy preconditioning must be immediate to administration of the cellular immunotherapies in order to maintain the cellular immunotherapies in the circulation, typically 48 hours before administration of the cellular immunotherapies. When cytotoxic chemotherapy preconditioning is given 4 weeks before or at a pretreatment time which allows bone marrow recovery, it is not effective to keep the cellular immunotherapies in the circulation Ritchie D S et al. *Mol Ther. November;* 21(11):2122-9 (2013).

The periarterial lymphoid sheaths (PALS) of the white pulp of the spleen are populated mainly by T cells, while the lymphoid portions are populated mainly by B cells. Germinal centers (GC) are sites within lymph nodes or lymph nodules in peripheral lymph tissues, and in the white pulp of the spleen where intense mature B lymphocytes, otherwise known as Centrocytes rapidly proliferate, differentiate, mutate through somatic hypermutation and class switch during antibody responses. Germinal centers are an important part of the B-cell humoral immune response. They develop dynamically after the activation of B-cells by T-dependent antigen. Histologically, the GCs describe microscopically distinguishable parts in lymphoid tissues. Activated B-cells migrate from the primary focus into the primary follicles follicular system and begin monoclonal expansion in the environment of follicular dendritic cells (FDC).

After several days of expansion the B cells mutate their antibody-encoding DNA and thus generate a diversity of clones in the germinal center. This involves random substitutions, deletions and insertions due to somatic hypermutation. Upon some unidentified stimulus from the FDC, the maturing B cells (Centroblasts) migrate from the dark zone to the light zone and start to expose their antibody to their surface and in this stage are referred to as Centrocytes. The Centrocytes are in a state of activated apoptosis and compete for survival signals from FDCs that present the antigen. This rescue process is believed to be dependent on the affinity of the antibody to the antigen. The functional B-cells have then to interact with helper T cells to get final differentiation signals. This also involves isotype switching for example from IgM to IgG. The interaction with T cells is believed to prevent the generation of autoreactive antibodies. The B cells become either a plasma cell spreading antibodies or a memory B cell that will be activated in subsequent contacts with the same antigen. They may also restart the whole process of proliferation, mutation and selection according to the recycling hypothesis.

The B cells contained within the white pulp region of the spleen can be further divided into specific areas, identified by staining with specific molecular markers. The marginal zone of the spleen contains noncirculating mature B cells that border on the white pulp creating a separation between the white and the red pulp and express high levels of CD21 and IgM and CD24 and CD79a, and measurable levels of CD9 and CD22. The mantle zone surrounds normal germinal center follicles and expresses CD21, CD23 and CD38. The follicular zone is contained within the germinal centers and expresses high levels of IgD and CD23, intermediate levels of CD21 and CD24, and can also be identified by PNA staining. The germinal center is best distinguished by PNA binding and expresses higher levels of CD54 than the follicular zone. Germinal centers have a special population of helper T cells that seem to distribute evenly in all germinal centers. Germinal centers are traditionally associated with immune responses that require T helper cells, although this is not absolute. Germinal centers are where hypervariable gene mutation occurs and high affinity IgG producing B cells are generated. Active germinal centers have tangible macrophages and CD21 expressing dendritic cells. Follicular centers can also be identified by the expression of CD45R (B220) (Cytotoxicologic Pathology, 35:366-375, 2007). CD45R follicular centers are found surrounding germinal centers expressing Bcl6 and Bcl2. BioEssays 29:166-177, 2007; Cytotoxicol Pathol 34(5): 648-655, (2006)]

Cells of the Immune System

The response to pathogens or cancer cells is orchestrated by the complex interactions and activities of the large number of diverse cell types involved in the immune response. The innate immune response is the first line of defense and occurs soon after pathogen exposure. It is carried out by phagocytic cells such as neutrophils and macrophages, cytocytotoxic natural killer (NK) cells, and granulocytes. The subsequent adaptive immune response elicits antigen-specific defense mechanisms and may take days to develop. Cell types with critical roles in adaptive immunity are antigen-presenting cells including macrophages and dendritic cells. Antigen-dependent stimulation of various cell types including T cell subsets, B cells, and macrophages all play critical roles in host defense. Immune cells non-exclusively relates to: B Cells, Dendritic Cells, Granulocytes, Innate Lymphoid Cells (ILCs), Megakaryocytes, Monocytes/Macrophages, Myeloid-derived Suppressor Cells (MDSC), Natural Killer (NK) Cells, Platelets, Red Blood Cells (RBCs), T Cells, Thymocytes.

Cell Types for Cellular Immunotherapy

In certain embodiments of the invention the cellular immunotherapy can be either autologous or allogeneic, endogenous or exogenous. The cell types used for cellular immunotherapy may non-exclusively, as single or combination cell therapies, be any of the following cell types: macrophages, phagocytes, toleragenic dendritic cells, tumor infiltrating lymphocytes, adoptive cell transfer, adoptive cell therapy, adoptive T cell therapy, chimeric antigen receptor cells, genetically engineered TCR cells, genetically engineered TCR-modified T cells, CAR T cells, regulatory T cell transfer, cellular adoptive immunotherapy, cellular immunotherapy, cellular immune-oncology, in vivo complex (IL-2C) consisting of IL-2 and anti-IL-2 monoclonal antibody (JES6-1) expanded Tregs, T-Cell receptor (TCR) immunogenicity for T-cell vaccinations, autological polyclonal T-cell vaccines (TCVs), adoptive transfer of Treg-of-B cells (B cells induced a particular subset of regulatory T), adoptive transfer of GC-induced or ATF3-deficient G-MDSCs (myeloid derived suppressor cells), genetically engineered lymphocytes, RNA redirected autologous T cells, T-cell Natural Killer cells, Receptor NKG2D cells, CD4+ cells, CD8+ cells, CD4+ T cells, CD8+ T cells, mixtures of CD4+ and CD8 T cells, MDSCs, CTLs, EBV-CTLs, virus specific cytocytotoxic T lymphocytes (CTLs), cytokine-induced killer cells, antigen pulsed dendritic cells, CMV-CTLs, natural dendritic cells, dendritic cells, third party donor derived CTL's, autologous γδ T lymphocyte therapy, CD45RA Depleted T-cell Infusion, Laboratory-treated T Cells, HER2Bi-armed activated T cells, autologous tumor DC vaccine, Dendritic Cell (DC)-Based Vaccines Loaded with Allogeneic Prostate Cell Lines, Dendritic Cell/AML Vaccine, Dendritic Cell vaccines, gene-modified lymphocytes, dendritic cell therapy, ESO-1 Lymphocytes, Tumor-Pulsed Dendritic Cells, Autologous Tumor Lysate-pulsed Dendritic Cell, gene-modified immune cells, Marrow Infiltrating Lymphocytes, Alpha-galactosylceramide-pulsed Dendritic Cells, Alpha-galactosylceramide-pulsed Natural Killer T (NKT) Cells, Alpha-galactosylceramide-pulsed Dendritic Cells and Natural Killer T (NKT) Cells, Autologous gamma/Delta T Cells, Activated Self-lymphocytes, Epstein-Barr Virus Immune T-Lymphocytes Derived From a Normal HLA-Compatible Or Partially-Matched Third-Party Donor, granulocyte macrophage colony-stimulating factor plus bi-shRNAi furin vector transfected autologous tumor cells, Alpha-galactosylceramide Pulsed Dendritic Cells (Chiba-NKT), P53-Pulsed Dendritic Cells, Primary Transplant Donor Derived CMVpp65 Specific T-cells, mixed T- and natural killer (NK) cell-like phenotype (CIK Cells), Antigen Pulsed Dendritic Cells (APDC), DC-CIK, Alpha-galcer Pulsed APC, Zoledronate-Activated Autologous Killer Lymphocytes (Zak Cells), Chiba NKT cells, Autologous Dendritic Cells Loaded with Autologous Tumor Lysate or Homogenate, Third Party Donor Derived CMVpp65 Specific T-cells, Autologous Tumor Lysate-pulsed D-CIK, Multi-epitope TARP Peptide Autologous Dendritic Cells, T-reg Adoptive Cell Transfer (TRACT), Modified DLI (Donor Double Negative T Cells), Type-1 Polarized Dendritic Cells (AlphaDC1), Autologous Tumor Tissue Antigen-sensitized DC-CIK Cells, Peptide Pulsed Dendritic Cells, Dendritic Cytocytotoxic Lymphocyte(DC-CTL) Cells, MTCR-transduced Autologous Peripheral Blood Lymphocytes, Cytokine Induced Memory-like NK Cells, LMP-specific T-cells, Modified DLI (Related-donor Double Negative T Cells), Autologous Dendritic Cells Loaded with Autologous Tumour Homogenate, Vigil® Engineered Autologous Tumor Cell (EATC) therapy, New Antigen Reactive Immune Cell Therapy (NRT), Autologous Cytokine-induced Killer Cells, Fused Autologous Dendritic Cells, Peptide Specific CTL, Allogeneic Cell Immunotherapy ACIT-1, PD-1 Knockout Engineered T Cells, DC/AML Fusion Cells, (DC/PC3), Laboratory-treated T Cells, Dendritic Cell Tumor Fusions, Lethally Irradiated, Autologous Breast Cancer Cells, CD4-ZETA Gene Modified T Cells, EBV-specific Immune Effector Cell (EBV-IE), Herpes Virus (HHV) Specific Immune Effector (IE) Cell, mRNA-transfected Dendritic Cells, Allogeneic Dendritic Cell Therapy, Cytomegalovirus (CMV) Pp65-specific Lyphocytes, Alpha-Galactosylceramide-Pulsed IL-2/GM-CSF-Cultured Peripheral Blood Mononuclear Cells, Depleted T Cells, Donor Cells Dendritic Vaccination, DCs Vaccine Combined with Cytokine-induced Killer Cells, DC Vaccine Combined with CIK Cells, HB-vac Activated-DCs, Haploidentical NK-cell Infusion, ZNK cell, WT1 and MUC1 Peptide-Pulsed Dendritic Cells, ONETreg1 cells, Alpha DC1, Autologous T Lymphocytes with ADCC, Memory T-cell Infusion, HER-2/Neu Pulsed DC1, Stimulated Autologous CD4+ T Cells, Gamma delta T cell, irradiated allogeneic lung adenocarcinoma cells, CD40LGVAX, irradiated allogeneic lung adenocarcinoma cells combined with a bystander cell line transfected with hCD40L and hGM-CSF, EGFRBi-armed Autologous T Cells, MiHA-loaded PD-L-silenced DC, MyDC/pDC, ROR-1.taNK, PDL1.taNK, Adjuvant Dendritic Cell-immunotherapy, D-CIK, DOT-Cells, Autologous Tumor Lysate (TL) plus Yeast Cell Wall Particles (YCWP) plus Dendritic Cells, Autologous EBV-specific Cytocytotoxic T Cells, Autologous TLPLDC vaccine (tumor lysate, particle loaded, dendritic cells), Regulatory T Cells, Personalized Cellular Vaccine (PERCELLVAC), CAR-pNK Cell, HER2.taNK, MUC16.taNK, DC1s-CTLs, (PERCELLVAC2), (PERCELLVAC3), MASCT, CAR-pNK Cells, CD33.taNK, Post Cord Blood HCT Dendritic Cells, Umbilical Cord Blood Regulatory T Cells, High-activity Natural Killer cells, PD-1 Knockout EBV-CTLs, DC-CTL Combined with CIK, Antigen-Bearing Dendritic Cells, Dendritic Cell/Tumor Fusions, Transfected Dendritic Cell, Her2 and TGFBeta CTLs, Blood T-cells and EBV Specific CTLs, Autologous Breast Cancer Cells Engineered to Secrete Granulocyte-macrophage Colony-Stimulating Factor (GM-CSF), Gene-modified White Blood Cells, Epitope-enhanced TARP Peptide and TARP Peptide-pulsed Dendritic Cells, Laboratory-treated Autologous Lymphocytes, Multi-virus CTLs, Cytomegalovirus-specific T-cell Adoptive Transfer (ERaDICATe), GM-K562 Cells, Kappa-CD28 T Lymphocytes, TGFB2-Antisense-GMCSF Gene Modified Autologous Tumor Cell, Bi-shRNA-furin and Granulocyte Macrophage Colony Stimulating Factor (GMCSF) Augmented Autologous Tumor Cells, Donor T Cells Sensitized with Pentadecapeptides of the CMV-PP65 Protein, Peptide-pulsed Monocyte-derived Dendritic Cell Vaccination to Expand Adoptively Transferred CMV-specific Cytocytotoxic T Lymphocytes, CMV Specific DLIs From 3-6/6 HLA Matched Family Member, CMV Specific DLIs, Autologous T-cells Combined With Autologous OC-DC, TAA-Specific CTLs, Autologous Lymphocytes, Autologous Tolerogenic Dendritic Cells, Langerhans-type Dendritic Cells, Langerhans-type Dendritic Cells Electroporated with mRNA Encoding a Tumor-associated Antigen, Autologous T Cells, Multi-virus Cytocytotoxic T-cells, Autologous IL2 and CD40 Ligand-Expressing Tumor Cells, Multiple Antigen-Engineered DC. WT1 And/Or Tumor Lysates-pulsed Dendritic Cells, Autologous Human Cytomegalovirus (HCMV)-specific T cell Therapy, Ad/HER2/Neu Dendritic Cell, WT1 Peptide (Peptivator)-pulsed Dendritic Cell, Donor Derived, Multi-virus-specific, Cytocytotoxic T-Lymphocytes, Ex-vivo Expanded Donor Regulatory T Cells, Alpha-Gal-Cer-Pulsed Antigen Presenting Cells (APCs), Cytokine-induced Memory-like NK Cells, "Re-stimulated" Tumor-infiltrating Lymphocytes, Autologous Langerhans-type Dendritic Cells, Memory Enriched T Cells, Expanded Multi-antigen Specifically Oriented Lymphocytes, TAA-Specific CTLs, Regulatory Dendritic Cells, Closely Matched Third Party Rapidly Generated LMP, BARF1 and EBNA1 Specific CTL, Activated Marrow Infiltrating Lymphocytes, Autologous Tumor Lysate-loaded Dendritic Cells, Multi-Epitope TARP Peptide Autologous Dendritic Cells, HPV-16/18 E6/E7-specific T Lymphocytes, Autologous Epstein-barr Virus-specific T Cells, Activated T-cells, Donor Multitaa-specific T Cells, Multitaa-specific T Cells, Type I-Polarized Autologous Dendritic Cells, Vaccine Enriched Autologous Activated T-cells, Multivirus-specific Cytocytotoxic T Lymphocytes (mCTL), Allogeneic Virus-specific T Cell Lines (VSTs), Donor Regulatory T Cells, TCR-modified T cells (TCRs), MIC Cell, Adoptive T Cell Therapy with Activated P53 Specific T Cells, MUC1-DC-CTL, T cell receptor-modified T cells, "Negative" Dendritic Cell-based Vaccine, tolDC, CD22 Redirected Autologous T Cells, Dendristim, Primary NK Cells, Lentiviral-based CART-EGFRvIII Gene-modified Cellular Therapy Products, Autologous Dendritic Cells Pulsed with Lysated Allegenic Tumor Lines, Expanded Multi-antigen Specific Lymphocytes, PD-1 Knockout Engineered T Cells, GSC-loaded Dendritic Cells, Treg Adoptive Cell Transfer (TRACT), E7 TCR T Cells, PD-1 Knockout Engineered T Cells, CAR-Treg (ENTX-DN), Chimeric Switch Receptor Modified T Cells, Neoantigen-primed Dendritic Cells (DC), Pre-activated T (PreT) Cells, TSA-CTL (Tumor Specific Antigen-induced Cytocytotoxic T Lymphocytes), Allogeneic Cell Immunotherapy (ACIT-1), Autologous OC-DC, Mature Dendritic Cells, CD8+NKG2D+ AKT Cell, Natural Killer (NK) cells—oNKord®, antigen presenting cells—sDCord®, Allogenic GM-CSF Transfected Pancreatic Tumor Vaccine.

The cellular immunotherapy can be genetically modified. The cellular immunotherapy can be CRISPR/Cas9, TALEN, piggy-bac transposon, transposase, Sleeping Beauty, serine recombinase, CRE-lox recombinase, RheoSwitch®, recombinase, lipofection, nucleofection, Zinc finger nuclease, chemically, plasmid, biologically, ARCUS, homing endonuclease or virally modified. The cellular immunotherapy cells can be engineered with a plasmid carrying the gene vector for shRNA Furin and GMCSF (VIGIL®).

In certain embodiments of the invention one would want to exclude and avoid using certain cell types for cellular immunotherapy including:

Macrophages, phagocytic cells, toleragenic dendritic cells, tumor infiltrating lymphocytes, adoptive cell transfer, adoptive cell therapy, chimeric antigen receptor cells, genetically engineered TCR cells, regulatory T cell transfer, cellular adoptive immunotherapy, cellular immunotherapy, cellular immune-oncology, in vivo complex (IL-2C) consisting of IL-2 and anti-IL-2 monoclonal antibody (JES6-1) expanded Tregs, T-Cell receptor (TCR) immunogenicity for T-cell vaccinations, autological polyclonal T-cell vaccines (TCVs), adoptive transfer of Treg-of-B cells (B cells induced a particular subset of regulatory T), adoptive transfer of GC-induced or ATF3-deficient G-MDSCs (myeloid derived suppressor cells), genetically engineered lymphocytes, RNA redirected autologous T cells, T-cell Natural Killer cells, Receptor NKG2D cells, CD4+ cells, CD8+ cells, CD4+ T cells, CD8+ T cells, mixtures of CD4+ and CD8 T cells, MDSCs, CTLs, EBV-CTLs, virus specific cytocytotoxic T lymphocytes (CTLs), cytokine-induced killer cells, antigen pulsed dendritic cells, CMV-CTLs, natural dendritic cells, dendritic cells, third party donor derived CTL's, autologous γδ T lymphocyte therapy, CD45RA Depleted T-cell Infusion, Laboratory-treated T Cells, HER2Bi-armed activated T cells, autologous tumor DC vaccine, Dendritic Cell (DC)-Based Vaccines Loaded with Allogeneic Prostate Cell Lines, Dendritic Cell/AML Vaccine, Dendritic Cell vaccines, gene-modified lymphocytes, dendritic cell therapy, ESO-1 Lymphocytes, Tumor-Pulsed Dendritic Cells, Autologous Tumor Lysate-pulsed Dendritic Cell, gene-modified immune cells, Marrow Infiltrating Lymphocytes, Alpha-galactosylceramide-pulsed Dendritic Cells, Alpha-galactosylceramide-pulsed Natural Killer T (NKT) Cells, Alpha-galactosylceramide-pulsed Dendritic Cells and Natural Killer T (NKT) Cells, Autologous gamma/Delta T Cells, Activated Self-lymphocytes, Epstein-Barr Virus Immune T-Lymphocytes Derived From a Normal HLA-Compatible Or Partially-Matched Third-Party Donor, granulocyte macrophage colony-stimulating factor plus bi-shRNAi furin vector transfected autologous tumor cells, Alpha-galactosylceramide Pulsed Dendritic Cells (Chiba-NKT), P53-Pulsed Dendritic Cells, Primary Transplant Donor Derived CMVpp65 Specific T-cells, mixed T- and natural killer (NK) cell-like phenotype (CIK Cells), Antigen Pulsed Dendritic Cells (APDC), DC-CIK, Alpha-galcer Pulsed APC, Zoledronate-Activated Autologous Killer Lymphocytes (Zak Cells), Chiba NKT cells, Autologous Dendritic Cells Loaded with Autologous Tumor Lysate or Homogenate, Third Party Donor Derived CMVpp65 Specific T-cells, Autologous Tumor Lysate-pulsed D-CIK, Multi-epitope TARP Peptide Autologous Dendritic Cells, T-reg Adoptive Cell Transfer (TRACT), Modified DLI (Donor Double Negative T Cells), Type-1 Polarized Dendritic Cells (AlphaDC1), Autologous Tumor Tissue Antigen-sensitized DC-CIK Cells, Peptide Pulsed Dendritic Cells, Dendritic Cytocytotoxic Lymphocyte(DC-CTL) Cells, MTCR-transduced Autologous Peripheral Blood Lymphocytes, Cytokine Induced Memory-like NK Cells, LMP-specific T-cells, Modified DLI (Related-donor Double Negative T Cells), Autologous Dendritic Cells Loaded with Autologous Tumour Homogenate, VIGIL® Engineered Autologous Tumor Cell (EATC) therapy, New Antigen Reactive Immune Cell Therapy (NRT), Autologous Cytokine-induced Killer Cells, Fused Autologous Dendritic Cells, Peptide Specific CTL, Allogeneic Cell Immunotherapy ACIT-1, PD-1 Knockout Engineered T Cells, DC/AML Fusion Cells, (DC/PC3), Laboratory-treated T Cells, Dendritic Cell Tumor Fusions, Lethally Irradiated, Autologous Breast Cancer Cells, CD4-ZETA Gene Modified T Cells, EBV-specific Immune Effector Cell (EBV-IE), Herpes Virus (HHV) Specific Immune Effector (IE) Cell, mRNA-transfected Dendritic Cells, Allogeneic Dendritic Cell Therapy, Cytomegalovirus (CMV) Pp65-specific Lyphocytes, Alpha-Galactosylceramide-Pulsed IL-2/GM-CSF-Cultured Peripheral Blood Mononuclear Cells, Depleted T Cells, Donor Cells Dendritic Vaccination, DCs Vaccine Combined with Cytokine-induced Killer Cells, DC Vaccine Combined with CIK Cells, HB-vac Activated-DCs, Haploidentical NK-cell Infusion, ZNK cell, WT1 and MUC1 Peptide-Pulsed Dendritic Cells, ONETreg1 cells, Alpha DC1, Autologous T Lymphocytes with ADCC, Memory T-cell Infusion, HER-2/Neu Pulsed DC1, Stimulated Autologous CD4+ T Cells, Gamma delta T cell, irradiated allogeneic lung adenocarcinoma cells, CD40LGVAX, irradiated allogeneic lung adenocarcinoma cells combined with a bystander cell line transfected with hCD40L and hGM-CSF, EGFRBi-armed Autologous T Cells, MiHA-loaded PD-L-silenced DC, MyDC/pDC, ROR-1.taNK, PDL1.taNK, Adjuvant Dendritic Cell-immunotherapy, D-CIK, DOT-Cells, Autologous Tumor Lysate (TL) plus Yeast Cell Wall Particles (YCWP) plus Dendritic Cells, Autologous EBV-specific Cytocytotoxic T Cells, Autologous TLPLDC vaccine (tumor lysate, particle loaded, dendritic cells), Regulatory T Cells, Personalized Cellular Vaccine (PERCELLVAC), CAR-pNK Cell, HER2.taNK, MUC16.taNK, DC1s-CTLs, (PERCELL-VAC2), (PERCELLVAC3), MASCT, CAR-pNK Cells, CD33.taNK, Post Cord Blood HCT Dendritic Cells, Umbilical Cord Blood Regulatory T Cells, High-activity Natural Killer cells, PD-1 Knockout EBV-CTLs, DC-CTL Combined with CIK, Antigen-Bearing Dendritic Cells, Dendritic Cell/Tumor Fusions, Transfected Dendritic Cell, Her2 and TGFBeta CTLs, Blood T-cells and EBV Specific CTLs, Autologous Breast Cancer Cells Engineered to Secrete Granulocyte-macrophage Colony-Stimulating Factor (GM-CSF), Gene-modified White Blood Cells, Epitope-enhanced TARP Peptide and TARP Peptide-pulsed Dendritic Cells, Laboratory-treated Autologous Lymphocytes, Multi-virus CTLs, Cytomegalovirus-specific T-cell Adoptive Transfer (ERaDICATe), GM-K562 Cells, Kappa-CD28 T Lymphocytes, TGFB2-Antisense-GMCSF Gene Modified Autologous Tumor Cell, Bi-shRNA-furin and Granulocyte Macrophage Colony Stimulating Factor (GMCSF) Augmented Autologous Tumor Cells, Donor T Cells Sensitized with Pentadecapeptides of the CMV-PP65 Protein, Peptide-pulsed Monocyte-derived Dendritic Cell Vaccination to Expand Adoptively Transferred CMV-specific Cytocytotoxic T Lymphocytes, CMV Specific DLIs From 3-6/6 HLA Matched Family Member, CMV Specific DLIs, Autologous T-cells Combined With Autologous OC-DC, TAA-Specific CTLs, Autologous Lymphocytes, Autologous Tolerogenic Dendritic Cells, Langerhans-type Dendritic Cells, Langerhans-type Dendritic Cells Electroporated with mRNA Encoding a Tumor-associated Antigen, Autologous T Cells, Multi-virus Cytocytotoxic T-cells, Autologous IL2 and CD40 Ligand-Expressing Tumor Cells, Multiple Antigen-Engineered DC. WT1 And/Or Tumor Lysates-pulsed Dendritic Cells, Autologous Human Cytomegalovirus (HCMV)-specific T cell Therapy, Ad/HER2/Neu Dendritic Cell, WT1 Peptide (Peptivator)-pulsed Dendritic Cell, Donor Derived, Multi-virus-specific, Cytocytotoxic T-Lymphocytes, Ex-vivo Expanded Donor Regulatory T Cells, Alpha-Gal-Cer-Pulsed Antigen Presenting Cells (APCs), Cytokine-induced Memory-like NK Cells, "Re-stimulated" Tumor-infiltrating Lymphocytes, Autologous Langerhans-type Dendritic Cells, Memory Enriched T Cells, Expanded Multi-antigen Specifically Oriented Lymphocytes, TAA-Specific CTLs, Regulatory Dendritic Cells, Closely Matched Third Party Rapidly Generated LMP, BARF1 and EBNA1 Specific CTL, Activated Marrow Infiltrating Lymphocytes, Autologous Tumor Lysate-loaded Dendritic Cells, Multi-Epitope TARP Peptide Autologous Dendritic Cells, HPV-16/18 E6/E7-specific T Lymphocytes, Autologous Epstein-barr Virus-specific T Cells, Activated T-cells, Donor Multitaa-specific T Cells, Multitaa-specific T Cells, Type I-Polarized Autologous Dendritic Cells, Vaccine Enriched Autologous Activated T-cells, Multivirus-specific Cytocytotoxic T Lymphocytes (mCTL), Allogeneic Virus-specific T Cell Lines (VSTs), Donor Regulatory T Cells, TCR-modified T cells (TCRs), MIC Cell, Adoptive T Cell Therapy with Activated P53 Specific T Cells, MUC1-DC-CTL, T cell receptor-modified T cells, "Negative" Dendritic Cell-based Vaccine, tolDC, CD22 Redirected Autologous T Cells, Dendristim, Primary NK Cells, Lentiviral-based CART-EGFRvIII Gene-modified Cellular Therapy Products, Autologous Dendritic Cells Pulsed with Lysated Allegenic Tumor Lines, Expanded Multi-antigen Specific Lymphocytes, PD-1 Knockout Engineered T Cells, GSC-loaded Dendritic Cells, Treg Adoptive Cell Transfer (TRACT), E7 TCR T Cells, PD-1 Knockout Engineered T Cells, CAR-Treg (ENTX-DN), Chimeric Switch Receptor Modified T Cells, Neoantigen-primed Dendritic Cells (DC), Pre-activated T (PreT) Cells, TSA-CTL (Tumor Specific Antigen-induced Cytocytotoxic T Lymphocytes), Allogeneic Cell Immunotherapy (ACIT-1), Autologous OC-DC, Mature Dendritic Cells, CD8+NKG2D+ AKT Cell, Natural Killer (NK) cells—oNKord®, antigen presenting cells—sDCord®, Allogenic GM-CSF Transfected Pancreatic Tumor Vaccine.

Chimeric Antigen Receptor Targets

In some embodiments of the invention the chimeric antigen receptor (CAR) T cells or genetically modified cellular immunotherapy may be to a single target or target multiple combinations of any of the targets listed below. The receptor/ligand or antibody expressed by the chimeric antigen receptor T cells or cellular immunotherapy can be mono- or bi-specific or multi-specific. In some embodiments of the invention the cellular immunotherapy may not be genetically modified to any specific target. In some embodiments of the present invention the cellular immunotherapy will be primed or activated in the laboratory to enhance the immune activity of the cellular immunotherapy prior to administering the cellular immunotherapy to a patient.

The expressed receptor/ligand or the antibody target or the cellular immunotherapy target may be chosen from the following list of receptors/ligands or targets including but not limited to; Proto-oncogene tyrosine-protein kinase ABL1, Citrullinated Antigen, ErbB2/HER2, CD16, WT-1, KRAS, glypican 3, CD3, CD20, CD226, CD155, CD123, HPV-16 E6, Melan-A/MART-1, TRAIL Bound to the DR4 Receptor, LMP, MTCR, ESO, NY-ESO-1, gp100, 4SCAR-GD2/CD56, Mesothelin (CAK1 Antigen or Pre Pro Megakaryocyte Potentiating Factor or MSLN); DNA Synthesis Inhibitor; Histamine H1 Receptor (HRH1) Antagonist; Prostaglandin G/H Synthase 2 (Cyclooxygenase 2 or COX2 or Prostaglandin Endoperoxide Synthase 2 or PHS II or Prostaglandin H2 Synthase 2 or PTGS2 or EC 1.14.99.1) Inhibitor, CD19 (B Lymphocyte Surface Antigen B4 or Differentiation Antigen CD19 or T Cell Surface Antigen Leu 12 or CD19), Cell Adhesion Molecule 5 (Carcinoembryonic Antigen or CEA or Meconium Antigen 100 or CD66e or CEACAM5); Interleukin 2 Receptor (IL2R) Agonist, Epidermal Growth Factor Receptor (Proto Oncogene c ErbB 1 or Receptor Tyrosine Protein Kinase erbB 1 or HER1 or ERBB1 or EGFR or EC 2.7.10.1); DNA Ligase (EC 6.5.1.) Inhibitor; DNA Ligase (EC 6.5.1.), DNA Polymerase Alpha (POLA or EC 2.7.7.7) Inhibitor; DNA Primase (EC 2.7.7.6) Inhibitor; Ribonucleoside Diphosphate Reductase (Ribonucleotide Reductase or RRM or EC 1.17.4.1) Inhibitor; RNA Polymerase II (RNAP II or Pol II or EC 2.7.7.6) Inhibitor, DNA Polymerase (EC 2.7.7.7) Inhibitor; DNA Topoisomerase II (EC 5.99.1.3) Inhibitor; CD22, meso, DNA Primase (EC 2.7.7.6); Programmed Cell Death 1 Ligand 1 (PD L or B7 Homolog 1 or CD274) Inhibitor; RNA Polymerase II (RNAP II or Pol II or EC 2.7.7.6), Histone Lysine N Methyltransferase EZH2 (ENX 1 or Enhancer Of Zeste Homolog 2 or Lysine N Methyltransferase 6 or EZH2 or EC 2.1.1.43) Inhibitor; Programmed Cell Death 1 Ligand 1 (PD L1 or B7 Homolog 1 or CD274), C-X-C Chemokine Receptor Type 4 (FB22 or Fusin or HM89 or LCR1 or Leukocyte Derived Seven Transmembrane Domain Receptor or Lipopolysaccharide Associated Protein 3 or Stromal Cell Derived Factor 1 Receptor or NPYRL or CD184 or CXCR4) Antagonist; Granulocyte Colony Stimulating Factor Receptor (CD114 or GCSFR or CSF3R) Agonist, Adenosine Deaminase (Adenosine Aminohydrolase or ADA or EC 3.5.4.4) Inhibitor; Tumor Necrosis Factor Receptor Superfamily Member 17 (B Cell Maturation Antigen or CD269 or TNFRSF17), Cytocytotoxic To Cells Expressing Inactive Tyrosine Protein Kinase Transmembrane Receptor ROR1 (Neurotrophic Tyrosine Kinase Receptor Related 1 or ROR1 or EC 2.7.10.1); T Cell Surface Glycoprotein CD3 Epsilon Chain (T Cell Surface Antigen T3/Leu 4 Epsilon Chain or CD3E); Dihydrofolate Reductase (DHFR or EC 1.5.1.3) Inhibitor; Ephrin Type A Receptor 2 (Epithelial Cell Kinase or Tyrosine Protein Kinase Receptor ECK or EPHA2 or EC 2.7.10.1) Inhibitor; Glucocorticoid Receptor (GR or Nuclear Receptor Subfamily 3 Group C Member 1 or NR3C1) Agonist; Mast/Stem Cell Growth Factor Receptor Kit (Proto Oncogene c Kit or Tyrosine Protein Kinase Kit or v Kit Hardy Zuckerman 4 Feline Sarcoma Viral Oncogene Homolog or Piebald Trait Protein or p145 c Kit or CD117 or KIT or EC 2.7.10.1) Inhibitor; Platelet Derived Growth Factor Receptor Beta (Beta Type Platelet Derived Growth Factor Receptor or CD140 Antigen Like Family Member B or Platelet Derived Growth Factor Receptor 1 or CD140b or PDGFRB or EC 2.7.10.1) Inhibitor; Tubulin Inhibitor; Tyrosine Protein Kinase CSK (C Src Kinase or Protein Tyrosine Kinase CYL or CSK or EC 2.7.10.2) Inhibitor; Tyrosine Protein Kinase Fyn (Proto Oncogene Syn or Proto Oncogene c Fyn or Src Like Kinase or p59 Fyn or FYN or EC 2.7.10.2) Inhibitor; Tyrosine Protein Kinase Lck (Leukocyte C Terminal Src Kinase or Protein YT16 or Proto Oncogene Lck or T Cell Specific Protein Tyrosine Kinase or Lymphocyte Cell Specific Protein Tyrosine Kinase or p56 LCK or LCK or EC 2.7.10.2) Inhibitor; Tyrosine Protein Kinase Yes (Proto Oncogene c Yes or p61 Yes or YES 1 or EC 2.7.10.2) Inhibitor, Tumor Necrosis Factor (Cachectin or TNF Alpha or Tumor Necrosis Factor Ligand Superfamily Member 2 or TNF a or TNF) Inhibitor, Signal Transducer And Activator Of Transcription 3 (Acute Phase Response Factor or DNA Binding Protein APRF or STAT3) Inhibitor, Bcr-Abl Tyrosine Kinase (EC 2.7.10.2) Inhibitor; Dihydrofolate Reductase (DHFR or EC 1.5.1.3); Ephrin Type A Receptor 2 (Epithelial Cell Kinase or Tyrosine Protein Kinase Receptor ECK or EPHA2 or EC 2.7.10.1); Mast/Stem Cell Growth Factor Receptor Kit (Proto Oncogene c Kit or Tyrosine Protein Kinase Kit or v Kit Hardy Zuckerman 4 Feline Sarcoma Viral Oncogene Homolog or Piebald Trait Protein or p145 c Kit or CD117 or KIT or EC 2.7.10.1); Platelet Derived Growth Factor Receptor Beta (Beta Type Platelet Derived Growth Factor Receptor or CD140 Antigen Like Family Member B or Platelet Derived Growth Factor Receptor 1 or CD140b or PDGFRB or EC 2.7.10.1); Tubulin; Tyrosine Protein Kinase CSK (C Src Kinase or Protein Tyrosine Kinase CYL or CSK or EC 2.7.10.2) Inhibitor; Tyrosine Protein Kinase Fyn (Proto Oncogene Syn or Proto Oncogene c Fyn or Src Like Kinase or p59 Fyn or FYN or EC 2.7.10.2) Inhibitor; Tyrosine Protein Kinase Lck (Leukocyte C Terminal Src Kinase or Protein YT16 or Proto Oncogene Lck or T Cell Specific Protein Tyrosine Kinase or Lymphocyte Cell Specific Protein Tyrosine Kinase or p56 LCK or LCK or EC 2.7.10.2) Inhibitor; Tyrosine Protein Kinase Yes (Proto Oncogene c Yes or p61 Yes or YES 1 or EC 2.7.10.2) Inhibitor, Caspase 9 (Apoptotic Protease Mch 6 or Apoptotic Protease Activating Factor 3 or ICE Like Apoptotic Protease 6 or CASP9 or EC 3.4.22.62) Activator; Prostate Stem Cell Antigen (PSCA), Melanoma Antigen Preferentially Expressed In Tumors (Cancer/Testis Antigen 130 or Opa Interacting Protein 4 or OIP4 or Preferentially Expressed Antigen Of Melanoma or PRAME), Signal Transducer And Activator Of Transcription 3 (Acute Phase Response Factor or DNA Binding Protein APRF or STAT3) Inhibitor, CD44 Antigen (CDw44 or Epican or Extracellular Matrix Receptor III or GP90 Lymphocyte Homing/Adhesion Receptor or HUTCH I or Heparan Sulfate Proteoglycan or Hermes Antigen or Hyaluronate Receptor or Phagocytic Glycoprotein 1 or CD44), AXL (anexelekto) receptor tyrosine kinase, GAS6, TAM receptor tyrosine kinases, TYRO-3 (also known as Brt, Dtk, Rse, Sky and Tif), AXL (also known as Ark, Tyro7 and Ufo), and MER (also known as Eyk, Nym and Tyro12), CTLA4, Tumor Necrosis Factor Receptor Superfamily Member 8 (CD30L Receptor or Ki 1 Antigen or Lymphocyte Activation Antigen CD30 or CD30 or TNFRSF8), Caspase 9 (Apoptotic Protease Mch 6 or Apoptotic Protease Activating Factor 3 or ICE Like Apoptotic Protease 6 or CASP9 or EC 3.4.22.62) Activator; Cytocytotoxic To Cells Expressing Ganglioside GD2; Prostaglandin G/H Synthase 1 (Cyclooxygenase 1 or COX1 or Prostaglandin Endoperoxide Synthase 1 or Prostaglandin H2 Synthase 1 or PTGS1 or EC 1.14.99.1) Inhibitor; cytokines, interleukins, Claudin 6 (Skullin or CLDN6), NKG2D, MICA, MICB and ULBP 1-6, NKp30, B7H6 (NCR3LG1), Bag6, B7 family, CD40 Ligand (T Cell Antigen Gp39 or TNF Related Activation Protein or Tumor Necrosis Factor Ligand Superfamily Member 5 or CD154 or CD40LG) Activator; Interleukin 12 (IL12) Activator, Interleukin 3 Receptor Subunit Alpha (IL3RAMast/Stem Cell Growth F), actor Receptor Kit (Proto Oncogene c Kit or Tyrosine Protein Kinase Kit or v Kit Hardy Zuckerman 4 Feline Sarcoma Viral Oncogene Homolog or Piebald Trait Protein or p145 c Kit or CD117 or KIT or EC 2.7.10.1) Antagonist; Proto Oncogene Tyrosine Protein Kinase Receptor Ret (Cadherin Family Member 12 or Proto Oncogene c Ret or RET or EC 2.7.10.1) Inhibitor; Receptor Type Tyrosine Protein Kinase FLT3 (FMS Like Tyrosine Kinase 3 or FL Cytokine Receptor or Stem Cell Tyrosine Kinase 1 or Fetal Liver Kinase 2 or CD135 or FLT3 or EC 2.7.10.1) Antagonist; Vascular Endothelial Growth Factor Receptor 1 (Fms Like Tyrosine Kinase 1 or Tyrosine Protein Kinase Receptor FLT or Tyrosine Protein Kinase FRT or Vascular Permeability Factor Receptor or VEGFR1 or FLT1 or EC 2.7.10.1) Antagonist; Vascular Endothelial Growth Factor Receptor 2 (Fetal Liver Kinase 1 or Kinase Insert Domain Receptor or Protein Tyrosine Kinase Receptor flk 1 or VEGFR2 or CD309 or KDR or EC 2.7.10.1) Antagonist; Vascular Endothelial Growth Factor Receptor 3 (Fms Like Tyrosine Kinase 4 or Tyrosine Protein Kinase Receptor FLT4 or VEGFR3 or FLT4 or EC 2.7.10.1) Antagonist, Caspase 9 (Apoptotic Protease Mch 6 or Apoptotic Protease Activating Factor 3 or ICE Like Apoptotic Protease 6 or CASP9 or EC 3.4.22.62) Activator, Cytocytotoxic T Lymphocyte Protein 4 (Cytocytotoxic T Lymphocyte Associated Antigen 4 or CD152 or CTLA4) Antagonist, Myeloid Cell Surface Antigen CD33 (Sialic Acid Binding Ig Like Lectin 3 or gp67 or CD33), Hepatocyte Growth Factor Receptor (Proto Oncogene c Met or Tyrosine Protein Kinase Met or HGF/SF Receptor or Scatter Factor Receptor or MET or EC 2.7.10.1), Epithelial Cell Adhesion Molecule (Adenocarcinoma Associated Antigen or Cell Surface Glycoprotein Trop 1 or Epithelial Cell Surface Antigen or Epithelial Glycoprotein 314 or KS 1/4 Antigen or KSA or Tumor Associated Calcium Signal Transducer 1 or CD326 or EPCAM), Ganglioside GD2, Lewis Y Antigen (CD174), Latent Membrane Protein 1 (Protein p63 or LMP1), Mucin 1 (Breast Carcinoma Associated Antigen DF3 or Episialin or H23AG or Krebs Von Den Lungen 6 or PEMT or Peanut Reactive Urinary Mucin or Polymorphic Epithelial Mucin or Tumor Associated Epithelial Membrane Antigen or Tumor Associated Mucin or CD227 or MUC1), T Cell Receptor Beta 1 Chain C Region (TRBC1), Vascular Endothelial Growth Factor Receptor 2 (Fetal Liver Kinase 1 or Kinase Insert Domain Receptor or Protein Tyrosine Kinase Receptor flk 1 or VEGFR2 or CD309 or KDR or EC 2.7.10.1), BCMA, PD-1, interleukin-6 receptor, NKR2, CX-072, T Lymphocyte Protein 4 (Cytocytotoxic T Lymphocyte Associated Antigen 4 or CD152 or CTLA4) Antagonist; Serine/Threonine Protein Kinase B Raf (p94 or Proto Oncogene B Raf or v Raf Murine Sarcoma Viral Oncogene Homolog B1 or BRAF or EC 2.7.11.1) Inhibitor, Mucin 16 (Ovarian Cancer Related Tumor Marker CA125 or Ovarian Carcinoma Antigen CA125 or MUC16); Bcr-Abl Tyrosine Kinase (EC 2.7.10.2) Inhibitor; Tyrosine Protein Kinase CSK (C Src Kinase or Protein Tyrosine Kinase CYL or CSK or EC 2.7.10.2) Inhibitor; Tyrosine Protein Kinase Fyn (Proto Oncogene Syn or Proto Oncogene c Fyn or Src Like Kinase or p59 Fyn or FYN or EC 2.7.10.2) Inhibitor; Tyrosine Protein Kinase Lck (Leukocyte C Terminal Src Kinase or Protein YT16 or Proto Oncogene Lck or T Cell Specific Protein Tyrosine Kinase or Lymphocyte Cell Specific Protein Tyrosine Kinase or p56 LCK or LCK or EC 2.7.10.2) Inhibitor; Tyrosine Protein Kinase Yes (Proto Oncogene c Yes or p61 Yes or YES 1 or EC 2.7.10.2) Inhibitor, Cyclin Dependent Kinase 1 (p34 Protein Kinase or Cell Division Protein Kinase 1 or Cell Division Control Protein 2 Homolog or CDK1 or EC 2.7.11.22 or EC 2.7.11.23) Inhibitor; Cyclin Dependent Kinase 2 (p33 Protein Kinase or Cell Division Protein Kinase 2 or CDK2 or EC 2.7.11.22) Inhibitor; Granulocyte Macrophage Colony Stimulating Factor Receptor Subunit Alpha (CDw116 or CD116 or CSF2RA) Agonist, EGFRVIII, Tyrosine Protein Kinase SYK (Spleen Tyrosine Kinase or p72 Syk or SYK or EC 2.7.10.2) Inhibitor, Alpha Fetoprotein (Alpha 1 Fetoprotein or Alpha Fetoglobulin or AFP), Cancer/Testis Antigen 1 (Autoimmunogenic Cancer/Testis Antigen or Cancer/Testis Antigen 6.1 or L Antigen Family Member 2 or CTAG1A or CTAG1B); HBV antigen, EGFR Family Member, Herin, Tyrosine Protein Kinase BTK (Bruton Tyrosine Kinase or B Cell Progenitor Kinase or Agammaglobulinemia Tyrosine Kinase or BTK or EC 2.7.10.2) Inhibitor, CD4, Epithelial Cell Adhesion Molecule (Adenocarcinoma Associated Antigen or Cell Surface Glycoprotein Trop 1 or Epithelial Cell Surface Antigen or Epithelial Glycoprotein 314 or KS 1/4 Antigen or KSA or Tumor Associated Calcium Signal Transducer 1 or CD326 or EPCAM), Prolyl Endopeptidase FAP (170 kDa Melanoma Membrane Bound Gelatinase or Dipeptidyl Peptidase FAP or Integral Membrane Serine Protease or Fibroblast Activation Protein Alpha or Gelatine Degradation Protease FAP or Seprase or FAP or EC 3.4.21.26 or EC 3.4.14.5), Neural Cell Adhesion Molecule 1 (Antigen Recognized By Monoclonal Antibody 5.1H11 or CD56 or NCAM1); Epidermal Growth Factor Receptor (Proto Oncogene c ErbB 1 or Receptor Tyrosine Protein Kinase erbB 1 or HER1 or ERBB1 or EGFR or EC 2.7.10.1) Antagonist, Tyrosine Protein Kinase Transmembrane Receptor ROR1 (Neurotrophic Tyrosine Kinase Receptor Related 1 or ROR1 or EC 2.7.10.1); Wilms Tumor Protein (WT33 or WT1); Interleukin 13 Receptor Subunit Alpha 2 (Interleukin 13 Binding Protein or CD213a2 or IL13RA2), Trophoblast Glycoprotein (M6P1 or 5T4 Oncofetal Antigen or 5T4 Oncofetal Trophoblast Glycoprotein or Wnt Activated Inhibitory Factor 1 or TPBG), SLAM Family Member 7 (CD319 or Membrane Protein FOAP 12 or CD2 Like Receptor Activating Cytocytotoxic Cells or Novel Ly9 or Protein 19A or CD2 Subset 1 or CS1 or SLAMF7), B Cell Lymphoma 2 (Bcl 2) Inhibitor; DNA (Cytosine 5) Methyltransferase 1 (CXXC Type Zinc Finger Protein 9 or DNA Methyltransferase HsaI or MCMT or DNMT1 or EC 2.1.1.37) Inhibitor, ROR1, CD19&CD40L, avidin (EGFRiiiv), a folate receptor, CD30, pmel CD*8 T, CD33, NKR2, Epithelial tumor antigen (ETA), Tyrosinase, Melanoma-associated antigen, abnormal products of ras, p53, Alphafetoprotein (AFP), CA-125, CA15-3, CA27-29, CA19-9, Calcitonin, Calretinin, CD34, CD99MIC 2, CD117, Chromogranin, Cytokeratin (various types: TPA, TPS, Cyfra21-1), Desmin, Epithelial membrane antigen (EMA), Factor VIII, CD31 FL1, Glial fibrillary acidic protein (GFAP), Gross cystic disease fluid protein (GCDFP-15), HMB-45, Human chorionic gonadotropin (hCG), immunoglobulin, inhibin, keratin (various types), lymphocyte marker (various types), BCR-ABL, Myo D1, muscle-specific actin (MSA), neurofilament, neuron-specific enolase (NSE), placental alkaline phosphatase (PLAP), prostate-specific antigen (PSA), PTPRC (CD45), S100 protein, smooth muscle actin (SMA), synaptophysin, thymidine kinase, thyroglobulin (Tg), thyroid transcription factor-1 (TTF-1), Tumor M2-PK, vimentin, SV40, Adenovirus E1b-58kd, IGF2B3, ubiquitous (low level), Kallikrein 4, KIF20A, Lengsin, Meloe, MUC5AC, Immature laminin receptor, TAG-72, HPV E6, HPV E7, BING-4, Calcium-activated chloride channel 2, Cyclin-B1, 9D7, Ep-CAM, EphA3, Telomerase, SAP-1, BAGE family, CAGE family, GAGE family, MAGE family, SAGE family, XAGE family, LAGE-1, PRAME, SSX-2, pmel17, Tyrosinase, TRP-1/-2, P. polypeptide, MC1R, β-catenin, Prostate-pecific antigen, BRCA1, BRCA2, CDK4, CML66, Fibronectin, MART-2, Ras, TGF-beta receptor II, T cell receptor (TCR), BLOC 1S6, CD10/Neprilysin, CD24, CD248, CD5/Cluster of Differentiation 5, CD63/Tspan-30/Tetraspanin-30, CEACAM5/CD66e, CT45A3, CTAG1A, CXORF61, DSE, GPA33, HPSE, KLK3, LCP1, LRIG3, LRRC15, megakaryocyte potentiating factor, MOK, MUC4, NDNL2, OCIAD1, PMPCB, PTOV1, RCAS 1/EBAG9, RNF43, ROPN1, RPLP1, SARNP, SBEM/MUCL1, TRP1/TYRP1, CA19-9, Inactive Tyrosine Protein Kinase Transmembrane Receptor ROR1 (Neurotrophic Tyrosine Kinase Receptor Related 1 or ROR1 or EC 2.7.10.1), ALK Tyrosine Kinase Receptor (Anaplastic Lymphoma Kinase or CD246 or ALK or EC 2.7.10.1), Prostate Stem Cell Antigen (PSCA), Melanoma Antigen Preferentially Expressed In Tumors (Cancer/Testis Antigen 130 or Opa Interacting Protein 4 or OIP4 or Preferentially Expressed Antigen Of Melanoma or PRAME), Signal Transducer And Activator Of Transcription 3 (Acute Phase Response Factor or DNA Binding Protein APRF or STAT3) Inhibitor, CD44 Antigen (CDw44 or Epican or Extracellular Matrix Receptor III or GP90 Lymphocyte Homing/Adhesion Receptor or HUTCH I or Heparan Sulfate Proteoglycan or Hermes Antigen or Hyaluronate Receptor or Phagocytic Glycoprotein 1 or CD44), CD40 Ligand (T Cell Antigen Gp39 or TNF Related Activation Protein or Tumor Necrosis Factor Ligand Superfamily Member 5 or CD154 or CD40LG) Activator; Tumor Necrosis Factor Receptor Superfamily Member 13B (Transmembrane Activator And CAML Interactor or CD267 or TACI or TNFRSF13B); Cytocytotoxic To Cells Expressing Tumor Necrosis Factor Receptor Superfamily Member 17 (B Cell Maturation Antigen or CD269 or TNFRSF17), CD276 Antigen (B7 Homolog 3 or 4Ig B7 H3 or Costimulatory Molecule or CD276), Myeloid Cell Surface Antigen CD33 (Sialic Acid Binding Ig Like Lectin 3 or gp67 or CD33), ADP Ribosyl Cyclase/Cyclic ADP Ribose Hydrolase 1 (Cyclic ADP Ribose Hydrolase 1 or T10 or 2' Phospho ADP Ribosyl Cyclase/2' Phospho Cyclic ADP Ribose Transferase or ADP Ribosyl Cyclase 1 or CD38 or EC 3.2.2.6 or EC 2.4.99.20), C Type Lectin Domain Family 14 Member A (Epidermal Growth Factor Receptor 5 or EGFR5 or CLEC14A), Hepatocyte Growth Factor Receptor (Proto Oncogene c Met or Tyrosine Protein Kinase Met or HGF/SF Receptor or Scatter Factor Receptor or MET or EC 2.7.10.1), Epithelial Cell Adhesion Molecule (Adenocarcinoma Associated Antigen or Cell Surface Glycoprotein Trop 1 or Epithelial Cell Surface Antigen or Epithelial Glycoprotein 314 or KS 1/4 Antigen or KSA or Tumor Associated Calcium Signal Transducer 1 or CD326 or EPCAM), Ganglioside GD3, Interleukin 13 Receptor Subunit Alpha 2 (Interleukin 13 Binding Protein or CD213a2 or IL13RA2); Kappa Myeloma Antigen (KMA), Lambda Myeloma Antigen (LMA), Latent Membrane Protein 1 (Protein p63 or LMP1), Melanoma Associated Antigen, Cytocytotoxic To Cells Expressing T Lymphocyte Activation Antigen CD80 (Activation B7-1 Antigen or CTLA 4 Counter Receptor B7.1 or CD80); Cytocytotoxic To Cells Expressing T Lymphocyte Activation Antigen CD86 (Activation B7-2 Antigen or CTLA 4 Counter Receptor B7.2 or CD86), Inactive Tyrosine Protein Kinase Transmembrane Receptor ROR1 (Neurotrophic Tyrosine Kinase Receptor Related 1 or ROR1 or EC 2.7.10.1), Fas Apoptotic Inhibitory Molecule 3 (IgM Fc Fragment Receptor or Regulator Of Fas Induced Apoptosis Toso or TOSO or FAIM3 or FCMR), T Cell Receptor Beta 1 Chain C Region (TRBC1), Vascular Endothelial Growth Factor Receptor 2 (Fetal Liver Kinase 1 or Kinase Insert Domain Receptor or Protein Tyrosine Kinase Receptor flk 1 or VEGFR2 or CD309 or KDR or EC 2.7.10.1), Alpha Fetoprotein (Alpha 1 Fetoprotein or Alpha Fetoglobulin or AFP), Cancer/Testis Antigen 1 (Autoimmunogenic Cancer/Testis Antigen NY ESO 1 or Cancer/Testis Antigen 6.1 or L Antigen Family Member 2 or CTAG1A or CTAG1B), T Cell Surface Glycoprotein CD5 (Lymphocyte Antigen T1/Leu 1 or CD5), Prolyl Endopeptidase FAP (170 kDa Melanoma Membrane Bound Gelatinase or Dipeptidyl Peptidase FAP or Integral Membrane Serine Protease or Fibroblast Activation Protein Alpha or Gelatine Degradation Protease FAP or Seprase or FAP or EC 3.4.21.26 or EC 3.4.14.5), Neural Cell Adhesion Molecule 1 (Antigen Recognized By Monoclonal Antibody 5.1H11 or CD56 or NCAM1), C Type Lectin Domain Family 12 Member A (Myeloid Inhibitory C Type Lectin Like Receptor or Dendritic Cell Associated Lectin 2 or C Type Lectin Like Molecule 1 or CLEC12A), Integrin Alpha V (Vitronectin Receptor Subunit Alpha or CD51 or ITGAV); Cytocytotoxic To Cells Expressing Integrin Beta 6 (ITGB6), Interleukin 13 Receptor Subunit Alpha 2 (Interleukin 13 Binding Protein or CD213a2 or IL13RA2), Trophoblast Glycoprotein (M6P1 or 5T4 Oncofetal Antigen or 5T4 Oncofetal Trophoblast Glycoprotein or Wnt Activated Inhibitory Factor 1 or TPBG), Trophoblast Glycoprotein (M6P1 or 5T4 Oncofetal Antigen or 5T4 Oncofetal Trophoblast Glycoprotein or Wnt Activated Inhibitory Factor 1 or TPBG), C Type Lectin Domain Family 12 Member A (Myeloid Inhibitory C Type Lectin Like Receptor or Dendritic Cell Associated Lectin 2 or C Type Lectin Like Molecule 1 or CLEC12A), SLAM Family Member 7 (CD319 or Membrane Protein FOAP 12 or CD2 Like Receptor Activating Cytocytotoxic Cells or Novel Ly9 or Protein 19A or CD2 Subset 1 or CS1 or SLAMF7), SLAM Family Member 7 (CD319 or Membrane Protein FOAP 12 or CD2 Like Receptor Activating Cytocytotoxic Cells or Novel Ly9 or Protein 19A or CD2 Subset 1 or CS1 or SLAMF7), immunoglobulin, Multidrug resistance-associated protein 3 (MRP3), Proto-oncogene tyrosine-protein kinase ABL1, Prostatic acid phosphatase, OY-TES-1, ACSM2A, Alpha-actinin-4, Perilipin-2, Alpha-fetoprotein, Lymphoid blast crisis oncogene (Lbc) oncoproptein, aldehyde dehydrogenase 1 family member A1 (ALDH1A1), AML, ANKRD17, NY-BR-1, Annexin II, ARHGAP17, ARHGAP30, ARID1B, Endoplasmic reticulum-resident protein, 5'-aminoimidazole-4-carboxamide-1-beta-d-ribonucleotide transfolmylase/inosinicase (AICRT/I), ATR, ATXN2, ATXN2L, BAGE1, BCL11A, Bcl-xL, Breakpoint cluster region, Survivin, Livin/ML-IAP, HM1.24, BTB domain containing 2 (BTBD2), C60RF89, Carbonic anhydrase IX, CLCA2, CRT2, CAMEL, CAN protein, Caspase-5, Caspase-8, KM-HN-1, CCDC88B, cyclin B1, Cyclin D1, CCNI, CDC2, CDC25A, CDC27, CDK12, intestinal carboxylesterase, CEP95, CHAF1A, Coactosin-like 1, CPSF, CRYBA1, TRAG-3, Macrophage colony stimulating factor, CSNK1A1, Melanoma-associated chondroitin sulfate proteoglycan (MCSP), Cathepsin H, Kita-kyushu lung cancer antigen 1, P450 1B1 or CYP1B1, DDR1, DEK oncogene, DEK-CAN, Dickkopf-1 (DKK1), DNAJC8, DSCAML1, EEF2, Elongation factor Tu GTP binding domain containing or SNRP116, EIF4EBP1, Human Mena protein, EP300, ETV5, TEL1 or ETV6, Polycomb group protein enhancer of zeste homolog 2 (EZH2), F2R, F4.2, FAM53C, Fibroblast growth factor 5 or FGF5, Formin-related protein in leukocytes 1 (FMNL1), Fibromodulin (FMOD), FNDC3B, FKHR, GDP-L-fucose, GAS7, GFI1, GIGYF2, GPNMB, O, A1, GPSM3, GRK2, GRM5, H3F3A, HAUS3, HERC1, HERV-K-MEL, HIVEP2, HMGN, HMHA1, heme oxygenase-1 (HO-1), HNRPL, Heparanase, HMSD-v-encoded mHA, HSPA1A, Hsp70, HSPB 1, immediate early response gene X-1 (IEX-1), insulin-like growth factor (IGF)-II mRNA binding protein 3 (IMP-3), IP6K1, IRS2, ITGB8, JUP, RU2AS, KANSL3, KLF10, KLF2, KLK4, KMT2A, K-ras, Low density lipid receptor (LDLR), LDLR-FUT, Mac-2-binding protein, KIAA0205, LPP, LRP1, LRRC41, LSP1, LUZP1, lymphocyte antigen 6 complex locus K (LY6K), MACF1, MAP1A, MAP3K11, MAP7D1, Matrilin-2, Mcl-1, MDM2, Malic enzyme, MEF2D, MEFV, Milk fat globule membrane protein BA46 (lactadherin), Melanotransferrin, GNT-V or N-acetylglucosaminytransferase V, MIIP, MMP14, Matrix metalloproteinase-2, MORC2, Melanoma antigen p15, MUC2, MUM, MYC, MYL9, Unconventional myosin class I gene, N4BP2, NCBP3, NCOA1, NCOR2, NFATC2, NFYC, NIFK, Ninein, NPM, NPM1-ALK1, N-ras, OAS3, P polypeptide, OGT, OS-9, ErbB3-binding protein 1, PAGE-4, P21-activated serine kinase 2 (PAK2), neo-PAP, PARP12, PAX3, PAX3-FKHR, PCBP2, phosphoglycerate kinase 1 (PKG1), PLEKHM2, promyelocytic leukemia or PML, PML-RARA, POLR2A, Cyclophilin B, PPP1CA, PPP1R3B, Peroxiredoxin 5, Proteinase 3, Parathyroid hormone-related protein (PTHrP), Receptor-like protein tyrosine phosphatase kappa, MG50, NY-MEL-1 or RAB38, RAGE, RALGAPB, RAR alpha, RBM, RCSD1, Recoverin, RERE, RGS5, RHAMM/CD168, RPA1, Ribosomal protein L10a, Ribosomal protein S2, RREB 1, RSRP1, RTCB, SART, SCAP, Mammaglobin A, Secernin 1, SDCBP, SETD2, SF3B1, Renal ubiquitous protein 1, SIK1, SIRT2, SKI, hairpin-binding protein, SLC35A4, Prostein, SLC46A1, SNRPD1, SOGA1, SON, SOX10, SOX11, SOX2, SOX-4, Sperm protein 17, SPEN, SRRM2, SRSF7, SRSF8, SSX1, SSX2 or HOM-MEL-40, SSX4, STAT1, STEAP, STRAP, ART-1, SVIL, HOM-TES-14/SCP1, CD138, SYNM, SYNPO, SYT, SYT15, SYT-SSX1, SYT-SSX2, SZT2, TAPBP, TBC1D10C, TBC1D9B, hTERT, THNSL2, THOC6, TLK1, TNS3, TOP2A, TOP2B, ATP-dependent interferon-responsive (ADIR), TP53, Triosephosphate isomerase or TPI1, Tropomyosin-4, TPX2, TRG, T-cell receptor gamma alternate reading frame protein (TARP), TRIM68, Prostate-specific protein transient receptor potential-p8 (trp-p8), TSC22D4, TTK protein kinase (TTK), Thymidylate synthase (TYMS), UBE2A, Ubiquitin-conjugating enzyme variant Kua, COA-1, USB1, NA88-A, VPS13D, BING4, WHSC1L1, WHSC2, WNK2, WT1, XBP1, XPO1, ZC3H14, ZNF106, ZNF219, Papillomavirus binding factor (PBF), E3 ubiquitin-protein ligase UBR4.

In certain embodiments of the invention one would want to exclude and avoid using certain expressed receptor/ligand or antibody target or cellular immunotherapy targets including but not limited to; Proto-oncogene tyrosine-protein kinase ABL1, Citrullinated Antigen, ErbB2/HER2, CD16, WT-1, KRAS, glypican 3, CD3, CD20, CD226, CD155, CD123, HPV-16 E6, Melan-A/MART-1, TRAIL Bound to the DR4 Receptor, LMP, MTCR, ESO, NY-ESO-1, gp100, 4SCAR-GD2/CD56, Mesothelin (CAK1 Antigen or Pre Pro Megakaryocyte Potentiating Factor or MSLN); DNA Synthesis Inhibitor; Histamine H1 Receptor (HRH1) Antagonist; Prostaglandin G/H Synthase 2 (Cyclooxygenase 2 or COX2 or Prostaglandin Endoperoxide Synthase 2 or PHS II or Prostaglandin H2 Synthase 2 or PTGS2 or EC 1.14.99.1) Inhibitor, CD19 (B Lymphocyte Surface Antigen B4 or Differentiation Antigen CD19 or T Cell Surface Antigen Leu 12 or CD19), Cell Adhesion Molecule 5 (Carcinoembryonic Antigen or CEA or Meconium Antigen 100 or CD66e or CEACAM5); Interleukin 2 Receptor (IL2R) Agonist, Epidermal Growth Factor Receptor (Proto Oncogene c ErbB 1 or Receptor Tyrosine Protein Kinase erbB 1 or HER1 or ERBB1 or EGFR or EC 2.7.10.1); DNA Ligase (EC 6.5.1.)

Inhibitor; DNA Ligase (EC 6.5.1.), DNA Polymerase Alpha (POLA or EC 2.7.7.7) Inhibitor; DNA Primase (EC 2.7.7.6) Inhibitor; Ribonucleoside Diphosphate Reductase (Ribonucleotide Reductase or RRM or EC 1.17.4.1) Inhibitor; RNA Polymerase II (RNAP II or Pol II or EC 2.7.7.6) Inhibitor, DNA Polymerase (EC 2.7.7.7) Inhibitor; DNA Topoisomerase II (EC 5.99.1.3) Inhibitor; CD22, meso, DNA Primase (EC 2.7.7.6); Programmed Cell Death 1 Ligand 1 (PD L or B7 Homolog 1 or CD274) Inhibitor; RNA Polymerase II (RNAP II or Pol II or EC 2.7.7.6), Histone Lysine N Methyltransferase EZH2 (ENX 1 or Enhancer Of Zeste Homolog 2 or Lysine N Methyltransferase 6 or EZH2 or EC 2.1.1.43) Inhibitor; Programmed Cell Death 1 Ligand 1 (PD L1 or B7 Homolog 1 or CD274), C-X-C Chemokine Receptor Type 4 (FB22 or Fusin or HM89 or LCR1 or Leukocyte Derived Seven Transmembrane Domain Receptor or Lipopolysaccharide Associated Protein 3 or Stromal Cell Derived Factor 1 Receptor or NPYRL or CD184 or CXCR4) Antagonist; Granulocyte Colony Stimulating Factor Receptor (CD114 or GCSFR or CSF3R) Agonist, Adenosine Deaminase (Adenosine Aminohydrolase or ADA or EC 3.5.4.4) Inhibitor; Tumor Necrosis Factor Receptor Superfamily Member 17 (B Cell Maturation Antigen or CD269 or TNFRSF17), Cytocytotoxic To Cells Expressing Inactive Tyrosine Protein Kinase Transmembrane Receptor ROR1 (Neurotrophic Tyrosine Kinase Receptor Related 1 or ROR1 or EC 2.7.10.1); T Cell Surface Glycoprotein CD3 Epsilon Chain (T Cell Surface Antigen T3/Leu 4 Epsilon Chain or CD3E); Dihydrofolate Reductase (DHFR or EC 1.5.1.3) Inhibitor; Ephrin Type A Receptor 2 (Epithelial Cell Kinase or Tyrosine Protein Kinase Receptor ECK or EPHA2 or EC 2.7.10.1) Inhibitor; Glucocorticoid Receptor (GR or Nuclear Receptor Subfamily 3 Group C Member 1 or NR3C1) Agonist; Mast/Stem Cell Growth Factor Receptor Kit (Proto Oncogene c Kit or Tyrosine Protein Kinase Kit or v Kit Hardy Zuckerman 4 Feline Sarcoma Viral Oncogene Homolog or Piebald Trait Protein or p145 c Kit or CD117 or KIT or EC 2.7.10.1) Inhibitor; Platelet Derived Growth Factor Receptor Beta (Beta Type Platelet Derived Growth Factor Receptor or CD140 Antigen Like Family Member B or Platelet Derived Growth Factor Receptor 1 or CD140b or PDGFRB or EC 2.7.10.1) Inhibitor; Tubulin Inhibitor; Tyrosine Protein Kinase CSK (C Src Kinase or Protein Tyrosine Kinase CYL or CSK or EC 2.7.10.2) Inhibitor; Tyrosine Protein Kinase Fyn (Proto Oncogene Syn or Proto Oncogene c Fyn or Src Like Kinase or p59 Fyn or FYN or EC 2.7.10.2) Inhibitor; Tyrosine Protein Kinase Lck (Leukocyte C Terminal Src Kinase or Protein YT16 or Proto Oncogene Lck or T Cell Specific Protein Tyrosine Kinase or Lymphocyte Cell Specific Protein Tyrosine Kinase or p56 LCK or LCK or EC 2.7.10.2) Inhibitor; Tyrosine Protein Kinase Yes (Proto Oncogene c Yes or p61 Yes or YES 1 or EC 2.7.10.2) Inhibitor, Tumor Necrosis Factor (Cachectin or TNF Alpha or Tumor Necrosis Factor Ligand Superfamily Member 2 or TNF a or TNF) Inhibitor, Signal Transducer And Activator Of Transcription 3 (Acute Phase Response Factor or DNA Binding Protein APRF or STAT3) Inhibitor, Bcr-Abl Tyrosine Kinase (EC 2.7.10.2) Inhibitor; Dihydrofolate Reductase (DHFR or EC 1.5.1.3); Ephrin Type A Receptor 2 (Epithelial Cell Kinase or Tyrosine Protein Kinase Receptor ECK or EPHA2 or EC 2.7.10.1); Mast/Stem Cell Growth Factor Receptor Kit (Proto Oncogene c Kit or Tyrosine Protein Kinase Kit or v Kit Hardy Zuckerman 4 Feline Sarcoma Viral Oncogene Homolog or Piebald Trait Protein or p145 c Kit or CD117 or KIT or EC 2.7.10.1); Platelet Derived Growth Factor Receptor Beta (Beta Type Platelet Derived Growth Factor Receptor or CD140 Antigen Like Family Member B or Platelet Derived Growth Factor Receptor 1 or CD140b or PDGFRB or EC 2.7.10.1); Tubulin; Tyrosine Protein Kinase CSK (C Src Kinase or Protein Tyrosine Kinase CYL or CSK or EC 2.7.10.2) Inhibitor; Tyrosine Protein Kinase Fyn (Proto Oncogene Syn or Proto Oncogene c Fyn or Src Like Kinase or p59 Fyn or FYN or EC 2.7.10.2) Inhibitor; Tyrosine Protein Kinase Lck (Leukocyte C Terminal Src Kinase or Protein YT16 or Proto Oncogene Lck or T Cell Specific Protein Tyrosine Kinase or Lymphocyte Cell Specific Protein Tyrosine Kinase or p56 LCK or LCK or EC 2.7.10.2) Inhibitor; Tyrosine Protein Kinase Yes (Proto Oncogene c Yes or p61 Yes or YES 1 or EC 2.7.10.2) Inhibitor, Caspase 9 (Apoptotic Protease Mch 6 or Apoptotic Protease Activating Factor 3 or ICE Like Apoptotic Protease 6 or CASP9 or EC 3.4.22.62) Activator; Prostate Stem Cell Antigen (PSCA), Melanoma Antigen Preferentially Expressed In Tumors (Cancer/Testis Antigen 130 or Opa Interacting Protein 4 or OIP4 or Preferentially Expressed Antigen Of Melanoma or PRAME), Signal Transducer And Activator Of Transcription 3 (Acute Phase Response Factor or DNA Binding Protein APRF or STAT3) Inhibitor, CD44 Antigen (CDw44 or Epican or Extracellular Matrix Receptor III or GP90 Lymphocyte Homing/Adhesion Receptor or HUTCH I or Heparan Sulfate Proteoglycan or Hermes Antigen or Hyaluronate Receptor or Phagocytic Glycoprotein 1 or CD44), AXL (anexelekto) receptor tyrosine kinase, GAS6, TAM receptor tyrosine kinases, TYRO-3 (also known as Brt, Dtk, Rse, Sky and Tif), AXL (also known as Ark, Tyro7 and Ufo), and MER (also known as Eyk, Nym and Tyro12), CTLA4, Tumor Necrosis Factor Receptor Superfamily Member 8 (CD30L Receptor or Ki 1 Antigen or Lymphocyte Activation Antigen CD30 or CD30 or TNFRSF8), Caspase 9 (Apoptotic Protease Mch 6 or Apoptotic Protease Activating Factor 3 or ICE Like Apoptotic Protease 6 or CASP9 or EC 3.4.22.62) Activator; Cytocytotoxic To Cells Expressing Ganglioside GD2; Prostaglandin G/H Synthase 1 (Cyclooxygenase 1 or COX1 or Prostaglandin Endoperoxide Synthase 1 or Prostaglandin H2 Synthase 1 or PTGS1 or EC 1.14.99.1) Inhibitor; cytokines, interleukins, Claudin 6 (Skullin or CLDN6), NKG2D, MICA, MICB and ULBP 1-6, NKp30, B7H6 (NCR3LG1), Bag6, B7 family, CD40 Ligand (T Cell Antigen Gp39 or TNF Related Activation Protein or Tumor Necrosis Factor Ligand Superfamily Member 5 or CD154 or CD40LG) Activator; Interleukin 12 (IL12) Activator, Interleukin 3 Receptor Subunit Alpha (IL3RAMast/Stem Cell Growth F), actor Receptor Kit (Proto Oncogene c Kit or Tyrosine Protein Kinase Kit or v Kit Hardy Zuckerman 4 Feline Sarcoma Viral Oncogene Homolog or Piebald Trait Protein or p145 c Kit or CD117 or KIT or EC 2.7.10.1) Antagonist; Proto Oncogene Tyrosine Protein Kinase Receptor Ret (Cadherin Family Member 12 or Proto Oncogene c Ret or RET or EC 2.7.10.1) Inhibitor; Receptor Type Tyrosine Protein Kinase FLT3 (FMS Like Tyrosine Kinase 3 or FL Cytokine Receptor or Stem Cell Tyrosine Kinase 1 or Fetal Liver Kinase 2 or CD135 or FLT3 or EC 2.7.10.1) Antagonist; Vascular Endothelial Growth Factor Receptor 1 (Fms Like Tyrosine Kinase 1 or Tyrosine Protein Kinase Receptor FLT or Tyrosine Protein Kinase FRT or Vascular Permeability Factor Receptor or VEGFR1 or FLT1 or EC 2.7.10.1) Antagonist; Vascular Endothelial Growth Factor Receptor 2 (Fetal Liver Kinase 1 or Kinase Insert Domain Receptor or Protein Tyrosine Kinase Receptor flk 1 or VEGFR2 or CD309 or KDR or EC 2.7.10.1) Antagonist; Vascular Endothelial Growth Factor Receptor 3 (Fms Like Tyrosine Kinase 4 or Tyrosine Protein Kinase Receptor FLT4 or VEGFR3 or FLT4 or EC 2.7.10.1) Antagonist, Caspase 9

(Apoptotic Protease Mch 6 or Apoptotic Protease Activating Factor 3 or ICE Like Apoptotic Protease 6 or CASP9 or EC 3.4.22.62) Activator, Cytocytotoxic T Lymphocyte Protein 4 (Cytocytotoxic T Lymphocyte Associated Antigen 4 or CD152 or CTLA4) Antagonist, Myeloid Cell Surface Antigen CD33 (Sialic Acid Binding Ig Like Lectin 3 or gp67 or CD33), Hepatocyte Growth Factor Receptor (Proto Oncogene c Met or Tyrosine Protein Kinase Met or HGF/SF Receptor or Scatter Factor Receptor or MET or EC 2.7.10.1), Epithelial Cell Adhesion Molecule (Adenocarcinoma Associated Antigen or Cell Surface Glycoprotein Trop 1 or Epithelial Cell Surface Antigen or Epithelial Glycoprotein 314 or KS 1/4 Antigen or KSA or Tumor Associated Calcium Signal Transducer 1 or CD326 or EPCAM), Ganglioside GD2, Lewis Y Antigen (CD174), Latent Membrane Protein 1 (Protein p63 or LMP1), Mucin 1 (Breast Carcinoma Associated Antigen DF3 or Episialin or H23AG or Krebs Von Den Lungen 6 or PEMT or Peanut Reactive Urinary Mucin or Polymorphic Epithelial Mucin or Tumor Associated Epithelial Membrane Antigen or Tumor Associated Mucin or CD227 or MUC1), T Cell Receptor Beta 1 Chain C Region (TRBC1), Vascular Endothelial Growth Factor Receptor 2 (Fetal Liver Kinase 1 or Kinase Insert Domain Receptor or Protein Tyrosine Kinase Receptor flk 1 or VEGFR2 or CD309 or KDR or EC 2.7.10.1), BCMA, PD-1, interleukin-6 receptor, NKR2, CX-072, T Lymphocyte Protein 4 (Cytocytotoxic T Lymphocyte Associated Antigen 4 or CD152 or CTLA4) Antagonist; Serine/Threonine Protein Kinase B Raf (p94 or Proto Oncogene B Raf or v Raf Murine Sarcoma Viral Oncogene Homolog B1 or BRAF or EC 2.7.11.1) Inhibitor, Mucin 16 (Ovarian Cancer Related Tumor Marker CA125 or Ovarian Carcinoma Antigen CA125 or MUC16); Bcr-Abl Tyrosine Kinase (EC 2.7.10.2) Inhibitor; Tyrosine Protein Kinase CSK (C Src Kinase or Protein Tyrosine Kinase CYL or CSK or EC 2.7.10.2) Inhibitor; Tyrosine Protein Kinase Fyn (Proto Oncogene Syn or Proto Oncogene c Fyn or Src Like Kinase or p59 Fyn or FYN or EC 2.7.10.2) Inhibitor; Tyrosine Protein Kinase Lck (Leukocyte C Terminal Src Kinase or Protein YT16 or Proto Oncogene Lck or T Cell Specific Protein Tyrosine Kinase or Lymphocyte Cell Specific Protein Tyrosine Kinase or p56 LCK or LCK or EC 2.7.10.2) Inhibitor; Tyrosine Protein Kinase Yes (Proto Oncogene Yes or p61 Yes or YES 1 or EC 2.7.10.2) Inhibitor, Cyclin Dependent Kinase 1 (p34 Protein Kinase or Cell Division Protein Kinase 1 or Cell Division Control Protein 2 Homolog or CDK1 or EC 2.7.11.22 or EC 2.7.11.23) Inhibitor; Cyclin Dependent Kinase 2 (p33 Protein Kinase or Cell Division Protein Kinase 2 or CDK2 or EC 2.7.11.22) Inhibitor; Granulocyte Macrophage Colony Stimulating Factor Receptor Subunit Alpha (CDw116 or CD116 or CSF2RA) Agonist, EGFRVIII, Tyrosine Protein Kinase SYK (Spleen Tyrosine Kinase or p72 Syk or SYK or EC 2.7.10.2) Inhibitor, Alpha Fetoprotein (Alpha 1 Fetoprotein or Alpha Fetoglobulin or AFP), Cancer/Testis Antigen 1 (Autoimmunogenic Cancer/Testis Antigen or Cancer/Testis Antigen 6.1 or L Antigen Family Member 2 or CTAG1A or CTAG1B); HBV antigen, EGFR Family Member, Herin, Tyrosine Protein Kinase BTK (Bruton Tyrosine Kinase or B Cell Progenitor Kinase or Agammaglobulinemia Tyrosine Kinase or BTK or EC 2.7.10.2) Inhibitor, CD4, Epithelial Cell Adhesion Molecule (Adenocarcinoma Associated Antigen or Cell Surface Glycoprotein Trop 1 or Epithelial Cell Surface Antigen or Epithelial Glycoprotein 314 or KS 1/4 Antigen or KSA or Tumor Associated Calcium Signal Transducer 1 or CD326 or EPCAM), Prolyl Endopeptidase FAP (170 kDa Melanoma Membrane Bound Gelatinase or Dipeptidyl Peptidase FAP or Integral Membrane Serine Protease or Fibroblast Activation Protein Alpha or Gelatine Degradation Protease FAP or Seprase or FAP or EC 3.4.21.26 or EC 3.4.14.5), Neural Cell Adhesion Molecule 1 (Antigen Recognized By Monoclonal Antibody 5.1H11 or CD56 or NCAM1); Epidermal Growth Factor Receptor (Proto Oncogene c ErbB 1 or Receptor Tyrosine Protein Kinase erbB 1 or HER1 or ERBB1 or EGFR or EC 2.7.10.1) Antagonist, Tyrosine Protein Kinase Transmembrane Receptor ROR1 (Neurotrophic Tyrosine Kinase Receptor Related 1 or ROR1 or EC 2.7.10.1); Wilms Tumor Protein (WT33 or WT1); Interleukin 13 Receptor Subunit Alpha 2 (Interleukin 13 Binding Protein or CD213a2 or IL13RA2), Trophoblast Glycoprotein (M6P1 or 5T4 Oncofetal Antigen or 5T4 Oncofetal Trophoblast Glycoprotein or Wnt Activated Inhibitory Factor 1 or TPBG), SLAM Family Member 7 (CD319 or Membrane Protein FOAP 12 or CD2 Like Receptor Activating Cytocytotoxic Cells or Novel Ly9 or Protein 19A or CD2 Subset 1 or CS1 or SLAMF7), B Cell Lymphoma 2 (Bcl 2) Inhibitor; DNA (Cytosine 5) Methyltransferase 1 (CXXC Type Zinc Finger Protein 9 or DNA Methyltransferase HsaI or MCMT or DNMT1 or EC 2.1.1.37) Inhibitor, ROR1, CD19&CD40L, avidin (EGFRiiv), a folate receptor, CD30, pmel CD*8 T, CD33, NKR2, Epithelial tumor antigen (ETA), Tyrosinase, Melanoma-associated antigen, abnormal products of ras, p53, Alphafetoprotein (AFP), CA-125, CA15-3, CA27-29, CA19-9, Calcitonin, Calretinin, CD34, CD99MIC 2, CD117, Chromogranin, Cytokeratin (various types: TPA, TPS, Cyfra21-1), Desmin, Epithelial membrane antigen (EMA), Factor VIII, CD31 FL1, Glial fibrillary acidic protein (GFAP), Gross cystic disease fluid protein (GCDFP-15), HMB-45, Human chorionic gonadotropin (hCG), immunoglobulin, inhibin, keratin (various types), lymphocyte marker (various types), BCR-ABL, Myo D1, muscle-specific actin (MSA), neurofilament, neuron-specific enolase (NSE), placental alkaline phosphatase (PLAP), prostate-specific antigen (PSA), PTPRC (CD45), S100 protein, smooth muscle actin (SMA), synaptophysin, thymidine kinase, thyroglobulin (Tg), thyroid transcription factor-1 (TTF-1), Tumor M2-PK, vimentin, SV40, Adenovirus E1b-58kd, IGF2B3, ubiquitous (low level), Kallikrein 4, KIF20A, Lengsin, Meloe, MUC5AC, Immature laminin receptor, TAG-72, HPV E6, HPV E7, BING-4, Calcium-activated chloride channel 2, Cyclin-B1, 9D7, Ep-CAM, EphA3, Telomerase, SAP-1, BAGE family, CAGE family, GAGE family, MAGE family, SAGE family, XAGE family, LAGE-1, PRAME, SSX-2, pmel17, Tyrosinase, TRP-1/-2, P. polypeptide, MC1R, β-catenin, Prostate-pecific antigen, BRCA1, BRCA2, CDK4, CML66, Fibronectin, MART-2, Ras, TGF-beta receptor II, T cell receptor (TCR), BLOC 1S6, CD10/Neprilysin, CD24, CD248, CD5/Cluster of Differentiation 5, CD63/Tspan-30/Tetraspanin-30, CEACAM5/CD66e, CT45A3, CTAG1A, CXORF61, DSE, GPA33, HPSE, KLK3, LCP1, LRIG3, LRRC15, megakaryocyte potentiating factor, MOK, MUC4, NDNL2, OCIAD1, PMPCB, PTOV1, RCAS 1/EBAG9, RNF43, ROPN1, RPLP1, SARNP, SBEM/MUCL1, TRP1/TYRP1, CA19-9, Inactive Tyrosine Protein Kinase Transmembrane Receptor ROR1 (Neurotrophic Tyrosine Kinase Receptor Related 1 or ROR1 or EC 2.7.10.1), ALK Tyrosine Kinase Receptor (Anaplastic Lymphoma Kinase or CD246 or ALK or EC 2.7.10.1), Prostate Stem Cell Antigen (PSCA), Melanoma Antigen Preferentially Expressed In Tumors (Cancer/Testis Antigen 130 or Opa Interacting Protein 4 or OIP4 or Preferentially Expressed Antigen Of Melanoma or PRAME), Signal Transducer And Activator Of Transcription 3 (Acute Phase Response Factor or DNA Binding Protein APRF or STAT3) Inhibitor, CD44 Antigen (CDw44 or Epican or Extracellular Matrix Receptor III or GP90 Lymphocyte Homing/Adhesion Receptor or HUTCH I or Heparan Sulfate Proteoglycan or Hermes Antigen or Hyaluronate Receptor or Phagocytic Glycoprotein 1 or CD44), CD40 Ligand (T Cell Antigen Gp39 or TNF Related Activation Protein or Tumor Necrosis Factor Ligand Superfamily Member 5 or CD154 or CD40LG) Activator; Tumor Necrosis Factor Receptor Superfamily Member 13B (Transmembrane Activator And CAML Interactor or CD267 or TACI or TNFRSF13B); Cytocytotoxic To Cells Expressing Tumor Necrosis Factor Receptor Superfamily Member 17 (B Cell Maturation Antigen or CD269 or TNFRSF17), CD276 Antigen (B7 Homolog 3 or 4Ig B7 H3 or Costimulatory Molecule or CD276), Myeloid Cell Surface Antigen CD33 (Sialic Acid Binding Ig Like Lectin 3 or gp67 or CD33), ADP Ribosyl Cyclase/Cyclic ADP Ribose Hydrolase 1 (Cyclic ADP Ribose Hydrolase 1 or T10 or 2' Phospho ADP Ribosyl Cyclase/2' Phospho Cyclic ADP Ribose Transferase or ADP Ribosyl Cyclase 1 or CD38 or EC 3.2.2.6 or EC 2.4.99.20), C Type Lectin Domain Family 14 Member A (Epidermal Growth Factor Receptor 5 or EGFR5 or CLEC14A), Hepatocyte Growth Factor Receptor (Proto Oncogene c Met or Tyrosine Protein Kinase Met or HGF/SF Receptor or Scatter Factor Receptor or MET or EC 2.7.10.1), Epithelial Cell Adhesion Molecule (Adenocarcinoma Associated Antigen or Cell Surface Glycoprotein Trop 1 or Epithelial Cell Surface Antigen or Epithelial Glycoprotein 314 or KS 1/4 Antigen or KSA or Tumor Associated Calcium Signal Transducer 1 or CD326 or EPCAM), Ganglioside GD3, Interleukin 13 Receptor Subunit Alpha 2 (Interleukin 13 Binding Protein or CD213a2 or IL13RA2); Kappa Myeloma Antigen (KMA), Lambda Myeloma Antigen (LMA), Latent Membrane Protein 1 (Protein p63 or LMP1), Melanoma Associated Antigen, Cytocytotoxic To Cells Expressing T Lymphocyte Activation Antigen CD80 (Activation B7-1 Antigen or CTLA 4 Counter Receptor B7.1 or CD80); Cytocytotoxic To Cells Expressing T Lymphocyte Activation Antigen CD86 (Activation B7-2 Antigen or CTLA 4 Counter Receptor B7.2 or CD86), Inactive Tyrosine Protein Kinase Transmembrane Receptor ROR1 (Neurotrophic Tyrosine Kinase Receptor Related 1 or ROR1 or EC 2.7.10.1), Fas Apoptotic Inhibitory Molecule 3 (IgM Fc Fragment Receptor or Regulator Of Fas Induced Apoptosis Toso or TOSO or FAIM3 or FCMR), T Cell Receptor Beta 1 Chain C Region (TRBC1), Vascular Endothelial Growth Factor Receptor 2 (Fetal Liver Kinase 1 or Kinase Insert Domain Receptor or Protein Tyrosine Kinase Receptor flk 1 or VEGFR2 or CD309 or KDR or EC 2.7.10.1), Alpha Fetoprotein (Alpha 1 Fetoprotein or Alpha Fetoglobulin or AFP), Cancer/Testis Antigen 1 (Autoimmunogenic Cancer/Testis Antigen NY ESO 1 or Cancer/Testis Antigen 6.1 or L Antigen Family Member 2 or CTAG1A or CTAG1B), T Cell Surface Glycoprotein CD5 (Lymphocyte Antigen T1/Leu 1 or CD5), Prolyl Endopeptidase FAP (170 kDa Melanoma Membrane Bound Gelatinase or Dipeptidyl Peptidase FAP or Integral Membrane Serine Protease or Fibroblast Activation Protein Alpha or Gelatine Degradation Protease FAP or Seprase or FAP or EC 3.4.21.26 or EC 3.4.14.5), Neural Cell Adhesion Molecule 1 (Antigen Recognized By Monoclonal Antibody 5.1H11 or CD56 or NCAM1), C Type Lectin Domain Family 12 Member A (Myeloid Inhibitory C Type Lectin Like Receptor or Dendritic Cell Associated Lectin 2 or C Type Lectin Like Molecule 1 or CLEC12A), Integrin Alpha V (Vitronectin Receptor Subunit Alpha or CD51 or ITGAV); Cytocytotoxic To Cells Expressing Integrin Beta 6 (ITGB6), Interleukin 13 Receptor Subunit Alpha 2 (Interleukin 13 Binding Protein or CD213a2 or IL13RA2), Trophoblast Glycoprotein (M6P1 or 5T4 Oncofetal Antigen or 5T4 Oncofetal Trophoblast Glycoprotein or Wnt Activated Inhibitory Factor 1 or TPBG), Trophoblast Glycoprotein (M6P1 or 5T4 Oncofetal Antigen or 5T4 Oncofetal Trophoblast Glycoprotein or Wnt Activated Inhibitory Factor 1 or TPBG), C Type Lectin Domain Family 12 Member A (Myeloid Inhibitory C Type Lectin Like Receptor or Dendritic Cell Associated Lectin 2 or C Type Lectin Like Molecule 1 or CLEC12A), SLAM Family Member 7 (CD319 or Membrane Protein FOAP 12 or CD2 Like Receptor Activating Cytocytotoxic Cells or Novel Ly9 or Protein 19A or CD2 Subset 1 or CS1 or SLAMF7), SLAM Family Member 7 (CD319 or Membrane Protein FOAP 12 or CD2 Like Receptor Activating Cytocytotoxic Cells or Novel Ly9 or Protein 19A or CD2 Subset 1 or CS1 or SLAMF7), immunoglobulin, Multidrug resistance-associated protein 3 (MRP3), Proto-oncogene tyrosine-protein kinase ABL1, Prostatic acid phosphatase, OY-TES-1, ACSM2A, Alpha-actinin-4, Perilipin-2, Alpha-fetoprotein, Lymphoid blast crisis oncogene (Lbc) oncoproptein, aldehyde dehydrogenase 1 family member A1 (ALDH1A1), AML, ANKRD17, NY-BR-1, Annexin II, ARHGAP17, ARHGAP30, ARID1B, Endoplasmic reticulum-resident protein, 5'-aminoimidazole-4-carboxamide-1-beta-d-ribonucleotide transfolmylase/inosinicase (AICRT/I), ATR, ATXN2, ATXN2L, BAGE1, BCL11A, Bcl-xL, Breakpoint cluster region, Survivin, Livin/ML-IAP, HM1.24, BTB domain containing 2 (BTBD2), C60RF89, Carbonic anhydrase IX, CLCA2, CRT2, CAMEL, CAN protein, Caspase-5, Caspase-8, KM-HN-1, CCDC88B, cyclin B1, Cyclin D1, CCNI, CDC2, CDC25A, CDC27, CDK12, intestinal carboxylesterase, CEP95, CHAF1A, Coactosin-like 1, CPSF, CRYBA1, TRAG-3, Macrophage colony stimulating factor, CSNK1A1, Melanoma-associated chondroitin sulfate proteoglycan (MCSP), Cathepsin H, Kita-kyushu lung cancer antigen 1, P450 1B1 or CYP1B1, DDR1, DEK oncogene, DEK-CAN, Dickkopf-1 (DKK1), DNAJC8, DSCAML1, EEF2, Elongation factor Tu GTP binding domain containing or SNRP116, EIF4EBP1, Human Mena protein, EP300, ETV5, TEL1 or ETV6, Polycomb group protein enhancer of zeste homolog 2 (EZH2), F2R, F4.2, FAM53C, Fibroblast g, rowth factor 5 or FGF5, Formin-related protein in leukocytes 1 (FMNL1), Fibromodulin (FMOD), FNDC3B, FKHR, GDP-L-fucose, GAS7, GFI1, GIGYF2, GPNMB, O, A1, GPSM3, GRK2, GRM5, H3F3A, HAUS3, HERC1, HERV-K-MEL, HIVEP2, HMGN, HMHA1, heme oxygenase-1 (HO-1), HNRPL, Heparanase, HMSD-v-encoded mHA, HSPA1A, Hsp70, HSPB 1, immediate early response gene X-1 (IEX-1), insulin-like growth factor (IGF)-II mRNA binding protein 3 (IMP-3), IP6K1, IRS2, ITGB8, JUP, RU2AS, KANSL3, KLF10, KLF2, KLK4, KMT2A, K-ras, Low density lipid receptor (LDLR), LDLR-FUT, Mac-2-binding protein, KIAA0205, LPP, LRP1, LRRC41, LSP1, LUZP1, lymphocyte antigen 6 complex locus K (LY6K), MACF1, MAP1A, MAP3K11, MAP7D1, Matrilin-2, Mcl-1, MDM2, Malic enzyme, MEF2D, MEFV, Milk fat globule membrane protein BA46 (lactadherin), Melanotransferrin, GNT-V or N-acetylglucosaminytransferase V, MIIP, MMP14, Matrix metalloproteinase-2, MORC2, Melanoma antigen p15, MUC2, MUM, MYC, MYL9, Unconventional myosin class I gene, N4BP2, NCBP3, NCOA1, NCOR2, NFATC2, NFYC, NIFK, Ninein, NPM, NPM1-ALK1, N-ras, OAS3, P polypeptide, OGT, OS-9, ErbB3-binding protein 1, PAGE-4, P21-activated serine kinase 2 (PAK2), neo-PAP, PARP12, PAX3, PAX3-FKHR, PCBP2, phosphoglycerate kinase 1 (PKG1), PLEKHM2, promyelocytic leukemia or PML, PML-RARA, POLR2A, Cyclophilin B, PPP1CA, PPP1R3B, Peroxiredoxin 5, Proteinase 3, Parathyroid hormone-related protein (PTHrP), Receptor-like protein tyrosine phosphatase kappa, MG50, NY-MEL-1 or RAB38, RAGE, RALGAPB, RAR alpha, RBM, RCSD1, Recoverin, RERE, RGS5, RHAMM/CD168, RPA1, Ribosomal protein L10a, Ribosomal protein S2, RREB 1, RSRP1, RTCB, SART, SCAP, Mammaglobin A, Secernin 1, SDCBP, SETD2, SF3B1, Renal ubiquitous protein 1, SIK1, SIRT2, SKI, hairpin-binding protein, SLC35A4, Prostein, SLC46A1, SNRPD1, SOGA1, SON, SOX10, SOX11, SOX2, SOX-4, Sperm protein 17, SPEN, SRRM2, SRSF7, SRSF8, SSX1, SSX2 or HOM-MEL-40, SSX4, STAT1, STEAP, STRAP, ART-1, SVIL, HOM-TES-14/SCP1, CD138, SYNM, SYNPO, SYT, SYT15, SYT-SSX1, SYT-SSX2, SZT2, TAPBP, TBC1D10C, TBC1D9B, hTERT, THNSL2, THOC6, TLK1, TNS3, TOP2A, TOP2B, ATP-dependent interferon-responsive (ADIR), TP53, Triosephosphate isomerase or TPI1, Tropomyosin-4, TPX2, TRG, T-cell receptor gamma alternate reading frame protein (TARP), TRIM68, Prostate-specific protein transient receptor potential-p8 (trp-p8), TSC22D4, TTK protein kinase (TTK), Thymidylate synthase (TYMS), UBE2A, Ubiquitin-conjugating enzyme variant Kua, COA-1, USB1, NA88-A, VPS13D, BING4, WHSC1L1, WHSC2, WNK2, WT1, XBP1, XPO1, ZC3H14, ZNF106, ZNF219, Papillomavirus binding factor (PBF), E3 ubiquitin-protein ligase UBR4.

T Cell Activator Domains

The T cell activator domain of the CAR T or other targeted cellular therapy can be 4-1BB, CD3, CD3 zeta, CD3 zeta cytoplasmic signalling domain and uses the natural co-stimulatory molecule DAP10, or any other appropriate T cell activator domain including but not limited to CD28, 41BB, ICOS, CD3z-CD28-41BB, CD3z-CD28-OX40, CD27 or any combination.

Production of the Antibody or Receptor to be Expressed by the Cellular Immunotherapeutic Production of the expressed receptor/ligand or antibody may be through any method including conditionally active biologics (CAB) technology. The antibody can be single chain or double chain. The antibody could be an Fc fusion protein, a Fab, F(ab')$_2$, Fab', single chain variable fragment, di-scFv, single domain antibody, tri-functional antibody, chemically linked, or bi-specific T cell engager.

Pretreatment of the Cellular Immunotherapy

In vitro or ex vivo pretreatment of the cellular immunotherapy can be done and non-exclusively relates to interleukin-1, interleukin 2, interleukin-7, interleukin-15, allogeneic PBMC, anti-CD3, anti-CD28, anti-CD3&28, HA 512-520 peptide, IL2&anti-CD3&CD28, PBMC activation, PMA/ionomycin, PHA, Con A, LPS, PWM, pokeweed mitogen, the comitogenic monoclonal antibodies (mAbs) CD2/CD2R, the superantigen staphylococcal enterotoxin B (SEB), and the specific antigen Candida albicans, SLAM, CD80 or CD86 crosslinking of CD28, dexamethasone or another steroid, or any combination of the above pretreatments.

In certain embodiments of the invention in vitro or ex vivo pretreatment of the cellular immunotherapy should exclude dexamethasone or other steroid treatments, interleukin-1, interleukin 2, interleukin-7, interleukin-15, allogeneic PBMC, anti-CD3, anti-CD28, anti-CD3&28, HA 512-520 peptide, IL2&anti-CD3&CD28, PBMC activation, PMA/ionomycin, PHA, Con A, LPS, PWM, pokeweed mitogen, the comitogenic monoclonal antibodies (mAbs) CD2/CD2R, the superantigen staphylococcal enterotoxin B (SEB), and the specific antigen Candida albicans, SLAM, CD80 or CD86 crosslinking of CD28, dexamethasone or another steroid, or any combination of the above pretreatments.

Diseases to be Treated Non-Exclusively Relates to all Cancers and Autoimmune Diseases and Infectious Diseases.

In certain embodiments of the invention a patient would be identified and/or selected who has one or more diseases of cancer or autoimmunity or infection. The following list and tables contains a list of diseases that may be used to identify and/or select a patient:

Hemophagocytic lymphohistiocytosis, multiple myeloma, allergen specific immunotherapy, autosomal dominant haploinsufficiency, anterior interosseous nerve syndrome, Churg-Strauss syndrome, Systemic vasculitis, chronic graft versus host disease, Opsoclonus-Myoclonus Syndrome, Necrotising Autoimmune Myopathy (NAM), Pulmonary Sarcomatoid carcinomas, Waldenstrom's macroglobulinaemia (WM), fertility, Behcets Disease, Alopecia areata (AA), Acute-on-chronic Liver Failure, melanoma, 'organizing bronchiolitis syndrome', encephalitis, minimal change disease, or a patient receiving Tumor flare reaction therapy or Sublingual immunotherapy (SLIT) or subcutaneous immunotherapy (SCIT), or having:

Disease (Source of Disease)

*Acinetobacter* infections (*Acinetobacter baumannii*), Actinomycosis (*Actinomyces israelii, Actinomyces gerencseriae* and *Propionibacterium propionicus*) African sleeping sickness or African trypanosomiasis (*Trypanosoma brucei*), AIDS (Acquired immunodeficiency syndrome) (Human immunodeficiency virus), Amebiasis (*Entamoeba histolytica*), Anaplasmosis (*Anaplasma* species), Angiostrongyliasis (*Angiostrongylus*), Anisakiasis (*Anisakis*), Anthrax (*Bacillus anthracis*), Arcanobacterium haemolyticum infection (*Arcanobacterium haemolyticum*), Argentine hemorrhagic fever (Junin virus), Ascariasis (*Ascaris lumbricoides*), Aspergillosis (*Aspergillus* species), Astrovirus infection (Astroviridae family), Babesiosis (*Babesia* species), *Bacillus cereus* infection (*Bacillus cereus*), Bacterial pneumonia (multiple bacteria), Bacterial vaginosis (List of bacterial vaginosis microbiota), *Bacteroides* infection (*Bacteroides* species), Balantidiasis (*Balantidium coli*), Bartonellosis (*Bartonella*), Baylisascaris infection (*Baylisascaris* species), BK virus infection (BK virus), Black *piedra* (*Piedraia hortae*), Blastocystosis (*Blastocystis* species), Blastomycosis (*Blastomyces dermatitidis*), Bolivian hemorrhagic fever (Machupo virus), Botulism (and Infant botulism) (*Clostridium botulinum*; Note: Botulism is not an infection by *Clostridium botulinum* but caused by the intake of botulinum toxin), Brazilian hemorrhagic fever (Sabiá virus), Brucellosis (*Brucella* species), Bubonic plague (the bacterial family Enterobacteriaceae), *Burkholderia* infection, usually *Burkholderia cepacia* and other *Burkholderia* species, Buruli ulcer (*Mycobacterium ulcerans*), Calicivirus infection (Norovirus and Sapovirus) (Caliciviridae family), Campylobacteriosis (*Campylobacter* species), Candidiasis (Moniliasis; Thrush) (usually *Candida albicans* and other *Candida* species), Capillariasis (Intestinal disease by *Capillaria philippinensis*, hepatic disease by *Capillaria hepatica* and pulmonary disease by *Capillaria* aerophila), Carrion's disease (*Bartonella bacilliformis*), Cat-scratch disease (*Bartonella henselae*), Cellulitis (usually Group A *Streptococcus* and *Staphylococcus*), Chagas Disease (American trypanosomiasis) (*Trypanosoma cruzi*), Chancroid (*Haemophilus ducreyi*), Chickenpox (Varicella zoster virus (VZV)), Chikungunya (*Alphavirus*), Chlamydia (*Chlamydia trachomatis*), *Chlamydophila pneumoniae* infection (Taiwan acute respiratory agent or TWAR) (*Chlamydophila pneumoniae*), Cholera (*Vibrio cholerae*), Chromoblastomycosis (usually *Fonsecaea pedrosoi*), Chytridiomycosis (*Batrachochytrium dendrabatidis*), Clonorchiasis (*Clonorchis sinensis*), *Clostridium difficile* colitis (*Clostridium difficile*), Coccidioidomycosis (*Coccidioides immitis* and *Coccidioides posadasii*), Colorado tick fever (CTF) (Colorado tick fever virus (CTFV)), Common cold (Acute viral rhinopharyngitis; Acute coryza) (usually rhinoviruses and coronaviruses), Creutzfeldt-Jakob disease (CJD) (PRNP), Crimean-Congo hemorrhagic fever (CCHF) (Crimean-Congo hemorrhagic fever virus), Cryptococcosis (*Cryptococcus neoformans*), Cryptosporidiosis (*Cryptosporidium* species), Cutaneous larva migrans (CLM) (usually *Ancylostoma braziliense*; multiple other parasites), Cyclosporiasis (*Cyclospora cayetanensis*), Cysticercosis (*Taenia solium*), Cytomegalovirus infection (Cytomegalovirus), Dengue fever (Dengue viruses (DEN-1, DEN-2, DEN-3 and DEN-4)—Flaviviruses), Desmodesmus infection (Green algae Desmodesmus armatus), Dientamoebiasis (*Dientamoeba fragilis*), Diphtheria (*Corynebacterium diphtheriae*), Diphyllobothriasis (*Diphyllobothrium*), Dracunculiasis (*Dracunculus medinensis*), Ebola hemorrhagic fever (Ebolavirus (EBOV)), Echinococcosis (*Echinococcus* species), Ehrlichiosis (*Ehrlichia* species), Enterobiasis (Pinworm infection) (*Enterobius vermicularis*), *Enterococcus* infection (*Enterococcus* species), Enterovirus infection (Enterovirus species), Epidemic typhus (*Rickettsia prowazekii*), Erythema infectiosum (Fifth disease) (Parvovirus B19), Exanthem subitum (Sixth disease) (Human herpesvirus 6 (HHV-6) and Human herpesvirus 7 (HHV-7)), Fasciolasis (*Fasciola hepatica* and *Fasciola gigantica*), Fasciolopsiasis (*Fasciolopsis buski*), Fatal familial insomnia (FFI) (PRNP), Filariasis (Filarioidea superfamily), Food poisoning by *Clostridium perfringens* (*Clostridium perfringens*), Free-living amebic infection (multiple), *Fusobacterium* infection (*Fusobacterium* species), Gas gangrene (Clostridial myonecrosis) (usually *Clostridium perfringens*; other *Clostridium* species), Geotrichosis (*Geotrichum candidum*), Gerstmann-Straussler-Scheinker syndrome (GSS) (PRNP), Giardiasis (*Giardia lamblia*) Glanders (*Burkholderia mallei*), Gnathostomiasis (*Gnathostoma spinigerum* and *Gnathostoma hispidum*), Gonorrhea (*Neisseria gonorrhoeae*), Granuloma inguinale (Donovanosis) (*Klebsiella granulomatis*), Group A streptococcal infection (*Streptococcus pyogenes*), Group B streptococcal infection (*Streptococcus agalactiae*), *Haemophilus influenzae* infection (*Haemophilus influenzae*) Hand, foot and mouth disease (HFMD) (Enteroviruses, mainly Coxsackie A virus and Enterovirus 71 (EV71)), Hantavirus Pulmonary Syndrome (HPS) (Sin Nombre virus), Heartland virus disease (Heartland virus), *Helicobacter pylori* infection (*Helicobacter pylori*), Hemolytic-uremic syndrome (HUS), *Escherichia coli* O157:H7, O111 and O104:H4, Hemorrhagic fever with renal syndrome (HFRS) (Bunyaviridae family), Hepatitis A (Hepatitis A virus), Hepatitis B (Hepatitis B virus), Hepatitis C (Hepatitis C virus), Hepatitis D (Hepatitis D Virus), Hepatitis E (Hepatitis E virus), Herpes simplex (Herpes simplex virus 1 and 2 (HSV-1 and HSV-2)), Histoplasmosis (*Histoplasma capsulatum*), Hookworm infection (*Ancylostoma duodenale* and *Necator americanus*), Human bocavirus infection (Human bocavirus (HBoV)), Human *ewingii* ehrlichiosis (*Ehrlichia ewingii*), Human granulocytic anaplasmosis (HGA) (*Anaplasma phagocytophilum*), Human metapneumovirus infection, Human metapneumovirus (hMPV), Human monocytic ehrlichiosis (*Ehrlichia chaffeensis*), Human papillomavirus (HPV) infection (Human papillomavirus (HPV)), Human parainfluenza virus infection (Human parainfluenza viruses (HPIV)), Hymenolepiasis (*Hymenolepis nana* and *Hymenolepis diminuta*), Epstein-Barr virus infectious mononucleosis (Mono) (Epstein-Barr virus (EBV)), Influenza (flu) (Orthomyxoviridae family) Isosporiasis (*Isospora belli*), Kawasaki disease (unknown; evidence supports that it is infectious) Keratitis (multiple), *Kingella kingae* infection (*Kingella kingae*), Kuru (PRNP), Lassa fever (Lassa virus), Legionellosis (Legionnaires' disease) (*Legionella pneumophila*), Legionellosis (Pontiac fever) (*Legionella pneumophila*), Leishmaniasis (*Leishmania* species), Leprosy (*Mycobacterium leprae* and *Mycobacterium lepromatosis*), Leptospirosis (*Leptospira* species), Listeriosis (*Listeria monocytogenes*), Lyme disease (Lyme borreliosis) (*Borrelia burgdorferi, Borrelia garinii*, and *Borrelia afzelii*), Lymphatic filariasis (Elephantiasis) (*Wuchereria bancrofti* and *Brugia malayi*), Lymphocytic choriomeningitis (Lymphocytic choriomeningitis virus (LCMV)), Malaria (*Plasmodium* species), Marburg hemorrhagic fever (MHF) (Marburg virus), Measles (Measles virus), Middle East respiratory syndrome (MERS) (Middle East respiratory syndrome coronavirus), Melioidosis (Whitmore's disease) (*Burkholderia pseudomallei*), Meningitis (multiple), Meningococcal disease (*Neisseria meningitidis*), Metagonimiasis (usually *Metagonimus yokagawai*), Microsporidiosis (Microsporidia phylum), Molluscum contagiosum (MC) (Molluscum contagiosum virus (MCV)), Monkeypox (Monkeypox virus), Mumps (Mumps virus), Murine typhus (Endemic typhus) (*Rickettsia typhi*), Mycoplasma pneumonia (*Mycoplasma pneumoniae*), Mycetoma (disambiguation) (numerous species of bacteria (Actinomycetoma) and fungi (Eumycetoma)), Myiasis (parasitic dipterous fly larvae), Neonatal conjunctivitis (Ophthalmia neonatorum) (most commonly *Chlamydia trachomatis* and *Neisseria gonorrhoeae*), Norovirus (children and babies) ((New) Variant Creutzfeldt-Jakob disease (vCJD, nvCJD), PRNP), Nocardiosis (usually *Nocardia asteroides* and other *Nocardia* species), Onchocerciasis (River blindness) (*Onchocerca volvulus*), Opisthorchiasis (*Opisthorchis viverrini* and *Opisthorchis felineus*), Paracoccidioidomycosis (South American blastomycosis) (*Paracoccidioides brasiliensis*), Paragonimiasis (usually *Paragonimus westermani* and other *Paragonimus* species), Pasteurellosis (*Pasteurella* species), Pediculosis capitis (Head lice) (*Pediculus humanus* capitis), Pediculosis corporis (Body lice) (*Pediculus humanus corporis*), Pediculosis pubis (Pubic lice, Crab lice) (*Phthirus pubis*), Pelvic inflammatory disease (PID) (multiple), Pertussis (Whooping cough) (*Bordetella pertussis*), Plague (*Yersinia pestis*), Pneumococcal infection (*Streptococcus pneumoniae*), *Pneumocystis* pneumonia (PCP) (*Pneumocystis jirovecii*), Pneumonia (multiple), Poliomyelitis (Poliovirus), *Prevotella* infection (*Prevotella* species), Primary amoebic meningoencephalitis (PAM) (usually *Naegleria fowleri*), Progressive multifocal leukoencephalopathy (JC virus), Psittacosis (*Chlamydophila psittaci*), Q fever (*Coxiella burnetii*), Rabies (Rabies virus), Relapsing fever (*Borrelia hermsii, Borrelia recurrentis*, and other *Borrelia* species), Respiratory syncytial virus infection (Respiratory syncytial virus (RSV)), Rhinosporidiosis (*Rhinosporidium seeberi*), Rhinovirus infection (Rhinovirus), Rickettsial infection (*Rickettsia* species), Rickettsialpox (*Rickettsia akari*), Rift Valley fever (RVF) (Rift Valley fever virus), Rocky Mountain spotted fever (RMSF) (*Rickettsia rickettsii*), Rotavirus infection (Rotavirus), Rubella (Rubella virus), Salmonellosis (*Salmonella* species), SARS (Severe Acute Respiratory Syndrome) (SARS coronavirus), Scabies (*Sarcoptes scabiei*), Schistosomiasis (*Schistosoma* species), Sepsis (multiple), Shigellosis (Bacillary dysentery) (*Shigella* species), Shingles (Herpes zoster) (Varicella zoster virus (VZV)), Smallpox (Variola) (Variola major or Variola minor), Sporotrichosis (*Sporothrix schenckii*), Staphylococcal food poisoning (*Staphylococcus* species), Staphylococcal infection (*Staphylococcus* species), Strongyloidiasis (*Strongyloides stercoralis*), Subacute sclerosing panencephalitis (Measles virus), Syphilis (*Treponema pallidum*), Taeniasis (*Taenia* species), Tetanus (Lockjaw) (*Clostridium tetani*), Tinea barbae (Barber's itch) (usually *Trichophyton* species), Tinea capitis (Ringworm of the Scalp) (usually *Trichophyton tonsurans*), Tinea corporis (Ringworm of the Body) (usually *Trichophyton* species), Tinea cruris (Jock itch) (usually Epidermophytonfloccosum, *Trichophyton rubrum*, and *Trichophyton mentagrophytes*), Tinea manum (Ringworm of the Hand) (*Trichophyton rubrum*), Tinea nigra (usually *Hortaea werneckii*), Tinea pedis (Athlete's foot) (usually *Trichophyton* species), Tinea unguium (Onychomycosis) (usually *Trichophyton* species), Tinea versicolor (*Pityriasis versicolor*) (*Malassezia* species), Toxocariasis (Ocular Larva Migrans (OLM)) (*Toxocara canis* or *Toxocara cati*), Toxocariasis (Visceral Larva Migrans (VLM)) (*Toxocara canis* or *Toxocara cati*), Trachoma (*Chlamydia trachomatis*), Toxoplasmosis (*Toxoplasma gondii*), Trichinosis (*Trichinella spiralis*), Trichomoniasis (*Trichomonas vaginalis*), Trichuriasis (Whipworm infection) (*Trichuris trichiura*), Tuberculosis (usually *Mycobacterium tuberculosis*), Tularemia (*Francisella tularensis*), Typhoid fever (*Salmonella enterica* subsp. *enterica*, serovar *typhi*), Typhus fever (*Rickettsia*), *Ureaplasma urealyticum* infection (*Ureaplasma urealyticum*), Valley fever (*Coccidioides immitis* or *Coccidioides posadasii*), Venezuelan equine encephalitis (Venezuelan equine encephalitis virus), Venezuelan hemorrhagic fever (Guanarito virus), *Vibrio vulnificus* infection (*Vibrio vulnificus*), *Vibrio parahaemolyticus* enteritis (*Vibrio parahaemolyticus*), Viral pneumonia (multiple viruses), West Nile Fever (West Nile virus), White *piedra* (Tinea blanca) (*Trichosporon beigelii*), *Yersinia pseudotuberculosis* infection (*Yersinia pseudotuberculosis*), Yersiniosis (*Yersinia enterocolitica*), Yellow fever (Yellow fever virus), Zygomycosis (Mucorales order (Mucormycosis) and Entomophthorales order (Entomophthoramycosis)) Human immunodeficiency virus [HIV] disease, HIV disease with infectious and parasitic diseases, HIV disease with mycobacterial infection, HIV disease with cytomegaloviral disease, HIV disease with other viral infections, HIV disease with candidiasis, HIV disease with other mycoses, HIV disease with Pneumocystic carinii pneumonia, HIV disease with malignant neoplasms, HIV disease with Kaposi's sarcoma, HIV disease with Burkitt's lymphoma, HIV disease with other type's of non-Hodgkin's lymphoma, HIV disease with other malignant neoplasms of lymphoid, hematopoietic and related tissue, HIV disease with multiple malignant neoplasms, HIV disease with other malignant neoplasms, HIV disease with unspecified malignant neoplasm, HIV disease with encephalopathy, HIV disease with lymphoid interstitial pneumonitis, HIV disease with wasting syndrome, HIV disease with multiple diseases classified elsewhere, HIV disease with other conditions, HIV disease Acute HIV infection syndrome, HIV disease with (persistent) generalized lymphadenopathy, HIV disease with hematological and immunological abnormalities, not elsewhere classified, HIV disease with other specified conditions, Unspecified HIV disease, Malignant neoplasm of lip, Malignant neoplasm of tonsil, Malignant neoplasm of tongue, Malignant neoplasm of gum, Malignant neoplasm of mouth, Malignant neoplasm of parotid gland, Malignant neoplasm of salivary glands, Malignant neoplasm of pharynx, Malignant neoplasm of esophagus, Malignant neoplasm of stomach, Malignant neoplasm of small intestine, Malignant neoplasm of colon, Malignant neoplasm of recto sigmoid junction, Malignant neoplasm of rectum, Malignant neoplasm of anus, Malignant neoplasm of liver, Malignant neoplasm of gallbladder, Malignant neoplasm of biliary tract, Malignant neoplasm of pancreas, Malignant neoplasm of intestinal tract, Malignant neoplasm of spleen, Malignant neoplasm of nasal cavity and middle ear, Malignant neoplasm of accessory sinuses, Malignant neoplasm of larynx, Malignant neoplasm of trachea, Malignant neoplasm of bronchus and lung, Malignant neoplasm of thymus, Malignant neoplasm of heart, mediastinum and pleura, Malignant neoplasm of sites in the respiratory system and intrathoracic organs, Malignant neoplasm of bone and articular cartilage of limbs, Malignant neoplasm of bones of skull and face, Malignant neoplasm of vertebral column, Malignant neoplasm of ribs, sternum and clavicle, Malignant neoplasm of pelvic bones, sacrum and coccyx, Malignant melanoma of skin, Malignant melanoma of lip, Malignant melanoma of eyelid, including canthus, Malignant melanoma of ear and external auricular canal, Malignant melanoma of face, Malignant melanoma of anal skin, Malignant melanoma of skin of breast, Malignant melanoma of limbs, including shoulder, Merkel cell carcinoma, Basal cell carcinoma of skin of lip, Squamous cell carcinoma of skin of lip, Other and unspecified malignant neoplasm skin/eyelid, including canthus, Malignant neoplasm skin/ear and external auric canal, Other and unspecified malignant neoplasm skin/and unspecified parts of face, Basal cell carcinoma of skin of other and unspecified parts of face, Squamous cell carcinoma of skin of and unspecified parts of face, Basal cell carcinoma of skin of scalp and neck, Squamous cell carcinoma of skin of scalp and neck, Basal cell carcinoma of skin of trunk, Basal cell carcinoma of anal skin, Basal cell carcinoma of skin of breast, Squamous cell carcinoma of skin of trunk, Squamous cell carcinoma of anal skin, Squamous cell carcinoma of skin of breast, Squamous cell carcinoma of skin of other part of trunk, Other and unspecified malignant neoplasm skin/limbs including shoulder, Basal cell carcinoma skin/limbs, including shoulder, Squamous cell carcinoma skin/limbs, including shoulder, Basal cell carcinoma of skin of limbs, including hip, Squamous cell carcinoma of skin of limbs, including hip, Mesothelioma, Kaposi's sarcoma, Malignant neoplasm of peripheral nerves and autonomic nervous sys, Malignant neoplasm of retroperitoneum and peritoneum, Malignant neoplasm of other connective and soft tissue, Malignant neoplasm of connective and soft tissue of thorax, Malignant neoplasm of connective and soft tissue of abdomen, Malignant neoplasm of connective and soft tissue of pelvis, Malignant neoplasm of conn and soft tissue of trunk, unspecified, Malignant neoplasm of overlapping sites of connective and soft tissue, Malignant neoplasm of connective and soft tissue, unspecified, Gastrointestinal stromal tumor, Malignant neoplasm of breast, Malignant neoplasm of vulva, Malignant neoplasm of vagina, Malignant neoplasm of cervix uteri, Malignant neoplasm of corpus uteri, Malignant neoplasm of uterus, part unspecified, Malignant neoplasm of ovary, Malignant neoplasm of other and unspecified female genital organs, Malignant neoplasm of placenta, Malignant neoplasm of penis, Malignant neoplasm of prostate, Malignant neoplasm of testis, Malignant neoplasm of other and unspecified male genital organs, Malignant neoplasm of kidney, Malignant neoplasm of renal pelvis, Malignant neoplasm of ureter, Malignant neoplasm of bladder, Malignant neoplasm of other and unspecified urinary organs, Malignant neoplasm of eye and adnexa, Malignant neoplasm of meninges, Malignant neoplasm of brain, Malignant neoplm of spinal cord, cranial nerves, Malignant neoplasm of optic nerve, Malignant neoplasm of other and unspecified cranial nerves, Malignant neoplasm of central nervous system, unspecified, Malignant neoplasm of thyroid gland, Malignant neoplasm of adrenal gland, Malignant neoplasm of endo glands and related structures, Malignant neuroendocrine tumors, Malignant carcinoid tumors, Secondary neuroendocrine tumors, Malignant neoplasm of head, face and neck, Malignant neoplasm of thorax, Malignant neoplasm of abdomen, Malignant neoplasm of pelvis, Malignant neoplasm of limbs, Malignant neoplasm of lower limb, Secondary and unspecified malignant neoplasm of lymph nodes, Secondary malignant neoplasm of respiratory and digestive organs, Secondary malignant neoplasm of kidney and renal pelvis, Secondary malignant neoplm of bladder and other and unspecified urinary organs, Secondary malignant neoplasm of skin, Secondary malignant neoplasm of brain and cerebral meninges, Secondary malignant neoplasm of and unspecified parts of nervous sys, Secondary malignant neoplasm of bone and bone marrow, Secondary malignant neoplasm of ovary, Secondary malignant neoplasm of adrenal gland, Hodgkin lymphoma, Follicular lymphoma, Non-follicular lymphoma, Small cell B-cell lymphoma, Mantle cell lymphoma, Diffuse large B-cell lymphoma, Lymphoblastic (diffuse) lymphoma, Burkitt lymphoma, Other non-follicular lymphoma, Non-follicular (diffuse) lymphoma, unspecified, Mature T/NK-cell lymphomas, Sezary disease, Peripheral T-cell lymphoma, not classified, Anaplastic large cell lymphoma, ALK-positive, Anaplastic large cell lymphoma, ALK-negative, Cutaneous T-cell lymphoma, unspecified, Other mature T/NK-cell lymphomas, Mature T/NK-cell lymphomas, unspecified, Other and unspecified types of non-Hodgkin lymphoma, Malignant immunoproliferative dis and certain other B-cell lymph, Multiple myeloma and malignant plasma cell neoplasms, Lymphoid leukemia, Acute lymphoblastic leukemia [ALL], Chronic lymphocytic leukemia of B-cell type, Prolymphocytic leukemia of B-cell type, Hairy cell leukemia, Adult T-cell lymphoma/leukemia (HTLV-1-associated), Prolymphocytic leukemia of T-cell type, Mature B-cell leukemia Burkitt-type, Other lymphoid leukemia, Lymphoid leukemia, unspecified, Myeloid leukemia, Acute myeloblastic leukemia, Chronic myeloid leukemia, BCR/ABL-positive, Atypical chronic myeloid leukemia, BCR/ABL-negative, Myeloid sarcoma, Acute promyelocytic leukemia, Acute myelomonocytic leukemia, Acute myeloid leukemia with 11q23-abnormality, Other myeloid leukemia, Myeloid leukemia, unspecified, Monocytic leukemia, Chronic myelomonocytic leukemia, Juvenile myelomonocytic leukemia, Other monocytic leukemia, Monocytic leukemia, unspecified, Other leukemias of specified cell type, Acute erythroid leukemia, Acute megakaryoblastic leukemia, Mast cell leukemia, Acute panmyelosis with myelofibrosis, Myelodysplastic disease, not classified, Other specified leukemias, Leukemia of unspecified cell type, Chronic leukemia of unspecified cell type, Leukemia, unspecified, Other & unspecified malignant neoplasm of lymphoid, hematopoietic tissue, Carcinoma in situ of oral cavity, esophagus and stomach, Carcinoma in situ of colon, Carcinoma in situ of recto sigmoid junction, Carcinoma in situ of rectum, Carcinoma in situ of anus and anal canal, Carcinoma in situ of other and unspecified parts of intestine, Carcinoma in situ of unspecified part of intestine, Carcinoma in situ of other parts of intestine, Carcinoma in situ of liver, gallbladder and bile ducts, Carcinoma in situ of other specified digestive organs, Carcinoma in situ of digestive organ, unspecified, Carcinoma in situ of middle ear and respiratory system, Carcinoma in situ of larynx, Carcinoma in situ of trachea, Carcinoma in situ of bronchus and lung, Carcinoma in situ of other parts of respiratory system, Melanoma in situ, Melanoma in situ of lip, Melanoma in situ of eyelid, including canthus, Melanoma in situ of ear and external auricular canal, Melanoma in situ of unspecified part of face, Melanoma in situ of scalp and neck, Melanoma in situ of trunk, Melanoma in situ of anal skin, Melanoma in situ of breast (skin) (soft tissue), Melanoma in situ of upper limb, including shoulder, Melanoma in situ of lower limb, including hip, Melanoma in situ of other sites, Carcinoma in situ of skin, Carcinoma in situ of skin of lip, Carcinoma in situ of skin of eyelid, including canthus, Carcinoma in situ skin of ear and external auricular canal, Carcinoma in situ of skin of other and unspecified parts of face, Carcinoma in situ of skin of scalp and neck, Carcinoma in situ of skin of trunk, Carcinoma in situ of skin of upper limb, including shoulder, Carcinoma in situ of skin of lower limb, including hip, Carcinoma in situ of skin of other sites, Carcinoma in situ of breast, Lobular carcinoma in situ of breast, Intraductal carcinoma in situ of breast, Other specified type of carcinoma in situ of breast, Unspecified type of carcinoma in situ of breast, Carcinoma in situ of cervix uteri, Carcinoma in situ of other parts of cervix, Carcinoma in situ of cervix, unspecified, Carcinoma in situ of other and unspecified genital organs, Carcinoma in situ of endometrium, Carcinoma in situ of vulva, Carcinoma in situ of vagina, Carcinoma in situ of other and unspecified female genital organs, Carcinoma in situ of penis, Carcinoma in situ of prostate, Carcinoma in situ of unspecified male genital organs, Carcinoma in situ of scrotum, Carcinoma in situ of other male genital organs, Carcinoma in situ of bladder, Carcinoma in situ of other and unspecified urinary organs, Carcinoma in situ of eye, Carcinoma in situ of thyroid and other endocrine glands, Benign neoplasm of mouth and pharynx, Benign neoplasm of major salivary glands, Benign neoplasm of colon, rectum, anus and anal canal, Benign neoplasm of and ill-defined parts of digestive system, Benign neoplasm of esophagus, Benign neoplasm of stomach, Benign neoplasm of duodenum, Benign neoplasm of other and unspecified parts of small intestine, Benign neoplasm of liver, Benign neoplasm of extrahepatic bile ducts, Benign neoplasm of pancreas, Benign neoplasm of endocrine pancreas, Benign neoplasm of ill-defined sites within the digestive system, Benign neoplasm of middle ear and respiratory system, Benign neoplasm of respiratory system, unspecified, Benign neoplasm of other and unspecified intrathoracic organs, Benign neoplasm of thymus, Benign neoplasm of heart, Benign neoplasm of mediastinum, Benign neoplasm of other specified intrathoracic organs, Benign neoplasm of intrathoracic organ, unspecified, Benign neoplasm of bone and articular cartilage, Benign neoplasm of short bones of upper limb, Benign neoplasm of long bones of lower limb, Benign neoplasm of short bones of lower limb, Benign neoplasm of bones of skull and face, Benign neoplasm of lower jaw bone, Benign neoplasm of vertebral column, Benign neoplasm of ribs, sternum and clavicle, Benign neoplasm of pelvic bones, sacrum and coccyx, Benign neoplasm of bone and articular cartilage, unspecified, Benign lipomatous neoplasm, Ben lipomatous neoplm of skin, subcutaneous of head, face and neck, Benign lipomatous neoplasm of intrathoracic organs, Benign lipomatous neoplasm of intra-abdominal organs, Benign lipomatous neoplasm of spermatic cord, Benign lipomatous neoplasm of other sites, Benign lipomatous neoplasm of kidney, Benign lipomatous neoplasm of other genitourinary organ, Hemangioma and lymphangioma, any site, Hemangioma, Hemangioma unspecified site, Hemangioma of skin and subcutaneous tissue, Hemangioma of intracranial structures, Hemangioma of intra-abdominal structures, Hemangioma of other sites, Lymphangioma, any site, Benign neoplasm of mesothelial tissue, Benign neoplm of soft tissue of retroperitoneum and peritoneum, Other benign neoplasms of connective and other soft tissue, Melanocytic nevi, Melanocytic nevi of lip, Melanocytic nevi of eyelid, including canthus, Melanocytic nevi of unspecified eyelid, including canthus, Melanocytic nevi of ear and external auricular canal, Melanocytic nevi of other and unspecified parts of face, Melanocytic nevi of scalp and neck, Melanocytic nevi of trunk, Melanocytic nevi of upper limb, including shoulder, Melanocytic nevi of lower limb, including hip, Melanocytic nevi, unspecified, Other benign neoplasm of skin of eyelid, including canthus, Other benign neoplasm skin/ear and external auricular canal, Other benign neoplasm skin/left ear and external auric canal, Other benign neoplasm of skin of other and unspecified parts of face, Other benign neoplasm of skin of other parts of face, Other benign neoplasm of skin of scalp and neck, Other benign neoplasm of skin of trunk, Other benign neoplasm skin/upper limb, including shoulder, Other benign neoplasm of skin of lower limb, including hip, Other benign neoplasm of skin, unspecified, Benign neoplasm of breast, Benign neoplasm of unspecified breast, Leiomyoma of uterus, Other benign neoplasms of uterus, Benign neoplasm of ovary, Benign neoplasm of other and unspecified female genital organs, Benign neoplasm of male genital organs, Benign neoplasm of urinary organs, Benign neoplasm of kidney, Benign neoplasm of renal pelvis, Benign neoplasm of ureter, Benign neoplasm of bladder, Benign neoplasm of urethra, Benign neoplasm of other specified urinary organs, Benign neoplasm of urinary organ, unspecified, Benign neoplasm of eye and adnexa, Benign neoplasm of conjunctiva, Benign neoplasm of cornea, Benign neoplasm of retina, Benign neoplasm of choroid, Benign neoplasm of ciliary body, Benign neoplasm of lacrimal gland and duct, Benign neoplasm of unspecified site of orbit, Benign neoplasm of unspecified part of eye, Benign neoplasm of meninges, Benign neoplasm of brain and central nervous system, Benign neoplasm of thyroid gland, Benign neoplasm of other and unspecified endocrine glands, Benign neoplasm of other and unspecified sites, Benign neoplasm of lymph nodes, Benign neoplasm of peripheral nerves and autonomic nervous sys, Benign neoplasm of other specified sites, Benign neuroendocrine tumors, Other benign neuroendocrine tumors, Neoplasm of uncertain behavior of oral cavity and digestive organs, Neoplasm of uncertain behavior of the major salivary glands, Neoplasm of uncertain behavior of pharynx, Neoplasm of uncertain behavior of sites of the oral cavity, Neoplasm of uncertain behavior of stomach, Neoplasm of uncertain behavior of small intestine, Neoplasm of uncertain behavior of appendix, Neoplasm of uncertain behavior of colon, Neoplasm of uncertain behavior of rectum, Neoplasm of uncertain behavior of liver, GB & bile duct, Neoplasm of uncertain behavior of other digestive organs, Neoplasm of uncertain behavior of digestive organ, Neoplm of mid ear and intrathoracic organs, Neoplasm of uncertain behavior of larynx, Neoplasm of uncertain behavior of trachea, bronchus and lung, Neoplasm of uncertain behavior of pleura, Neoplasm of uncertain behavior of mediastinum, Neoplasm of uncertain behavior of thymus, Neoplasm of uncertain behavior of other respiratory organs, Neoplasm of uncertain behavior of respiratory organ, unspecified, Neoplasm of uncertain behavior of female genital organs, Neoplasm of uncertain behavior of uterus, Neoplasm of uncertain behavior of ovary, Neoplasm of uncertain behavior of unspecified ovary, Neoplasm of uncertain behavior of placenta, Neoplasm of uncertain behavior of male genital organs, Neoplasm of uncertain behavior of urinary organs, Neoplasm of uncertain behavior of kidney, Neoplasm of uncertain behavior of unspecified kidney, Neoplasm of uncertain behavior of renal pelvis, Neoplasm of uncertain behavior of ureter, Neoplasm of uncertain behavior of bladder, Neoplasm of uncertain behavior of other urinary organs, Neoplasm of uncertain behavior of unspecified urinary organ, Neoplasm of uncertain behavior of meninges, Neoplasm of uncertain behavior of cerebral meninges, Neoplasm of uncertain behavior of spinal meninges, Neoplasm of uncertain behavior of meninges, unspecified, Neoplasm of uncertain behavior of brain, Neoplasm of uncertain behavior of brain, Neoplasm of uncertain behavior of brain, infratentorial, Neoplasm of uncertain behavior of brain, unspecified, Neoplasm of uncertain behavior of cranial nerves, Neoplasm of uncertain behavior of spinal cord, Neoplasm of uncertain behavior of central nervous system, Neoplasm of uncertain behavior of endocrine glands, Neoplasm of uncertain behavior of thyroid gland, Neoplasm of uncertain behavior of adrenal gland, Neoplasm of uncertain behavior of unspecified adrenal gland, Neoplasm of uncertain behavior of parathyroid gland, Neoplasm of uncertain behavior of pituitary gland, Neoplasm of uncertain behavior of craniopharyngeal duct, Neoplasm of uncertain behavior of pineal gland, Neoplasm of uncertain behavior of carotid body, Neoplasm of uncertain behavior of aortic body and other paraganglia, Neoplasm of uncertain behavior of unspecified endocrine gland, Polycythemia vera, Myelodysplastic syndromes, Refractory anemia without ring sideroblasts, so stated, Refractory anemia with ring sideroblasts, Refractory anemia with excess of blasts [RAEB], Myelodysplastic syndrome, unspecified, Other neoplm of uncertain behavior of lymphoid, hematopoietic tissue, Histiocytic and mast cell tumors of uncertain behavior, Chronic myeloproliferative disease, Monoclonal gammopathy, Essential (hemorrhagic) thrombocythemia, Osteomyelofibrosis, Other neoplasm of uncertain behavior of lymphoid, hematopoietic tissue, Neoplasm of uncertain behavior of lymphoid, hematopoietic & unspecified, Neoplasm of uncertain behavior of other and unspecified sites, Neoplasm of uncertain behavior of bone/artic cartilage, Neoplasm of uncertain behavior of connective/soft tissue, Neoplasm of uncertain behavior of peripheral nerves and autonomous nervous sys, Neoplasm of uncertain behavior of retroperitoneum, Neoplasm of uncertain behavior of peritoneum, Neoplasm of uncertain behavior of skin, Neoplasm of uncertain behavior of breast, Neoplasm of unspecified behavior of digestive system, Neoplasm of unspecified behavior of respiratory system, Neoplasm of unspecified behavior of bone, soft tissue, and skin, Neoplasm of unspecified behavior of breast, Neoplasm of unspecified behavior of bladder, Neoplasm of unspecified behavior of other genitourinary organs, Neoplasm of unspecified behavior of kidney, Neoplasm of unspecified behavior of other GU organ, Neoplasm of unspecified behavior of brain, Neoplasm of unspecified behavior of endo glands and other parts of nervous sys, Neoplasm of unspecified behavior of retina and choroid, Neoplasm of unspecified behavior of unspecified site, Iron deficiency anemia, Vitamin B12 deficiency anemia, Folate deficiency anemia, Protein deficiency anemia, Other megaloblastic anemias, not elsewhere classified, Scorbutic anemia, Other specified nutritional anemias, Nutritional anemia, unspecified, Anemia due to enzyme disorders, Anemia, Thalassemia, Hereditary persistence of fetal hemoglobin [HPFH], Hemoglobin E-beta thalassemia, Other thalassemia's, Thalassemia, unspecified, Sickle-cell disorders, Other hereditary hemolytic anemias, Acquired hemolytic anemia, Acquired pure red cell aplasia [erythroblastopenia], Acquired pure red cell aplasia, unspecified, Other aplastic anemias and other bone marrow failure syndromes, Drug-induced aplastic anemia, Aplastic anemia due to other external agents, Idiopathic aplastic anemia, Other aplastic anemias and other bone marrow failure syndromes, Aplastic anemia, unspecified, Acute posthemorrhagic anemia, Anemia, Disseminated intravascular coagulation, Hereditary factor VIII deficiency, Hereditary factor IX deficiency, Other coagulation defects, Acquired coagulation factor deficiency, Primary thrombophilia, Other thrombophilia, Purpura and other hemorrhagic conditions, Secondary thrombocytopenia, Thrombocytopenia, unspecified, Other specified hemorrhagic conditions, Hemorrhagic condition, unspecified, Neutropenia, Congenital agranulocytosis, Agranulocytosis secondary to cancer chemotherapy, Other drug-induced agranulocytosis, Neutropenia due to infection, Cyclic neutropenia, Other neutropenia, Other disorders of white blood cells, Genetic anomalies of leukocytes, Eosinophilia, Other specified disorders of white blood cells, Decreased white blood cell count, Lymphocytosis (symptomatic), Diseases of spleen, Methemoglobinemia, Congenital methemoglobinemia, Other methemoglobinemias, Methemoglobinemia, unspecified, Other and unspecified diseases of blood and blood-forming organs, Familial erythrocytosis, Secondary polycythemia, Other specified diseases of blood and blood-forming organs, Myelofibrosis, Heparin induced thrombocytopenia (HIT), Other specified diseases of blood and blood-forming organs, Other dis with lymphoreticular and reticulohistiocytic tissue, Intraoperative and postprocedural complications of the spleen, Immunodeficiency with predominantly antibody defects, Hereditary hypogammaglobulinemia, Nonfamilial hypogammaglobulinemia, Selective deficiency of immunoglobulin A [IgA], Selective deficiency of immunoglobulin G [IgG] subclasses, Selective deficiency of immunoglobulin M [IgM], Immunodeficiency with increased immunoglobulin M [IgM], Antibody deficiency w near-norm immunoglobulin or w hyperimmunoglobulin, Transient hypogammaglobulinemia of infancy, Other immunodeficiencies with predominantly antibody defects, Immunodeficiency with predominantly antibody defects, unspecified, Combined immunodeficiencies, Severe combined immunodeficiency with reticular dysgenesis, Severe combined immunodeficiency w low T- and B-cell numbers, Severe combined immunodeficiencies w low or normal B-cell numbers, Adenosine deaminase [ADA] deficiency, Nezelofs syndrome, Purine nucleoside phosphorylase [PNP] deficiency, Major histocompatibility complex class I deficiency, Major histocompatibility complex class II deficiency, Other combined immunodeficiencies, Combined immunodeficiency, unspecified, Immunodeficiency associated with other major defects, Wiskott-Aldrich syndrome, Di George's syndrome, Immunodeficiency with short-limbed stature, Immunodeficiency following response to Epstein-Barr virus, Hyperimmunoglobulin E [IgE] syndrome, Immunodeficiency associated with other major defects, Immunodeficiency associated with major defect, unspecified, Common variable immunodeficiency, Other immunodeficiencies, Lymphocyte function antigen-1 [LFA-1] defect, Defects in the complement system, Other specified immunodeficiencies, Sarcoidosis, Other disorders involving the immune mechanism, NEC, Polyclonal hypergammaglobulinemia, Cryoglobulinemia, Hypergammaglobulinemia, unspecified, Immune reconstitution syndrome, Mast cell activation syndrome and related disorders, Mast cell activation, unspecified, Monoclonal mast cell activation syndrome, Idiopathic mast cell activation syndrome, Secondary mast cell activation, Other mast cell activation disorder, Other disorders involving the immune mechanism, NEC, Graft-versus-host disease, Acute graft-versus-host disease, Chronic graft-versus-host disease, Acute on chronic graft-versus-host disease, Graft-versus-host disease, unspecified, Autoimmune lymphoproliferative syndrome [ALPS], Other disorders involving the immune mechanism, NEC, Disorder involving the immune mechanism, unspecified, Autoimmune thyroiditis, Type 1 diabetes mellitus, Other diabetes mellitus with other specified complication, Primary adrenocortical insufficiency, Autoimmune polyglandabular failure, Dementia in human immunodeficiency virus [HIV] disease (B22.0), Multiple sclerosis, Guillain-Barre syndrome, Myasthenia gravis without (acute) exacerbation, Myasthenia gravis with (acute) exacerbation, Cytotoxic myoneural disorders, Congenital and developmental myasthenia, Lambert-Eaton syndrome, unspecified, Lambert-Eaton syndrome in disease classified elsewhere, Other specified myoneural disorders, Myoneural disorder, unspecified, Unspecified acute and subacute iridocyclitis, Crohn's disease, Ulcerative (chronic) pancolitis, Inflammatory polyps of colon, Left sided colitis, Other ulcerative colitis without/with complications, Chronic persistent hepatitis, Chronic lobular hepatitis, Chronic active hepatitis, Other chronic hepatitis, Chronic hepatitis, unspecified, Primary biliary cirrhosis, Autoimmune hepatitis, Celiac disease, Pemphigus, Bullous pemphigoid, Cicatricial pemphigoid, Chronic bullous disease of childhood, Acquired epidermolysis bullosa, unspecified, Other acquired epidermolysis bullosa, Other pemphigoid, Psoriasis vulgaris, Other psoriatic arthropathy, Alopecia (capitis) totalis, Alopecia universalis, Ophiasis, Other alopecia areata, Alopecia areata, unspecified, Vitiligo, Felty's syndrome, Rheumatoid lung disease w rheumatoid arthritis, Rheumatoid vasculitis with rheumatoid arthritis of unspecified site, Rheumatoid vasculitis w rheumatoid arthritis, Rheumatoid heart disease w rheumatoid arthritis, Rheumatoid myopathy with rheumatoid arthritis, Rheumatoid polyneurop w rheumatoid arthritis, rheumatoid arthritis, Rheumatoid arthritis with/without rheumatoid factor, Adult-onset Still's disease, Rheumatoid bursitis, Rheumatoid nodule, Inflammatory polyarthropathy, Other specified rheumatoid arthritis, Juvenile rheumatoid arthritis, Juvenile ankylosing spondylitis, Juvenile arthritis, Wegener's granulomatosis without renal involvement, Wegener's granulomatosis with renal involvement, Juvenile dermatopolymyositis, Polymyositis, Dermatopolymyositis, Giant cell arteritis with polymyalgia rheumatica, Systemic lupus erythematosus, Endocarditis in systemic lupus erythematosus, Pericarditis in systemic lupus erythematosus, Lung involvement in systemic lupus erythematosus, Glomerular disease in systemic lupus erythematosus, Tubulo-interstitial neuropath in sys lupus erythematosus, Progressive systemic sclerosis, CR(E)ST syndrome, Systemic sclerosis, Sicca syndrome, Polymyalgia rheumatica, Systemic involvement of connective tissue, Ankylosing spondylitis, Laboratory evidence of human immunodeficiency virus [HIV].

In certain embodiments of the invention one would want to exclude and avoid treating certain patients who have one or more diseases of cancer or autoimmunity or infection in the list and tables below:

Hemophagocytic lymphohistiocytosis, multiple myeloma, allergen specific immunotherapy, autosomal dominant haploinsufficiency, anterior interosseous nerve syndrome, Churg-Strauss syndrome, Systemic vasculitis, chronic graft versus host disease, Opsoclonus-Myoclonus Syndrome, Necrotising Autoimmune Myopathy (NAM), Pulmonary Sarcomatoid carcinomas, Waldenstrom's macroglobulinaemia (WM), fertility, Behcets Disease, Alopecia areata (AA), Acute-on-chronic Liver Failure, melanoma, 'organizing bronchiolitis syndrome', encephalitis, minimal change disease, or a patient receiving Tumor flare reaction therapy or Sublingual immunotherapy (SLIT) or subcutaneous immunotherapy (SCIT), or having:

Disease (Source of Disease)

Acinetobacter infections (Acinetobacter baumannii), Actinomycosis (Actinomyces israelii, Actinomyces gerencseriae and Propionibacterium propionicus) African sleeping sickness or African trypanosomiasis (Trypanosoma brucei), AIDS (Acquired immunodeficiency syndrome) (Human immunodeficiency virus), Amebiasis (Entamoeba histolytica), Anaplasmosis (Anaplasma species), Angiostrongyliasis (Angiostrongylus), Anisakiasis (Anisakis), Anthrax (Bacillus anthracis), Arcanobacterium haemolyticum infection (Arcanobacterium haemolyticum), Argentine hemorrhagic fever (Junin virus), Ascariasis (Ascaris lumbricoides), Aspergillosis (Aspergillus species), Astrovirus infection (Astroviridae family), Babesiosis (Babesia species), Bacillus cereus infection (Bacillus cereus), Bacterial pneumonia (multiple bacteria), Bacterial vaginosis (List of bacterial vaginosis microbiota), Bacteroides infection (Bacteroides species), Balantidiasis (Balantidium coli), Bartonellosis (Bartonella), Baylisascaris infection (Baylisascaris species), BK virus infection (BK virus), Black piedra (Piedraia hortae), Blastocystosis (Blastocystis species), Blastomycosis (Blastomyces dermatitidis), Bolivian hemorrhagic fever (Machupo virus), Botulism (and Infant botulism) (Clostridium botulinum; Note: Botulism is not an infection by Clostridium botulinum but caused by the intake of botulinum toxin), Brazilian hemorrhagic fever (Sabiá virus), Brucellosis (Brucella species), Bubonic plague (the bacterial family Enterobacteriaceae), Burkholderia infection, usually Burkholderia cepacia and other Burkholderia species, Buruli ulcer (Mycobacterium ulcerans), Calicivirus infection (Norovirus and Sapovirus) (Caliciviridae family), Campylobacteriosis (Campylobacter species), Candidiasis (Moniliasis; Thrush) (usually Candida albicans and other Candida species), Capillariasis (Intestinal disease by Capillaria philippinensis, hepatic disease by Capillaria hepatica and pulmonary disease by Capillaria aerophila), Carrion's disease (Bartonella bacilliformis), Cat-scratch disease (Bartonella henselae), Cellulitis (usually Group A Streptococcus and Staphylococcus), Chagas Disease (American trypanosomiasis) (Trypanosoma cruzi), Chancroid (Haemophilus ducreyi), Chickenpox (Varicella zoster virus (VZV)), Chikungunya (Alphavirus), Chlamydia (Chlamydia trachomatis), Chlamydophila pneumoniae infection (Taiwan acute respiratory agent or TWAR) (Chlamydophila pneumoniae), Cholera (Vibrio cholerae), Chromoblastomycosis (usually Fonsecaea pedrosoi), Chytridiomycosis (Batrachochytrium dendrabatidis), Clonorchiasis (Clonorchis sinensis), Clostridium difficile colitis (Clostridium difficile), Coccidioidomycosis (Coccidioides immitis and Coccidioides posadasii), Colorado tick fever (CTF) (Colorado tick fever virus (CTFV)), Common cold (Acute viral rhinopharyngitis; Acute coryza) (usually rhinoviruses and coronaviruses), Creutzfeldt-Jakob disease (CJD) (PRNP), Crimean-Congo hemorrhagic fever (CCHF) (Crimean-Congo hemorrhagic fever virus), Cryptococcosis (Cryptococcus neoformans), Cryptosporidiosis (Cryptosporidium species), Cutaneous larva migrans (CLM) (usually Ancylostoma braziliense; multiple other parasites), Cyclosporiasis (Cyclospora cayetanensis), Cysticercosis (Taenia solium), Cytomegalovirus infection (Cytomegalovirus), Dengue fever (Dengue viruses (DEN-1, DEN-2, DEN-3 and DEN-4)—Flaviviruses), Desmodesmus infection (Green algae Desmodesmus armatus), Dientamoebiasis (Dientamoeba fragilis), Diphtheria (Corynebacterium diphtheriae), Diphyllobothriasis (Diphyllobothrium), Dracunculiasis (Dracunculus medinensis), Ebola hemorrhagic fever (Ebolavirus (EBOV)), Echinococosis (Echinococcus species), Ehrlichiosis (Ehrlichia species), Enterobiasis (Pinworm infection) (Enterobius vermicularis), Enterococcus infection (Enterococcus species), Enterovirus infection (Enterovirus species), Epidemic typhus (Rickettsia prowazekii), Erythema infectiosum (Fifth disease) (Parvovirus B19), Exanthem subitum (Sixth disease) (Human herpesvirus 6 (HHV-6) and Human herpesvirus 7 (HHV-7)), Fasciolasis (Fasciola hepatica and Fasciola gigantica), Fasciolopsiasis (Fasciolopsis buski), Fatal familial insomnia (FFI) (PRNP), Filariasis (Filarioidea superfamily), Food poisoning by Clostridium perfringens (Clostridium perfringens), Free-living amebic infection (multiple), Fusobacterium infection (Fusobacterium species), Gas gangrene (Clostridial myonecrosis) (usually Clostridium perfringens; other Clostridium species), Geotrichosis (Geotrichum candidum), Gerstmann-Straussler-Scheinker syndrome (GSS) (PRNP), Giardiasis (Giardia lamblia) Glanders (Burkholderia mallei), Gnathostomiasis (Gnathostoma spinigerum and Gnathostoma hispidum), Gonorrhea (Neisseria gonorrhoeae), Granuloma inguinale (Donovanosis) (Klebsiella granulomatis), Group A streptococcal infection (Streptococcus pyogenes), Group B streptococcal infection (Streptococcus agalactiae), Haemophilus influenzae infection (Haemophilus influenzae) Hand, foot and mouth disease (HFMD) (Enteroviruses, mainly Coxsackie A virus and Enterovirus 71 (EV71)), Hantavirus Pulmonary Syndrome (HPS) (Sin Nombre virus), Heartland virus disease (Heartland virus), Helicobacter pylori infection (Helicobacter pylori), Hemolytic-uremic syndrome (HUS), Escherichia coli O157:H7, O111 and O104:H4, Hemorrhagic fever with renal syndrome (HFRS) (Bunyaviridae family), Hepatitis A (Hepatitis A virus), Hepatitis B (Hepatitis B virus), Hepatitis C (Hepatitis C virus), Hepatitis D (Hepatitis D Virus), Hepatitis E (Hepatitis E virus), Herpes simplex (Herpes simplex virus 1 and 2 (HSV-1 and HSV-2)), Histoplasmosis (Histoplasma capsulatum), Hookworm infection (Ancylostoma duodenale and Necator americanus), Human bocavirus infection (Human bocavirus (HBoV)), Human ewingii ehrlichiosis (Ehrlichia ewingii), Human granulocytic anaplasmosis (HGA) (Anaplasma phagocytophilum), Human metapneumovirus infection, Human metapneumovirus (hMPV), Human monocytic ehrlichiosis (Ehrlichia chaffeensis), Human papillomavirus (HPV) infection (Human papillomavirus (HPV)), Human parainfluenza virus infection (Human parainfluenza viruses (HPIV)), Hymenolepiasis (Hymenolepis nana and Hymenolepis diminuta), Epstein-Barr virus infectious mononucleosis (Mono) (Epstein-Barr virus (EBV)), Influenza (flu) (Orthomyxoviridae family) Isosporiasis (Isospora belli), Kawasaki disease (unknown; evidence supports that it is infectious) Keratitis (multiple), Kingella kingae infection (Kingella kingae), Kuru (PRNP), Lassa fever (Lassa virus), Legionellosis (Legionnaires' disease) (Legionella pneumophila), Legionellosis (Pontiac fever) (Legionella pneumophila), Leishmaniasis (Leishmania species), Leprosy (Mycobacterium leprae and Mycobacterium lepromatosis), Leptospirosis (Leptospira species), Listeriosis (Listeria monocytogenes), Lyme disease (Lyme borreliosis) (*Borrelia burgdorferi, Borrelia garinii*, and *Borrelia afzelii*), Lymphatic filariasis (Elephantiasis) (*Wuchereria bancrofti* and *Brugia malayi*), Lymphocytic choriomeningitis (Lymphocytic choriomeningitis virus (LCMV)), Malaria (*Plasmodium* species), Marburg hemorrhagic fever (MHF) (Marburg virus), Measles (Measles virus), Middle East respiratory syndrome (MERS) (Middle East respiratory syndrome coronavirus), Melioidosis (Whitmore's disease) (*Burkholderia pseudomallei*), Meningitis (multiple), Meningococcal disease (*Neisseria meningitidis*), Metagonimiasis (usually *Metagonimus yokagawai*), Microsporidiosis (Microsporidia phylum), Molluscum contagiosum (MC) (Molluscum contagiosum virus (MCV)), Monkeypox (Monkeypox virus), Mumps (Mumps virus), Murine typhus (Endemic typhus) (*Rickettsia typhi*), *Mycoplasma* pneumonia (*Mycoplasma pneumoniae*), Mycetoma (disambiguation) (numerous species of bacteria (Actinomycetoma) and fungi (Eumycetoma)), Myiasis (parasitic dipterous fly larvae), Neonatal conjunctivitis (Ophthalmia neonatorum) (most commonly *Chlamydia trachomatis* and *Neisseria gonorrhoeae*), Norovirus (children and babies) ((New) Variant Creutzfeldt-Jakob disease (vCJD, nvCJD), PRNP), Nocardiosis (usually *Nocardia asteroides* and other *Nocardia* species), Onchocerciasis (River blindness) (*Onchocerca volvulus*), Opisthorchiasis (*Opisthorchis viverrini* and *Opisthorchis felineus*), Paracoccidioidomycosis (South American blastomycosis) (*Paracoccidioides brasiliensis*), Paragonimiasis (usually *Paragonimus westermani* and other *Paragonimus* species), Pasteurellosis (*Pasteurella* species), Pediculosis capitis (Head lice) (*Pediculus humanus* capitis), Pediculosis corporis (Body lice) (*Pediculus humanus* corporis), Pediculosis pubis (Pubic lice, Crab lice) (*Phthirus pubis*), Pelvic inflammatory disease (PID) (multiple), Pertussis (Whooping cough) (*Bordetella pertussis*), Plague (*Yersinia pestis*), Pneumococcal infection (*Streptococcus pneumoniae*), *Pneumocystis* pneumonia (PCP) (*Pneumocystis jirovecii*), Pneumonia (multiple), Poliomyelitis (Poliovirus), *Prevotella* infection (*Prevotella* species), Primary amoebic meningoencephalitis (PAM) (usually *Naegleria fowleri*), Progressive multifocal leukoencephalopathy (JC virus), Psittacosis (*Chlamydophila psittaci*), Q fever (*Coxiella burnetii*), Rabies (Rabies virus), Relapsing fever (*Borrelia hermsii, Borrelia recurrentis,* and other *Borrelia* species), Respiratory syncytial virus infection (Respiratory syncytial virus (RSV)), Rhinosporidiosis (*Rhinosporidium seeberi*), Rhinovirus infection (Rhinovirus), Rickettsial infection (*Rickettsia* species), Rickettsialpox (*Rickettsia akari*), Rift Valley fever (RVF) (Rift Valley fever virus), Rocky Mountain spotted fever (RMSF) (*Rickettsia rickettsii*), Rotavirus infection (Rotavirus), Rubella (Rubella virus), Salmonellosis (*Salmonella* species), SARS (Severe Acute Respiratory Syndrome) (SARS coronavirus), Scabies (*Sarcoptes scabiei*), Schistosomiasis (*Schistosoma* species), Sepsis (multiple), Shigellosis (Bacillary dysentery) (*Shigella* species), Shingles (Herpes zoster) (Varicella zoster virus (VZV)), Smallpox (Variola) (Variola major or Variola minor), Sporotrichosis (*Sporothrix schenckii*), Staphylococcal food poisoning (*Staphylococcus* species), Staphylococcal infection (*Staphylococcus* species), Strongyloidiasis (*Strongyloides stercoralis*), Subacute sclerosing panencephalitis (Measles virus), Syphilis (*Treponema pallidum*), Taeniasis (*Taenia* species), Tetanus (Lockjaw) (*Clostridium tetani*), Tinea barbae (Barber's itch) (usually *Trichophyton* species), Tinea capitis (Ringworm of the Scalp) (usually *Trichophyton tonsurans*), Tinea corporis (Ringworm of the Body) (usually *Trichophyton* species), Tinea cruris (Jock itch) (usually Epidermophytonfloccosum, *Trichophyton rubrum,* and *Trichophyton mentagrophytes*), Tinea manum (Ringworm of the Hand) (*Trichophyton rubrum*), Tinea nigra (usually *Hortaea werneckii*), Tinea pedis (Athlete's foot) (usually *Trichophyton* species), Tinea unguium (Onychomycosis) (usually *Trichophyton* species), Tinea versicolor (*Pityriasis versicolor*) (*Malassezia* species), Toxocariasis (Ocular Larva Migrans (OLM)) (*Toxocara canis* or *Toxocara cati*), Toxocariasis (Visceral Larva Migrans (VLM)) (*Toxocara canis* or *Toxocara cati*), Trachoma (*Chlamydia trachomatis*), Toxoplasmosis (*Toxoplasma gondii*), Trichinosis (*Trichinella spiralis*), Trichomoniasis (*Trichomonas vaginalis*), Trichuriasis (Whipworm infection) (*Trichuris trichiura*), Tuberculosis (usually *Mycobacterium tuberculosis*), Tularemia (*Francisella tularensis*), Typhoid fever (*Salmonella enterica* subsp. *enterica*, serovar *typhi*), Typhus fever (*Rickettsia*), *Ureaplasma urealyticum* infection (*Ureaplasma urealyticum*), Valley fever (*Coccidioides immitis* or *Coccidioides posadasii*), Venezuelan equine encephalitis (Venezuelan equine encephalitis virus), Venezuelan hemorrhagic fever (Guanarito virus), *Vibrio vulnificus* infection (*Vibrio vulnificus*), *Vibrio parahaemolyticus* enteritis (*Vibrio parahaemolyticus*), Viral pneumonia (multiple viruses), West Nile Fever (West Nile virus), White *piedra* (Tinea blanca) (*Trichosporon beigelii*), *Yersinia pseudotuberculosis* infection (*Yersinia pseudotuberculosis*), Yersiniosis (*Yersinia enterocolitica*), Yellow fever (Yellow fever virus), Zygomycosis (Mucorales order (Mucormycosis) and Entomophthorales order (Entomophthoramycosis)) Human immunodeficiency virus [HIV] disease, HIV disease with infectious and parasitic diseases, HIV disease with mycobacterial infection, HIV disease with cytomegaloviral disease, HIV disease with other viral infections, HIV disease with candidiasis, HIV disease with other mycoses, HIV disease with Pneumocystic carinii pneumonia, HIV disease with malignant neoplasms, HIV disease with Kaposi's sarcoma, HIV disease with Burkitt's lymphoma, HIV disease with other type's of non-Hodgkin's lymphoma, HIV disease with other malignant neoplasms of lymphoid, hematopoietic and related tissue, HIV disease with multiple malignant neoplasms, HIV disease with other malignant neoplasms, HIV disease with unspecified malignant neoplasm, HIV disease with encephalopathy, HIV disease with lymphoid interstitial pneumonitis, HIV disease with wasting syndrome, HIV disease with multiple diseases classified elsewhere, HIV disease with other conditions, HIV disease Acute HIV infection syndrome, HIV disease with (persistent) generalized lymphadenopathy, HIV disease with hematological and immunological abnormalities, not elsewhere classified, HIV disease with other specified conditions, Unspecified HIV disease, Malignant neoplasm of lip, Malignant neoplasm of tonsil, Malignant neoplasm of tongue, Malignant neoplasm of gum, Malignant neoplasm of mouth, Malignant neoplasm of parotid gland, Malignant neoplasm of salivary glands, Malignant neoplasm of pharynx, Malignant neoplasm of esophagus, Malignant neoplasm of stomach, Malignant neoplasm of small intestine, Malignant neoplasm of colon, Malignant neoplasm of recto sigmoid junction, Malignant neoplasm of rectum, Malignant neoplasm of anus, Malignant neoplasm of liver, Malignant neoplasm of gallbladder, Malignant neoplasm of biliary tract, Malignant neoplasm of pancreas, Malignant neoplasm of intestinal tract, Malignant neoplasm of spleen, Malignant neoplasm of nasal cavity and middle ear, Malignant neoplasm of accessory sinuses, Malignant neoplasm of larynx, Malignant neoplasm of trachea, Malignant neoplasm of bronchus and lung, Malignant neoplasm of thymus, Malignant neoplasm of heart, mediastinum and pleura, Malignant neoplasm of sites in the respiratory system and intrathoracic organs, Malignant neoplasm of bone and articular cartilage of limbs, Malignant neoplasm of bones of skull and face, Malignant neoplasm of vertebral column, Malignant neoplasm of ribs, sternum and clavicle, Malignant neoplasm of pelvic bones, sacrum and coccyx, Malignant melanoma of skin, Malignant melanoma of lip, Malignant melanoma of eyelid, including canthus, Malignant melanoma of ear and external auricular canal, Malignant melanoma of face, Malignant melanoma of anal skin, Malignant melanoma of skin of breast, Malignant melanoma of limbs, including shoulder, Merkel cell carcinoma, Basal cell carcinoma of skin of lip, Squamous cell carcinoma of skin of lip, Other and unspecified malignant neoplasm skin/eyelid, including canthus, Malignant neoplasm skin/ear and external auric canal, Other and unspecified malignant neoplasm skin/and unspecified parts of face, Basal cell carcinoma of skin of other and unspecified parts of face, Squamous cell carcinoma of skin of and unspecified parts of face, Basal cell carcinoma of skin of scalp and neck, Squamous cell carcinoma of skin of scalp and neck, Basal cell carcinoma of skin of trunk, Basal cell carcinoma of anal skin, Basal cell carcinoma of skin of breast, Squamous cell carcinoma of skin of trunk, Squamous cell carcinoma of anal skin, Squamous cell carcinoma of skin of breast, Squamous cell carcinoma of skin of other part of trunk, Other and unspecified malignant neoplasm skin/limbs including shoulder, Basal cell carcinoma skin/limbs, including shoulder, Squamous cell carcinoma skin/limbs, including shoulder, Basal cell carcinoma of skin of limbs, including hip, Squamous cell carcinoma of skin of limbs, including hip, Mesothelioma, Kaposi's sarcoma, Malignant neoplasm of peripheral nerves and autonomic nervous sys, Malignant neoplasm of retroperitoneum and peritoneum, Malignant neoplasm of other connective and soft tissue, Malignant neoplasm of connective and soft tissue of thorax, Malignant neoplasm of connective and soft tissue of abdomen, Malignant neoplasm of connective and soft tissue of pelvis, Malignant neoplasm of conn and soft tissue of trunk, unspecified, Malignant neoplasm of overlapping sites of connective and soft tissue, Malignant neoplasm of connective and soft tissue, unspecified, Gastrointestinal stromal tumor, Malignant neoplasm of breast, Malignant neoplasm of vulva, Malignant neoplasm of vagina, Malignant neoplasm of cervix uteri, Malignant neoplasm of corpus uteri, Malignant neoplasm of uterus, part unspecified, Malignant neoplasm of ovary, Malignant neoplasm of other and unspecified female genital organs, Malignant neoplasm of placenta, Malignant neoplasm of penis, Malignant neoplasm of prostate, Malignant neoplasm of testis, Malignant neoplasm of other and unspecified male genital organs, Malignant neoplasm of kidney, Malignant neoplasm of renal pelvis, Malignant neoplasm of ureter, Malignant neoplasm of bladder, Malignant neoplasm of other and unspecified urinary organs, Malignant neoplasm of eye and adnexa, Malignant neoplasm of meninges, Malignant neoplasm of brain, Malignant neoplm of spinal cord, cranial nerves, Malignant neoplasm of optic nerve, Malignant neoplasm of other and unspecified cranial nerves, Malignant neoplasm of central nervous system, unspecified, Malignant neoplasm of thyroid gland, Malignant neoplasm of adrenal gland, Malignant neoplasm of endo glands and related structures, Malignant neuroendocrine tumors, Malignant carcinoid tumors, Secondary neuroendocrine tumors, Malignant neoplasm of head, face and neck, Malignant neoplasm of thorax, Malignant neoplasm of abdomen, Malignant neoplasm of pelvis, Malignant neoplasm of limbs, Malignant neoplasm of lower limb, Secondary and unspecified malignant neoplasm of lymph nodes, Secondary malignant neoplasm of respiratory and digestive organs, Secondary malignant neoplasm of kidney and renal pelvis, Secondary malignant neoplm of bladder and other and unspecified urinary organs, Secondary malignant neoplasm of skin, Secondary malignant neoplasm of brain and cerebral meninges, Secondary malignant neoplasm of and unspecified parts of nervous sys, Secondary malignant neoplasm of bone and bone marrow, Secondary malignant neoplasm of ovary, Secondary malignant neoplasm of adrenal gland, Hodgkin lymphoma, Follicular lymphoma, Non-follicular lymphoma, Small cell B-cell lymphoma, Mantle cell lymphoma, Diffuse large B-cell lymphoma, Lymphoblastic (diffuse) lymphoma, Burkitt lymphoma, Other non-follicular lymphoma, Non-follicular (diffuse) lymphoma, unspecified, Mature T/NK-cell lymphomas, Sezary disease, Peripheral T-cell lymphoma, not classified, Anaplastic large cell lymphoma, ALK-positive, Anaplastic large cell lymphoma, ALK-negative, Cutaneous T-cell lymphoma, unspecified, Other mature T/NK-cell lymphomas, Mature T/NK-cell lymphomas, unspecified, Other and unspecified types of non-Hodgkin lymphoma, Malignant immunoproliferative dis and certain other B-cell lymph, Multiple myeloma and malignant plasma cell neoplasms, Lymphoid leukemia, Acute lymphoblastic leukemia [ALL], Chronic lymphocytic leukemia of B-cell type, Prolymphocytic leukemia of B-cell type, Hairy cell leukemia, Adult T-cell lymphoma/leukemia (HTLV-1-associated), Prolymphocytic leukemia of T-cell type, Mature B-cell leukemia Burkitt-type, Other lymphoid leukemia, Lymphoid leukemia, unspecified, Myeloid leukemia, Acute myeloblastic leukemia, Chronic myeloid leukemia, BCR/ABL-positive, Atypical chronic myeloid leukemia, BCR/ABL-negative, Myeloid sarcoma, Acute promyelocytic leukemia, Acute myelomonocytic leukemia, Acute myeloid leukemia with 11q23-abnormality, Other myeloid leukemia, Myeloid leukemia, unspecified, Monocytic leukemia, Chronic myelomonocytic leukemia, Juvenile myelomonocytic leukemia, Other monocytic leukemia, Monocytic leukemia, unspecified, Other leukemias of specified cell type, Acute erythroid leukemia, Acute megakaryoblastic leukemia, Mast cell leukemia, Acute panmyelosis with myelofibrosis, Myelodysplastic disease, not classified, Other specified leukemias, Leukemia of unspecified cell type, Chronic leukemia of unspecified cell type, Leukemia, unspecified, Other & unspecified malignant neoplasm of lymphoid, hematopoietic tissue, Carcinoma in situ of oral cavity, esophagus and stomach, Carcinoma in situ of colon, Carcinoma in situ of recto sigmoid junction, Carcinoma in situ of rectum, Carcinoma in situ of anus and anal canal, Carcinoma in situ of other and unspecified parts of intestine, Carcinoma in situ of unspecified part of intestine, Carcinoma in situ of other parts of intestine, Carcinoma in situ of liver, gallbladder and bile ducts, Carcinoma in situ of other specified digestive organs, Carcinoma in situ of digestive organ, unspecified, Carcinoma in situ of middle ear and respiratory system, Carcinoma in situ of larynx, Carcinoma in situ of trachea, Carcinoma in situ of bronchus and lung, Carcinoma in situ of other parts of respiratory system, Melanoma in situ, Melanoma in situ of lip, Melanoma in situ of eyelid, including canthus, Melanoma in situ of ear and external auricular canal, Melanoma in situ of unspecified part of face, Melanoma in situ of scalp and neck, Melanoma in situ of trunk, Melanoma in situ of anal skin, Melanoma in situ of breast (skin) (soft tissue), Melanoma in situ of upper limb, including shoulder, Melanoma in situ of lower limb, including hip, Melanoma in situ of other sites, Carcinoma in situ of skin, Carcinoma in situ of skin of lip, Carcinoma in situ of skin of eyelid, including canthus, Carcinoma in situ skin of ear and external auricular canal, Carcinoma in situ of skin of other and unspecified parts of face, Carcinoma in situ of skin of scalp and neck, Carcinoma in situ of skin of trunk, Carcinoma in situ of skin of upper limb, including shoulder, Carcinoma in situ of skin of lower limb, including hip, Carcinoma in situ of skin of other sites, Carcinoma in situ of breast, Lobular carcinoma in situ of breast, Intraductal carcinoma in situ of breast, Other specified type of carcinoma in situ of breast, Unspecified type of carcinoma in situ of breast, Carcinoma in situ of cervix uteri, Carcinoma in situ of other parts of cervix, Carcinoma in situ of cervix, unspecified, Carcinoma in situ of other and unspecified genital organs, Carcinoma in situ of endometrium, Carcinoma in situ of vulva, Carcinoma in situ of vagina, Carcinoma in situ of other and unspecified female genital organs, Carcinoma in situ of penis, Carcinoma in situ of prostate, Carcinoma in situ of unspecified male genital organs, Carcinoma in situ of scrotum, Carcinoma in situ of other male genital organs, Carcinoma in situ of bladder, Carcinoma in situ of other and unspecified urinary organs, Carcinoma in situ of eye, Carcinoma in situ of thyroid and other endocrine glands, Benign neoplasm of mouth and pharynx, Benign neoplasm of major salivary glands, Benign neoplasm of colon, rectum, anus and anal canal, Benign neoplasm of and ill-defined parts of digestive system, Benign neoplasm of esophagus, Benign neoplasm of stomach, Benign neoplasm of duodenum, Benign neoplasm of other and unspecified parts of small intestine, Benign neoplasm of liver, Benign neoplasm of extrahepatic bile ducts, Benign neoplasm of pancreas, Benign neoplasm of endocrine pancreas, Benign neoplasm of ill-defined sites within the digestive system, Benign neoplasm of middle ear and respiratory system, Benign neoplasm of respiratory system, unspecified, Benign neoplasm of other and unspecified intrathoracic organs, Benign neoplasm of thymus, Benign neoplasm of heart, Benign neoplasm of mediastinum, Benign neoplasm of other specified intrathoracic organs, Benign neoplasm of intrathoracic organ, unspecified, Benign neoplasm of bone and articular cartilage, Benign neoplasm of short bones of upper limb, Benign neoplasm of long bones of lower limb, Benign neoplasm of short bones of lower limb, Benign neoplasm of bones of skull and face, Benign neoplasm of lower jaw bone, Benign neoplasm of vertebral column, Benign neoplasm of ribs, sternum and clavicle, Benign neoplasm of pelvic bones, sacrum and coccyx, Benign neoplasm of bone and articular cartilage, unspecified, Benign lipomatous neoplasm, Ben lipomatous neoplm of skin, subcutaneous of head, face and neck, Benign lipomatous neoplasm of intrathoracic organs, Benign lipomatous neoplasm of intra-abdominal organs, Benign lipomatous neoplasm of spermatic cord, Benign lipomatous neoplasm of other sites, Benign lipomatous neoplasm of kidney, Benign lipomatous neoplasm of other genitourinary organ, Hemangioma and lymphangioma, any site, Hemangioma, Hemangioma unspecified site, Hemangioma of skin and subcutaneous tissue, Hemangioma of intracranial structures, Hemangioma of intra-abdominal structures, Hemangioma of other sites, Lymphangioma, any site, Benign neoplasm of mesothelial tissue, Benign neoplm of soft tissue of retroperitoneum and peritoneum, Other benign neoplasms of connective and other soft tissue, Melanocytic nevi, Melanocytic nevi of lip, Melanocytic nevi of eyelid, including canthus, Melanocytic nevi of unspecified eyelid, including canthus, Melanocytic nevi of ear and external auricular canal, Melanocytic nevi of other and unspecified parts of face, Melanocytic nevi of scalp and neck, Melanocytic nevi of trunk, Melanocytic nevi of upper limb, including shoulder, Melanocytic nevi of lower limb, including hip, Melanocytic nevi, unspecified, Other benign neoplasm of skin of eyelid, including canthus, Other benign neoplasm skin/ear and external auricular canal, Other benign neoplasm skin/left ear and external auric canal, Other benign neoplasm of skin of other and unspecified parts of face, Other benign neoplasm of skin of other parts of face, Other benign neoplasm of skin of scalp and neck, Other benign neoplasm of skin of trunk, Other benign neoplasm skin/ upper limb, including shoulder, Other benign neoplasm of skin of lower limb, including hip, Other benign neoplasm of skin, unspecified, Benign neoplasm of breast, Benign neoplasm of unspecified breast, Leiomyoma of uterus, Other benign neoplasms of uterus, Benign neoplasm of ovary, Benign neoplasm of other and unspecified female genital organs, Benign neoplasm of male genital organs, Benign neoplasm of urinary organs, Benign neoplasm of kidney, Benign neoplasm of renal pelvis, Benign neoplasm of ureter, Benign neoplasm of bladder, Benign neoplasm of urethra, Benign neoplasm of other specified urinary organs, Benign neoplasm of urinary organ, unspecified, Benign neoplasm of eye and adnexa, Benign neoplasm of conjunctiva, Benign neoplasm of cornea, Benign neoplasm of retina, Benign neoplasm of choroid, Benign neoplasm of ciliary body, Benign neoplasm of lacrimal gland and duct, Benign neoplasm of unspecified site of orbit, Benign neoplasm of unspecified part of eye, Benign neoplasm of meninges, Benign neoplasm of brain and central nervous system, Benign neoplasm of thyroid gland, Benign neoplasm of other and unspecified endocrine glands, Benign neoplasm of other and unspecified sites, Benign neoplasm of lymph nodes, Benign neoplasm of peripheral nerves and autonomic nervous sys, Benign neoplasm of other specified sites, Benign neuroendocrine tumors, Other benign neuroendocrine tumors, Neoplasm of uncertain behavior of oral cavity and digestive organs, Neoplasm of uncertain behavior of the major salivary glands, Neoplasm of uncertain behavior of pharynx, Neoplasm of uncertain behavior of sites of the oral cavity, Neoplasm of uncertain behavior of stomach, Neoplasm of uncertain behavior of small intestine, Neoplasm of uncertain behavior of appendix, Neoplasm of uncertain behavior of colon, Neoplasm of uncertain behavior of rectum, Neoplasm of uncertain behavior of liver, GB & bile duct, Neoplasm of uncertain behavior of other digestive organs, Neoplasm of uncertain behavior of digestive organ, Neoplm of mid ear and intrathoracic organs, Neoplasm of uncertain behavior of larynx, Neoplasm of uncertain behavior of trachea, bronchus and lung, Neoplasm of uncertain behavior of pleura, Neoplasm of uncertain behavior of mediastinum, Neoplasm of uncertain behavior of thymus, Neoplasm of uncertain behavior of other respiratory organs, Neoplasm of uncertain behavior of respiratory organ, unspecified, Neoplasm of uncertain behavior of female genital organs, Neoplasm of uncertain behavior of uterus, Neoplasm of uncertain behavior of ovary, Neoplasm of uncertain behavior of unspecified ovary, Neoplasm of uncertain behavior of placenta, Neoplasm of uncertain behavior of male genital organs, Neoplasm of uncertain behavior of urinary organs, Neoplasm of uncertain behavior of kidney, Neoplasm of uncertain behavior of unspecified kidney, Neoplasm of uncertain behavior of renal pelvis, Neoplasm of uncertain behavior of ureter, Neoplasm of uncertain behavior of bladder, Neoplasm of uncertain behavior of other urinary organs, Neoplasm of uncertain behavior of unspecified urinary organ, Neoplasm of uncertain behavior of meninges, Neoplasm of uncertain behavior of cerebral meninges, Neoplasm of uncertain behavior of spinal meninges, Neoplasm of uncertain behavior of meninges, unspecified, Neoplasm of uncertain behavior of brain, Neoplasm of uncertain behavior of brain, Neoplasm of uncertain behavior of brain, infratentorial, Neoplasm of uncertain behavior of brain, unspecified, Neoplasm of uncertain behavior of cranial nerves, Neoplasm of uncertain behavior of spinal cord, Neoplasm of uncertain behavior of central nervous system, Neoplasm of uncertain behavior of endocrine glands, Neoplasm of uncertain behavior of thyroid gland, Neoplasm of uncertain behavior of adrenal gland, Neoplasm of uncertain behavior of unspecified adrenal gland, Neoplasm of uncertain behavior of parathyroid gland, Neoplasm of uncertain behavior of pituitary gland, Neoplasm of uncertain behavior of craniopharyngeal duct, Neoplasm of uncertain behavior of pineal gland, Neoplasm of uncertain behavior of carotid body, Neoplasm of uncertain behavior of aortic body and other paraganglia, Neoplasm of uncertain behavior of unspecified endocrine gland, Polycythemia vera, Myelodysplastic syndromes, Refractory anemia without ring sideroblasts, so stated, Refractory anemia with ring sideroblasts, Refractory anemia with excess of blasts [RAEB], Myelodysplastic syndrome, unspecified, Other neoplm of uncertain behavior of lymphoid, hematopoietic tissue, Histiocytic and mast cell tumors of uncertain behavior, Chronic myeloproliferative disease, Monoclonal gammopathy, Essential (hemorrhagic) thrombocythemia, Osteomyelofibrosis, Other neoplasm of uncertain behavior of lymphoid, hematopoietic tissue, Neoplasm of uncertain behavior of lymphoid, hematopoietic & unspecified, Neoplasm of uncertain behavior of other and unspecified sites, Neoplasm of uncertain behavior of bone/artic cartilage, Neoplasm of uncertain behavior of connective/soft tissue, Neoplasm of uncertain behavior of peripheral nerves and autonomous nervous sys, Neoplasm of uncertain behavior of retroperitoneum, Neoplasm of uncertain behavior of peritoneum, Neoplasm of uncertain behavior of skin, Neoplasm of uncertain behavior of breast, Neoplasm of unspecified behavior of digestive system, Neoplasm of unspecified behavior of respiratory system, Neoplasm of unspecified behavior of bone, soft tissue, and skin, Neoplasm of unspecified behavior of breast, Neoplasm of unspecified behavior of bladder, Neoplasm of unspecified behavior of other genitourinary organs, Neoplasm of unspecified behavior of kidney, Neoplasm of unspecified behavior of other GU organ, Neoplasm of unspecified behavior of brain, Neoplasm of unspecified behavior of endo glands and other parts of nervous sys, Neoplasm of unspecified behavior of retina and choroid, Neoplasm of unspecified behavior of unspecified site, Iron deficiency anemia, Vitamin B12 deficiency anemia, Folate deficiency anemia, Protein deficiency anemia, Other megaloblastic anemias, not elsewhere classified, Scorbutic anemia, Other specified nutritional anemias, Nutritional anemia, unspecified, Anemia due to enzyme disorders, Anemia, Thalassemia, Hereditary persistence of fetal hemoglobin [HPFH], Hemoglobin E-beta thalassemia, Other thalassemia's, Thalassemia, unspecified, Sickle-cell disorders, Other hereditary hemolytic anemias, Acquired hemolytic anemia, Acquired pure red cell aplasia [erythroblastopenia], Acquired pure red cell aplasia, unspecified, Other aplastic anemias and other bone marrow failure syndromes, Drug-induced aplastic anemia, Aplastic anemia due to other external agents, Idiopathic aplastic anemia, Other aplastic anemias and other bone marrow failure syndromes, Aplastic anemia, unspecified, Acute posthemorrhagic anemia, Anemia, Disseminated intravascular coagulation, Hereditary factor VIII deficiency, Hereditary factor IX deficiency, Other coagulation defects, Acquired coagulation factor deficiency, Primary thrombophilia, Other thrombophilia, Purpura and other hemorrhagic conditions, Secondary thrombocytopenia, Thrombocytopenia, unspecified, Other specified hemorrhagic conditions, Hemorrhagic condition, unspecified, Neutropenia, Congenital agranulocytosis, Agranulocytosis secondary to cancer chemotherapy, Other drug-induced agranulocytosis, Neutropenia due to infection, Cyclic neutropenia, Other neutropenia, Other disorders of white blood cells, Genetic anomalies of leukocytes, Eosinophilia, Other specified disorders of white blood cells, Decreased white blood cell count, Lymphocytosis (symptomatic), Diseases of spleen, Methemoglobinemia, Congenital methemoglobinemia, Other methemoglobinemias, Methemoglobinemia, unspecified, Other and unspecified diseases of blood and blood-forming organs, Familial erythrocytosis, Secondary polycythemia, Other specified diseases of blood and blood-forming organs, Myelofibrosis, Heparin induced thrombocytopenia (HIT), Other specified diseases of blood and blood-forming organs, Other dis with lymphoreticular and reticulohistiocytic tissue, Intraoperative and postprocedural complications of the spleen, Immunodeficiency with predominantly antibody defects, Hereditary hypogammaglobulinemia, Nonfamilial hypogammaglobulinemia, Selective deficiency of immunoglobulin A [IgA], Selective deficiency of immunoglobulin G [IgG] subclasses, Selective deficiency of immunoglobulin M [IgM], Immunodeficiency with increased immunoglobulin M [IgM], Antibody deficiency w near-norm immunoglobulin or w hyperimmunoglobulin, Transient hypogammaglobulinemia of infancy, Other immunodeficiencies with predominantly antibody defects, Immunodeficiency with predominantly antibody defects, unspecified, Combined immunodeficiencies, Severe combined immunodeficiency with reticular dysgenesis, Severe combined immunodeficiency w low T- and B-cell numbers, Severe combined immunodeficiencies w low or normal B-cell numbers, Adenosine deaminase [ADA] deficiency, Nezelofs syndrome, Purine nucleoside phosphorylase [PNP] deficiency, Major histocompatibility complex class I deficiency, Major histocompatibility complex class II deficiency, Other combined immunodeficiencies, Combined immunodeficiency, unspecified, Immunodeficiency associated with other major defects, Wiskott-Aldrich syndrome, Di George's syndrome, Immunodeficiency with short-limbed stature, Immunodeficiency following response to Epstein-Barr virus, Hyperimmunoglobulin E [IgE] syndrome, Immunodeficiency associated with other major defects, Immunodeficiency associated with major defect, unspecified, Common variable immunodeficiency, Other immunodeficiencies, Lymphocyte function antigen-1 [LFA-1] defect, Defects in the complement system, Other specified immunodeficiencies, Sarcoidosis, Other disorders involving the immune mechanism, NEC, Polyclonal hypergammaglobulinemia, Cryoglobulinemia, Hypergammaglobulinemia, unspecified, Immune reconstitution syndrome, Mast cell activation syndrome and related disorders, Mast cell activation, unspecified, Monoclonal mast cell activation syndrome, Idiopathic mast cell activation syndrome, Secondary mast cell activation, Other mast cell activation disorder, Other disorders involving the immune mechanism, NEC, Graft-versus-host disease, Acute graft-versus-host disease, Chronic graft-versus-host disease, Acute on chronic graft-versus-host disease, Graft-versus-host disease, unspecified, Autoimmune lymphoproliferative syndrome [ALPS], Other disorders involving the immune mechanism, NEC, Disorder involving the immune mechanism, unspecified, Autoimmune thyroiditis, Type 1 diabetes mellitus, Other diabetes mellitus with other specified complication, Primary adrenocortical insufficiency, Autoimmune polyglandabular failure, Dementia in human immunodeficiency virus [HIV] disease (B22.0), Multiple sclerosis, Guillain-Barre syndrome, Myasthenia gravis without (acute) exacerbation, Myasthenia gravis with (acute) exacerbation, Cytotoxic myoneural disorders, Congenital and developmental myasthenia, Lambert-Eaton syndrome, unspecified, Lambert-Eaton syndrome in disease classified elsewhere, Other specified myoneural disorders, Myoneural disorder, unspecified, Unspecified acute and subacute iridocyclitis, Crohn's disease, Ulcerative (chronic) pancolitis, Inflammatory polyps of colon, Left sided colitis, Other ulcerative colitis without/with complications, Chronic persistent hepatitis, Chronic lobular hepatitis, Chronic active hepatitis, Other chronic hepatitis, Chronic hepatitis, unspecified, Primary biliary cirrhosis, Autoimmune hepatitis, Celiac disease, Pemphigus, Bullous pemphigoid, Cicatricial pemphigoid, Chronic bullous disease of childhood, Acquired epidermolysis bullosa, unspecified, Other acquired epidermolysis bullosa, Other pemphigoid, Psoriasis vulgaris, Other psoriatic arthropathy, Alopecia (capitis) totalis, Alopecia universalis, Ophiasis, Other alopecia areata, Alopecia areata, unspecified, Vitiligo, Felty's syndrome, Rheumatoid lung disease w rheumatoid arthritis, Rheumatoid vasculitis with rheumatoid arthritis of unspecified site, Rheumatoid vasculitis w rheumatoid arthritis, Rheumatoid heart disease w rheumatoid arthritis, Rheumatoid myopathy with rheumatoid arthritis, Rheumatoid polyneurop w rheumatoid arthritis, rheumatoid arthritis, Rheumatoid arthritis with/without rheumatoid factor, Adult-onset Still's disease, Rheumatoid bursitis, Rheumatoid nodule, Inflammatory polyarthropathy, Other specified rheumatoid arthritis, Juvenile rheumatoid arthritis, Juvenile ankylosing spondylitis, Juvenile arthritis, Wegener's granulomatosis without renal involvement, Wegener's granulomatosis with renal involvement, Juvenile dermatopolymyositis, Polymyositis, Dermatopolymyositis, Giant cell arteritis with polymyalgia rheumatica, Systemic lupus erythematosus, Endocarditis in systemic lupus erythematosus, Pericarditis in systemic lupus erythematosus, Lung involvement in systemic lupus erythematosus, Glomerular disease in systemic lupus erythematosus, Tubulo-interstitial neuropath in sys lupus erythematosus, Progressive systemic sclerosis, CR(E)ST syndrome, Systemic sclerosis, Sicca syndrome, Polymyalgia rheumatica, Systemic involvement of connective tissue, Ankylosing spondylitis, Laboratory evidence of human immunodeficiency virus [HIV].

Route of Administration

In certain embodiments of the invention the cellular immunotherapy may be administered to the patient by the following but not limiting routes: via nasal submucosa, lingual, via bronchoscopy, intravenous, intra-tumor, intra-arterial, intra-muscular, intro-ocular, intra-striatal, subcutaneous, intradermal, by dermal patch, by skin patch, by patch, into the cerebrospinal fluid, intra-peritoneal, into the portal vein, into the spleen, into the brain, into the lymphatic system, intra-pleural, retro-orbital, intralymphatic, intra-dermal, by systemic among others. The cellular immunotherapy can be administered by systemic injection or site of injection as defined previously.

In certain embodiments of the present invention applications to apply the cellular immunotherapies directly to an organ or tumor non-exclusively relates to collagen matrices, extracellular matrix compositions, biopolymer microthreads made of fibrin or other extracellular matrix material, patches containing extracellular matrix and biodegradable materials, fibrin patches, alginateor agarose based patches, scaffolds composed of extracellular matrix materials and biodegradable physiologically inert material that could non-exclusively relates tocomponents such as dextrans, coating stem cells with organ specific antigens or binding molecules, remnant extracellular matrices also known as scaffolds or decellularized organs from ex vivo digested organ donors or cadaveric organs, and contact lenses among others.

Catheter based delivery systems that can be used to deliver cellular immunotherapies non-exclusively relates tostandard balloon angioplasty infusion catheters, percutaneous coronary artery delivery catheters, stop flow inflations of over-the-wire balloon catheters, Swan Ganz type catheters, Hickman type catheters, Foley type catheters, central venous catheters, pigtail type catheters, SmartPort® systems, metal-tipped magnet guided catheters such as the Gentle Touch™ Magnetic Navigation System developed by Stereotaxis Inc or Mitralign, the Accucinch System®, and by catheters that inject directly into an organ such as the HELIX™, the MyoCath™, NOGA R-guided Myostar™, the Stiletto™, or the intravascular ultrasound (IVUS) guided TransAccess Delivery System™, or catheters that deliver via arterial routes such as the OpenSail™, Concerto™, Microsyringe infusion catheter from Mercator, and Maverick™, or via implantable device therapies such left ventricular assist devices (LVADs), biventricular assist devices (Bi-VADs), the Optimizer™, cell-delivery catheters such as described in US 2009/0299269.

In administering the antibody therapeutic agents that inhibit binding of the cellular immunotherapies to secondary lymphatic tissue it is preferable to administer them systemically, repeatedly about three weeks before administering the cellular immunotherapy. In administering the small molecule therapeutic agents that inhibit binding of the cellular immunotherapies to secondary lymphatic tissue it is preferable to administer them systemically, repeatedly for about 1 to about 4 weeks. For dexamethasone containing agents it is preferable to administer them systemically about 12 to about 72 hours before administering the cellular immunotherapy and most preferable to administer dexamethasone containing NTLA systemically about 36 to about 48 hours before administering the cellular immunotherapy.

Example 1: T Cell Immunotherapies Bind to the Germinal Center and Marginal Zone Regions of the Spleen and Secondary Lymphatics and the Binding is Reduced by NTLA Dexamethasone Dosing Mice are IV injected with NK cells isolated from syngeneic mice (using commercially available kits), with NK cell line KIL (from ATCC), with CD4+/CD8+ mixtures of T cells isolated from syngeneic mice (using commercially available kits) or with other ACTs, labeled with vital dyes such as DiR and CTO. Mice are intravenously injected by tail vein with between about $1\times10^5$ cells/kg to about $1\times10^7$ cells/kg. Between 1 to 48 hours later mice are sacrificed by exsanguination and then residual blood cells flushed out with 5 U heparin/ml PBS via retrograde flush into the thoracic jugular vein. The spleens are removed, weighed wet, and then fixed in 10% formalin. Subsequently the spleens are sectioned via proprietary methods that do not fix or later the temperature of the spleen, and then incubated with FITC-PNA to co-label germinal centers or FITC-anti-CD21 (10 ugs) to colabel marginal zones at 4 deg C. for 24 hours, are washed, placed on slides and immunofluorescent images are captured. Metamorph software is used to quantify the immunofluorescent signal. T cell, NK cell and KIL binding fluorescence co-localizes with FITC-PNA and FITC-anti-CD21 fluorescence, indicating the cells are sequestered in the marginal zones and germinal centers of the secondary lymphatics.

C57B1/6 male mice weighing approximately 25 gms were treated orally on day −2 with Placebo or HED 12 mg/kg Dexamethasone. Naïve T cells were isolated on day −1 from the spleens of donor C57B1/6 mice using EasySep™ Mouse Pan-Naïve T Cell Isolation Kits from Miltenyi. The resulting CD4+/CD8+ T cells were incubated overnight at 37 degree C. in 5% $CO_2$. On day 0, fresh CMPTX dye solution was made for a concentration of 5 µM. T cells isolated on day −1 were incubated with CMPTX dye solution for 40 minutes at 37 degrees C. in 5% $CO_2$. Mice treated orally on day −2 were each tail vein injected with 5M labeled T cells in 80 uls volume. Three hours later the mice were euthanized by exsanguination, spleens were weighed and then cut into thick sections to visual T cell binding regions. The spleen sections were incubated overnight at 4 degrees with FITC-PNA to label germinal centers and anti-CD21/CD35 to label marginal zones. The next day the sections were rinsed, fixed with 4% PFA/PBS 5% sucrose and images were collected using an EVOS fluorescent microscope.

The labeled T cells were visualized bound in clusters on germinal centers and marginal zone areas of the spleen sections. Compared to Placebo treated mice, the spleens from Dexamethasone pretreated mice were significantly smaller and T cell total binding measured by fluorescence intensity was dramatically reduced.

C57B1/6 male mice weighing approximately 25 gms were treated orally on day −2 with Placebo or HED 12 mg/kg Dexamethasone. Splenic NK cells were isolated on day −1 from the spleens of donor C57B1/6 mice using MojoSort™ Mouse NK Cell Isolation Kit from BioLegend. The resulting NK cells were incubated overnight at 37 degree C. in 5% $CO_2$. On day 0, fresh CMPTX dye solution was made for a concentration of 5 µM. NK cells isolated on day −1 were incubated with CMPTX dye solution for 40 minutes at 37 degrees C. in 5% $CO_2$. Mice treated orally on day −2 were each tail vein injected with 3M labeled NK cells in 80 uls volume. Three hours later the mice were euthanized by exsanguination, spleens were weighed and then cut into thick sections to visual NK cell binding regions. The sections were rinsed, fixed with 4% PFA/PBS 5% sucrose and images were collected using an EVOS fluorescent microscope.

The labeled NK cells were visualized bound in clusters along marginal zone areas of the spleen sections. Compared to Placebo treated mice, the spleens from Dexamethasone pretreated mice were significantly smaller and NK cell total binding measured by fluorescence intensity was dramatically reduced.

Example 2: Immunesuppressant Reduction of the Sites in the Secondary Lymphatics where Cellular Immunotherapies are Bound and Sequestered For mice, male mice were intraperitoneally injected with dexamethasone sodium phosphate for 114.6 mg/kg dexamethasone base (HED 9.32 mg/kg) day 0 and were sacrificed 96 hours after the dexamethasone injection. Acute high dose Dexamethasone is also referred to herein as Dex, AugmenStem™, PlenaStem™ or AVM0703. The mice were sacrificed by exsanguination and then residual blood cells flushed out with 5 U heparin/ml PBS via retrograde flush into the thoracic jugular vein. The spleens were removed, weighed wet, and then fixed in 10% formalin. Subsequently the spleens were sectioned via proprietary methods and then incubated with FITC-PNA at 4 deg C. for 24 hours, washed, placed on slides and immunofluorescent images were captured. Metamorph software was used to quantify the immunofluorescent signal. Sample images and the results, normalized to spleen area, are shown in FIG. 1. Control mice have significant FITC-PNA immunofluorescence, while mice who were injected with dexamethasone sodium phosphate have almost no immunoflurescent signal. FITC-PNA labels germinal centers, the site where cellular immunotherapies bind in the secondary lymphatics, which nonexclusively relates to the spleen and lymph nodes. This example demonstrates that cellular immunotherapies cannot bind and sequester in the secondary lymphatics after being treated with an immunesuppressant at effective doses to eliminate germinal centers. When the cellular immunotherapies cannot bind to the secondary lymphatics they remain at the site of injection or in the circulation for extended periods of time where they are able to locate and kill their cancer, autoimmune cell or pathogenic target. Additionally, long term engraftment of the cellular immunotherapy is enhanced.

Figure 2:
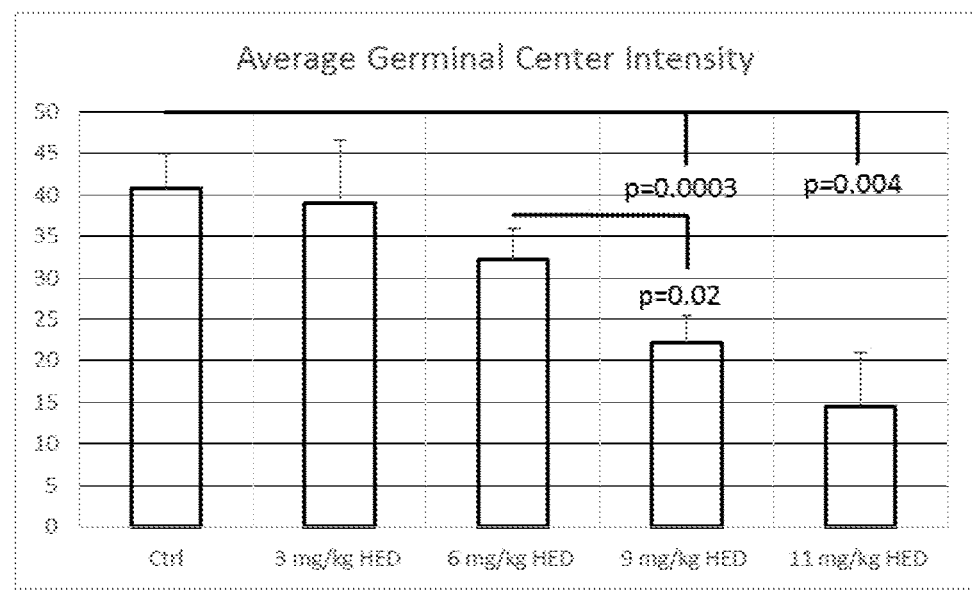
FIG. 2: Acute high dose Dex dose-dependently eliminates ACT binding niches in the mouse spleen. A graph of column plots of average Germinal Center staining intensity measured using immunofluorescent staining of fresh tichk spleen sections stained with FITC-PNA is shown. Immunofluorescent intensity was calculated using thresholding and MetaMorph Image Analysis. Columns are average plus SEM. The mice were administered placebo, 3 mg/kg HED dexamethasone base, 6 mg/kg HED dexamethasone base, 9 mg/kg HED dexamethasone base or 12 mg/kg HED dexamethasone base 48 hours before spleen harvest.

FIG. 2 shows the dose response of acute high dose Dexamethasone (in HED) effect on germinal center number in spleens of mice. Germinal center reduction is apparent at HED 6 mg/kg but not significantly reduced until HED of 9 and 12 mg/kg doses.

Figure 3:
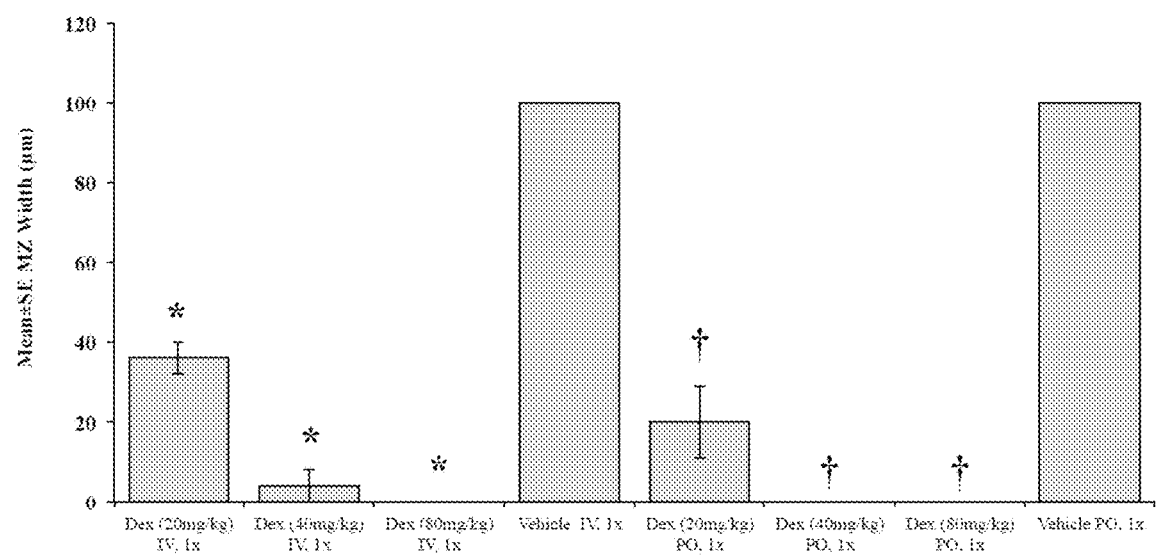
FIG. 3: Acute high dose Dex eliminates ACT binding niches in the rat spleen (MZ: marginal zone). A graph of column plots of marginal zone widths measured on 5 micron spleen sections from rats treated IV or PO with placebo, 20 mg/kg (HED 3.23 mg/kg), 40 mg/kg (HED 6.45) or 80 mg/kg (HED 12.9 mg/kg) dexamethasone base 48 hours before spleen harvest is shown.
Figure 4:
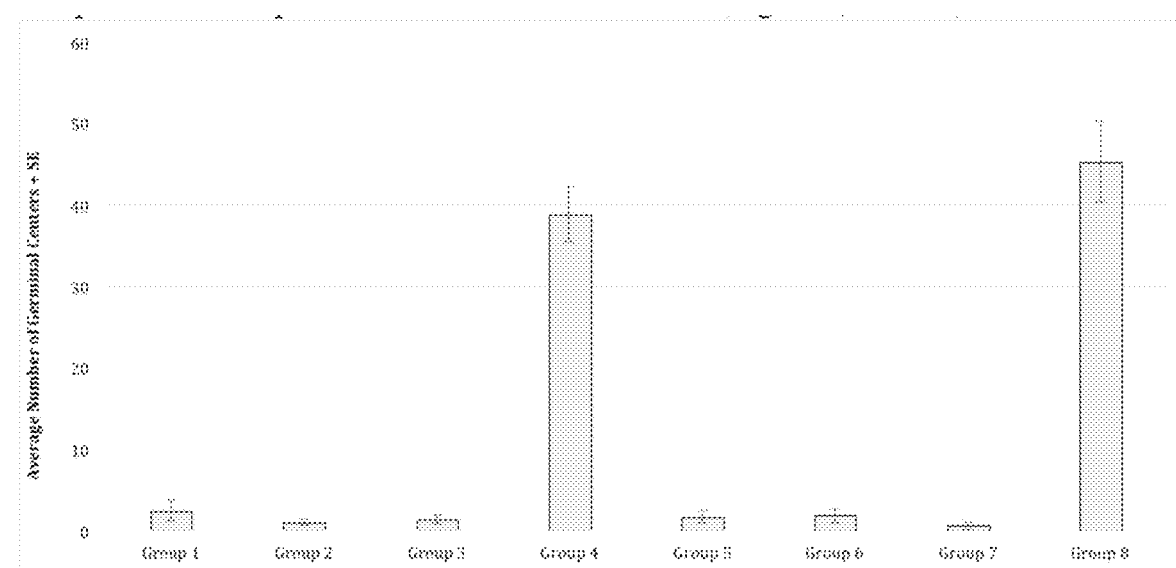
FIG. 4: Acute high dose Dex eliminates ACT binding niches in the rat spleen. A graph of column plots of the area per spleen are of BCL-6 staining of 5 micron fixed spleen sections as a measure of germinal center numbers given as average per section is shown. The rats treated IV or PO with placebo, 20 mg/kg (HED 3.23 mg/kg), 40 mg/kg (HED 6.45) or 80 mg/kg (HED 12.9 mg/kg) dexamethasone base 48 hours before spleen harvest.

For the rat, Dex HED between 3.23, 6.45 and 12.9 mg/kg (rat doses 20, 40 and 80 mg/kg) was administered (IV or PO) to determine GC and marginal zone inhibition 48 hours later. In the rat, the HED Dex dose of 12.9 mg/kg maximally inhibited both GC and marginal zone number and area as shown in FIG. 3 and FIG. 4. Formalin-fixed spleens were cross-sectioned in 5 pieces, trimmed and embedded in paraffin, sectioned and stained with hematoxylin and eosin (H&E). Measurements of the periarteriolar lymphoid sheath (PAL) diameter and the width of the marginal zone (MZ) in areas of white pulp that had PAL with the greatest diameter were measured using an ocular micrometer. BCL-6 immunohistochemical staining in rat spleens was evaluated to determine GC area using automated image analysis methods.

Figure 5:
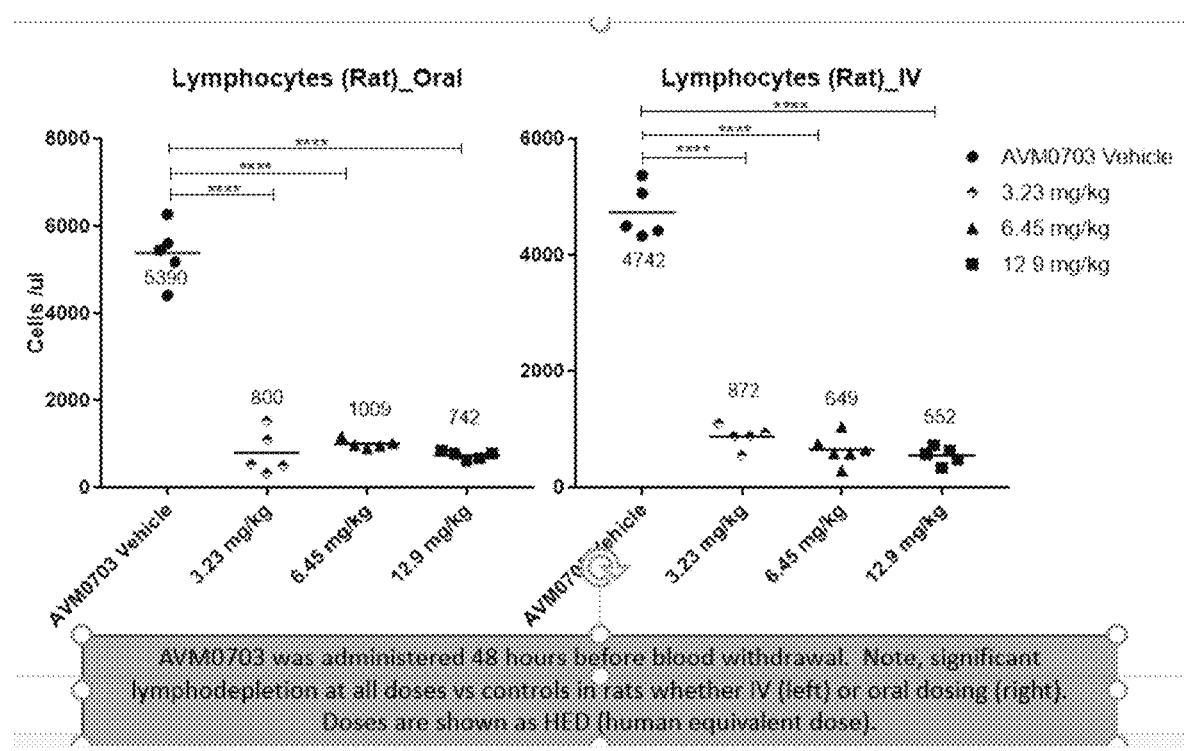
FIG. 5: Acute high dose Dex reduces rat lymphocyte number. Graphs of individual absolute lymphocyte numbers and averages measured by complete blood chemistries 48 hours after rats were treated IV or PO with placebo, 20 mg/kg (HED 3.23 mg/kg), 40 mg/kg (HED 6.45) or 80 mg/kg (HED 12.9 mg/kg) dexamethasone base are shown.
Figure 6:
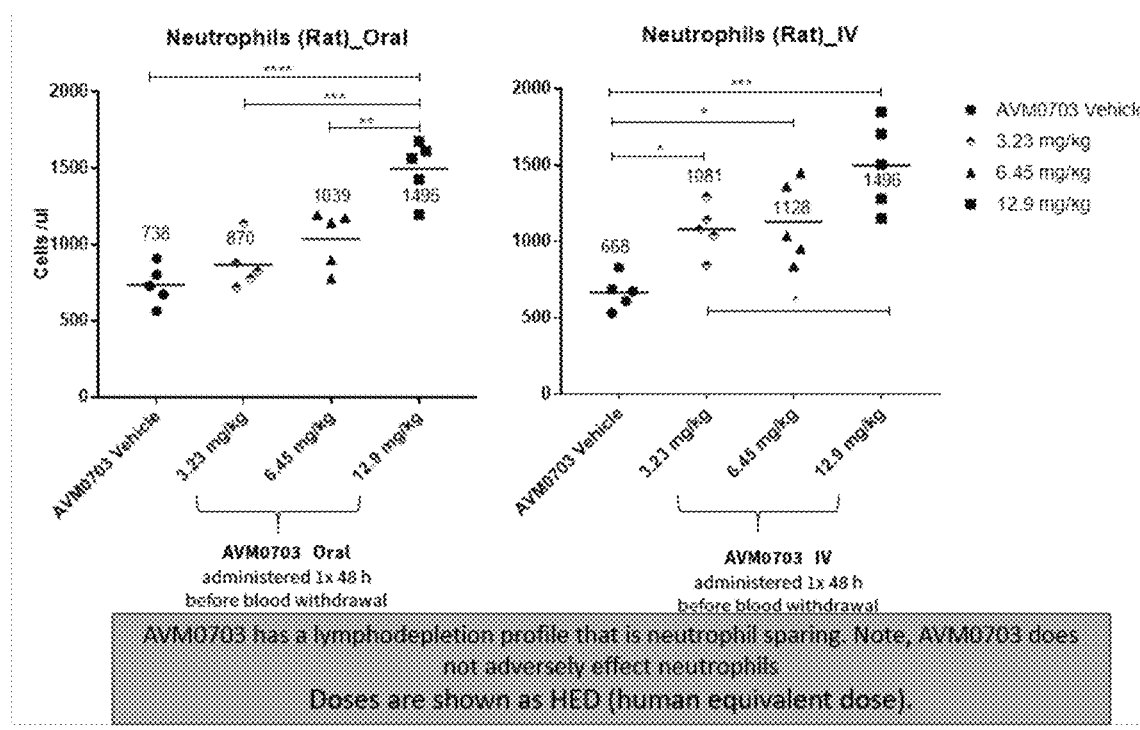
FIG. 6: Acute high dose Dex does not reduce rat neutrophil number. Graphs of individual absolute neutrophil numbers and averages measured by complete blood chemistries 48 hours after rats were treated IV or PO with placebo, 20 mg/kg (HED 3.23 mg/kg), 40 mg/kg (HED 6.45) or 80 mg/kg (HED 12.9 mg/kg) dexamethasone base are shown. Data in FIGS. 3, 4, 5 and 6 are from the same rats.

Example 3: Immunesuppressant Lymphodepletion in Mice, Rats, and Humans 36-48 Hours after Acute Administration of Dexamethasone, with Neutrophil, RBC, Platelet and Stem Cell Sparing Properties As shown in FIG. 5, IV or PO administration of dexamethasone at 20 (3.2 HED), 40 (6.5 HED) or 80 (12.9 HED) mg/kg to male Lewis rats weighing 250-300 grams significantly reduced lymphocyte count at all doses compared to Placebo 48 hours after administration. In contrast, as shown in FIG. 6, neutrophils were not reduced by acute high dose dexamethasone. Neutrophil number are actually increased by all doses of dexamethasone, likely via a demargination effect. RBCs, platelets, Hct, HgB were not affected by the dexamethasone treatment.

Figure 7:
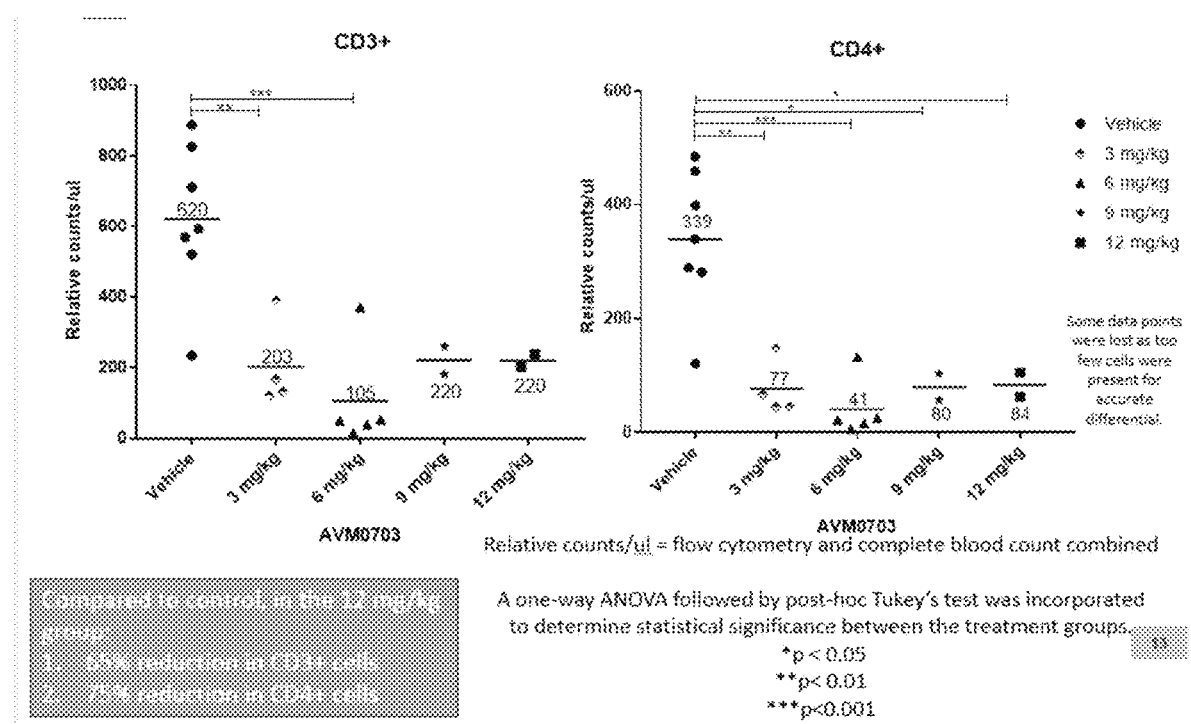
FIG. 7: Acute high dose Dex reduces mouse CD3 and CD4 positive lymphocytes (Dexamethasone (AVM0703) doses are shown as HED). Graphs of individual CD3+ and CD4+ lymphocytes and averages measured by flow cytometry as relative counts and normalized to relative absolute counts using complete blood chemistries 48 hours after mice were treated PO with placebo, HED 3 mg/kg, HED 6 mg/kg, HED 9 mg/kg or HED 12.mg/kg dexamethasone base.
Figure 8:
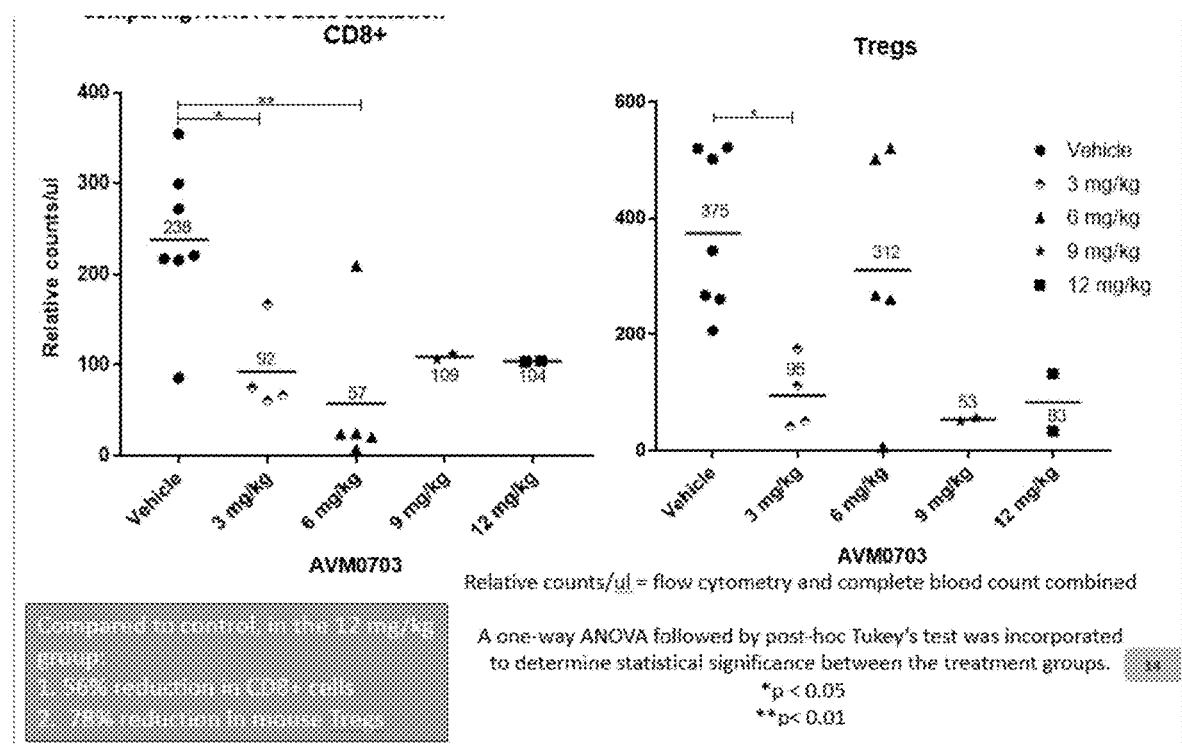
FIG. 8: Acute high dose Dex reduces mouse CD8 positive lymphocytes and Tregs (Dexamethasone (AVM0703) doses are shown as HED). Graphs of individual CD8+ and Treg lymphocytes and averages measured by flow cytometry as relative counts and normalized to relative absolute counts using complete blood chemistries 48 hours after mice were treated PO with placebo, HED 3 mg/kg, HED 6 mg/kg, HED 9 mg/kg or HED 12.mg/kg dexamethasone base. Treg lymphocytes were identified by being CD3+CD4+CD25+FoxP3+.
Figure 9:
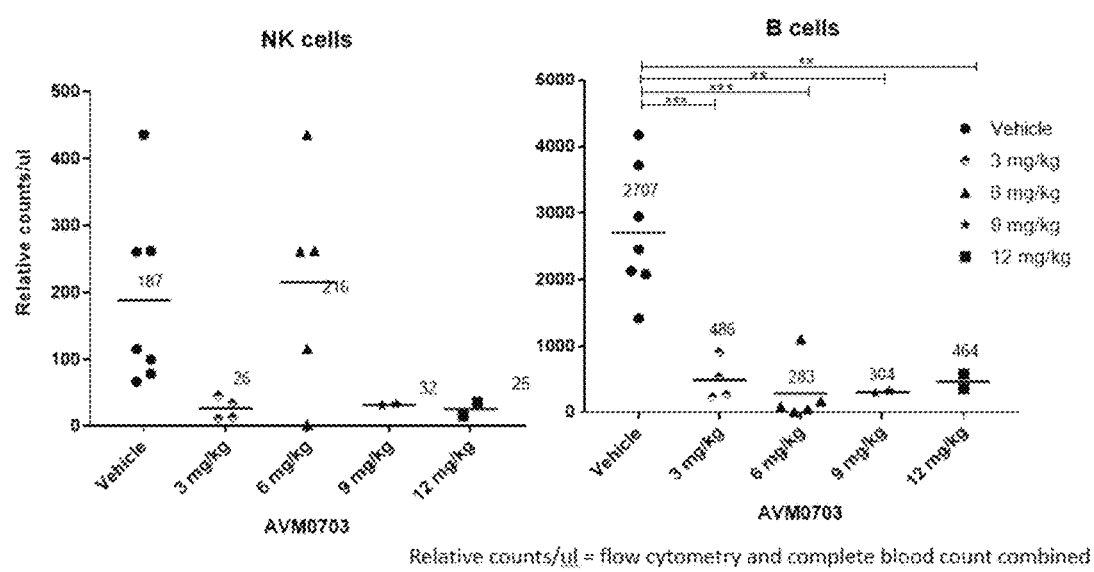
FIG. 9: Acute high dose Dex reduces mouse NK cells and B lymphocytes (Dexamethasone (AVM0703) doses are shown as HED). Graphs of individual natural killer (NK) cells and B lymphocytes and averages measured by flow cytometry as relative counts and normalized to relative absolute counts using complete blood chemistries 48 hours after mice were treated PO with placebo, HED 3 mg/kg, HED 6 mg/kg, HED 9 mg/kg or HED 12.mg/kg dexamethasone base. NK cells were identified by being CD3−CD49b+. B lymphocytes were identified by being CD3−B220+.
Figure 10:
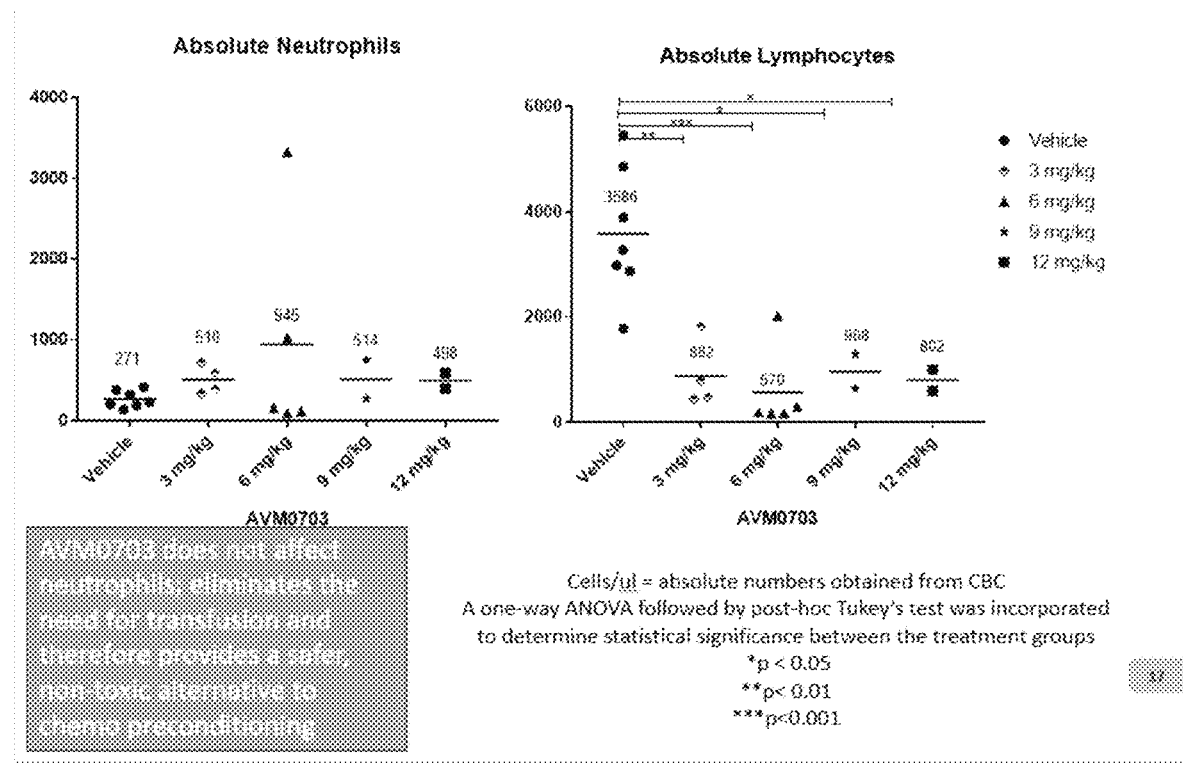
FIG. 10: Acute high dose Dex reduces mouse absolute lymphocyte numbers while sparing neutrophils (Dexamethasone (AVM0703) doses are shown as HED). Graphs of individual absolute neutrophils and total lymphocytes and averages measured by complete blood chemistries 48 hours after mice were treated PO with placebo, HED 3 mg/kg, HED 6 mg/kg, HED 9 mg/kg or HED 12.mg/kg dexamethasone base.
Figure 11:
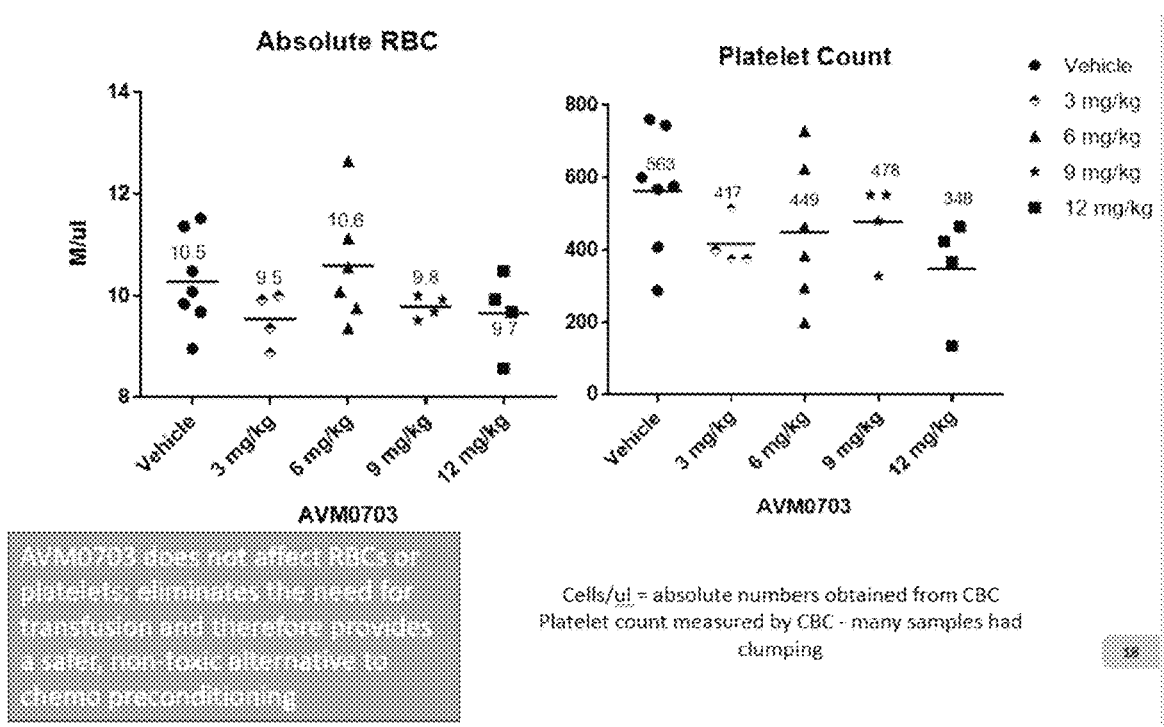
FIG. 11: Acute high dose Dex spares mouse RBCs and Platelets (Dexamethasone (AVM0703) doses are shown as HED). Graphs of individual absolute RBC and platelet and averages measured by complete blood chemistries 48 hours after mice were treated PO with placebo, HED 3 mg/kg, HED 6 mg/kg, HED 9 mg/kg or HED 12.mg/kg dexamethasone base. Data in FIG. 8, FIG. 9, FIG. 10, FIG. 11 are from the same cohorts of mice.

Oral acute administration of dexamethasone to C57B1 male mice at HED of 3 mg/kg (n=4), HED 6 mg/kg (n=6), 9 mg/kg (n=4) or 12 mg/kg (n=4) compared to placebo (n=7) reduced CD3+ T lymphocytes by 65% and CD4+ T lymphocytes by 75% (FIG. 7), reduced CD8+ T lymphocytes by 56% and Tregs by 78% (FIG. 8), reduced natural killer cells (NK) by 87% and B lymphocytes by 83% (FIG. 9), reduced absolute lymphocyte count by 84% but spared neutrophils (FIG. 10), RBCs (FIG. 11) and platelets (FIG. 11). Blood was drawn for CBC and flow cytometry 48 hours after dexamethasone administration by oral gavage.

Figure 13:
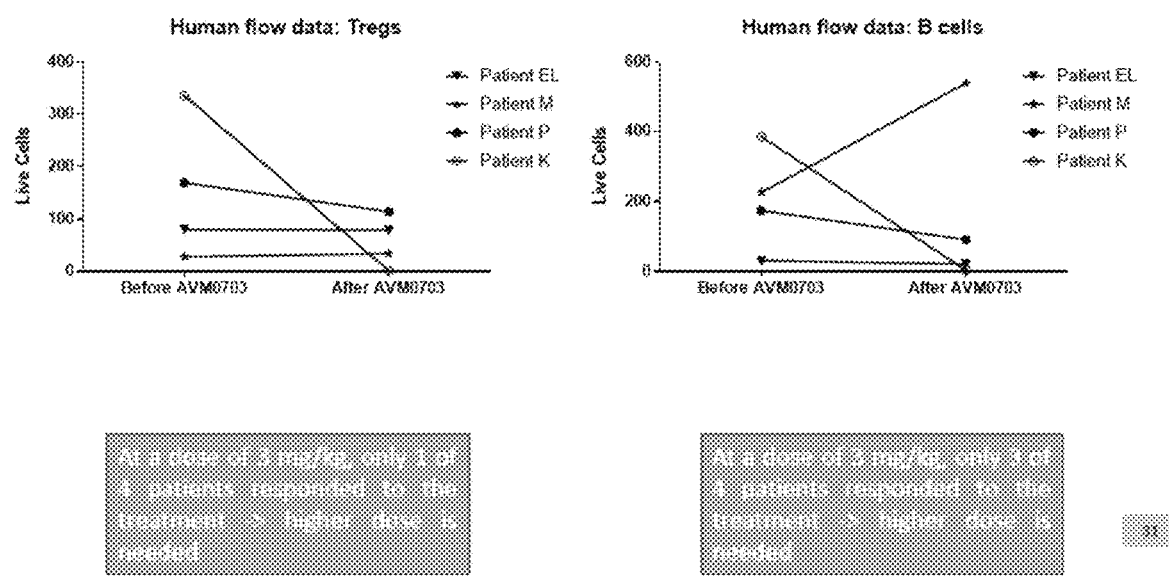
FIG. 13: Twenty-five percent (1 of 4) of human patients treated with 3 mg/kg dexamethasone base depleted Tregs and B lymphocytes. Line are individual pre- and post-, 48 hours after oral administration of 3 mg/kg dexamethasone base to four human patients, values and line plots of Treg and B lymphocytes measured by flow cytometry. Each patient's pre-treatment values are connected to post-treatment values by a connecting line. Tregs are identified by being CD3+CD4+CD25+FoxP3+. B lymphocytes are identified by being CD3-CD19+.
Figure 14:
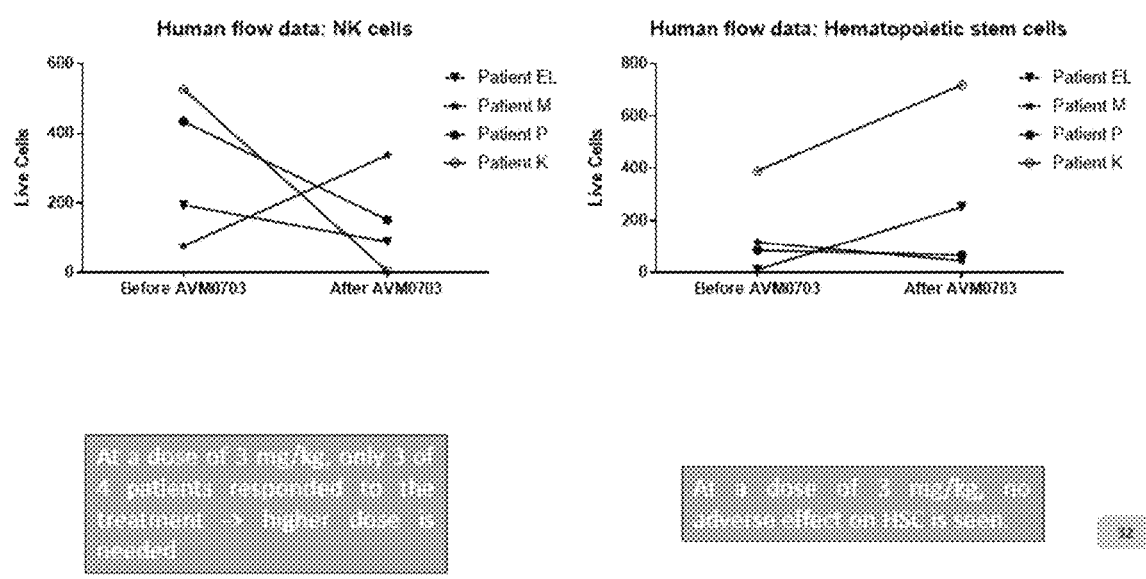
FIG. 14: Seventy-five percent (3 of 4) of human patients treated with 3 mg/kg dexamethasone base depleted NK cells while hematopoietic stem cells were spared. Line are individual pre- and post-treatment, 48 hours after oral administration of 3 mg/kg dexamethasone base to four human patients, values and line plots of NK cells and Hematopoietic Stem Cells (HSCs) measured by flow cytometry. Each patient's pre-treatment values are connected to post-treatment values by a connecting line. NK cells are identified by being CD3-CD16/56+. HSCs are identified by being CD34+CD38-.

Oral acute administration of 3 mg/kg dexamethasone base equivalent (all doses given are dexamethasone base equivalent in these examples) to four human patients, three with knee osteoarthritis and one with aortic aneurysm, was administered. Blood was drawn before drug treatment and 48 hours post-treatment for CBC analysis and flow cytometry to determine lymphocyte and other blood cell populations. Serum was analyzed for cytokine levels. For one patient, pre-treatment CBCs were not drawn and thus normalized flow cytometry data is shown for only 3 patients. By un-normalized flow cytometry data only 2 of the 4 patients responded to the dexamethasone with lymphodepletion (FIGS. 12, 13, and 14), while 2 of 4 patients showed a lymphocytosis response in CD3 and CD4 lymphocytes and 1 of 4 patients showed a lymphocytosis response in CD8, B lymphocytes and NK cells, to this dose of dexamethasone. 3 of 4 patients showed elevated levels of IL-2 and 4 of 4 showed elevated levels of IL-15 48 hours after acute oral dexamethasone base (3 mg/kg) (FIG. 15). IL-6, a cytokine known to be the primary driver of potentially fatal cytokine release syndrome (CRS) was not elevated in any patient. Based on the lymphocytosis response observed in 2 of 4 non cancer patients at the 3 mg/kg dose, preferred lymphodepleting preconditioning doses prior to ACT will be 3 mg/kg or higher based on the increased sensitivity of tumor bearing mice to Dexamethasone where the lowest lethal dose was HED 43 mg/kg in tumor bearing mice compared to HED 114 mg/kg in healthy mice (P. Scorza Barcellona, Arch. Toxiccl., Supp!. 7, 90-93 (1984)).

Figure 16:
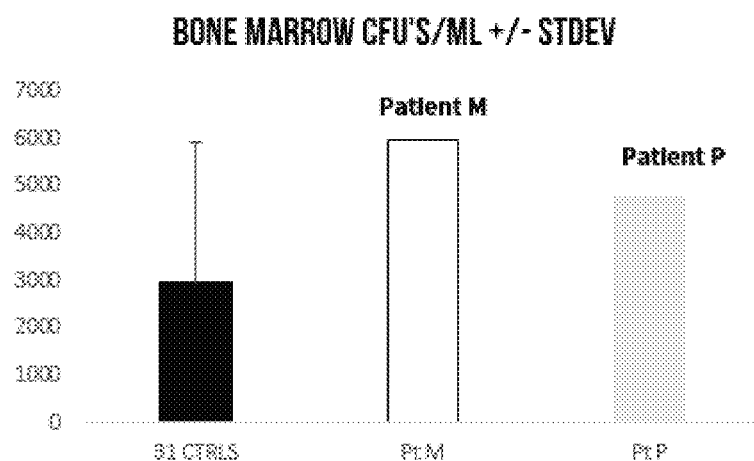
FIG. 16: Oral administration of 3 mg/kg dexamethasone base increased bone marrow MSC number 48 hours later. Column plots of data from 31 historical naïve control humans plus standard deviation, and two human patients treated with 3 mg/kg dexamethasone base 48 hours before aspiration of concentrated bone marrow from the ileac crest using a MarrowCellution™ needle. Bone marrow was added to directly to colony forming unit assay fibroblast (CFU-F) media without further manipulation 24 hours after harvest and shipment at controlled room temperature. CFU-F colony number is a measure of mesenchymal stem cell (MSC) number in the starting material. 48 hours after oral administration of 3 mg/kg dexamethasone base, ileac crest bone marrow MSC numbers appear about twice as high as 31 historical controls.
Figure 17:
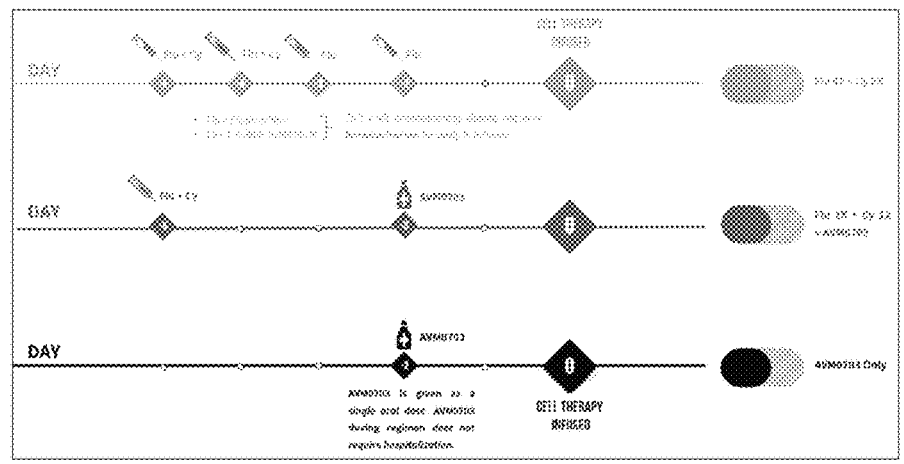
FIG. 17: Comparison of a 12 mg/kg Dex base oral dose on day −2 to a single dose of Cyclophosphamide 166 mg/kg (HED 500 mg/m2) and Fludarabine 10 mg/kg on day −5 combined with 12 mg/kg Dex base on day −2, and to 2 days of repeat Cyclophosphamide 166 mg/kg on day −5 and −4 and 4 days of Fludarabine 10 mg/kg (HED 30 mg/m2) on days −5, −4, −3, −2.
Figure 17:
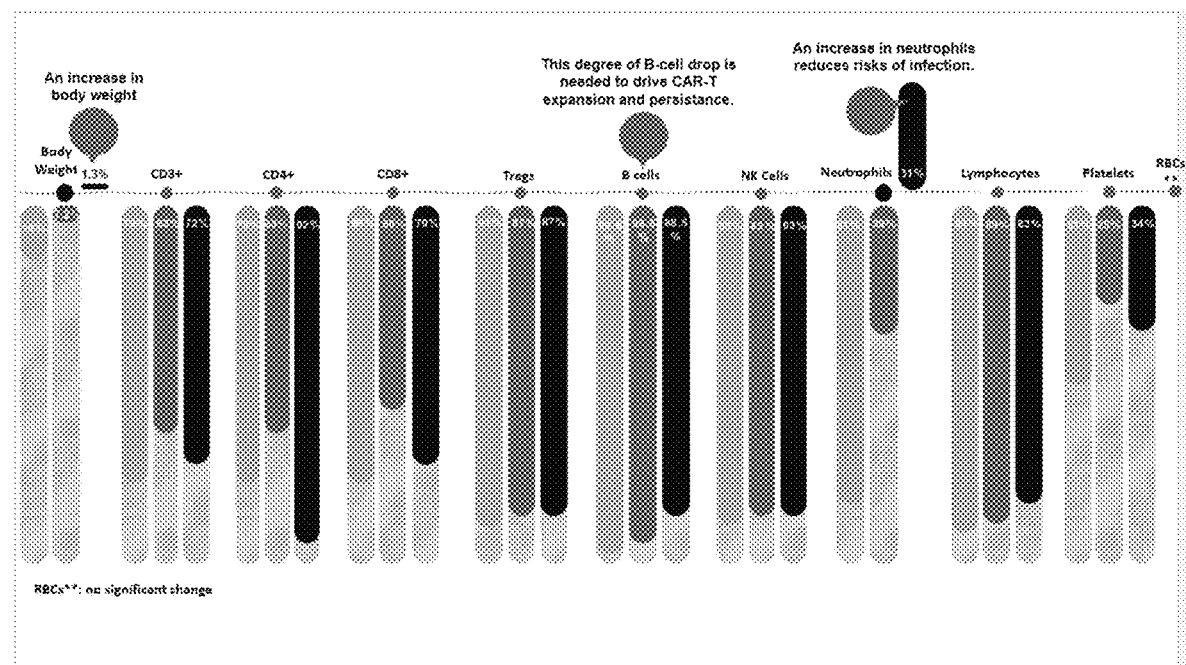
Figure 18:
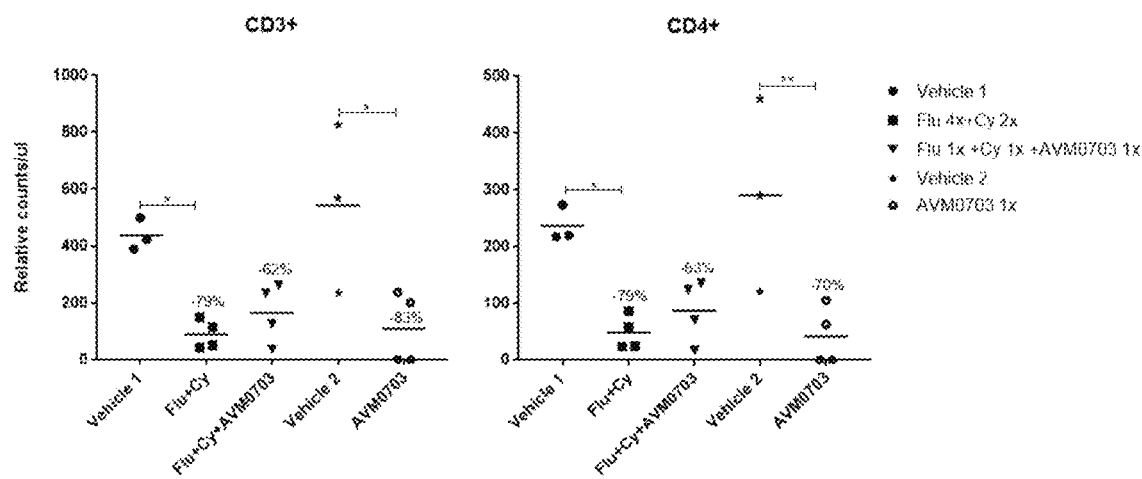
FIG. 18: A single dose of Cyclophosphamide 166 mg/kg (HED 500 mg/m2) and Fludarabine 10 mg/kg on day −5 combined with 12 mg/kg Dex base on day −2 equivalently lymphodepleted CD3+ and CD4+ lymphocytes compared to 2 days of repeat Cyclophosphamide 166 mg/kg on day −5 and −4 and 4 days of Fludarabine 10 mg/kg (HED 30 mg/m2) on days −5, −4, −3, −2.
Figure 19:
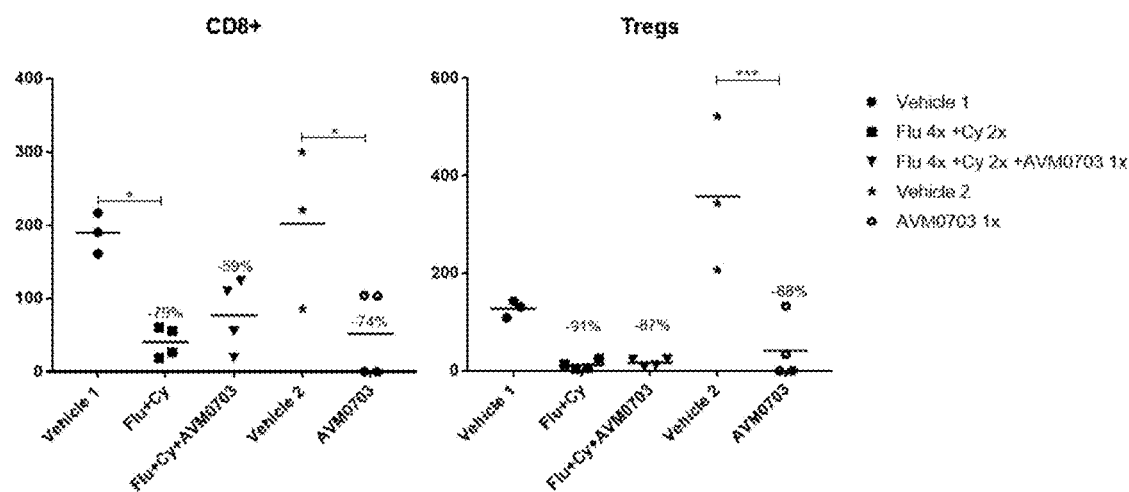
FIG. 19: A single dose of Cyclophosphamide 166 mg/kg (HED 500 mg/m2) and Fludarabine 10 mg/kg on day −5 combined with 12 mg/kg Dex base on day −2 equivalently lymphodepleted CD8+ lymphocytes and Tregs compared to 2 days of repeat Cyclophosphamide 166 mg/kg on day −5 and −4 and 4 days of Fludarabine 10 mg/kg (HED 30 mg/m2) on days −5, −4, −3, −2.
Figure 20:
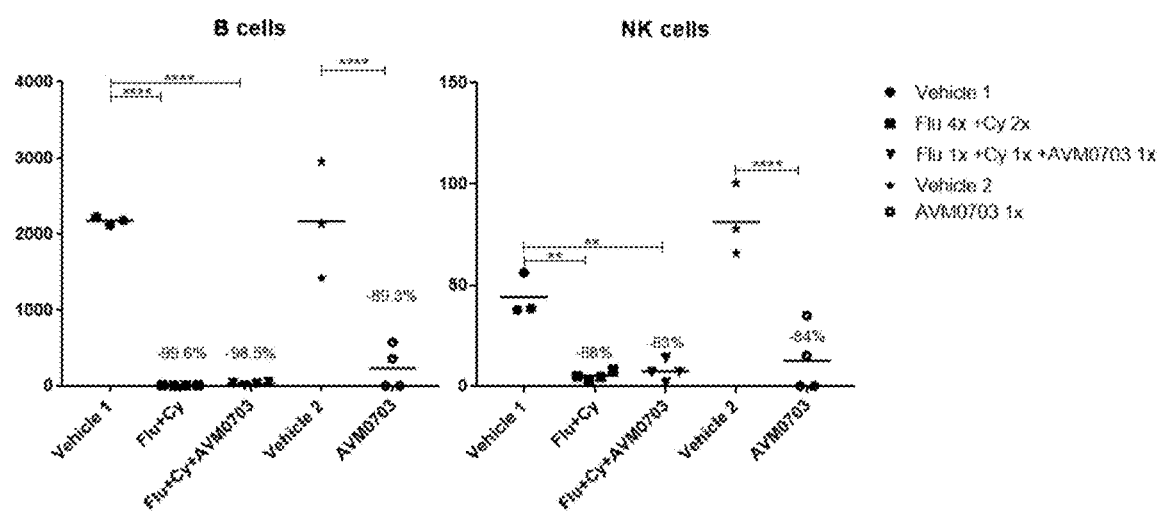
FIG. 20: A single dose of Cyclophosphamide 166 mg/kg (HED 500 mg/m2) and Fludarabine 10 mg/kg on day −5 combined with 12 mg/kg Dex base on day −2 equivalently lymphodepleted NK cells and B lymphocytes compared to 2 days of repeat Cyclophosphamide 166 mg/kg on day −5 and −4 and 4 days of Fludarabine 10 mg/kg (HED 30 mg/m2) on days −5, −4, −3, −2.
Figure 21:
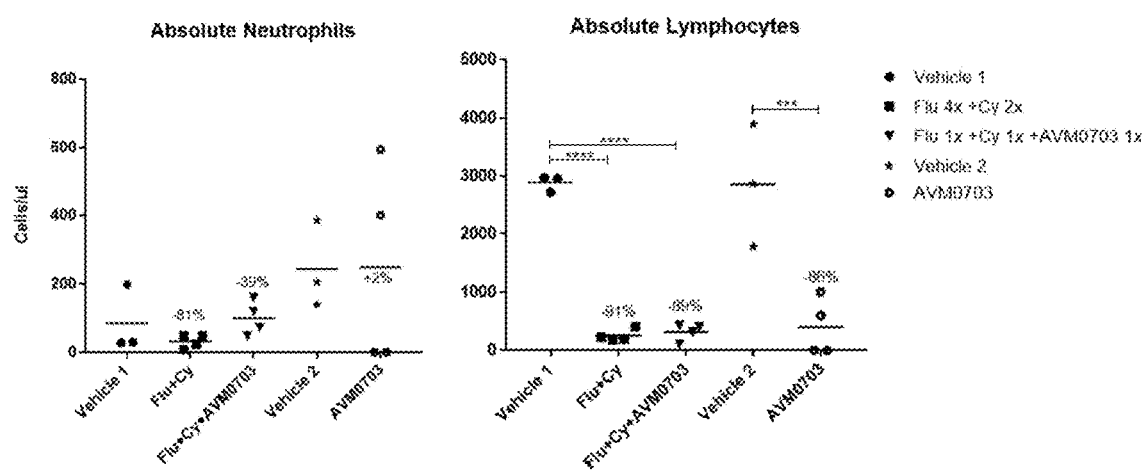
FIG. 21: A single dose of Cyclophosphamide 166 mg/kg (HED 500 mg/m2) and Fludarabine 10 mg/kg on day −5 combined with 12 mg/kg Dex base on day −2 equivalently lymphodepleted absolute lymphocytes, but spared neutrophils, compared to 2 days of repeat Cyclophosphamide 166 mg/kg on day −5 and −4 and 4 days of Fludarabine 10 mg/kg (HED 30 mg/m2) on days −5, −4, −3, −2.
Figure 22:
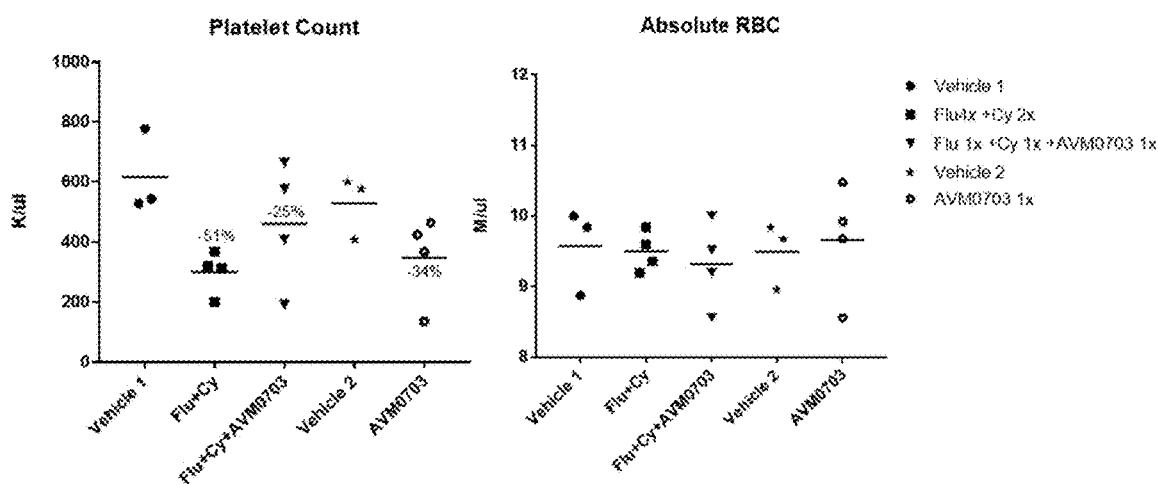
FIG. 22: A single dose of Cyclophosphamide 166 mg/kg (500 mg/m2) and Fludarabine 10 mg/kg (HED 30 mg/m2) on day −5 combined with 12 mg/kg Dex base on day −2 spared RBCs and platelets.

Bone marrow was drawn 48 hours after dexamethasone administration and mesenchymal stem cell (MSC) number was determined by colony-forming assay fibroblast (CFU-F). Oral administration of dexamethasone base 3 mg/kg increased ileac crest BM MSC almost two fold (FIG. 16). Trilineage differentiation capacity of the BM MSC was also determined in a study in horses. A 6 mg/kg HED doubled sternal BM MSC stem cell number 48 hours after a one hour IV infusion administration to horses, but did not alter trilineage differentiation capacity of the MSC towards osteocytes, chondrocytes or adipocytes.

Figure 23:
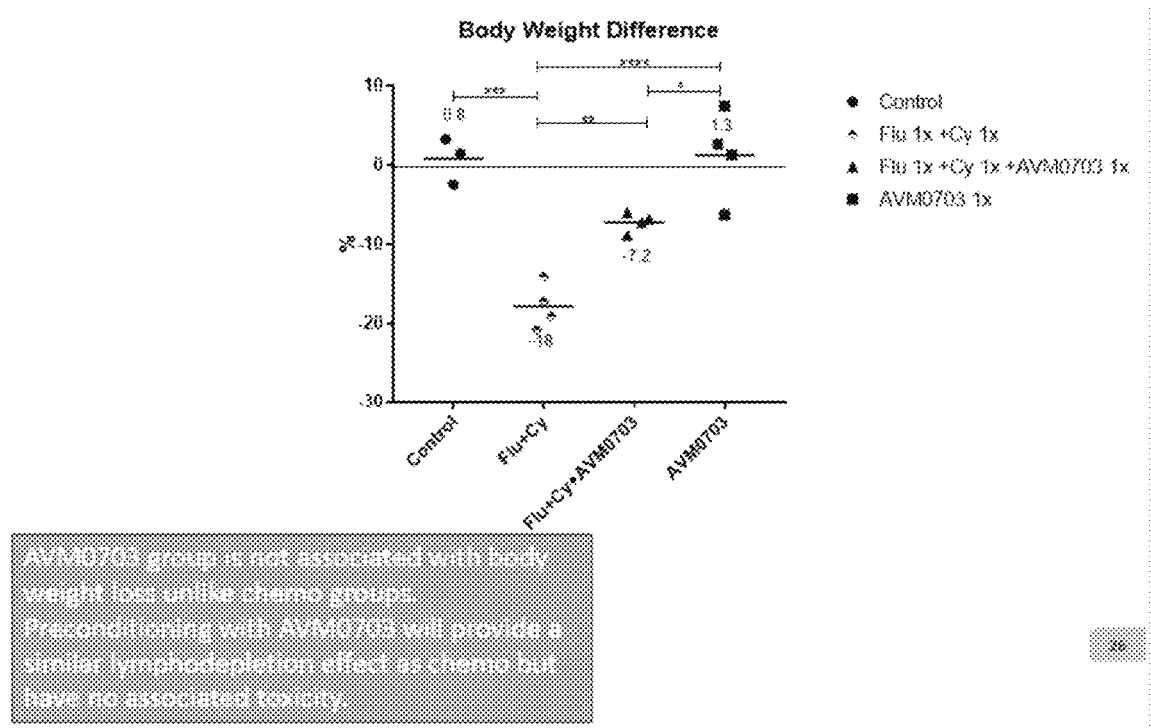
FIG. 23: A single dose of Cyclophosphamide 166 mg/kg (500 mg/m2) and Fludarabine 10 mg/kg on day −5 combined with 12 mg/kg Dex base on day −2 spared body weight, a measure of toxicity, compared to 2 days of repeat Cyclophosphamide 166 mg/kg on day −5 and −4 and 4 days of Fludarabine 10 mg/kg on days −5, −4, −3, −2.

Example 4: Comparison of Acute 12 mg/kg Dexamethasone Base HED to a Standard Cy (Cyclophosphamide) Flu (Fludarabine) Preconditioning Regimen Dexamethasone base was administered by oral gavage to adult male mice at 12 mg/kg HED on day −2. To another group of mice Cy was administered IP at 166 mg/kg (HED 500 mg/m$^2$) on day −5 and day −4 and Fludarabine 10 mg/kg (HED 30 mg/m$^2$) on days −5, −4, −3, −2. To a third group of mice Cy was administered IP at 166 mg/kg (HED 500 mg/m$^2$) on day −5 and Fludarabine 10 mg/kg (HED 30 mg/m$^2$) on days −5, then 12 mg/kg HED dexamethasone base was administered orally on day −2. CBC and flow cytometry results are shown in FIGS. 17-22, and body weights are shown in FIG. 23. Dexamethasone base 12 mg/kg HED given between 12-72 hours before blood draw leads to a comparable lymphodepletion profile compared to standard 2 day Cy with 4 day Flu, as does the combination of a single Cy on day −5 and a single Flu on day −5 with 12 mg/kg dexamethasone HED on day −2. The single Cy and single Flu dose can be administered on day −6, day −4, or day−3 with equal effect. The lymphodepletion profile of dexamethasone alone may be preferable because absolute lymphocytes are not depleted as dramatically as with CyFlu, and the degree of lymphodepletion may be related to neuroedema when ACT is given after CyFlu.

The standard repeat CyFlu preconditioning significantly reduced body weight as a general measure of toxicity, while 12 mg/kg dexamethasone base HED did not impact body weight, and the combination of one Cy and one Flu dose on day −5 with 12 mg/kg dexamethasone HED impacted body weight significantly less than the standard CyFlu regimen.

Other standard preconditioning agents that can given as a single dose(s) on day −1 or day −2 or day −3 or day −4 or day −5 and be combined with Dexamethasone between about 3 to about 12 mg/kg on day −2 include: Cy 120 mg/kg and Flu 75 mg/m$^2$; 30 mg/m$^2$ flu and 50 mg/kg Cy and 200 cGy TBI; Cy 1500 mg/m2 and Bendamustine 120 mg/m2; Cy between about 300 mg/m$^2$ and about 2300 mg/m$^2$; Flu between about 10 mg/m$^2$ and about 900 mg/m$^2$; Cy 600 mg/m$^2$ and Flu 30 mg/m$^2$; Busulfan and Melphalan and Flu; Busulfan (dose adjusted according to weight) and Thiotepa (10 mg/kg) and Fludarabine (160 mg/m$^2$); Flu 30 mg/m$^2$ andCy 300 mg/m$^2$ and Mensa 300 mg/m$^2$; Flu 30 mg/m$^2$ and Cy 60 mg/m$^2$ and Alemtuzumab 0.2 mg/kg.

Example 5: Immunocompetent Mouse Model of Multiple Myeloma

The mouse multiple myeloma MOPC315 cell line available from ATCC is tail vein inoculated to immunocompetent Balbc mice at 2×10$^6$ cells. Approximately 21 days later symptoms begin to show which include hind limb paralysis. Between day 21 and day 67 after inoculation greater than 90% of inoculated mice will be affected with disease.

Mice are preconditioned with standard CyFlu (Cy 300 mg/m2 to 2100 mg/m2 for 2 to 5 days on about days −6, −5, −4, −3, −2, or −1 before ACT and Flu 10 mg/m2 to 30 mg/m2 for 2 to 5 days on about days −6, −5, −4, −3, −2, or −1 before ACT); other mice are preconditioned with Dexamethasone base HED between 3-12 mg/kg administered either orally or over a 15-60 minute intravenous infusion; other mice are preconditioned with a single dose of Cy (300 mg/m2 to 2100 mg/m2 between day −6 to day −2 and Flu (10 mg/m2 to 30 mg/m2 between day −6 to day −2) plus Dexamethasone base HED between 3-12 mg/kg administered either orally or over a 15–60 minute intravenous infusion between 12-72 hours before allogeneic HSCT or Natural Killer (NK) cell administration, which is considered day 0 for the purpose of planning the timing of preconditioning.

Mice can also be preconditioned with: An agent containing hydrocortisone is administered intravenously or orally about every 12 hours at a dose of about 75 to about 300 mg/kg between about 12 to about 72 hours before administration of the cellular immunotherapy. An agent containing cortisone is administered intravenously or orally about every 12 hours at a dose of about 93 to about 375 mg/kg between about 12 to about 72 hours before administration of the cellular immunotherapy. An agent containing prednisolone is administered intravenously or orally about every 24 hours at a dose of about 19 to about 75 mg/kg between about 12 to about 60 hours before administration of the cellular immunotherapy. An agent containing methylprednisolone is administered intravenously or orally about every 24 hours at a dose of about 15 to about 60 mg/kg between about 12 to about 60 hours before administration of the cellular immunotherapy. An agent containing triamcinolone is administered intravenously or orally about every 24 hours at a dose of about 15 to about 60 mg/kg between about 12 to about 60 hours before administration of the cellular immunotherapy. An agent containing paramethasone is administered in either a single acute dose or cumulative doses of about 7.5 to about 30 mg/kg, given between about 12-72 hours prior to cellular immunotherapy. An agent containing betamethasone is administered in either a single acute dose or cumulative doses of about 2.5 to 10 mg/kg, given between about 12-72 hours prior to cellular immunotherapy.

Balb/cJ (H-2d) and B10.D2 (H-2d) mice were purchased from Jackson Laboratory (Bar Harbor, Me., USA). Mice were used when they were between 10- to 14-wk-old. For allogeneic HSCT, spleens and bone marrows (femurs and tibias) from donor B10.D2 mice are harvested and homogenized in RPMI 1640 medium containing 10% FBS and 1% Penicillin/Streptomycin (5complete medium). Red blood cells are lysed using sterile filtered RBC lysis buffer (eBioscience, San Diego, USA) and cells are washed, resuspended in phosphate buffered saline (PBS) containing 3% FBS, and filtered through a 70 mM nylon membrane. For CD8 T-cell depletion, the "Mouse CD8a positive selection kit" (Stem Cell, Grenoble, France) are used according to the manufacturer's EASYSEP depletion protocol. Finally, cells are suspended in 200 ml PBS for i.v. injection. Balbc mice are transplanted by i.v. tail vein injection of $1\times10^7$ bone marrow cells and $7\times10^7$ splenocytes from donor B10.D2 mice between 10 and 30 days after MOPC315 inoculation. 94% of the mice will show complete elimination of MOPC315 cells after alloHSCT. The group that received Dexamethasone preconditioning will have a similar elimination of MOPC315 cells after alloHSCT compared to standard CyFlu, but less toxicity as body weights are reduced 20% by the CyFlu preconditioning, but not reduced by the Dex preconditioning. The combination of one dose CyFlu plus Dex is also effective and has lower toxicity than standard repeat CyFlu preconditioning. The Dexa preconditioned group will have similar or better anti-tumor effect, improved progression-free survival, reduced Disease progression, enhanced duration of response, improved overall survival, reduced minimal residual disease compared to mice who were preconditioned with CyFlu for 2 to 5 days.

For allogeneic NK cell administration, fully functional NK cells are isolated from donor B10.D2 mice using commercially available kits such as the one from Miltenyi. Alternatively, mouse NK cells can be purchased from ATCC (KIL cells). The NK Cell Isolation Kit was developed for the isolation of untouched NK cells from single-cell suspensions of murine spleen. Non-NK cells, i.e. T cells, dendritic cells, B cells, granulocytes, macrophages, and erythroid cells are magnetically labeled by using a cocktail of biotin-conjugated antibodies and Anti-Biotin MicroBeads. Isolation of highly pure unlabeled NK cells is achieved by depletion of non-target cells. The kit has been optimized to give outstanding purities in C57BL/6J mice. $1\times10^7$ isolated NK cells are transplanted by IV tail vein injection between 10 and 30 days after MOPC315 inoculation. NK cell eradication of MOPC315 cells is as effective when Dexa preconditioning was used as when standard CyFlu preconditioning is used, with much less toxicity. The combination of one dose CyFlu plus Dex is also effective and has lower toxicity than standard repeat CyFlu preconditioning. The Dexa preconditioned group will have similar or better anti-tumor effect, improved progression-free survival, reduced Disease progression, enhanced duration of response, improved overall survival, reduced minimal residual disease compared to mice who were preconditioned with CyFlu for 2 to 5 days.

Example 6: A Patient with a Condition Selected from the Group Consisting of

Hemophagocytic lymphohistiocytosis, multiple myeloma, allergen specific immunotherapy, autosomal dominant haploinsufficiency, anterior interosseous nerve syndrome, Churg-Strauss syndrome, Systemic vasculitis, chronic graft versus host disease, Opsoclonus-Myoclonus Syndrome, Necrotising Autoimmune Myopathy (NAM), Pulmonary Sarcomatoid carcinomas, Waldenstrom's macroglobulinaemia (WM), fertility, Behcets Disease, Alopecia areata (AA), Acute-on-chronic Liver Failure, melanoma, 'organizing bronchiolitis syndrome', encephalitis, minimal change disease, or a patient receiving Tumor flare reaction therapy or Sublingual immunotherapy (SLIT) or subcutaneous immunotherapy (SCIT), or having: Disease (source of Disease)

*Acinetobacter* infections (*Acinetobacter baumannii*), Actinomycosis (*Actinomyces israelii, Actinomyces gerencseriae* and *Propionibacterium propionicus*) African sleeping sickness or African trypanosomiasis (*Trypanosoma brucei*), AIDS (Acquired immunodeficiency syndrome) (Human immunodeficiency virus), Amebiasis (*Entamoeba histolytica*), Anaplasmosis (*Anaplasma* species), Angiostrongyliasis (*Angiostrongylus*), Anisakiasis (*Anisakis*), Anthrax (*Bacillus anthracis*), Arcanobacterium haemolyticum infection (*Arcanobacterium haemolyticum*), Argentine hemorrhagic fever (Junin virus), Ascariasis (*Ascaris lumbricoides*), Aspergillosis (*Aspergillus* species), Astrovirus infection (Astroviridae family), Babesiosis (*Babesia* species), *Bacillus cereus* infection (*Bacillus cereus*), Bacterial pneumonia (multiple bacteria), Bacterial vaginosis (List of bacterial vaginosis microbiota), *Bacteroides* infection (*Bacteroides* species), Balantidiasis (*Balantidium coli*), Bartonellosis (*Bartonella*), Baylisascaris infection (*Baylisascaris* species), BK virus infection (BK virus), Black *piedra* (*Piedraia hortae*), Blastocystosis (*Blastocystis* species), Blastomycosis (*Blastomyces dermatitidis*), Bolivian hemorrhagic fever (Machupo virus), Botulism (and Infant botulism) (*Clostridium botulinum*; Note: Botulism is not an infection by *Clostridium botulinum* but caused by the intake of botulinum toxin), Brazilian hemorrhagic fever (Sabiá virus), Brucellosis (*Brucella* species), Bubonic plague (the bacterial family Enterobacteriaceae), *Burkholderia* infection, usually *Burkholderia cepacia* and other *Burkholderia* species, Buruli ulcer (*Mycobacterium ulcerans*), Calicivirus infection (Norovirus and Sapovirus) (Caliciviridae family), Campylobacteriosis (*Campylobacter* species), Candidiasis (Moniliasis; Thrush) (usually *Candida albicans* and other *Candida* species), Capillariasis (Intestinal disease by *Capillaria philippinensis*, hepatic disease by *Capillaria hepatica* and pulmonary disease by *Capillaria aerophila*), Carrion's disease (*Bartonella bacilliformis*), Cat-scratch disease (*Bartonella henselae*), Cellulitis (usually Group A *Streptococcus* and *Staphylococcus*), Chagas Disease (American trypanosomiasis) (*Trypanosoma cruzi*), Chancroid (*Haemophilus ducreyi*), Chickenpox (Varicella zoster virus (VZV)), Chikungunya (*Alphavirus*), Chlamydia (*Chlamydia trachomatis*), *Chlamydophila pneumoniae* infection (Taiwan acute respiratory agent or TWAR) (*Chlamydophila pneumoniae*), Cholera (*Vibrio cholerae*), Chromoblastomycosis (usually *Fonsecaea pedrosoi*), Chytridiomycosis (*Batrachochytrium dendrabatidis*), Clonorchiasis (*Clonorchis sinensis*), *Clostridium difficile* colitis (*Clostridium difficile*), Coccidioidomycosis (*Coccidioides immitis* and *Coccidioides posadasii*), Colorado tick fever (CTF) (Colorado tick fever virus (CTFV)), Common cold (Acute viral rhinopharyngitis; Acute coryza) (usually rhinoviruses and coronaviruses), Creutzfeldt-Jakob disease (CJD) (PRNP), Crimean-Congo hemorrhagic fever (CCHF) (Crimean-Congo hemorrhagic fever virus), Cryptococcosis (*Cryptococcus neoformans*), Cryptosporidiosis (*Cryptosporidium* species), Cutaneous larva migrans (CLM) (usually *Ancylostoma braziliense*; multiple other parasites), Cyclosporiasis (*Cyclospora cayetanensis*), Cysticercosis (*Taenia solium*), Cytomegalovirus infection (Cytomegalovirus), Dengue fever (Dengue viruses (DEN-1, DEN-2, DEN-3 and DEN-4)—Flaviviruses), Desmodesmus infection (Green algae Desmodesmus armatus), Dientamoebiasis (*Dientamoeba fragilis*), Diphtheria (*Corynebacterium diphtheriae*), Diphyllobothriasis (*Diphyllobothrium*), Dracunculiasis (*Dracunculus medinensis*), Ebola hemorrhagic fever (Ebolavirus (EBOV)), Echinococcosis (*Echinococcus* species), Ehrlichiosis (*Ehrlichia* species), Enterobiasis (Pinworm infection) (*Enterobius vermicularis*), *Enterococcus* infection (*Enterococcus* species), Enterovirus infection (Enterovirus species), Epidemic typhus (*Rickettsia prowazekii*), Erythema infectiosum (Fifth disease) (Parvovirus B19), Exanthem subitum (Sixth disease) (Human herpesvirus 6 (HHV-6) and Human herpesvirus 7 (HHV-7)), Fasciolasis (*Fasciola hepatica* and *Fasciola gigantica*), Fasciolopsiasis (*Fasciolopsis buski*), Fatal familial insomnia (FFI) (PRNP), Filariasis (Filarioidea superfamily), Food poisoning by *Clostridium perfringens* (*Clostridium perfringens*), Free-living amebic infection (multiple), *Fusobacterium* infection (*Fusobacterium* species), Gas gangrene (Clostridial myonecrosis) (usually *Clostridium perfringens*; other *Clostridium* species), Geotrichosis (*Geotrichum candidum*), Gerstmann-Straussler-Scheinker syndrome (GSS) (PRNP), Giardiasis (*Giardia lamblia*) Glanders (*Burkholderia mallei*), Gnathostomiasis (*Gnathostoma spinigerum* and *Gnathostoma hispidum*), Gonorrhea (*Neisseria gonorrhoeae*), Granuloma inguinale (Donovanosis) (*Klebsiella granulomatis*), Group A streptococcal infection (*Streptococcus pyogenes*), Group B streptococcal infection (*Streptococcus agalactiae*), *Haemophilus influenzae* infection (*Haemophilus influenzae*) Hand, foot and mouth disease (HFMD) (Enteroviruses, mainly Coxsackie A virus and Enterovirus 71 (EV71)), Hantavirus Pulmonary Syndrome (HPS) (Sin Nombre virus), Heartland virus disease (Heartland virus), *Helicobacter pylori* infection (*Helicobacter pylori*), Hemolytic-uremic syndrome (HUS), *Escherichia coli* O157:H7, O111 and O104:H4, Hemorrhagic fever with renal syndrome (HFRS) (Bunyaviridae family), Hepatitis A (Hepatitis A virus), Hepatitis B (Hepatitis B virus), Hepatitis C (Hepatitis C virus), Hepatitis D (Hepatitis D Virus), Hepatitis E (Hepatitis E virus), Herpes simplex (Herpes simplex virus 1 and 2 (HSV-1 and HSV-2)), Histoplasmosis (*Histoplasma capsulatum*), Hookworm infection (*Ancylostoma duodenale* and *Necator americanus*), Human bocavirus infection (Human bocavirus (HBoV)), Human *ewingii* ehrlichiosis (*Ehrlichia ewingii*), Human granulocytic anaplasmosis (HGA) (*Anaplasma phagocytophilum*), Human metapneumovirus infection, Human metapneumovirus (hMPV), Human monocytic ehrlichiosis (*Ehrlichia chaffeensis*), Human papillomavirus (HPV) infection (Human papillomavirus (HPV)), Human parainfluenza virus infection (Human parainfluenza viruses (HPIV)), Hymenolepiasis (*Hymenolepis nana* and *Hymenolepis diminuta*), Epstein-Barr virus infectious mononucleosis (Mono) (Epstein-Barr virus (EBV)), Influenza (flu) (Orthomyxoviridae family) Isosporiasis (*Isospora belli*), Kawasaki disease (unknown; evidence supports that it is infectious) Keratitis (multiple), *Kingella kingae* infection (*Kingella kingae*), Kuru (PRNP), Lassa fever (Lassa virus), Legionellosis (Legionnaires' disease) (*Legionella pneumophila*), Legionellosis (Pontiac fever) (*Legionella pneumophila*), Leishmaniasis (*Leishmania* species), Leprosy (*Mycobacterium leprae* and *Mycobacterium lepromatosis*), Leptospirosis (*Leptospira* species), Listeriosis (*Listeria monocytogenes*), Lyme disease (Lyme borreliosis) (*Borrelia burgdorferi, Borrelia garinii*, and *Borrelia afzelii*), Lymphatic filariasis (Elephantiasis) (*Wuchereria bancrofti* and *Brugia malayi*), Lymphocytic choriomeningitis (Lymphocytic choriomeningitis virus (LCMV)), Malaria (*Plasmodium* species), Marburg hemorrhagic fever (MHF) (Marburg virus), Measles (Measles virus), Middle East respiratory syndrome (MERS) (Middle East respiratory syndrome coronavirus), Melioidosis (Whitmore's disease) (*Burkholderia pseudomallei*), Meningitis (multiple), Meningococcal disease (*Neisseria meningitidis*), Metagonimiasis (usually *Metagonimus yokagawai*), Microsporidiosis (Microsporidia phylum), Molluscum contagiosum (MC) (Molluscum contagiosum virus (MCV)), Monkeypox (Monkeypox virus), Mumps (Mumps virus), Murine typhus (Endemic typhus) (*Rickettsia typhi*), *Mycoplasma* pneumonia (*Mycoplasma pneumoniae*), Mycetoma (disambiguation) (numerous species of bacteria (Actinomycetoma) and fungi (Eumycetoma)), Myiasis (parasitic dipterous fly larvae), Neonatal conjunctivitis (Ophthalmia neonatorum) (most commonly *Chlamydia trachomatis* and *Neisseria gonorrhoeae*), Norovirus (children and babies) ((New) Variant Creutzfeldt-Jakob disease (vCJD, nvCJD), PRNP), Nocardiosis (usually *Nocardia asteroides* and other *Nocardia* species), Onchocerciasis (River blindness) (*Onchocerca volvulus*), Opisthorchiasis (*Opisthorchis viverrini* and *Opisthorchis felineus*), Paracoccidioidomycosis (South American blastomycosis) (*Paracoccidioides brasiliensis*), Paragonimiasis (usually *Paragonimus westermani* and other *Paragonimus* species), Pasteurellosis (*Pasteurella* species), Pediculosis capitis (Head lice) (*Pediculus humanus* capitis), Pediculosis corporis (Body lice) (*Pediculus humanus* corporis), Pediculosis pubis (Pubic lice, Crab lice) (*Phthirus pubis*), Pelvic inflammatory disease (PID) (multiple), Pertussis (Whooping cough) (*Bordetella pertussis*), Plague (*Yersinia pestis*), Pneumococcal infection (*Streptococcus pneumoniae*), *Pneumocystis* pneumonia (PCP) (*Pneumocystis jirovecii*), Pneumonia (multiple), Poliomyelitis (Poliovirus), *Prevotella* infection (*Prevotella* species), Primary amoebic meningoencephalitis (PAM) (usually *Naegleria fowleri*), Progressive multifocal leukoencephalopathy (JC virus), Psittacosis (*Chlamydophila psittaci*), Q fever (*Coxiella burnetii*), Rabies (Rabies virus), Relapsing fever (*Borrelia hermsii, Borrelia recurrentis*, and other *Borrelia* species), Respiratory syncytial virus infection (Respiratory syncytial virus (RSV)), Rhinosporidiosis (*Rhinosporidium seeberi*), Rhinovirus infection (Rhinovirus), Rickettsial infection (*Rickettsia* species), Rickettsialpox (*Rickettsia akari*), Rift Valley fever (RVF) (Rift Valley fever virus), Rocky Mountain spotted fever (RMSF) (*Rickettsia rickettsii*), Rotavirus infection (Rotavirus), Rubella (Rubella virus), Salmonellosis (*Salmonella* species), SARS (Severe Acute Respiratory Syndrome) (SARS coronavirus), Scabies (*Sarcoptes scabiei*), Schistosomiasis (*Schistosoma* species), Sepsis (multiple), Shigellosis (Bacillary dysentery) (*Shigella* species), Shingles (Herpes zoster) (Varicella zoster virus (VZV)), Smallpox (Variola) (Variola major or Variola minor), Sporotrichosis (*Sporothrix schenckii*), Staphylococcal food poisoning (*Staphylococcus* species), Staphylococcal infection (*Staphylococcus* species), Strongyloidiasis (*Strongyloides stercoralis*), Subacute sclerosing panencephalitis (Measles virus), Syphilis (*Treponema pallidum*), Taeniasis (*Taenia* species), Tetanus (Lockjaw) (*Clostridium tetani*), Tinea barbae (Barber's itch) (usually *Trichophyton* species), Tinea capitis (Ringworm of the Scalp) (usually *Trichophyton tonsurans*), Tinea corporis (Ringworm of the Body) (usually *Trichophyton* species), Tinea cruris (Jock itch) (usually Epidermophytonfloccosum, *Trichophyton rubrum*, and *Trichophyton mentagrophytes*), Tinea manum (Ringworm of the Hand) (*Trichophyton rubrum*), Tinea nigra (usually *Hortaea werneckii*), Tinea pedis (Athlete's foot) (usually *Trichophyton* species), Tinea unguium (Onychomycosis) (usually *Trichophyton* species), Tinea versicolor (*Pityriasis versicolor*) (*Malassezia* species), Toxocariasis (Ocular Larva Migrans (OLM)) (*Toxocara canis* or *Toxocara cati*), Toxocariasis (Visceral Larva Migrans (VLM)) (*Toxocara canis* or *Toxocara cati*), Trachoma (*Chlamydia trachomatis*), Toxoplasmosis (*Toxoplasma gondii*), Trichinosis (*Trichinella spiralis*), Trichomoniasis (*Trichomonas vaginalis*), Trichuriasis (Whipworm infection) (*Trichuris trichiura*), Tuberculosis (usually *Mycobacterium tuberculosis*), Tularemia (*Francisella tularensis*), Typhoid fever (*Salmonella enterica* subsp. *enterica*, serovar *typhi*), Typhus fever (*Rickettsia*), *Ureaplasma urealyticum* infection (*Ureaplasma urealyticum*), Valley fever (*Coccidioides immitis* or *Coccidioides posadasii*), Venezuelan equine encephalitis (Venezuelan equine encephalitis virus), Venezuelan hemorrhagic fever (Guanarito virus), *Vibrio vulnificus* infection (*Vibrio vulnificus*), *Vibrio parahaemolyticus* enteritis (*Vibrio parahaemolyticus*), Viral pneumonia (multiple viruses), West Nile Fever (West Nile virus), White *piedra* (Tinea blanca) (*Trichosporon beigelii*), *Yersinia pseudotuberculosis* infection (*Yersinia pseudotuberculosis*), Yersiniosis (*Yersinia enterocolitica*), Yellow fever (Yellow fever virus), Zygomycosis (Mucorales order (Mucormycosis) and Entomophthorales order (Entomophthoramycosis)) Human immunodeficiency virus [HIV] disease, HIV disease with infectious and parasitic diseases, HIV disease with mycobacterial infection, HIV disease with cytomegaloviral disease, HIV disease with other viral infections, HIV disease with candidiasis, HIV disease with other mycoses, HIV disease with Pneumocystic carinii pneumonia, HIV disease with malignant neoplasms, HIV disease with Kaposi's sarcoma, HIV disease with Burkitt's lymphoma, HIV disease with other type's of non-Hodgkin's lymphoma, HIV disease with other malignant neoplasms of lymphoid, hematopoietic and related tissue, HIV disease with multiple malignant neoplasms, HIV disease with other malignant neoplasms, HIV disease with unspecified malignant neoplasm, HIV disease with encephalopathy, HIV disease with lymphoid interstitial pneumonitis, HIV disease with wasting syndrome, HIV disease with multiple diseases classified elsewhere, HIV disease with other conditions, HIV disease Acute HIV infection syndrome, HIV disease with (persistent) generalized lymphadenopathy, HIV disease with hematological and immunological abnormalities, not elsewhere classified, HIV disease with other specified conditions, Unspecified HIV disease, Malignant neoplasm of lip, Malignant neoplasm of tonsil, Malignant neoplasm of tongue, Malignant neoplasm of gum, Malignant neoplasm of mouth, Malignant neoplasm of parotid gland, Malignant neoplasm of salivary glands, Malignant neoplasm of pharynx, Malignant neoplasm of esophagus, Malignant neoplasm of stomach, Malignant neoplasm of small intestine, Malignant neoplasm of colon, Malignant neoplasm of recto sigmoid junction, Malignant neoplasm of rectum, Malignant neoplasm of anus, Malignant neoplasm of liver, Malignant neoplasm of gallbladder, Malignant neoplasm of biliary tract, Malignant neoplasm of pancreas, Malignant neoplasm of intestinal tract, Malignant neoplasm of spleen, Malignant neoplasm of nasal cavity and middle ear, Malignant neoplasm of accessory sinuses, Malignant neoplasm of larynx, Malignant neoplasm of trachea, Malignant neoplasm of bronchus and lung, Malignant neoplasm of thymus, Malignant neoplasm of heart, mediastinum and pleura, Malignant neoplasm of sites in the respiratory system and intrathoracic organs, Malignant neoplasm of bone and articular cartilage of limbs, Malignant neoplasm of bones of skull and face, Malignant neoplasm of vertebral column, Malignant neoplasm of ribs, sternum and clavicle, Malignant neoplasm of pelvic bones, sacrum and coccyx, Malignant melanoma of skin, Malignant melanoma of lip, Malignant melanoma of eyelid, including canthus, Malignant melanoma of ear and external auricular canal, Malignant melanoma of face, Malignant melanoma of anal skin, Malignant melanoma of skin of breast, Malignant melanoma of limbs, including shoulder, Merkel cell carcinoma, Basal cell carcinoma of skin of lip, Squamous cell carcinoma of skin of lip, Other and unspecified malignant neoplasm skin/eyelid, including canthus, Malignant neoplasm skin/ear and external auric canal, Other and unspecified malignant neoplasm skin/and unspecified parts of face, Basal cell carcinoma of skin of other and unspecified parts of face, Squamous cell carcinoma of skin of and unspecified parts of face, Basal cell carcinoma of skin of scalp and neck, Squamous cell carcinoma of skin of scalp and neck, Basal cell carcinoma of skin of trunk, Basal cell carcinoma of anal skin, Basal cell carcinoma of skin of breast, Squamous cell carcinoma of skin of trunk, Squamous cell carcinoma of anal skin, Squamous cell carcinoma of skin of breast, Squamous cell carcinoma of skin of other part of trunk, Other and unspecified malignant neoplasm skin/limbs including shoulder, Basal cell carcinoma skin/limbs, including shoulder, Squamous cell carcinoma skin/limbs, including shoulder, Basal cell carcinoma of skin of limbs, including hip, Squamous cell carcinoma of skin of limbs, including hip, Mesothelioma, Kaposi's sarcoma, Malignant neoplasm of peripheral nerves and autonomic nervous sys, Malignant neoplasm of retroperitoneum and peritoneum, Malignant neoplasm of other connective and soft tissue, Malignant neoplasm of connective and soft tissue of thorax, Malignant neoplasm of connective and soft tissue of abdomen, Malignant neoplasm of connective and soft tissue of pelvis, Malignant neoplasm of conn and soft tissue of trunk, unspecified, Malignant neoplasm of overlapping sites of connective and soft tissue, Malignant neoplasm of connective and soft tissue, unspecified, Gastrointestinal stromal tumor, Malignant neoplasm of breast, Malignant neoplasm of vulva, Malignant neoplasm of vagina, Malignant neoplasm of cervix uteri, Malignant neoplasm of corpus uteri, Malignant neoplasm of uterus, part unspecified, Malignant neoplasm of ovary, Malignant neoplasm of other and unspecified female genital organs, Malignant neoplasm of placenta, Malignant neoplasm of penis, Malignant neoplasm of prostate, Malignant neoplasm of testis, Malignant neoplasm of other and unspecified male genital organs, Malignant neoplasm of kidney, Malignant neoplasm of renal pelvis, Malignant neoplasm of ureter, Malignant neoplasm of bladder, Malignant neoplasm of other and unspecified urinary organs, Malignant neoplasm of eye and adnexa, Malignant neoplasm of meninges, Malignant neoplasm of brain, Malignant neoplm of spinal cord, cranial nerves, Malignant neoplasm of optic nerve, Malignant neoplasm of other and unspecified cranial nerves, Malignant neoplasm of central nervous system, unspecified, Malignant neoplasm of thyroid gland, Malignant neoplasm of adrenal gland, Malignant neoplasm of endo glands and related structures, Malignant neuroendocrine tumors, Malignant carcinoid tumors, Secondary neuroendocrine tumors, Malignant neoplasm of head, face and neck, Malignant neoplasm of thorax, Malignant neoplasm of abdomen, Malignant neoplasm of pelvis, Malignant neoplasm of limbs, Malignant neoplasm of lower limb, Secondary and unspecified malignant neoplasm of lymph nodes, Secondary malignant neoplasm of respiratory and digestive organs, Secondary malignant neoplasm of kidney and renal pelvis, Secondary malignant neoplm of bladder and other and unspecified urinary organs, Secondary malignant neoplasm of skin, Secondary malignant neoplasm of brain and cerebral meninges, Secondary malignant neoplasm of and unspecified parts of nervous sys, Secondary malignant neoplasm of bone and bone marrow, Secondary malignant neoplasm of ovary, Secondary malignant neoplasm of adrenal gland, Hodgkin lymphoma, Follicular lymphoma, Non-follicular lymphoma, Small cell B-cell lymphoma, Mantle cell lymphoma, Diffuse large B-cell lymphoma, Lymphoblastic (diffuse) lymphoma, Burkitt lymphoma, Other non-follicular lymphoma, Non-follicular (diffuse) lymphoma, unspecified, Mature T/NK-cell lymphomas, Sezary disease, Peripheral T-cell lymphoma, not classified, Anaplastic large cell lymphoma, ALK-positive, Anaplastic large cell lymphoma, ALK-negative, Cutaneous T-cell lymphoma, unspecified, Other mature T/NK-cell lymphomas, Mature T/NK-cell lymphomas, unspecified, Other and unspecified types of non-Hodgkin lymphoma, Malignant immunoproliferative dis and certain other B-cell lymph, Multiple myeloma and malignant plasma cell neoplasms, Lymphoid leukemia, Acute lymphoblastic leukemia [ALL], Chronic lymphocytic leukemia of B-cell type, Prolymphocytic leukemia of B-cell type, Hairy cell leukemia, Adult T-cell lymphoma/leukemia (HTLV-1-associated), Prolymphocytic leukemia of T-cell type, Mature B-cell leukemia Burkitt-type, Other lymphoid leukemia, Lymphoid leukemia, unspecified, Myeloid leukemia, Acute myeloblastic leukemia, Chronic myeloid leukemia, BCR/ABL-positive, Atypical chronic myeloid leukemia, BCR/ABL-negative, Myeloid sarcoma, Acute promyelocytic leukemia, Acute myelomonocytic leukemia, Acute myeloid leukemia with 11q23-abnormality, Other myeloid leukemia, Myeloid leukemia, unspecified, Monocytic leukemia, Chronic myelomonocytic leukemia, Juvenile myelomonocytic leukemia, Other monocytic leukemia, Monocytic leukemia, unspecified, Other leukemias of specified cell type, Acute erythroid leukemia, Acute megakaryoblastic leukemia, Mast cell leukemia, Acute panmyelosis with myelofibrosis, Myelodysplastic disease, not classified, Other specified leukemias, Leukemia of unspecified cell type, Chronic leukemia of unspecified cell type, Leukemia, unspecified, Other & unspecified malignant neoplasm of lymphoid, hematopoietic tissue, Carcinoma in situ of oral cavity, esophagus and stomach, Carcinoma in situ of colon, Carcinoma in situ of recto sigmoid junction, Carcinoma in situ of rectum, Carcinoma in situ of anus and anal canal, Carcinoma in situ of other and unspecified parts of intestine, Carcinoma in situ of unspecified part of intestine, Carcinoma in situ of other parts of intestine, Carcinoma in situ of liver, gallbladder and bile ducts, Carcinoma in situ of other specified digestive organs, Carcinoma in situ of digestive organ, unspecified, Carcinoma in situ of middle ear and respiratory system, Carcinoma in situ of larynx, Carcinoma in situ of trachea, Carcinoma in situ of bronchus and lung, Carcinoma in situ of other parts of respiratory system, Melanoma in situ, Melanoma in situ of lip, Melanoma in situ of eyelid, including canthus, Melanoma in situ of ear and external auricular canal, Melanoma in situ of unspecified part of face, Melanoma in situ of scalp and neck, Melanoma in situ of trunk, Melanoma in situ of anal skin, Melanoma in situ of breast (skin) (soft tissue), Melanoma in situ of upper limb, including shoulder, Melanoma in situ of lower limb, including hip, Melanoma in situ of other sites, Carcinoma in situ of skin, Carcinoma in situ of skin of lip, Carcinoma in situ of skin of eyelid, including canthus, Carcinoma in situ skin of ear and external auricular canal, Carcinoma in situ of skin of other and unspecified parts of face, Carcinoma in situ of skin of scalp and neck, Carcinoma in situ of skin of trunk, Carcinoma in situ of skin of upper limb, including shoulder, Carcinoma in situ of skin of lower limb, including hip, Carcinoma in situ of skin of other sites, Carcinoma in situ of breast, Lobular carcinoma in situ of breast, Intraductal carcinoma in situ of breast, Other specified type of carcinoma in situ of breast, Unspecified type of carcinoma in situ of breast, Carcinoma in situ of cervix uteri, Carcinoma in situ of other parts of cervix, Carcinoma in situ of cervix, unspecified, Carcinoma in situ of other and unspecified genital organs, Carcinoma in situ of endometrium, Carcinoma in situ of vulva, Carcinoma in situ of vagina, Carcinoma in situ of other and unspecified female genital organs, Carcinoma in situ of penis, Carcinoma in situ of prostate, Carcinoma in situ of unspecified male genital organs, Carcinoma in situ of scrotum, Carcinoma in situ of other male genital organs, Carcinoma in situ of bladder, Carcinoma in situ of other and unspecified urinary organs, Carcinoma in situ of eye, Carcinoma in situ of thyroid and other endocrine glands, Benign neoplasm of mouth and pharynx, Benign neoplasm of major salivary glands, Benign neoplasm of colon, rectum, anus and anal canal, Benign neoplasm of and ill-defined parts of digestive system, Benign neoplasm of esophagus, Benign neoplasm of stomach, Benign neoplasm of duodenum, Benign neoplasm of other and unspecified parts of small intestine, Benign neoplasm of liver, Benign neoplasm of extrahepatic bile ducts, Benign neoplasm of pancreas, Benign neoplasm of endocrine pancreas, Benign neoplasm of ill-defined sites within the digestive system, Benign neoplasm of middle ear and respiratory system, Benign neoplasm of respiratory system, unspecified, Benign neoplasm of other and unspecified intrathoracic organs, Benign neoplasm of thymus, Benign neoplasm of heart, Benign neoplasm of mediastinum, Benign neoplasm of other specified intrathoracic organs, Benign neoplasm of intrathoracic organ, unspecified, Benign neoplasm of bone and articular cartilage, Benign neoplasm of short bones of upper limb, Benign neoplasm of long bones of lower limb, Benign neoplasm of short bones of lower limb, Benign neoplasm of bones of skull and face, Benign neoplasm of lower jaw bone, Benign neoplasm of vertebral column, Benign neoplasm of ribs, sternum and clavicle, Benign neoplasm of pelvic bones, sacrum and coccyx, Benign neoplasm of bone and articular cartilage, unspecified, Benign lipomatous neoplasm, Ben lipomatous neoplm of skin, subcutaneous of head, face and neck, Benign lipomatous neoplasm of intrathoracic organs, Benign lipomatous neoplasm of intra-abdominal organs, Benign lipomatous neoplasm of spermatic cord, Benign lipomatous neoplasm of other sites, Benign lipomatous neoplasm of kidney, Benign lipomatous neoplasm of other genitourinary organ, Hemangioma and lymphangioma, any site, Hemangioma, Hemangioma unspecified site, Hemangioma of skin and subcutaneous tissue, Hemangioma of intracranial structures, Hemangioma of intra-abdominal structures, Hemangioma of other sites, Lymphangioma, any site, Benign neoplasm of mesothelial tissue, Benign neoplm of soft tissue of retroperitoneum and peritoneum, Other benign neoplasms of connective and other soft tissue, Melanocytic nevi, Melanocytic nevi of lip, Melanocytic nevi of eyelid, including canthus, Melanocytic nevi of unspecified eyelid, including canthus, Melanocytic nevi of ear and external auricular canal, Melanocytic nevi of other and unspecified parts of face, Melanocytic nevi of scalp and neck, Melanocytic nevi of trunk, Melanocytic nevi of upper limb, including shoulder, Melanocytic nevi of lower limb, including hip, Melanocytic nevi, unspecified, Other benign neoplasm of skin of eyelid, including canthus, Other benign neoplasm skin/ear and external auricular canal, Other benign neoplasm skin/left ear and external auric canal, Other benign neoplasm of skin of other and unspecified parts of face, Other benign neoplasm of skin of other parts of face, Other benign neoplasm of skin of scalp and neck, Other benign neoplasm of skin of trunk, Other benign neoplasm skin/upper limb, including shoulder, Other benign neoplasm of skin of lower limb, including hip, Other benign neoplasm of skin, unspecified, Benign neoplasm of breast, Benign neoplasm of unspecified breast, Leiomyoma of uterus, Other benign neoplasms of uterus, Benign neoplasm of ovary, Benign neoplasm of other and unspecified female genital organs, Benign neoplasm of male genital organs, Benign neoplasm of urinary organs, Benign neoplasm of kidney, Benign neoplasm of renal pelvis, Benign neoplasm of ureter, Benign neoplasm of bladder, Benign neoplasm of urethra, Benign neoplasm of other specified urinary organs, Benign neoplasm of urinary organ, unspecified, Benign neoplasm of eye and adnexa, Benign neoplasm of conjunctiva, Benign neoplasm of cornea, Benign neoplasm of retina, Benign neoplasm of choroid, Benign neoplasm of ciliary body, Benign neoplasm of lacrimal gland and duct, Benign neoplasm of unspecified site of orbit, Benign neoplasm of unspecified part of eye, Benign neoplasm of meninges, Benign neoplasm of brain and central nervous system, Benign neoplasm of thyroid gland, Benign neoplasm of other and unspecified endocrine glands, Benign neoplasm of other and unspecified sites, Benign neoplasm of lymph nodes, Benign neoplasm of peripheral nerves and autonomic nervous sys, Benign neoplasm of other specified sites, Benign neuroendocrine tumors, Other benign neuroendocrine tumors, Neoplasm of uncertain behavior of oral cavity and digestive organs, Neoplasm of uncertain behavior of the major salivary glands, Neoplasm of uncertain behavior of pharynx, Neoplasm of uncertain behavior of sites of the oral cavity, Neoplasm of uncertain behavior of stomach, Neoplasm of uncertain behavior of small intestine, Neoplasm of uncertain behavior of appendix, Neoplasm of uncertain behavior of colon, Neoplasm of uncertain behavior of rectum, Neoplasm of uncertain behavior of liver, GB & bile duct, Neoplasm of uncertain behavior of other digestive organs, Neoplasm of uncertain behavior of digestive organ, Neoplm of mid ear and intrathoracic organs, Neoplasm of uncertain behavior of larynx, Neoplasm of uncertain behavior of trachea, bronchus and lung, Neoplasm of uncertain behavior of pleura, Neoplasm of uncertain behavior of mediastinum, Neoplasm of uncertain behavior of thymus, Neoplasm of uncertain behavior of other respiratory organs, Neoplasm of uncertain behavior of respiratory organ, unspecified, Neoplasm of uncertain behavior of female genital organs, Neoplasm of uncertain behavior of uterus, Neoplasm of uncertain behavior of ovary, Neoplasm of uncertain behavior of unspecified ovary, Neoplasm of uncertain behavior of placenta, Neoplasm of uncertain behavior of male genital organs, Neoplasm of uncertain behavior of urinary organs, Neoplasm of uncertain behavior of kidney, Neoplasm of uncertain behavior of unspecified kidney, Neoplasm of uncertain behavior of renal pelvis, Neoplasm of uncertain behavior of ureter, Neoplasm of uncertain behavior of bladder, Neoplasm of uncertain behavior of other urinary organs, Neoplasm of uncertain behavior of unspecified urinary organ, Neoplasm of uncertain behavior of meninges, Neoplasm of uncertain behavior of cerebral meninges, Neoplasm of uncertain behavior of spinal meninges, Neoplasm of uncertain behavior of meninges, unspecified, Neoplasm of uncertain behavior of brain, Neoplasm of uncertain behavior of brain, Neoplasm of uncertain behavior of brain, infratentorial, Neoplasm of uncertain behavior of brain, unspecified, Neoplasm of uncertain behavior of cranial nerves, Neoplasm of uncertain behavior of spinal cord, Neoplasm of uncertain behavior of central nervous system, Neoplasm of uncertain behavior of endocrine glands, Neoplasm of uncertain behavior of thyroid gland, Neoplasm of uncertain behavior of adrenal gland, Neoplasm of uncertain behavior of unspecified adrenal gland, Neoplasm of uncertain behavior of parathyroid gland, Neoplasm of uncertain behavior of pituitary gland, Neoplasm of uncertain behavior of craniopharyngeal duct, Neoplasm of uncertain behavior of pineal gland, Neoplasm of uncertain behavior of carotid body, Neoplasm of uncertain behavior of aortic body and other paraganglia, Neoplasm of uncertain behavior of unspecified endocrine gland, Polycythemia vera, Myelodysplastic syndromes, Refractory anemia without ring sideroblasts, so stated, Refractory anemia with ring sideroblasts, Refractory anemia with excess of blasts [RAEB], Myelodysplastic syndrome, unspecified, Other neoplm of uncertain behavior of lymphoid, hematopoietic tissue, Histiocytic and mast cell tumors of uncertain behavior, Chronic myeloproliferative disease, Monoclonal gammopathy, Essential (hemorrhagic) thrombocythemia, Osteomyelofibrosis, Other neoplasm of uncertain behavior of lymphoid, hematopoietic tissue, Neoplasm of uncertain behavior of lymphoid, hematopoietic & unspecified, Neoplasm of uncertain behavior of other and unspecified sites, Neoplasm of uncertain behavior of bone/artic cartilage, Neoplasm of uncertain behavior of connective/soft tissue, Neoplasm of uncertain behavior of peripheral nerves and autonomous nervous sys, Neoplasm of uncertain behavior of retroperitoneum, Neoplasm of uncertain behavior of peritoneum, Neoplasm of uncertain behavior of skin, Neoplasm of uncertain behavior of breast, Neoplasm of unspecified behavior of digestive system, Neoplasm of unspecified behavior of respiratory system, Neoplasm of unspecified behavior of bone, soft tissue, and skin, Neoplasm of unspecified behavior of breast, Neoplasm of unspecified behavior of bladder, Neoplasm of unspecified behavior of other genitourinary organs, Neoplasm of unspecified behavior of kidney, Neoplasm of unspecified behavior of other GU organ, Neoplasm of unspecified behavior of brain, Neoplasm of unspecified behavior of endo glands and other parts of nervous sys, Neoplasm of unspecified behavior of retina and choroid, Neoplasm of unspecified behavior of unspecified site, Iron deficiency anemia, Vitamin B12 deficiency anemia, Folate deficiency anemia, Protein deficiency anemia, Other megaloblastic anemias, not elsewhere classified, Scorbutic anemia, Other specified nutritional anemias, Nutritional anemia, unspecified, Anemia due to enzyme disorders, Anemia, Thalassemia, Hereditary persistence of fetal hemoglobin [HPFH], Hemoglobin E-beta thalassemia, Other thalassemia's, Thalassemia, unspecified, Sickle-cell disorders, Other hereditary hemolytic anemias, Acquired hemolytic anemia, Acquired pure red cell aplasia [erythroblastopenia], Acquired pure red cell aplasia, unspecified, Other aplastic anemias and other bone marrow failure syndromes, Drug-induced aplastic anemia, Aplastic anemia due to other external agents, Idiopathic aplastic anemia, Other aplastic anemias and other bone marrow failure syndromes, Aplastic anemia, unspecified, Acute posthemorrhagic anemia, Anemia, Disseminated intravascular coagulation, Hereditary factor VIII deficiency, Hereditary factor IX deficiency, Other coagulation defects, Acquired coagulation factor deficiency, Primary thrombophilia, Other thrombophilia, Purpura and other hemorrhagic conditions, Secondary thrombocytopenia, Thrombocytopenia, unspecified, Other specified hemorrhagic conditions, Hemorrhagic condition, unspecified, Neutropenia, Congenital agranulocytosis, Agranulocytosis secondary to cancer chemotherapy, Other drug-induced agranulocytosis, Neutropenia due to infection, Cyclic neutropenia, Other neutropenia, Other disorders of white blood cells, Genetic anomalies of leukocytes, Eosinophilia, Other specified disorders of white blood cells, Decreased white blood cell count, Lymphocytosis (symptomatic), Diseases of spleen, Methemoglobinemia, Congenital methemoglobinemia, Other methemoglobinemias, Methemoglobinemia, unspecified, Other and unspecified diseases of blood and blood-forming organs, Familial erythrocytosis, Secondary polycythemia, Other specified diseases of blood and blood-forming organs, Myelofibrosis, Heparin induced thrombocytopenia (HIT), Other specified diseases of blood and blood-forming organs, Other dis with lymphoreticular and reticulohistiocytic tissue, Intraoperative and postprocedural complications of the spleen, Immunodeficiency with predominantly antibody defects, Hereditary hypogammaglobulinemia, Nonfamilial hypogammaglobulinemia, Selective deficiency of immunoglobulin A [IgA], Selective deficiency of immunoglobulin G [IgG] subclasses, Selective deficiency of immunoglobulin M [IgM], Immunodeficiency with increased immunoglobulin M [IgM], Antibody deficiency w near-norm immunoglobulin or w hyperimmunoglobulin, Transient hypogammaglobulinemia of infancy, Other immunodeficiencies with predominantly antibody defects, Immunodeficiency with predominantly antibody defects, unspecified, Combined immunodeficiencies, Severe combined immunodeficiency with reticular dysgenesis, Severe combined immunodeficiency w low T- and B-cell numbers, Severe combined immunodeficiencies w low or normal B-cell numbers, Adenosine deaminase [ADA] deficiency, Nezelofs syndrome, Purine nucleoside phosphorylase [PNP] deficiency, Major histocompatibility complex class I deficiency, Major histocompatibility complex class II deficiency, Other combined immunodeficiencies, Combined immunodeficiency, unspecified, Immunodeficiency associated with other major defects, Wiskott-Aldrich syndrome, Di George's syndrome, Immunodeficiency with short-limbed stature, Immunodeficiency following response to Epstein-Barr virus, Hyperimmunoglobulin E [IgE] syndrome, Immunodeficiency associated with other major defects, Immunodeficiency associated with major defect, unspecified, Common variable immunodeficiency, Other immunodeficiencies, Lymphocyte function antigen-1 [LFA-1] defect, Defects in the complement system, Other specified immunodeficiencies, Sarcoidosis, Other disorders involving the immune mechanism, NEC, Polyclonal hypergammaglobulinemia, Cryoglobulinemia, Hypergammaglobulinemia, unspecified, Immune reconstitution syndrome, Mast cell activation syndrome and related disorders, Mast cell activation, unspecified, Monoclonal mast cell activation syndrome, Idiopathic mast cell activation syndrome, Secondary mast cell activation, Other mast cell activation disorder, Other disorders involving the immune mechanism, NEC, Graft-versus-host disease, Acute graft-versus-host disease, Chronic graft-versus-host disease, Acute on chronic graft-versus-host disease, Graft-versus-host disease, unspecified, Autoimmune lymphoproliferative syndrome [ALPS], Other disorders involving the immune mechanism, NEC, Disorder involving the immune mechanism, unspecified, Autoimmune thyroiditis, Type 1 diabetes mellitus, Other diabetes mellitus with other specified complication, Primary adrenocortical insufficiency, Autoimmune polyglandabular failure, Dementia in human immunodeficiency virus [HIV] disease (B22.0), Multiple sclerosis, Guillain-Barre syndrome, Myasthenia gravis without (acute) exacerbation, Myasthenia gravis with (acute) exacerbation, Cytotoxic myoneural disorders, Congenital and developmental myasthenia, Lambert-Eaton syndrome, unspecified, Lambert-Eaton syndrome in disease classified elsewhere, Other specified myoneural disorders, Myoneural disorder, unspecified, Unspecified acute and subacute iridocyclitis, Crohn's disease, Ulcerative (chronic) pancolitis, Inflammatory polyps of colon, Left sided colitis, Other ulcerative colitis without/with complications, Chronic persistent hepatitis, Chronic lobular hepatitis, Chronic active hepatitis, Other chronic hepatitis, Chronic hepatitis, unspecified, Primary biliary cirrhosis, Autoimmune hepatitis, Celiac disease, Pemphigus, Bullous pemphigoid, Cicatricial pemphigoid, Chronic bullous disease of childhood, Acquired epidermolysis bullosa, unspecified, Other acquired epidermolysis bullosa, Other pemphigoid, Psoriasis vulgaris, Other psoriatic arthropathy, Alopecia (capitis) totalis, Alopecia universalis, Ophiasis, Other alopecia areata, Alopecia areata, unspecified, Vitiligo, Felty's syndrome, Rheumatoid lung disease w rheumatoid arthritis, Rheumatoid vasculitis with rheumatoid arthritis of unspecified site, Rheumatoid vasculitis w rheumatoid arthritis, Rheumatoid heart disease w rheumatoid arthritis, Rheumatoid myopathy with rheumatoid arthritis, Rheumatoid polyneurop w rheumatoid arthritis, rheumatoid arthritis, Rheumatoid arthritis with/without rheumatoid factor, Adult-onset Still's disease, Rheumatoid bursitis, Rheumatoid nodule, Inflammatory polyarthropathy, Other specified rheumatoid arthritis, Juvenile rheumatoid arthritis, Juvenile ankylosing spondylitis, Juvenile arthritis, Wegener's granulomatosis without renal involvement, Wegener's granulomatosis with renal involvement, Juvenile dermatopolymyositis, Polymyositis, Dermatopolymyositis, Giant cell arteritis with polymyalgia rheumatica, Systemic lupus erythematosus, Endocarditis in systemic lupus erythematosus, Pericarditis in systemic lupus erythematosus, Lung involvement in systemic lupus erythematosus, Glomerular disease in systemic lupus erythematosus, Tubulo-interstitial neuropath in sys lupus erythematosus, Progressive systemic sclerosis, CR(E)ST syndrome, Systemic sclerosis, Sicca syndrome, Polymyalgia rheumatica, Systemic involvement of connective tissue, Ankylosing spondylitis, Laboratory evidence of human immunodeficiency virus [HIV], Other abnormal immunological findings in serum, Immunosuppressive agents, Immunoglobulin is treated with an NTLA immune suppressant, or an antagonist to CD26 prior to administration of a cellular immunotherapy. The NTLA can be chosen from the list consisting of: Dexamethasone base HED between 3-12 mg/kg administered either orally or over a 15-60 minute intravenous infusion between 12-72 hours before administration of a cellular immunotherapy. Mice can also be preconditioned with: An agent containing hydrocortisone is administered intravenously or orally about every 12 hours at a dose of about 75 to about 300 mg/kg between about 12 to about 72 hours before administration of the cellular immunotherapy. An agent containing cortisone is administered intravenously or orally about every 12 hours at a dose of about 93 to about 375 mg/kg between about 12 to about 72 hours before administration of the cellular immunotherapy. An agent containing prednisolone is administered intravenously or orally about every 24 hours at a dose of about 19 to about 75 mg/kg between about 12 to about 60 hours before administration of the cellular immunotherapy. An agent containing methylprednisolone is administered intravenously or orally about every 24 hours at a dose of about 15 to about 60 mg/kg between about 12 to about 60 hours before administration of the cellular immunotherapy. An agent containing triamcinolone is administered intravenously or orally about every 24 hours at a dose of about 15 to about 60 mg/kg between about 12 to about 60 hours before administration of the cellular immunotherapy. An agent containing paramethasone is administered in either a single acute dose or cumulative doses of about 7.5 to about 30 mg/kg, given between about 12-72 hours prior to cellular immunotherapy. An agent containing betamethasone is administered in either a single acute dose or cumulative doses of about 2.5 to 10 mg/kg, given between about 12-72 hours prior to cellular immunotherapy.

Cellular immunotherapy is administered on day 0 and can be chosen from the list of: toleragenic dendritic cells, tumor infiltrating lymphocytes, adoptive cell transfer, adoptive cell therapy, chimeric antigen receptor cells, genetically engineered TCR cells, regulatory T cell transfer, cellular adoptive immunotherapy, cellular immunotherapy, cellular immune-oncology, in vivo complex (IL-2C) consisting of IL-2 and anti-IL-2 monoclonal antibody (JES6-1) expanded Tregs, T-Cell receptor (TCR) immunogenicity for T-cell vaccinations, autological polyclonal T-cell vaccines (TCVs), adoptive transfer of Treg-of-B cells (B cells induced a particular subset of regulatory T), adoptive transfer of GC-induced or ATF3-deficient G-MDSCs (myeloid derived suppressor cells), genetically engineered lymphocytes, RNA redirected autologous T cells, T-cell Natural Killer cells, Receptor NKG2D cells, CD4+ cells, CD8+ cells, CD4+ T cells, CD8+ T cells, mixtures of CD4+ and CD8 T cells, MDSCs, CTLs, EBV-CTLs, virus specific cytocytotoxic T lymphocytes (CTLs), cytokine-induced killer cells, antigen pulsed dendritic cells, CMV-CTLs, natural dendritic cells, dendritic cells, third party donor derived CTL's, autologous γδ T lymphocyte therapy, CD45RA Depleted T-cell Infusion, Laboratory-treated T Cells, HER2Bi-armed activated T cells, autologous tumor DC vaccine, Dendritic Cell (DC)-Based Vaccines Loaded with Allogeneic Prostate Cell Lines, Dendritic Cell/AML Vaccine, Dendritic Cell vaccines, gene-modified lymphocytes, dendritic cell therapy, ESO-1 Lymphocytes, Tumor-Pulsed Dendritic Cells, Autologous Tumor Lysate-pulsed Dendritic Cell, gene-modified immune cells, Marrow Infiltrating Lymphocytes, Alpha-galactosylceramide-pulsed Dendritic Cells, Alpha-galactosylceramide-pulsed Natural Killer T (NKT) Cells, Alpha-galactosylceramide-pulsed Dendritic Cells and Natural Killer T (NKT) Cells, Autologous gamma/Delta T Cells, Activated Self-lymphocytes, Epstein-Barr Virus Immune T-Lymphocytes Derived From a Normal HLA-Compatible Or Partially-Matched Third-Party Donor, granulocyte macrophage colony-stimulating factor plus bi-shRNAi furin vector transfected autologous tumor cells, Alpha-galactosylceramide Pulsed Dendritic Cells (Chiba-NKT), P53-Pulsed Dendritic Cells, Primary Transplant Donor Derived CMVpp65 Specific T-cells, mixed T- and natural killer (NK) cell-like phenotype (CIK Cells), Antigen Pulsed Dendritic Cells (APDC), DC-CIK, Alpha-galcer Pulsed APC, Zoledronate-Activated Autologous Killer Lymphocytes (Zak Cells), Chiba NKT cells, Autologous Dendritic Cells Loaded with Autologous Tumor Lysate or Homogenate, Third Party Donor Derived CMVpp65 Specific T-cells, Autologous Tumor Lysate-pulsed D-CIK, Multi-epitope TARP Peptide Autologous Dendritic Cells, T-reg Adoptive Cell Transfer (TRACT), Modified DLI (Donor Double Negative T Cells), Type-1 Polarized Dendritic Cells (AlphaDC1), Autologous Tumor Tissue Antigen-sensitized DC-CIK Cells, Peptide Pulsed Dendritic Cells, Dendritic Cytocytotoxic Lymphocyte(DC-CTL) Cells, MTCR-transduced Autologous Peripheral Blood Lymphocytes, Cytokine Induced Memory-like NK Cells, LMP-specific T-cells, Modified DLI (Related-donor Double Negative T Cells), Autologous Dendritic Cells Loaded with Autologous Tumour Homogenate, Vigil® Engineered Autologous Tumor Cell (EATC) therapy, New Antigen Reactive Immune Cell Therapy (NRT), Autologous Cytokine-induced Killer Cells, Fused Autologous Dendritic Cells, Peptide Specific CTL, Allogeneic Cell Immunotherapy ACIT-1, PD-1 Knockout Engineered T Cells, DC/AML Fusion Cells, (DC/PC3), Laboratory-treated T Cells, Dendritic Cell Tumor Fusions, Lethally Irradiated, Autologous Breast Cancer Cells, CD4-ZETA Gene Modified T Cells, EBV-specific Immune Effector Cell (EBV-IE), Herpes Virus (HHV) Specific Immune Effector (IE) Cell, mRNA-transfected Dendritic Cells, Allogeneic Dendritic Cell Therapy, Cytomegalovirus (CMV) Pp65-specific Lyphocytes, Alpha-Galactosylceramide-Pulsed IL-2/GM-CSF-Cultured Peripheral Blood Mononuclear Cells, Depleted T Cells, Donor Cells Dendritic Vaccination, DCs Vaccine Combined with Cytokine-induced Killer Cells, DC Vaccine Combined with CIK Cells, HB-vac Activated-DCs, Haploidentical NK-cell Infusion, ZNK cell, WT1 and MUC1 Peptide-Pulsed Dendritic Cells, ONETreg1 cells, Alpha DC1, Autologous T Lymphocytes with ADCC, Memory T-cell Infusion, HER-2/Neu Pulsed DC1, Stimulated Autologous CD4+ T Cells, Gamma delta T cell, irradiated allogeneic lung adenocarcinoma cells, CD40LGVAX, irradiated allogeneic lung adenocarcinoma cells combined with a bystander cell line transfected with hCD40L and hGM-CSF, EGFRBi-armed Autologous T Cells, MiHA-loaded PD-L-silenced DC, MyDC/pDC, ROR-1.taNK, PDL1.taNK, Adjuvant Dendritic Cell-immunotherapy, D-CIK, DOT-Cells, Autologous Tumor Lysate (TL) plus Yeast Cell Wall Particles (YCWP) plus Dendritic Cells, Autologous EBV-specific Cytocytotoxic T Cells, Autologous TLPLDC vaccine (tumor lysate, particle loaded, dendritic cells), Regulatory T Cells, Personalized Cellular Vaccine (PERCELLVAC), CAR-pNK Cell, HER2.taNK, MUC16.taNK, DC1s-CTLs, (PERCELLVAC2), (PERCELLVAC3), MASCT, CAR-pNK Cells, CD33.taNK, Post Cord Blood HCT Dendritic Cells, Umbilical Cord Blood Regulatory T Cells, High-activity Natural Killer cells, PD-1 Knockout EBV-CTLs, DC-CTL Combined with CIK, Anti-gen-Bearing Dendritic Cells, Dendritic Cell/Tumor Fusions, Transfected Dendritic Cell, Her2 and TGFBeta CTLs, Blood T-cells and EBV Specific CTLs, Autologous Breast Cancer Cells Engineered to Secrete Granulocyte-macrophage Colony-Stimulating Factor (GM-CSF), Gene-modified White Blood Cells, Epitope-enhanced TARP Peptide and TARP Peptide-pulsed Dendritic Cells, Laboratory-treated Autologous Lymphocytes, Multi-virus CTLs, Cytomegalovirus-specific T-cell Adoptive Transfer (ERaDICATe), GM-K562 Cells, Kappa-CD28 T Lymphocytes, TGFB2-Antisense-GMCSF Gene Modified Autologous Tumor Cell, Bi-shRNA-furin and Granulocyte Macrophage Colony Stimulating Factor (GMCSF) Augmented Autologous Tumor Cells, Donor T Cells Sensitized with Pentadecapeptides of the CMV-PP65 Protein, Peptide-pulsed Monocyte-derived Dendritic Cell Vaccination to Expand Adoptively Transferred CMV-specific Cytocytotoxic T Lymphocytes, CMV Specific DLIs From 3-6/6 HLA Matched Family Member, CMV Specific DLIs, Autologous T-cells Combined With Autologous OC-DC, TAA-Specific CTLs, Autologous Lymphocytes, Autologous Tolerogenic Dendritic Cells, Langerhans-type Dendritic Cells, Langerhans-type Dendritic Cells Electroporated with mRNA Encoding a Tumor-associated Antigen, Autologous T Cells, Multi-virus Cytocytotoxic T-cells, Autologous IL2 and CD40 Ligand-Expressing Tumor Cells, Multiple Antigen-Engineered DC. WT1 And/Or Tumor Lysates-pulsed Dendritic Cells, Autologous Human Cytomegalovirus (HCMV)-specific T cell Therapy, Ad/HER2/Neu Dendritic Cell, WT1 Peptide (Peptivator)-pulsed Dendritic Cell, Donor Derived, Multi-virus-specific, Cytocytotoxic T-Lymphocytes, Ex-vivo Expanded Donor Regulatory T Cells, Alpha-GalCer-Pulsed Antigen Presenting Cells (APCs), Cytokine-induced Memory-like NK Cells, "Re-stimulated" Tumor-infiltrating Lymphocytes, Autologous Langerhans-type Dendritic Cells, Memory Enriched T Cells, Expanded Multi-antigen Specifically Oriented Lymphocytes, TAA-Specific CTLs, Regulatory Dendritic Cells, Closely Matched Third Party Rapidly Generated LMP, BARF1 and EBNA1 Specific CTL, Activated Marrow Infiltrating Lymphocytes, Autologous Tumor Lysate-loaded Dendritic Cells, Multi-Epitope TARP Peptide Autologous Dendritic Cells, HPV-16/18 E6/E7-specific T Lymphocytes, Autologous Epstein-barr Virus-specific T Cells, Activated T-cells, Donor Multitaa-specific T Cells, Multitaa-specific T Cells, Type I-Polarized Autologous Dendritic Cells, Vaccine Enriched Autologous Activated T-cells, Multivirus-specific Cytocytotoxic T Lymphocytes (mCTL), Allogeneic Virus-specific T Cell Lines (VSTs), Donor Regulatory T Cells, TCR-modified T cells (TCRs), MIC Cell, Adoptive T Cell Therapy with Activated P53 Specific T Cells, MUC1-DC-CTL, T cell receptor-modified T cells, "Negative" Dendritic Cell-based Vaccine, tolDC, CD22 Redirected Autologous T Cells, Dendristim, Primary NK Cells, Lentiviral-based CART-EGFRvIII Gene-modified Cellular Therapy Products, Autologous Dendritic Cells Pulsed with Lysated Allegenic Tumor Lines, Expanded Multi-antigen Specific Lymphocytes, PD-1 Knockout Engineered T Cells, GSC-loaded Dendritic Cells, Treg Adoptive Cell Transfer (TRACT), E7 TCR T Cells, PD-1 Knockout Engineered T Cells, CAR-Treg (ENTX-DN), Chimeric Switch Receptor Modified T Cells, Neoantigen-primed Dendritic Cells (DC), Pre-activated T (PreT) Cells, TSA-CTL (Tumor Specific Antigen-induced Cytotoxic T Lymphocytes), Allogeneic Cell Immunotherapy (ACIT-1), Autologous OC-DC, Mature Dendritic Cells, CD8+NKG2D+ AKT Cell, Natural Killer (NK) cells—oNKord®, antigen presenting cells—sD-Cord®.

In comparison to administering the cellular immunotherapy without pretreatment with an NTLA immunesuppressant, with NTLA dexamethasone doses, or an antagonist to CD26, when the patient is pretreated with an NTLA immunesuppressant, with NTLA dexamethasone doses, or an antagonist to CD26 the administered cellular immunotherapy remains in the circulation or at the site of injection where it can find and kill its target, resulting in greater killing or slower growth of the cancer or tumor or autoimmune cell, or pathogen. The NTLA preconditioned patients will have similar or better anti-tumor effect, improved progression-free survival, reduced Disease progression, enhanced duration of response, improved overall survival, or reduced minimal residual disease compared to patients who are preconditioned with radiation or repetitive doses of cytotoxic chemotherapy.

Example 7: Post-Surgical Treatment of Solid Tumors with NTLA and Cellular Immunotherapy to Prevent Relapse A patient with a solid tumor undergoes surgical removal or reduction, which can release cancer blasts and cause ultimate relapse. Relapse can occur in the short term, for cancers such as pancreatic cancer, or in the long term for cancers such as breast cancer, which may relapse as long as 20 years following surgery. After recovery from surgery, between about 1 to about 3 days to about 1 year after surgery, the patient is preconditioned with NTLA as Tacrolimus delivered as an injection or oral dose of about 0.48 mg/kg/day to about 10 mgs/kg/day for about 1 to about 4 weeks, or as Cyclosporine administered at about 15 to about 100 mgs/kg/daily for about 7 to about 28 days (the daily dose is divided by two and administered every 12 hours), or as Dexamethasone base, or an equivalent dose of another glucocorticoid, between about 3 mg/kg and about 26 mg/kg single acute dose about 12 to about 72 hours prior to cell immunotherapy administration or total dose of about 3 mg/kg to about 26 mg/kg given between about 12 to about 72 hours prior to cell therapy administration (the single acute dose would most preferably be given about 36 to about 48 hours prior to cell immunotherapy administration), or as a TNF inhibitor administered for about 3 to about 4 weeks, or as an immunotherapy of the class of Rituximab administered between about 375 mg/m2 to about 500 mg/m2 administered about every 7 days on about day −7 and day −1. After preconditioning, between about 1 day to about 4 days after preconditioning, the patient is administered a cellular immunotherapy between about $1 \times 10^5$ cells/kg body weight to about $1 \times 10^7$ cells/kg body weight. The preferred cellular therapy is an NK cell product, a TCR cell product, a TAC cell product, or a CarT cell product. Relapse free survival is increased and overall survival time is enhanced. The NTLA preconditioned patients will have similar or better anti-tumor effect, improved progression-free survival, reduced Disease progression, enhanced duration of response, improved overall survival, or reduced minimal residual disease compared to patients who are preconditioned with radiation or repetitive doses of cytotoxic chemotherapy.

Example 8: Treatment of Post-Surgical Breast Tumors in Mice

Eight groups of BALB/c mice each are injected with 4T1 cells into the mammary fat pad for the generation of breast tumor mouse model. After 9-11 days or until the tumor size reach a diameter of 3.5-5 mm, tumors will be surgically removed. One day after primary tumor removal, preconditioning schedule will be followed according to Table I below. Either syngeneic (NK cells isolated from BALB/c mice; 3 groups) or allogenic (KIL cell; 3 groups) NK cells are transplanted by IV tail vein injection after preconditioning. Mice are sacrificed between day 30 and day 60. The groups in this study are found in Table I below.

TABLE I

Preconditioning schedule for Example 8:
Treatment of post-surgical breast tumors in mice

| Group | Preconditioning | NK cell | Protocol |
|---|---|---|---|
| 1 | Cy/Flu* | allogeneic | Cyclophosphamide 166 mg/kg, dosing at days −5, −4, −3<br>Fludarabine Phosphate 10 mg/kg, dosing at days −5, −4, −3 |
| 2 | AVM0703 | allogeneic | AVM0703 148 mg/kg, dosing at day −2 |
| 3 | CyFlu + AVM0703 | allogeneic | Cyclophosphamide 166 mg/kg, dosing at day −5<br>Fludarabine Phosphate 10 mg/kg, dosing at day −5<br>AVM0703 148 mg/kg, dosing day −2 |
| 4 | Cy/Flu* | syngeneic | Cyclophosphamide 166 mg/kg, dosing at days −5, −4, −3<br>Fludarabine Phosphate 10 mg/kg, dosing at days −5, −4, −3 |
| 5 | AVM0703 | syngeneic | AVM0703 148 mg/kg, dosing at day −2 |
| 6 | CyFlu + AVM0703 | syngeneic | Cyclophosphamide 166 mg/kg, dosing at day −5<br>Fludarabine Phosphate 10 mg/kg, dosing at day −5<br>AVM0703 148 mg/kg, dosing day −2 |
| 7 | Vehicle | allogeneic | Vehicle only, dosing at day −2 (AVM Placebo) |
| 8 | Vehicle | syngeneic | Vehicle only, dosing at day −2 (AVM Placebo) |

Method of investigation: Body weight, blood, and spleen collection for further analysis. Lungs are excised and perfused with India Ink for visual counts of metastasis. Mice survival plot will be made to compare the survival benefit between different treatments.

Expected outcome: Efficacy of NK-cell therapy after AVM0703 preconditioning demonstrated to be equivalent or superior to therapy after chemotherapy preconditioning in breast cancer mouse model.

Example 9: Treatment of Post-Surgical Solid Tumors in Mice

Mice are injected subcutaneously in the flank with solid tumor cells. C57Bl6 mice are injected with B16 or B16-F10 melanoma cells or LLC lung cancer cells; Balb/c mice are injected with RENCA renal cancer cells or CT26 colon cancer cells. When the tumor reaches a palpable size of 3.5-5 mm the tumors are completely excised. One day after primary tumor removal, preconditioning schedule is followed according to the table II schedule. Either syngeneic (NK cells isolated from BALB/c mice or C57Bl6) or allogenic (NK cells isolated from BALB/c mice or C57Bl6 or the KIL cell line) NK cells are transplanted by IV tail vein injection after preconditioning. Mice are sacrificed between day 30 and day 60. The groups in this study are found in Table II below.

TABLE II

Preconditioning schedule for Example 9:
Treatment of post-surgical solid tumors in mice

| Group | Preconditioning | NK cell | Protocol |
|---|---|---|---|
| 1 | Cy/Flu* | allogeneic | Cyclophosphamide 166 mg/kg, dosing at days −5, −4, −3<br>Fludarabine Phosphate 10 mg/kg, dosing at days −5, −4, −3 |
| 2 | AVM0703 | allogeneic | AVM0703 148 mg/kg, dosing at day −2 |
| 3 | CyFlu + AVM0703 | allogeneic | Cyclophosphamide 166 mg/kg, dosing at day −5<br>Fludarabine Phosphate 10 mg/kg, dosing at day −5<br>AVM0703 148 mg/kg, dosing day −2 |
| 4 | Cy/Flu* | syngeneic | Cyclophosphamide 166 mg/kg, dosing at days −5, −4, −3<br>Fludarabine Phosphate 10 mg/kg, dosing at days −5, −4, −3 |
| 5 | AVM0703 | syngeneic | AVM0703 148 mg/kg, dosing at day −2 |
| 6 | CyFlu + AVM0703 | syngeneic | Cyclophosphamide 166 mg/kg, dosing at day −5<br>Fludarabine Phosphate 10 mg/kg, dosing at day −5<br>AVM0703 148 mg/kg, dosing day −2 |
| 7 | Vehicle | allogeneic | Vehicle only, dosing at day −2 (AVM Placebo) |
| 8 | Vehicle | syngeneic | Vehicle only, dosing at day −2 (AVM Placebo) |

Method of investigation: Body weight, blood, and spleen collection for further analysis. Lungs are excised and perfused with India Ink for visual counts of metastasis. Mice survival plot will be made to compare the survival benefit between different treatments.

Expected outcome: Efficacy of NK-cell therapy after AVM0703 preconditioning demonstrated to be equivalent or superior to therapy after chemotherapy preconditioning in solid tumor mouse models.

Example 10: Treatment of Patients with Solid Tumors

A patient with a solid tumor including but not limited to prostate cancer, pancreatic cancer, colon cancer, breast cancer, a sarcoma, a carcinoma, a neuroblastoma, blastomas, fibromas, chondromas, lymphomas, adenomas, lung cancer, ependymomas, chromocytomas, histiocytomas, seminomas, uterine cancer, cervical cancer is identified. The patient is preconditioned with NTLA as Tacrolimus delivered as an injection or oral dose of about 0.1 mg/kg/day to about 10 mgs/kg/day but preferably about 0.48 mg/kg to about 10 mg/kg for about 1 to about 4 weeks, or as Cyclosporine administered at about 15 to about 100 mgs/kg/daily for about 7 to about 28 days (the daily dose is divided by two and administered every 12 hours), or as Dexamethasone base, or an equivalent dose of another glucocorticoid, between about 3 mg/kg and about 26 mg/kg single acute dose about 12 to about 72 hours prior to cell immunotherapy administration or total dose of about 3 mg/kg to about 26 mg/kg given between about 12 to about 72 hours prior to cell therapy administration (the single acute dose would most preferably be given about 36 to about 48 hours prior to cell immunotherapy administration), or as a TNF inhibitor administered for about 3 to about 4 weeks, or as an immunotherapy of the class of Rituximab administered between about 375 mg/m2 to about 500 mg/m2 administered about every 7 days on about day −7 and day −1. After preconditioning, between about 1 days to about 4 days, the patient is administered a cellular immunotherapy between about $1\times10^5$ cells/kg body weight to about $1\times10^7$ cells/kg body weight. The preferred cellular therapy is an NK cell product, a TCR cell product, a TAC cell product, or a CarT cell product. Minimal residual disease (MRD) is reduced, complete remission rates are increased, partial remission rates are increased, relapse free survival is increased and overall survival time is enhanced. The NTLA preconditioned patients will have similar or better anti-tumor effect, improved progression-free survival, reduced Disease progression, enhanced duration of response, improved overall survival, or reduced minimal residual disease compared to patients who are preconditioned with radiation or repetitive doses of cytotoxic chemotherapy.

Example 11: Treatment of Patients with Leukemias or Lymphomas or Myelomas

A patient with multiple myeloma, acute lymphoblastic leukemia, chronic lymphoblastic leukemia, acute myelogenous leukemia or any leukemia or lymphoma or myeloma is preconditioned with NTLA as Tacrolimus delivered as an injection or oral dose of about 0.1 mg/kg/day to about 10 mgs/kg/day but preferably 0.48 mg/kg to about 10 mg/kg for about 1 to about 4 weeks, or as Cyclosporine administered at about 15 to about 100 mgs/kg/daily for about 7 to about 28 days (the daily dose is divided by two and administered every 12 hours), or as Dexamethasone base, or an equivalent dose of another glucocorticoid, between about 3 mg/kg and about 26 mg/kg single acute dose about 12 to about 72 hours prior to cell immunotherapy administration or total dose of about 3 mg/kg to about 26 mg/kg given between about 12 to about 72 hours prior to cell therapy administration (the single acute dose would most preferably be given about 36 to about 48 hours prior to cell immunotherapy administration), or as a TNF inhibitor administered for about 3 to about 4 weeks, or as an immunotherapy of the class of Rituximab administered between about 375 mg/m2 to about 500 mg/m2 administered about every 7 days on about day −7 and day −1. After preconditioning, between about 1 days to about 4 days after, the patient is administered a cellular immunotherapy between about $1\times10^5$ cells/kg body weight to about $1\times10^7$ cells/kg body weight. The preferred cellular therapy is an NK cell product, a TCR cell product, a TAC cell product, or a CarT cell product. Minimal residual disease (MRD) is reduced, complete remission rates are increased, partial remission rates are increased, relapse free survival is increased and overall survival time is enhanced. The NTLA preconditioned patients will have similar or better anti-tumor effect, improved progression-free survival, reduced Disease progression, enhanced duration of response, improved overall survival, or reduced minimal residual disease compared to patients who are preconditioned with radiation or repetitive doses of cytotoxic chemotherapy.

Example 12: Treatment of Patients with Autoimmune Diseases

A patient with an autoimmune disease such as, but not limited to: SLE, psoriasis, rheumatoid arthritis, sporiatic arthritis, type I diabetes, multiple sclerosis, Sjogren's Syndrome, scleroderma, Grave's Disease, Hashimoto's thyroiditis, Celiac Disease, Addison's Disease, Myasthenia Gravis, Autoimmune hepatitis, Antiphospholipid syndrome, biliary cholangitis, is treated with NTLA immune suppressant, with NTLA dexamethasone doses, or an antagonist to CD26. NTLA dexamethasone (as base) doses range from about 3 mg/kg to about 12 mg/kg, with doses between about 9 mg/kg and about 12 mg/kg being preferred.

B lymphocyte numbers are reduced by greater than 90% with the NTLA dexamethasone dose, and as memory B cells make up approximately 50% of the B cell compartment in people over age 20, memory B cell populations are also reduced by greater than 90%. The patient's autoimmune attacking B cells have apoptosed and the patient ceases to have active self-immune attacks. The patient's physical symptoms are improved or eliminated. Remission from the autoimmune disease lasts indefinitely in most patients, however, should the patient relapse then a repeat dose of the NTLA immune suppressant, with NTLA dexamethasone doses, or an antagonist to CD26. Repeat treatments can occur as often as once per month if necessary, but preferably not more than one a year, and most preferably not more than once every 5 years.

Example 13: Treatment of Residual HIV

A patient with residual HIV is treated with NTLA immune suppressant, with NTLA dexamethasone doses, or an antagonist to CD26. NTLA dexamethasone (as base) doses range from about 3 mg/kg to about 12 mg/kg, with doses between about 9 mg/kg and about 12 mg/kg being preferred. The treatment eliminates the nuches in the spleen where HIV hides and sends the infected T cells into the circulation where they can be killed by standard HIV therapies that include anti-retroviral drugs, including but not limited to nucleoside reverse transcriptase inhibitors (NTRIs), non-nucleoside reverse transcriptase inhibitors (NNRTIs), protease inhibitors (PIs), fusion and entry inhibitors, pharmacokinetic enhances and integrase strand transfer inhibitors (INSTIs).

Example 14: Treatment of Germinal Center Lymphomas, for Example Burkitts Lymphoma A patient with a germinal center lymphoma such as but not limited to Burkitt's Lymphoma or diffuse large B-cell lymphoma (DLBCL) is treated with NTLA immune suppressant, with NTLA dexamethasone doses, or an antagonist to CD26. NTLA dexamethasone (as base) doses range from about 3 mg/kg to about 12 mg/kg, with doses between about 9 mg/kg and about 12 mg/kg being preferred. The treatment eliminates the nuches in the spleen where the germinal center lymphomas bind and sends the cells into the circulation where they can be eliminated more completely, or with lower doses, of standard chemotherapy such as R-CHOP, or by antibodies to CD20 such as Rituxan, Bexxar, or Zevalin, or by antibodies to CD22 or CD70 such as Lymphocide or Vorsetuzumab mafodotin, or by Bcl-2 inhibitors such as Oblimersen sodium, ABT-737 (oral form navitoclax, ABT-263), or Fenretinide, or by Syk inhibitors such as Fostamatinib or Tamatinib, or by proteasome inhibitors such as Bortezomib (Velcade), or COMPADME, CODOX-M/IVAC. Relapse rates are reduced and disease free survival rates are increased.

Example 15: Conversion of a Dexamethasone Dose to an Equivalent Dose of Another Glucocorticoid To calculate the equivalent dosing for another glucocorticoid, the dose of dexamethasone is entered into a publicly available glucocorticoid conversion calculator, preferably www.medcalc.com. Then the total dosing is determined based on the half-life of the glucocorticoid. For instance, 3 to 12 mg/kg dexamethasone converts to 19 to 75 mg/kg prednisone. Since prednisone's biologic half-life is about 20 hours, while dexamethasone's biologic half-life is about 36 to 54 hours. Therefore, prednisone would be dosed between 19 to 75 mg/kg every 24 hours for equivalent biologic dosing.

The invention claimed is:

1. A method of enhancing adoptive cellular therapy (ACT) in a human patient suffering from cancer, the method comprising:
   administering to the human patient dexamethasone or another glucocorticoid at a dose that is effective to cause lymphodepletion and/or cause ablation of secondary lymphatic germinal centers,
   and administering ACT to the patient, wherein the ACT comprises a cell from an immune lineage which directly treats the cancer,
   wherein the method does not include the administration of radiotherapy nor a chemotherapeutic agent for a duration of more than 1 day within about 2 weeks preceding the start of ACT administration,
   wherein the dose of dexamethasone or another glucocorticoid that is effective to cause lymphodepletion and/or cause ablation of secondary lymphatic germinal centers is between 5-26 mg/kg dexamethasone or dexamethasone base or a dose of another glucocorticoid that is equivalent to between 5-26 mg/kg of dexamethasone,
   and wherein the dexamethasone or another glucocorticoid is administered before ACT commences.

2. The method of claim 1, wherein dexamethasone, dexamethasone base, prednisone, betamethasone, or methylprednisolone is administered to the patient.

3. The method of claim 2, wherein dexamethasone is administered to the patient.

4. The method of claim 1, wherein the effective dose achieves at least 60% CD3+ lymphodepletion.

5. The method of claim 3, wherein the dexamethasone is administered at a dose of about 12 mg/kg.

6. The method of claim 3, wherein the dexamethasone is administered at a dose of between about 9 mg/kg to 26 mg/kg.

7. The method of claim 3, wherein the dexamethasone is administered at a dose of between about 9 mg/kg to about 12 mg/kg.

8. The method of claim 1, wherein the enhanced ACT comprises enhanced cancer killing in the patient with cancer.

9. The method of claim 1, wherein dexamethasone or another glucocorticoid is administered at least 12 hours before ACT commences.

10. The method of claim 9, wherein dexamethasone or another glucocorticoid is administered at one or more time points between about 72 to about 12 hours prior to commencement of ACT.

11. The method of claim 1, wherein the ACT comprises administration of T cells.

12. The method of claim 1, wherein the dose is between about 9 mg/kg to 26 mg/kg of dexamethasone or dexamethasone base or a dose of another glucocorticoid that is equivalent to between about 9 mg/kg to 26 mg/kg of dexamethasone.

13. The method of claim 1, wherein the dose is between about 9 mg/kg to about 12 mg/kg of dexamethasone or dexamethasone base or a dose of another glucocorticoid that is equivalent to between about 9 mg/kg to about 12 mg/kg of dexamethasone.

14. The method of claim 1, wherein the dose is between about 12 mg/kg to 26 mg/kg of dexamethasone or dexamethasone base or a dose of another glucocorticoid that is equivalent to between about 12 mg/kg to 26 mg/kg of dexamethasone.

15. The method of claim 1, wherein the dose is about 12 mg/kg of dexamethasone or dexamethasone base or a dose of another glucocorticoid that is equivalent to about 12 mg/kg of dexamethasone.

16. A method of ameliorating the binding and accumulation of a cellular immunotherapy in secondary lymphatic binding sites comprising:
   administering to a human patient suffering from cancer an adoptive cellular therapy (ACT) comprising a cell from an immune lineage which directly treats the cancer; and
   administering a non-toxic lymphodepleting agent (NTLA), which lymphodepletes and ablates the secondary lymphatic binding sites where said cellular immunotherapy binds and accumulates, wherein the NTLA is dexamethasone administered at a dose of between 5-26 mg/kg for a single acute dose or the NTLA is another glucocorticoid administered at a dose that is equivalent to between 5-26 mg/kg of dexamethasone for a single acute dose, wherein the administration of the NTLA occurs about 12-72 hours before administration of said ACT to ameliorate the binding and accumulation of said ACT cells in secondary lymphatic binding sites.

17. The method of claim 16, wherein administering the dexamethasone or another glucocorticoid achieves at least 60% CD3+ lymphodepletion.

18. The method of claim 16, wherein the ACT comprises the administration of T cells.

19. The method of claim 16, wherein the method does not include the administration of radiotherapy or a chemotherapeutic agent for a duration of more than 1 day within about 2 weeks preceding the start of ACT.

* * * * *